United States Patent
Dzierba et al.

(10) Patent No.: US 10,035,777 B2
(45) Date of Patent: Jul. 31, 2018

(54) HETEROCYCLIC KINASE INHIBITORS

(71) Applicant: BRISTOL-MYERS SQUIBB COMPANY, Princeton, NJ (US)

(72) Inventors: Carolyn Diane Dzierba, Middletown, CT (US); Joanne J. Bronson, Durham, CT (US); John E. Macor, Washington Crossing, PA (US); Bireshwar Dasgupta, East Hampton, CT (US); Susheel Jethanand Nara, Mumbai (IN); Vivekananda M. Vrudhula, Killingworth, CT (US); Senliang Pan, Woodbridge, CT (US); Richard A. Hartz, Middletown, CT (US); Ramkumar Rajamani, Woodbridge, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/500,116

(22) PCT Filed: Jul. 27, 2015

(86) PCT No.: PCT/US2015/042165
§ 371 (c)(1),
(2) Date: Jan. 30, 2017

(87) PCT Pub. No.: WO2016/022312
PCT Pub. Date: Feb. 11, 2016

(65) Prior Publication Data
US 2017/0260145 A1    Sep. 14, 2017

Related U.S. Application Data

(60) Provisional application No. 62/033,425, filed on Aug. 5, 2014.

(51) Int. Cl.
| C07D 235/14 | (2006.01) |
| C07D 401/04 | (2006.01) |
| C07D 403/04 | (2006.01) |
| C07D 413/04 | (2006.01) |
| C07D 417/04 | (2006.01) |
| C07D 471/04 | (2006.01) |
| C07D 487/04 | (2006.01) |
| C07D 401/14 | (2006.01) |

(52) U.S. Cl.
CPC ......... *C07D 235/14* (2013.01); *C07D 401/04* (2013.01); *C07D 401/14* (2013.01); *C07D 403/04* (2013.01); *C07D 413/04* (2013.01); *C07D 417/04* (2013.01); *C07D 471/04* (2013.01); *C07D 487/04* (2013.01)

(58) Field of Classification Search
None
See application file for complete search history.

(56) References Cited

U.S. PATENT DOCUMENTS

| 2004/0224952 A1 | 11/2004 | Cowart et al. |
| 2004/0224953 A1 | 11/2004 | Cowart et al. |
| 2014/0336190 A1* | 11/2014 | Aktoudianakis ..... C07D 471/04 514/234.5 |

FOREIGN PATENT DOCUMENTS

| JP | 10036361 A2 | 2/1998 |
| WO | WO 2010/024903 A1 | 3/2010 |
| WO | WO 2013/042137 A1 | 3/2013 |
| WO | WO 2013/134336 A2 | 9/2013 |
| WO | WO 2014/182929 A1 | 11/2014 |

OTHER PUBLICATIONS

Buonanno, A., "The neuregulin signaling pathway and schizophrenia: From genes to synapses and neural circuits", Brain Research Bulletin, vol. 83, pp. 122-131 (2010).
Conner, S.D. et al., "AAK-1 Mediated μ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor μ2 kinase", The Journal of Cell Biology, vol. 163, No. 2, pp. 231-236 (2003).
Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", BMC Medical Genetics, 10:98 (2009).
Motley, A.M. et al., Functional Analysis of AP2 α and μ2 Subunits, Molecular Biology of the Cell, vol. 17, pp. 5298-5308 (2006).
Ricotta, D. et al., "Phosphorylation of the AP2 μ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).
Yin, Y. et al., "Benzothiazoles as Rho-associated kinase (ROCK-II) inhibitors," Bioorganic & Medicinal Chemistry Letters, 19, pp. 6686-6690 (2009).

* cited by examiner

*Primary Examiner* — Alicia L Otton
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

12 Claims, No Drawings

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: fluoresceinated peptide

<400> SEQUENCE: 1

Lys Glu Glu Gln Ser Gln Ile Thr Ser Gln Val Thr Gly Gln Ile Gly
1               5                   10                  15

Trp Arg

HETEROCYCLIC KINASE INHIBITORS

CROSS-REFERENCE TO RELATED APPLICATIONS

This application claims priority to U.S. Provisional Patent Application Ser. No. 62/033,425, filed Aug. 5, 2014, which is incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In a first aspect the present disclosure provides a compound of formula (I)

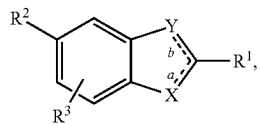

or a pharmaceutically acceptable salt thereof, wherein
one of $a$ and $b$ is a double bond and the other is a single bond;
when $a$ is a double bond, X is N;
when $a$ is a single bond, X is selected from $NR^4$, O, and S;
when $b$ is a double bond, Y is N;
when $b$ is a single bond, Y is selected from $NR^4$, O, and S;
$R^1$ is selected from $C_3$-$C_6$cycloalkyl optionally substituted with one or two methyl groups; $C_3$-$C_6$cycloalkyl$C_1$-$C_3$alkyl, wherein the $C_1$-$C_3$alkyl part is optionally substituted with an amino or methylamino group and wherein the $C_3$-$C_6$cycloalkyl part is optionally substituted with a methyl group;

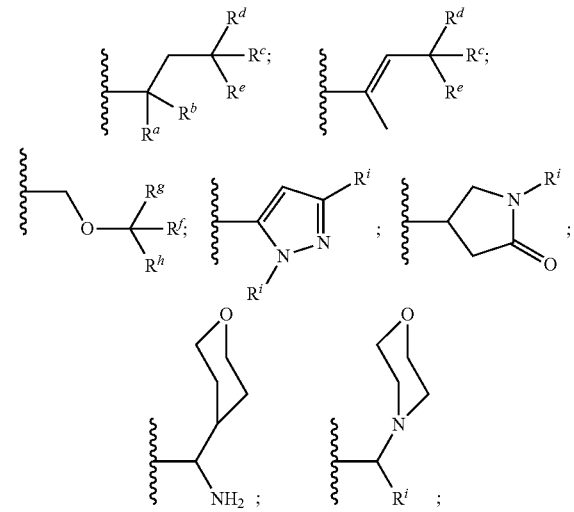

wherein
$R^a$ is selected from hydrogen, amino, aminomethyl, methoxyethylamino, methyl, methylamino, trifluoroacyl, and 2,2,2-trifluoroethyl;
$R^b$ is selected from hydrogen and methyl;
$R^c$ is selected from hydrogen, fluoro, and methyl;
$R^d$ is selected from methyl and trifluoromethyl;
$R^e$ is selected from hydrogen, methyl, trifluoromethyl;
$R^f$ is selected from hydrogen and methyl;
$R^g$ is selected from hydrogen and methyl;
$R^h$ is methyl; and
$R^i$ is $C_1$-$C_6$alkyl;
$R^2$ is a five- or six-membered monocyclic heteroaromatic ring or an eight, nine-, or ten-membered bicyclic heteroaromatic ring system containing one nitrogen atom and optionally one or two additional heteroatoms independently selected from nitrogen, oxygen and sulfur; wherein the ring or ring system is optionally substituted with one or two groups independently selected from acylamino, $C_1$-$C_3$alkoxy, $C_1$-$C_3$alkyl, amino, cyano, dimethylamino, halo, methyl, and methylamino;

$R^3$ is selected from hydrogen, $C_1$-$C_3$alkoxy, $C_1$-$C_3$alkyl, and halo; and $R^4$ is selected from hydrogen, $C_1$-$C_3$alkoxy$C_1$-$C_3$alkyl, $C_1$-$C_3$alkyl, halo$C_1$-$C_3$alkyl, hydroxy$C_1$-$C_3$alkyl.

In a first embodiment of the first aspect the present disclosure provides a compound of formula (I), or a pharmaceutically acceptable salt thereof, wherein $R^1$ is

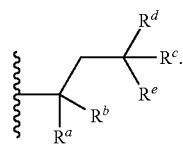

In a second embodiment of the first aspect the present disclosure provides a compound of formula (I), or a pharmaceutically acceptable salt thereof, wherein $R^2$ is optionally substituted pyridinyl.

In a third embodiment of the first aspect the present disclosure provides a compound of formula (I), or a pharmaceutically acceptable salt thereof, wherein $R^2$ is optionally substituted oxazolyl.

In a fourth embodiment of the first aspect the present disclosure provides a compound of formula (I), or a pharmaceutically acceptable salt thereof, wherein $R^2$ is pyrrazolyl.

In a second aspect the present disclosure provides a composition comprising a pharmaceutically acceptable amount of a compound of formula (I), or a pharmaceutically acceptable salt thereof, and a pharmaceutically acceptable carrier.

In a third aspect the present disclosure provides a method of inhibiting adaptor associated kinase 1 (AAK1) activity, comprising contacting AAK1 with a compound of formula (I), or a pharmaceutically acceptable salt thereof.

In a fourth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fourth aspect the disease or disorder is selected from Alzheimer's disease, bipolar disorder, pain, Parkinson's disease, and schizophrenia. In a second embodiment wherein the pain is neuropathic pain. In a third embodiment the neuropathic pain is fibromyalgia or peripheral neuropathy.

Other aspects of the present disclosure may include suitable combinations of embodiments disclosed herein.

Yet other aspects and embodiments may be found in the description provided herein.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "halo," as used herein, refers to Br, Cl, and/or F.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.
One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals. Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: HATU for O-(7-azabenzotriazole-1-yl)-1,1,3,3-tetramethyluronium hexafluorophosphate; EDC for 1-ethyl-3-(3-dimethylaminopropyl)carbodiimide; TBTU for O-benzotriazole-1-yl-1,1,3,3-tetramethyluronium tetrafluoroborate; $PPh_3$ for triphenylphosphine; OAc for acetate; DME for 1,2-dimethoxyethane; DMF for N,N-dimethylformamide; THF for tetrahydrofuran; TOSMIC or TosMIC for tosylmethyl isocyanide; Bu for butyl; NBS for N-bromosuccinimide; EtOH for ethanol; DCM for dichloromethane; Me for methyl; BOC or Boc for tert-butoxycarbonyl; DIPA for diisopropylamine; TFA for trifluoroacetic acid; min for minutes; h for hours; ACN or MeCN for acetonitrile; MeOH for methanol; DEA for diethylamine; EtOAc for ethyl acetate; DMSO for dimethylsulfoxide; MeOD for $CD_4OD$; DMA for dimethylacetamide; TBAB for tetra-n-butylammonium bromide; RT or R.T. or r.t. for room temperature or retention time (context will dictate); DMAP for 4-N,N-dimethylaminopyridine; DMC for dimethylcarbonate; and DIEA or DIPEA for diisopropylethylamine.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 5, wherein $R^2$ is aryl, are prepared by the methods outlined in Scheme 1. A diaminohalide such as bromide 1, can be condensed with an acid 2, utilizing a coupling agent such as HATU, EDC, or TBTU, followed by treatment with a protic acid such as acetic acid to provide benzimidazoles 3. Suzuki coupling of compounds of formula 3 with aryl and heteroarylboronic acids or esters in the presence of a palladium catalyst such as $Pd(PPh_3)_4$, $Pd(OAc)_2$, or 1,1'-bis(diphenylphosphino)ferrocene palladium (II) chloride complex and a base such as sodium carbonate, cesium carbonate, potassium carbonate, or potassium phosphate in the presence or absence of a ligand such as SPhos or XPhos and in a solvent such as DME, DMF, toluene, acetonitrile, THF, dioxane, methanol, ethanol, butanol or water or a combination thereof at temperatures ranging from 20 to 150° C. to give analogs of the formula 5. If $R^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 5.

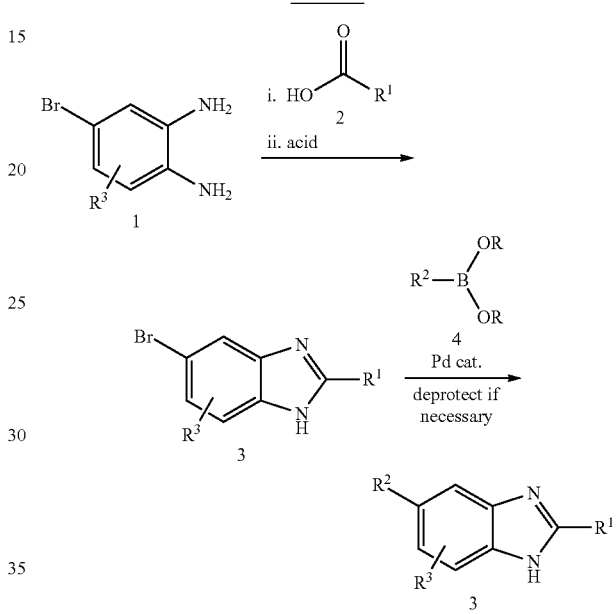

Scheme 1

Compounds of formula 9, wherein $R^2$ is oxazole, are prepared by the methods outlined in Scheme 2. Suzuki coupling of compounds of formula 3 with vinylboronic acids or esters in the presence of a palladium catalyst such as $Pd(PPh_3)_4$, $Pd(OAc)_2$, or 1,1'-bis(diphenylphosphino)ferrocene palladium (II) chloride complex and a base such as sodium carbonate, cesium carbonate, potassium carbonate, or potassium phosphate in the presence or absence of a ligand such as SPhos or XPhos and in a solvent such as DME, DMF, toluene, acetonitrile, THF, dioxane, methanol, ethanol, butanol or water or a combination thereof at temperatures ranging from 20 to 150° C. can give analogs of the formula 7. The vinyl group can be oxidized with reagents such as osmium tetroxide and sodium periodate followed by treatment with TOSMIC to afford compounds of the formula 9.

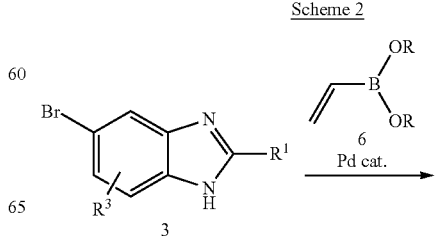

Scheme 2

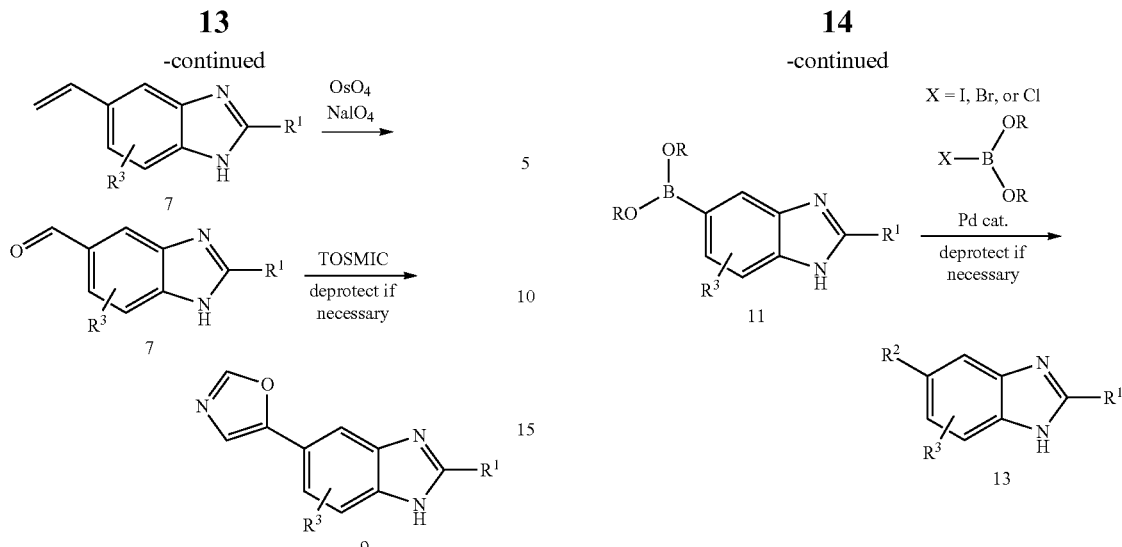

Compounds of formula 13, wherein $R^2$ is aryl, are prepared by the methods outlined in Scheme 3. Bromide 3 can be converted into the boronic acid or ester 11 via standard Suzuki coupling conditions under standard Suzuki coupling conditions employing a base such as cesium carbonate and a catalyst such as $Pd(PPh_3)_4$ as described by Zhang, Lei et. al. (Journal of Medicinal Chemistry, 2011, 54, 1724-1739) or by treatment with a base such as N-butyl lithium, followed by trialkoxyboronate. The boronic acid or ester 11 and be coupled via Suzuki coupling to an aryl halide 12 utilizing standard Suzuki coupling conditions in the presence of a palladium catalyst such as $Pd(PPh_3)_4$, $Pd(OAc)_2$, or 1,1'-bis(diphenylphosphino)ferrocene palladium (II) chloride complex and a base such as sodium carbonate, cesium carbonate, potassium carbonate, or potassium phosphate in the presence or absence of a ligand such as SPhos or XPhos and in a solvent such as DME, DMF, toluene, acetonitrile, THF, dioxane, methanol, ethanol, butanol or water or a combination thereof at temperatures ranging from 20 to 150° C. to give compounds of the formula 13. If $R^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 13.

Scheme 3

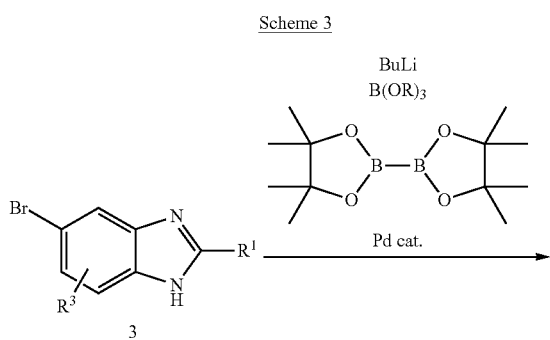

Intermediates of formula 16 are prepared by the methods outlined in Scheme 4. Nitro anilines 14 can be halogenated with a reagent such as NBS to give bromides 15. Reduction of the nitro group can be carried out using standard conditions such as hydrogenation with palladium on carbon or treatment with reducing agents such as ammonium chloride and zinc powder in a solvent such as methanol or ethanol to afford intermediates of the formula 16.

Scheme 4

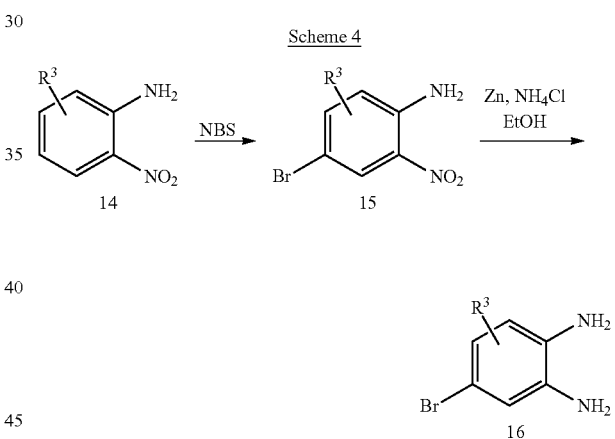

Intermediates of formula 20 and 23 are prepared by the methods outlined in Scheme 5. The fluorine of ortho-fluoro nitro compounds 17 and 21 can displaced with amines 18 to give compounds of the formula 19 and 22, respectively. Reduction of the nitro group can be carried out using standard conditions such as hydrogenation with palladium on carbon or treatment with reducing agents such as ammonium chloride and zinc powder in a solvent such as methanol or ethanol to afford intermediates of the formula 20 and 23.

Scheme 5

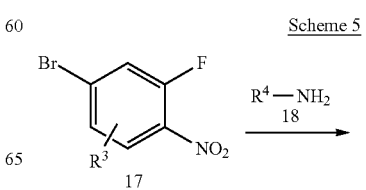

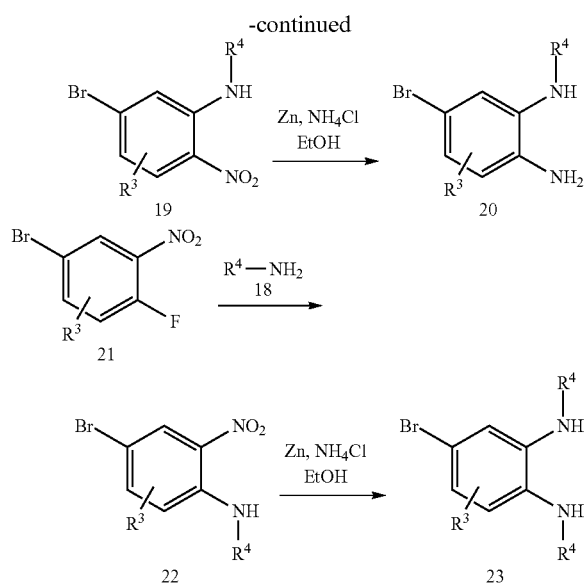

Intermediates of formula 26, wherein $R^2$ is aryl, are prepared by the methods outlined in Scheme 6. The boronic acid or ester 4 and be coupled via Suzuki coupling to aryl halide 24 utilizing standard Suzuki coupling conditions in the presence of a palladium catalyst such as $Pd(PPh_3)_4$, $Pd(OAc)_2$, or 1,1'-bis(diphenylphosphino)ferrocene palladium (II) chloride complex and a base such as sodium carbonate, cesium carbonate, potassium carbonate, or potassium phosphate in the presence or absence of a ligand such as SPhos or XPhos and in a solvent such as DME, DMF, toluene, acetonitrile, THF, dioxane, methanol, ethanol, butanol or water or a combination thereof at temperatures ranging from 20 to 150° C. to give compounds of the formula 25. In cases where $R^2$ is oxazole, bromide 24 and be converted in to oxazole 25 via the route described in Scheme 2. Reduction of the nitro group can be carried out using standard conditions such as hydrogenation with palladium on carbon or treatment with reducing agents such as ammonium chloride and zinc powder in a solvent such as methanol or ethanol to afford intermediates of the formula 26.

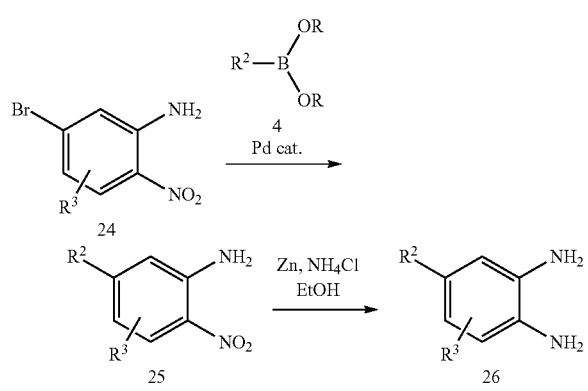

Compounds of formula 31, wherein X is O in formula (I), are prepared by the methods outlined in Scheme 7. Alkoxyphenyls 27 can be nitrated with nitric acid followed by cleavage of the alkoxy group with reagents such as boron tribromide to afford nitro phenols 28. Reduction of the nitro group can be carried out using standard conditions such as hydrogenation with palladium on carbon or treatment with reducing agents such as ammonium chloride and zinc powder in a solvent such as methanol or ethanol to afford amino alcohols 30. Coupling with an acid 2, utilizing a coupling agent such as HATU, EDC, or TBTU, followed by treatment with a protic acid such as acetic acid to provide compounds of the formula 31. If $R^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 31.

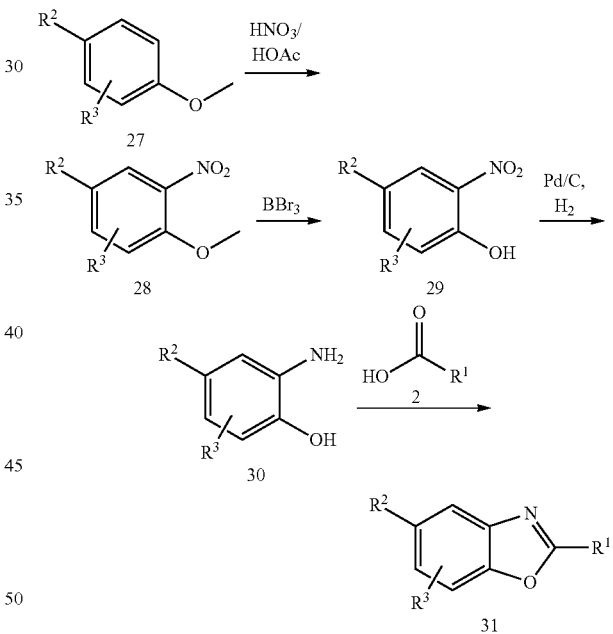

Intermediates of formula 30, are also prepared by the methods outlined in Scheme 8. Benzimidazole 32 can be coupled to boronic acid or ester 4 via standard Suzuki coupling conditions in the presence of a palladium catalyst such as $Pd(PPh_3)_4$, $Pd(OAc)_2$, or 1,1'-bis(diphenylphosphino)ferrocene palladium (II) chloride complex and a base such as sodium carbonate, cesium carbonate, potassium carbonate, or potassium phosphate in the presence or absence of a ligand such as Sphos, XPhos or 2-dicyclohexylphosphino-2',6'-dimethoxy-1,1'-biphenyl and in a solvent such as DME, DMF, toluene, acetonitrile, THF, dioxane, methanol, ethanol, butanol or water or a combination thereof at temperatures ranging from 20 to 150° C. to give intermediates of the formula 30.

Scheme 8

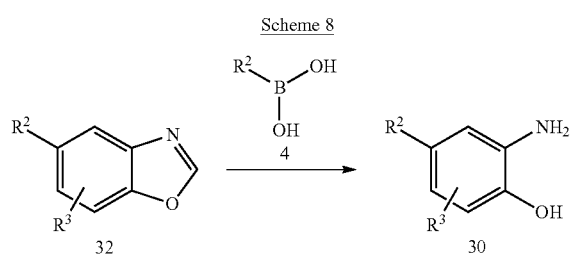

Compounds of formula 37, wherein X is O in formula (II), are prepared by the methods outlined in Scheme 9. The boronic acid or ester 4 and be coupled to compounds of formula 33 via standard Suzuki coupling conditions in the presence of a palladium catalyst such as Pd(PPh$_3$)$_4$, Pd(OAc)$_2$, or bis(triphenylphosphine)palladium(II) chloride and a base such as sodium carbonate, cesium carbonate, potassium carbonate, or potassium phosphate in the presence or absence of a ligand such as Sphos, XPhos or 2-dicyclohexylphosphino-2',6'-dimethoxy-1,1'-biphenyl and in a solvent such as DME, DMF, toluene, acetonitrile, THF, dioxane, methanol, ethanol, butanol or water or a combination thereof at temperatures ranging from 20 to 150° C. to give intermediates of the formula 34. The alkoxy group of 34 can be removed with reagents such as boron tribromide to afford nitro phenols 35. Reduction of the nitro group can be carried out using standard conditions such as hydrogenation with palladium on carbon or treatment with reducing agents such as ammonium chloride and zinc powder in a solvent such as methanol or ethanol to afford amino alcohols 36. Coupling with an acid 2, utilizing a coupling agent such as HATU, EDC, or TBTU, followed by treatment with a protic acid such as acetic acid to provide compounds of the formula 37. If R$^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 37.

Scheme 9

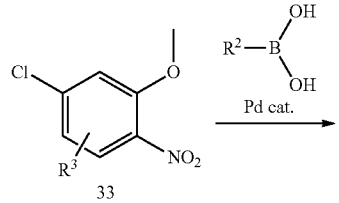

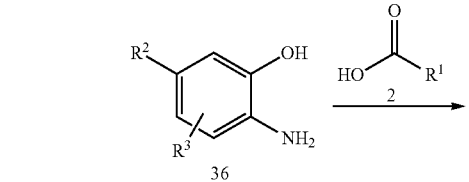

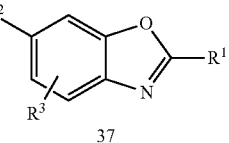

Compounds of formula 40, wherein X is S in formula (I), are prepared by the methods outlined in Scheme 10. Aryl halides 38 can be condensed with an acid 2, utilizing a coupling agent such as HATU, EDC, or TBTU, followed by treatment with a protic acid such as acetic acid to provide benzthiazoles 9. Suzuki coupling of intermediates of the formula 9 with a boronic acid or ester 4 can be carried out via standard Suzuki coupling conditions in the presence of a palladium catalyst such as Pd(PPh$_3$)$_4$, Pd(OAc)$_2$, or bis(triphenylphosphine)palladium(II) chloride and a base such as sodium carbonate, cesium carbonate, potassium carbonate, or potassium phosphate in the presence or absence of a ligand such as Sphos, XPhos or 2-dicyclohexylphosphino-2',6'-dimethoxy-1,1'-biphenyl and in a solvent such as DME, DMF, toluene, acetonitrile, THF, dioxane, methanol, ethanol, butanol or water or a combination thereof at temperatures ranging from 20 to 150° C. to give intermediates of the formula 40. If R$^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 40.

Scheme 10

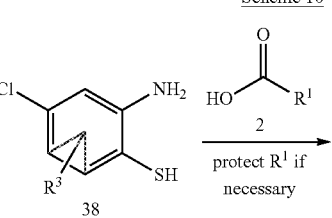

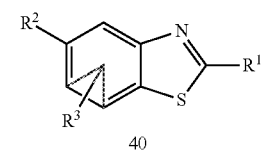

Compounds of formula 43, wherein X is S in formula (II), are prepared by the methods outlined in Scheme 11. Suzuki coupling of halo benzthiazoles 41 with a boronic acid or ester 4, can be carried out via standard Suzuki coupling conditions in the presence of a palladium catalyst such as Pd(PPh$_3$)$_4$, Pd(OAc)$_2$, or bis(triphenylphosphine)palladium(II) chloride and a base such as sodium carbonate, cesium carbonate, potassium carbonate, or potassium phosphate in the presence or absence of a ligand such as Sphos, XPhos or 2-dicyclohexylphosphino-2',6'-dimethoxy-1,1'-biphenyl and in a solvent such as DME, DMF, toluene, acetonitrile, THF, dioxane, methanol, ethanol, butanol or water or a combination thereof at temperatures ranging from 20 to 150° C. to give intermediates of the formula 42 which may exist as the disulfide. Intermediate 42 can condensed with an acid 2, utilizing a coupling agent such as HATU, EDC, or TBTU, followed by treatment with a protic acid such as acetic acid to provide benzthiazoles 43. If $R^1$ contains an amine group or another functional group that is protected, the protecting group can be removed after the Suzuki coupling by treating the substrate with the appropriate reagents as described in Protective Groups in Organic Synthesis (Greene, Wuts; 3rd ed., 1999, John Wiley & Sons, Inc.) to provide compounds of the formula 43.

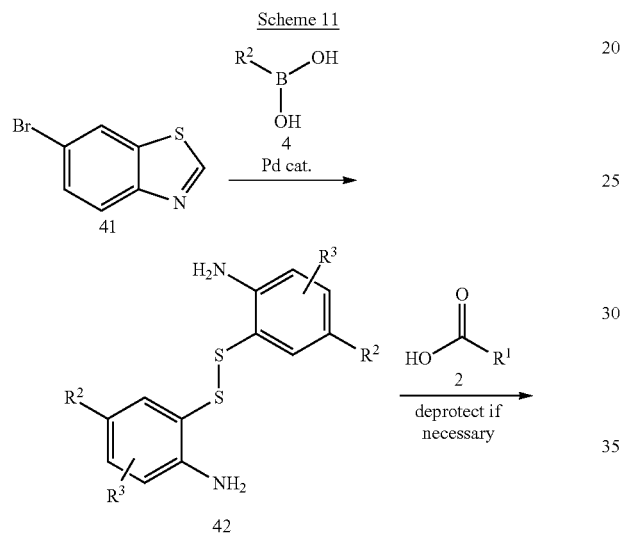

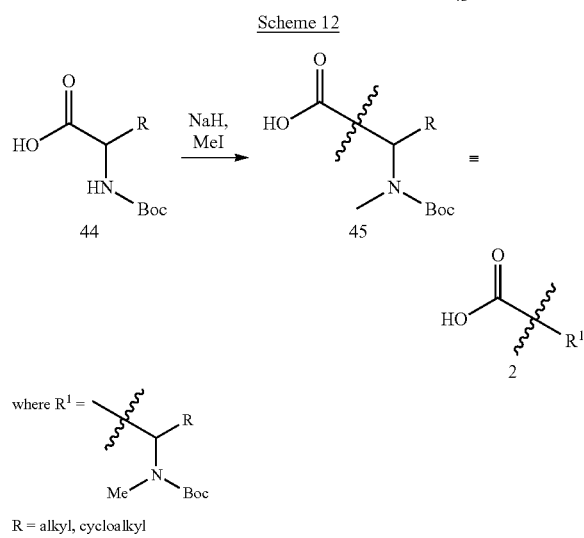

Intermediate of the formula 45, where in R is alkyl or cycloalkyl, is prepared by the method outlined in Scheme 12. The acid of the formula 44 can be treated with a base such as sodium hydride and in solvents such as THF or DCM followed by addition of an electrophile such as methyl iodide to afford the intermediate of the formula 45. The intermediate of the formula 45 is equivalent to the intermediate of formula 2, wherein $R^1$=—CH(R)(NMeBoc). The intermediates of the formula 2 can be used for the synthesis of compounds of the formula 5 and 9 as described in Schemes 1 and 2 respectively.

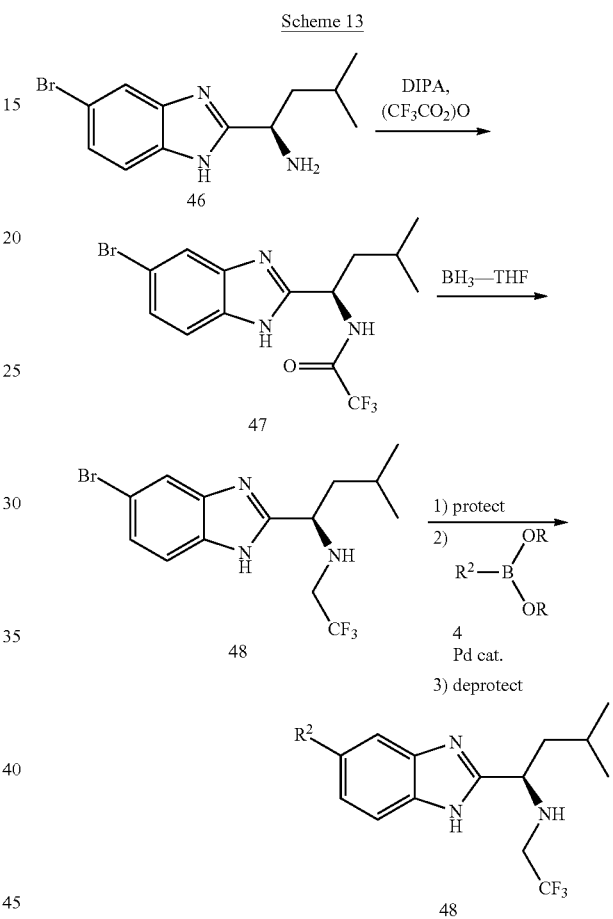

Intermediate of the formula 48 can be prepared from intermediate of the formula 46 as outlined in Scheme 13. Bromo intermediate of the formula 46 can be treated with base such as diisopropyl ethyl amine and acylating agent such as trifluoroacetic anhydride using standard acylation conditions to afford intermediate of the formula 47. Trifluoroacyl intermediate of the formula 47 can be reduced with a reducing agent such as borane in solvents such as THF or diethyl ether to afford intermediate of the formula 48. The intermediate of formula 48 can be protected using groups such as Boc following the standard protection chemistry with the appropriate reagents as described in Protective Groups in Organic Synthesis (Greene, Wuts; 3rd ed., 1999, John Wiley & Sons, Inc.). Suzuki coupling with aryl and heteroarylboronic acids or esters in the presence of a palladium catalyst such as Pd(PPh$_3$)$_4$, Pd(OAc)$_2$, or 1,1'-bis(diphenylphosphino)ferrocene palladium (II) chloride complex and a base such as sodium carbonate, cesium carbonate, potassium carbonate, or potassium phosphate in a solvent such as DME, DMF, acetonitrile, THF, dioxane, methanol, ethanol, butanol or water or a combination thereof at temperatures ranging from 20 to 150° C. affords the aryl substituent R². The protecting group can be removed after the Suzuki coupling by treating the substrate with the appropriate reagents as described in Protective Groups in Organic Synthesis (Greene, Wuts; 3rd ed., 1999, John Wiley & Sons, Inc.) to give analogs of the formula 49.

Scheme 14

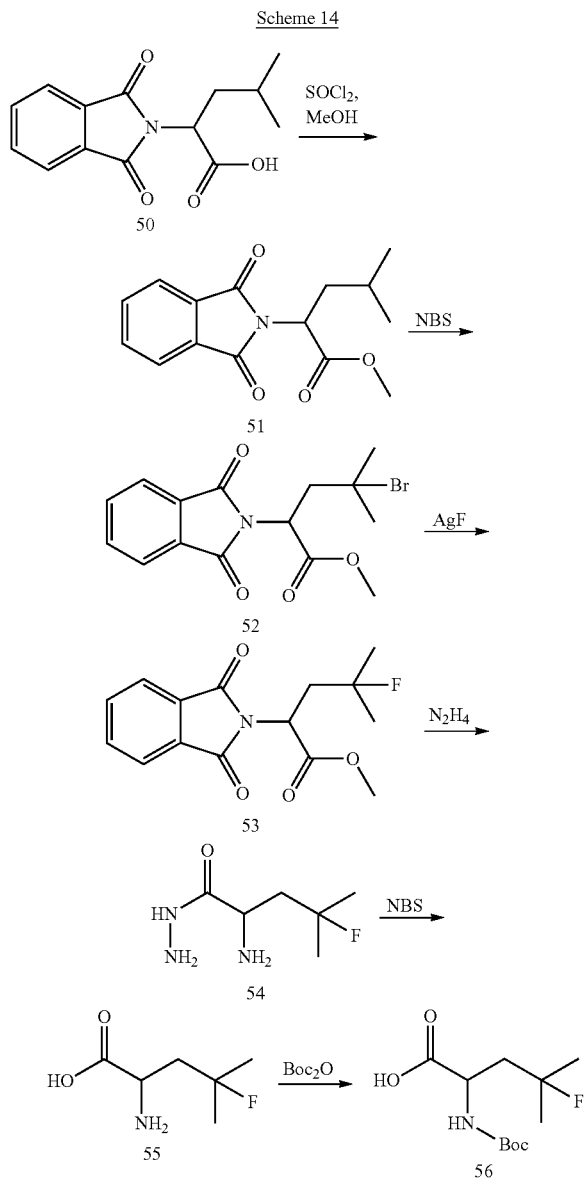

Intermediate of the formula 56 was prepared by the methods outlined in Scheme 14. Compound of the formula 50 can be converted to methyl ester 51 using reagent such as thionyl chloride or oxalyl chloride in methanol. Intermediate 51 can be brominated using reagents such as NBS in solvents such as $CCl_4$ to afford intermediate 52. Bromo intermediate 52 can be converted to fluoro intermediate 53 by using reagents such as silver fluoride in solvents such as acetonitrile. Phthalimide group of the intermediate 53 can be deprotected using a reagent such as hydrazine hydrate in solvent such as ethanol to afford intermediate 54. Hydrazide intermediate of the formula 54 can be hydrolyzed to car-boxylic acid 55 by using reagent such as NBS in water. Boc intermediate 55 can be prepared from intermediate 54 by reaction with a reagent such as Boc anhydride in a solvent such as dioxane and water as described in Protective Groups in Organic Synthesis (Greene, Wuts; 3rd ed., 1999, John Wiley & Sons, Inc.). The carboxylic acid intermediate 56 can be used for the synthesis of compounds of the formula 5 and 9 as described in Schemes 1 and 2 respectively.

Various analogues synthesized using procedures and intermediates outlined in Schemes 1-14 are listed in Table 1. AAK1 functional (AAK1 $IC_{50}$ (nM)) and cellular (cell $IC_{50}$ (nM)) potency for select compounds are listed.

In the following examples, proton NMR spectra were recorded on either a Bruker 400 or 500 MHz NMR spectrometer. Chemical shifts are reported in δ values relative to tetramethylsilane. Multiplicity patterns are designated as follows: s, singlet; d, doublet; t, triplet; q, quartet; quin, quintet; sept or spt, septet; m, multiplet; br, broad peak; dd, doublet of doublet; br d, broad doublet; dt, doublet of triplet; br s, broad singlet; dq, doublet of quartet. Optical rotations $[\alpha]_D$ were determined on a Rudolph Scientific Autopol IV polarimeter in the solvents indicated; concentrations are given in mg/mL. Liquid chromatography (LC)/mass spectra were run on a Shimadzu LC coupled to a Waters Micromass ZQ. HPLC retention times were obtained using at least one of the following methods:

Analytical HPLC methods:
Method A:
Waters analytical C18 Sunfire column (3.0×150 mm, 3.5 m); mobile phase: A=$H_2O$ with 0.1% TFA, B=acetonitrile with 0.1% TFA; 1-20 min, 10% B→40% B; 20-23 min, 95% B; flow rate=1 mL/min; λ=254 nm; run time=23 min.

Method B:
Waters analytical Phenyl Xbridge column (3.0×150 mm, 3.5 m), mobile phase: A=$H_2O$ with 0.1% TFA, B=acetonitrile with 0.1% TFA, 1-20 min, 5% B→40% B; 20-23 min, 95% B; flow rate=1 mL/min; λ=254 nm; run time=23 min.

Method C:
Waters analytical C18 Sunfire column (3.0×150 mm, 3.5 m); mobile phase: A=$H_2O$ with 0.1% TFA, B=acetonitrile with 0.1% TFA; 1-20 min, 10% B→100% B; 20-23 min, 100% B; flow rate=1 mL/min; λ=254 nm; run time=23 min.

Method D:
Waters analytical Phenyl Xbridge column (3.0×150 mm, 3.5 m), mobile phase: A=$H_2O$ with 0.1% TFA, B=acetonitrile with 0.1% TFA, 1-20 min, 10% B→100% B; 20-23 min, 100% B; flow rate=1 mL/min; λ=254 nm; run time=23 min.

Method E:
Waters analytical C18 Sunfire column (3.0×150 mm, 3.5 m); mobile phase: A=$H_2O$ with 0.1% TFA, B=acetonitrile with 0.1% TFA, 1-15 min, 10% B→100% B; 15-18 min, 100% B; flow rate=1 mL/min; λ=254 nm; run time=18 min.

Method F:
Waters analytical Phenyl Xbridge column (3.0×150 mm, 3.5 m), mobile phase: A=$H_2O$ with 0.1% TFA, B=acetonitrile with 0.1% TFA, 1-15 min, 10% B→100% B; 15-18 min, 100% B; flow rate=1 mL/min; λ=254 nm; run time=18 min.

Method G:
YMC C18 S5 analytical column (4.6×50 mm, 3.5 m); mobile phase: A=10% MeOH—90% $H_2O$—0.2% $H_3PO_4$, B=90% MeOH—10% $H_2O$—0.2% $H_3PO_4$; 1-19 min, 0% B→100% B; 19-20 min, 100% B; flow rate=4 mL/min; λ=220 and 254 nm; run time=20 min.

Method H:

Waters analytical C18 Sunfire column (3.0×150 mm, 3.5 m); mobile phase: A=H$_2$O with 0.1% TFA, B=acetonitrile with 0.1% TFA; 1-15 min, 10% B→40% B; 15-18 min, 95% B; flow rate=1 mL/min; λ=254 nm; run time=18 min.

Method I:

Waters analytical Phenyl Xbridge column (3.0×150 mm, 3.5 m), mobile phase: A=H$_2$O with 0.1% TFA, B=acetonitrile with 0.1% TFA, 1-15 min, 5% B→40% B; 15-18 min, 95% B; flow rate=1 mL/min; λ=254 nm; run time=18 min.

Method J:

Waters analytical C18 Sunfire column (3.0×150 mm, 3.5 m); mobile phase: A=H$_2$O with 0.1% TFA, B=acetonitrile with 0.1% TFA; 1-15 min, 5% B→40% B; 15-18 min, 100% B; flow rate=1 mL/min; λ=254 nm; run time=18 min.

Method K:

Waters analytical Phenyl Xbridge column (3.0×150 mm, 3.5 m), mobile phase: A=H$_2$O with 0.1% TFA, B=acetonitrile with 0.1% TFA, 1-15 min, 5% B→40% B; 15-18 min, 100% B; flow rate=1 mL/min; λ=254 nm; run time=18 min.

Method L:

Waters analytical C18 Sunfire column (3.0×150 mm, 3.5 m); mobile phase: A=H$_2$O with 0.1% TFA, B=acetonitrile with 0.1% TFA; 1-10 min, 10% B→100% B; 10-12 min, 100% B; flow rate=1 mL/min; λ=254 nm; run time=10 min.

Method M:

Waters analytical Phenyl Xbridge column (3.0×150 mm, 3.5 m), mobile phase: A=H$_2$O with 0.1% TFA, B=acetonitrile with 0.1% TFA, 1-10 min, 10% B→100% B; 10-12 min, 100% B; flow rate=1 mL/min; λ=254 nm; run time=10 min.

Method N:

Waters analytical Phenyl Xbridge column (3.0×150 mm, 3.5 m), mobile phase: A=10 mM NH$_4$OAc, pH6.8, in Water/ACN (95/5), B=10 mM NH$_4$OAc, pH6.8, in Water/ACN (5/95), 1-10 min, 10% B→100% B; 10-12 min, 100% B; flow rate=0.5 mL/min; λ=254 nm; run time=10 min.

Method O:

Waters analytical Phenyl Xbridge column (3.0×150 mm, 3.5 m), mobile phase: A=10 mM Ammonium Bicarbonate, pH 9.5, in Water/MeOH (95/5), B=10 mM Ammonium Bicarbonate, pH 9.5, in Water/MeOH (5/95), 1-10 min, 40% B→100% B; 10-12 min, 100% B; flow rate=0.5 mL/min; λ=254 nm; run time=10 min.

Method P:

Sunfire C18 (3.0×150 mm, 3.5 m), mobile phase: A=10 mM Ammonium Bicarbonate, pH 9.5, in Water/MeOH (95/5), B=10 mM Ammonium Bicarbonate, pH 9.5, in Water/MeOH (5/95), 1-15 min, 40% B→100% B; 15-18 min, 100% B; flow rate=0.5 mL/min; λ=254 nm; run time=15 min.

Method Q:

Waters analytical Phenyl Xbridge column (3.0×150 mm, 3.5 m), mobile phase: A=10 mM Ammonium Bicarbonate, pH 9.5, in Water/MeOH (95/5), B=10 mM Ammonium Bicarbonate, pH 9.5, in Water/MeOH (5/95), 1-15 min, 40% B→100% B; 15-18 min, 100% B; flow rate=0.5 mL/min; λ=254 nm; run time=15 min.

Method R:

Sunfire C18 (3.0×150 mm, 3.5 m), mobile phase: A=10 mM Ammonium Bicarbonate, pH 9.5, in Water/MeOH (95/5), B=10 mM Ammonium Bicarbonate, pH 9.5, in Water/MeOH (5/95), 1-10 min, 40% B→100% B; 10-12 min, 100% B; flow rate=0.5 mL/min; λ=254 nm; run time=10 min.

Method S: Waters analytical C18 sunfire column (4.6×150 mm, 3.5 m); mobile phase: Buffer: 0.05% TFA in H$_2$O pH=2.5 adjusted with ammonia; A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method T: Waters analytical phenyl xbridge column (4.6×150 mm, 3.5 m), mobile phase: Buffer: 0.05% TFA in H$_2$O pH=2.5 adjusted with ammonia; A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method U: Waters analytical C18 sunfire column (4.6×150 mm, 3.5 m); mobile phase: Buffer: 0.05% TFA in H$_2$O pH=2.5 adjusted with ammonia; A=buffer and acetonitrile (95:5), B=acetonitrile and buffer (95:5); 0-12 min, 10% B→100% B; 12-15 min, 100% B; flow rate=1 mL/min; λ=254 nm and 220 nm; run time=17 min.

Method V: Waters analytical phenyl xbridge column (4.6×150 mm, 3.5 m), mobile phase: Buffer: 0.05% TFA in H$_2$O pH=2.5 adjusted with ammonia; VA=buffer and acetonitrile (95:5), B=acetonitrile and buffer (95:5); 0-12 min, 10% B→100% B; 12-15 min, B→100% B; flow rate=1 mL/min; λ=254 nm and 220 nm; run time=17 min.

Method W: Waters analytical phenyl xbridge column (4.6×150 mm, 3.5 μm), mobile phase: A=10 m M NH$_4$HCO$_3$ in H$_2$O pH=9.5 adjusted with ammonia, B=methanol; 0-12 min, 10% B→100% B; 12-20 min, B→100% B; flow rate=1 mL/min; λ=254 nm and 220 nm; run time=23 min.

Method X: ECLIPSE XDB C18 (4.6×150 mm, 5 μm); mobile phase A=20 mM NH$_4$OAc in H$_2$O, B=acetonitrile; 0-25 min, 10% B→100% B; 25-30 min, 100% B; flow rate=1 mL/min; λ=254 nm and 220 nm; run time=30 min.

Method Y: ATLANTIS T3 column (4.6×150 mm, 5 m); mobile phase: Buffer: 0.05% TFA in H$_2$O pH=2.5 adjusted with ammonia; A=buffer and acetonitrile (95:5), B=acetonitrile and buffer (95:5); 0-15 min, 0% B→50% B; 15-18 min, 50% B-100% B 18-23 min 100% B; flow rate=1 mL/min; λ=254 nm and 220 nm; run time=23 min.

Chiral HPLC methods:

Method A:

Chiralcel OD-H analytical column, 4.6×250 mm, 5 m; Mobile Phase: 15% Methanol with 0.1% DEA Temp: 35° C.; Flow rate: 2.0 mL/min. for 30 min; UV monitored @ 230 nm; Injection: 5 uL of ~1 mg/mL solution in MeOH.

Method B: CHIRALCEL ODH (250×4.6) mm 5 micron; Mob. phase: 0.2% DEA in n-hexane: ethanol (60:40)

Chiral SFC Methods:

Method A1 (A): Column: CHIRALPAK IC; Co Solvent: 0.5% DEA in Methanol; Co Solvent %: 30; Total flow: 3 g/min; Back pressure: 107 bar; Instrument: THAR SFC Method B: Column: CHIRALCEL OD H; Co Solvent: 0.5% DEA in Methanol; Co Solvent %: 30; Total flow: 3 g/min; Column Temperature: 34.8; Back pressure: 100 bar; Instrument: THAR SFC Method C: Column: CHIRALCEL OD H; Co Solvent: 0.5% DEA in Methanol; Co Solvent %: 15; Total flow: 3 g/min; Back pressure: 100 bar; Instrument: THAR SFC Method D: Column: CHIRALPAK AS H; Co Solvent: 0.5% DEA in Methanol; Co Solvent %: 25; Total flow: 3 g/min; Back pressure: 100 bar; Instrument: THAR SFC LC-MS methods:

LC/MS Method A=Column: PUROSPHER@star RP-18 (4×55 mm), 3 μm; Buffer: 20 mM NH$_4$OAC IN WATER; Mphase A: Buffer+ACN(90+10); Mphase B: Buffer+MeCN (10+90); Flow: 2.5 ml/min)

LC/MS Method B=Column: ZORBAX SB C18 (4.6×50 mm), 5 μm; Positive mode Mphase A: 10% MeOH—90% H$_2$O—0.1% TFA; Mphase B: 90% MeOH—10% H$_2$O—0.1% TFA; Flow: 5 ml/min)

LC/MS Method C=Column—Ascentis Express C8 (5×2.1 mm), 2.7 μm; Mphase A: 2% MeCN—98% H$_2$O—10 mM NH$_4$COOH; Mphase B: 98% ACN—2% H$_2$O—10 mM NH$_4$COOH; Flow: 1/min)

LC/MS Method D=Column—ACQUITY UPLC BEH C18 (2.1×50 mm), 1.7 μm; Mphase A: 0.1% TFA in water; Mphase B: ACN; Flow: 1/min)

LC/MS Method E=Column—X Bridge Phe (4.6×30 mm), 3.5 μm; Mphase A: 2% MeCN—98% H$_2$O—10 mM NH$_4$COOH; Mphase B: 98% ACN—2% H$_2$O—10 mM NH$_4$COOH; Flow: 1.8 mL/min)

LC/MS Method F=Column—Ascentis Express C18 (5×2.1 mm), 2.7 μm; Mphase A: 2% MeCN—98% H$_2$O—10 mM NH$_4$COOH; Mphase B: 98% ACN—2% H$_2$O—10 mM NH$_4$COOH; Flow: 1 mL/min)

LC/MS Method J=Column—ZORBAX SB AQ (4.6×50 mm), 3.5 μm; Mphase A: 0.1% HCOOH; Mphase B: MeCN Flow: 1 mL/min)

Example 1

(R)-3-methyl-1-(5-(pyridin-4-yl)-1H-benzo[d]imidazol-2-yl)butan-1-amine

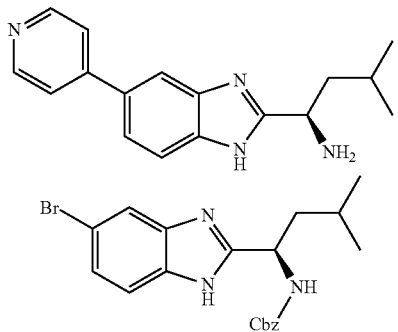

Part A: (R)-benzyl 1-(5-bromo-1H-benzo[d]imidazol-2-yl)-3-methylbutylcarbamate

To a solution of 4-bromobenzene-1,2-diamine (1.614 g, 8.63 mmol), (R)-2-(benzyloxycarbonylamino)-4-methylpentanoic acid (2.29 g, 8.63 mmol) and O-(1H-Benzotriazol-1-yl)-N,N,N,N-tetramethyluronium hexafluorophosphate (3.27 g, 8.63 mmol) in DMF (10.79 mL) at 0° C. was added DIEA (4.52 mL, 25.9 mmol). The solution was stirred at 0° C. for 1.5 h. The reaction mixture was diluted with water and extracted with EtOAc (3×25 mL). The combined organic layers were washed with brine (4×25 mL), dried over MgSO$_4$, filtered and concentrated under reduced pressure. Acetic acid (19.77 mL, 345 mmol) was added to the residue and the solution was heated to 65° C. for 2 h. The reaction was cooled to room temperature and concentrated under reduced pressure. The residue was purified via silica gel chromatography (5%-50% EtOAc in hexanes). Obtained (R)-benzyl 1-(5-bromo-1H-benzo[d]imidazol-2-yl)-3-methylbutylcarbamate (2.48 g, 5.18 mmol, 60% yield) as a pale yellow amorphous solid. $^1$H NMR (400 MHz, CHLOROFORM-d) δ 11.33 (br. s., 2H), 7.52-7.26 (m, 4H), 7.22 (m, 3H), 6.99-6.88 (m, 1H), 5.11-5.02 (m, 2H), 4.92 (d, J=12.3 Hz, 1H), 2.00-1.84 (m, 2H), 1.71-1.61 (m, 1H), 0.91 (d, J=6.8 Hz, 3H), 0.86 (d, J=6.5 Hz, 3H); LC/MS (ESI) m/e 416.0 [(M+H)+, calcd for C20H23BrN3O2 416.1].

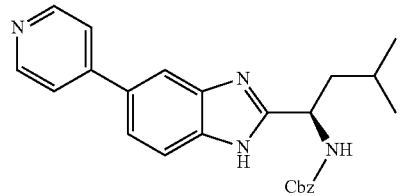 [SMILES: CC(C)C[C@@H](NC(=O)OCc1ccccc1)c1nc2cc(-c3ccncc3)ccc2[nH]1]

Part B: (R)-benzyl 3-methyl-1-(5-(pyridin-4-yl)-1H-benzo[d]imidazol-2-yl)butylcarbamate A solution of (R)-benzyl 1-(5-bromo-1H-benzo[d]imidazol-2-yl)-3-methylbutylcarbamate (125 mg, 0.300 mmol), 1,1'-bis(diphenylphosphino)ferrocene palladium (II) chloride complex with dichloromethane (12.35 mg, 0.015 mmol) and pyridine-4-boronic acid (36.9 mg, 0.300 mmol) in saturated aqueous sodium bicarbonate (2224 μL, 0.300 mmol) and acetonitrile (2224 μL) was heated to 100° C. for 3 h in a microwave. The reaction mixture was diluted with water and extracted with EtOAc (3×10 mL). The combined organic layers were washed with brine (1×10 mL), dried over MgSO$_4$, filtered and concentrated. The crude material was purified by reverse phase HPLC (30%-80% MeOH/H$_2$O/0.1% TFA over 25 min). Obtained (R)-benzyl 3-methyl-1-(5-(pyridin-4-yl)-1H-benzo[d]imidazol-2-yl)butylcarbamate (36 mg, 0.087 mmol, 29% yield) as a pale tan oil. $^1$H NMR (400 MHz, DMSO-d$_6$) δ 12.49 (d, J=18.8 Hz, 1H), 8.63 (d, J=4.5 Hz, 2H), 8.09-7.81 (m, 2H), 7.78-7.57 (m, 4H), 7.42-7.13 (m, 5H), 5.18-5.00 (m, 2H), 4.97-4.85 (m, 1H), 1.91-1.74 (m, 2H), 1.65 (dt, J=13.0, 6.4 Hz, 1H), 0.94 (m, 6H); LC/MS (ESI) m/e 415.1 [(M+H)+, calcd for C25H27N4O2 415.2].

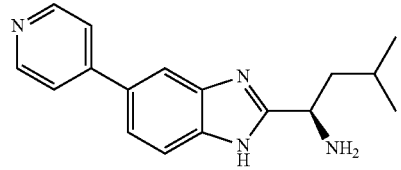 [SMILES: CC(C)C[C@@H](N)c1nc2cc(-c3ccncc3)ccc2[nH]1]

Part C: (R)-3-methyl-1-(5-(pyridin-4-yl)-1H-benzo[d]imidazol-2-yl)butan-1-amine

To a solution of (R)-benzyl 3-methyl-1-(5-(pyridin-4-yl)-1H-benzo[d]imidazol-2-yl)butylcarbamate (35 mg, 0.066 mmol) and anisole (15.83 μL, 0.146 mmol) in DCM (602 μL) was added methanesulfonic acid (150 μL, 2.318 mmol). The solution was stirred at room temperature for 2 h. The solution was concentrated under reduced pressure and purified by reverse phase HPLC (5%-60% MeOH/H$_2$O/0.1% TFA over 20 min). Obtained (R)-3-methyl-1-(5-(pyridin-4-yl)-1H-benzo[d]imidazol-2-yl)butan-1-amine, 2 TFA (29 mg, 0.056 mmol, 84% yield) as a colorless oil. ¹H NMR (400 MHz, MeOD) δ ppm 8.84 (d, J=7.0 Hz, 2H), 8.45 (d, J=7.0 Hz, 2H), 8.32 (d, J=1.3 Hz, 1H), 7.95 (dd, J=8.4, 1.3 Hz, 1H), 7.81-7.91 (m, 1H), 4.74 (dd, J=8.3, 6.8 Hz, 1H), 2.15 (ddd, J=13.7, 8.4, 6.8 Hz, 1H), 1.96 (dt, J=13.9, 7.0 Hz, 1 H), 1.63 (sept, J=6.5 Hz, 1 H), 1.03 (d, J=6.5 Hz, 3H), 1.00 (d, J=6.5 Hz, 3H); LC/MS (ESI) m/e 281.2 [(M+H)+, calcd for C17H21N4 281.2]; HPLC (method A): $t_R$=4.68 min; HPLC (method B): $t_R$=4.54 min.

Example 2

(S)-3-methyl-1-(6-(pyridin-4-yl)-1H-benzo[d]imidazol-2-yl)butan-1-amine

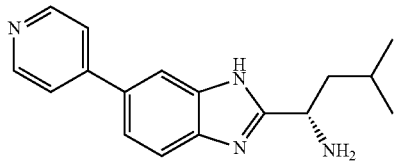 [SMILES: CC(C)C[C@H](N)c1nc2ccc(-c3ccncc3)cc2[nH]1]

Prepared in a similar fashion as described in Example 1, using (S)-2-(benzyloxycarbonylamino)-4-methylpentanoic acid in Part A to give the title compound (0.0956 g, 0.334 mmol, 90% yield) as a yellow solid. ¹H NMR (400 MHz, METHANOL-d₄) δ 8.67-8.48 (m, 2H), 7.91 (d, J=0.8 Hz, 1H), 7.76-7.68 (m, 2H), 7.68-7.57 (m, 2H), 4.22 (t, J=7.4 Hz, 1H), 1.91-1.79 (m, 1H), 1.79-1.68 (m, 1H), 1.67-1.55 (m, 1H), 0.98 (d, J=6.5 Hz, 3H), 0.93 (d, J=6.3 Hz, 3H), LC/MS (ESI) m/e 281.2 [(M+H)+, calcd for C17H21N4 281.2], optical rotation: $[\alpha]^{20}_D$ (MeOH)=−14.1°.

Example 3

(R)-1-(5-(1H-pyrazol-3-yl)-1H-benzo[d]imidazol-2-yl)-3-methylbutan-1-amine

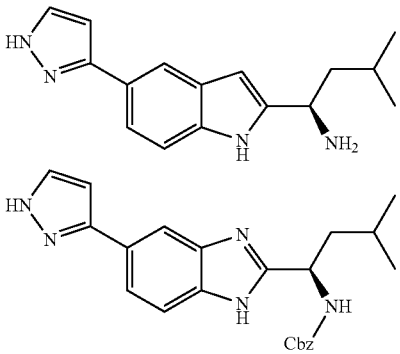

Part A: (R)-benzyl 1-(5-(1H-pyrazol-4-yl)-1H-benzo[d]imidazol-2-yl)-3-methylbutylcarbamate A solution of (R)-benzyl 1-(5-bromo-1H-benzo[d]imidazol-2-yl)-3-methylbutylcarbamate (70 mg, 0.168 mmol) prepared as in Example 1, Part A, 1,1'-bis(diphenylphosphino)ferrocene palladium (II) chloride complex with dichloromethane (4.15 mg, 5.04 μmol) and 4-(4,4,5,5-tetramethyl-1,3,2-dioxaborolan-2-yl)-1H-pyrazole (39.2 mg, 0.202 mmol) in saturated aqueous sodium bicarbonate (1246 μL, 0.168 mmol) and acetonitrile (1246 μL) was heated to 90° C. for 15 min in a microwave. Added additional 1,1'-bis(diphenylphosphino)ferrocene palladium (II) chloride complex with dichloromethane (4.15 mg, 5.04 μmol) and continued heating in the microwave at 100° C. for 1 h. The mixture was diluted with water and extracted with EtOAc (3×5 mL). The combined organics were washed with brine (1×5 mL), dried (MgSO₄), filtered and concentrated under reduced pressure. The crude material was purified by reverse phase HPLC (30%-80% MeOH/H₂O/0.1% TFA over 25 min). Obtained (R)-benzyl 1-(5-(1H-pyrazol-4-yl)-1H-benzo[d]imidazol-2-yl)-3-methylbutylcarbamate (19 mg, 0.047 mmol, 28% yield) as a pale brown oil. LC/MS (ESI) m/e 404.1 [(M+H)+, calcd for C23H26N5O2 404.2].

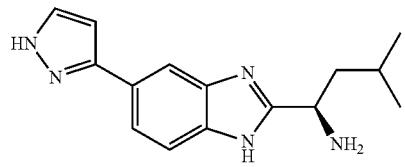 [SMILES: CC(C)C[C@@H](N)c1nc2cc(-c3cc[nH]n3)ccc2[nH]1]

Part B: (R)-1-(5-(1H-pyrazol-3-yl)-1H-benzo[d]imidazol-2-yl)-3-methylbutan-1-amine To a solution of (R)-benzyl 1-(5-(1H-pyrazol-4-yl)-1H-benzo[d]imidazol-2-yl)-3-methylbutylcarbamate (19 mg, 0.047 mmol) and anisole (11.26 μl, 0.104 mmol) in DCM (428 μL) was added methanesulfonic acid (107 μl, 1.648 mmol).

The solution was stirred at room temperature for 1 h. The solution was concentrated under reduced pressure and the residue purified by reverse phase HPLC (10%-70% MeOH/H₂O/0.1% TFA over 20 min). Obtained (R)-1-(5-(1H-pyrazol-4-yl)-1H-benzo[d]imidazol-2-yl)-3-methylbutan-1-amine, TFA (13 mg, 0.034 mmol, 72% yield) as a colorless oil. ¹H NMR (400 MHz, MeOD) δ ppm 8.06 (s, 2H), 7.87 (s, 1 H), 7.58-7.76 (m, 2H), 4.74 (dd, J=8.8, 6.5 Hz, 1H), 2.17 (ddd, J=13.7, 8.9, 6.3 Hz, 1H), 1.97 (ddd, J=13.7, 7.6, 6.5 Hz, 1H), 1.60 (sept, J=6.5 Hz, 1 H), 1.03 (d, J=6.8 Hz, 3H), 0.99 (d, J=6.5 Hz, 3H); LC/MS (ESI) m/e 270.1 [(M+H)+, calcd for C15H20N5 270.2]. HPLC (method A): $t_R$=6.28 min; HPLC (method B): $t_R$=5.53 min.

Example 4

(R)-3-methyl-1-(5-(oxazol-5-yl)-1H-benzo[d]imidazol-2-yl)butan-1-amine

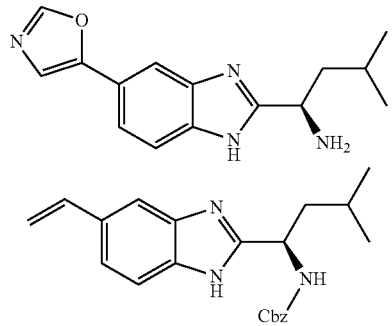

Part A: (R)-benzyl 3-methyl-1-(5-vinyl-1H-benzo[d]imidazol-2-yl)butylcarbamate A solution of (R)-benzyl 1-(5-bromo-1H-benzo[d]imidazol-2-yl)-3-methylbutylcarbamate (500 mg, 1.201 mmol) prepared as in Example 1, Part A, vinylboronic anhydride pyridine complex (289 mg, 1.201 mmol), and saturated aqueous sodium bicarbonate (1201 µL, 2.402 mmol) in toluene (6405 µL) and EtOH (1601 µL) was sealed and purged with $N_2$ for 10 min.

Tetrakis(triphenylphosphine)palladium(0) (69.4 mg, 0.060 mmol) was added and the solution heated to 95° C. for 2.5 h. The mixture was cooled to room temperature and diluted with water and extracted with EtOAc (2×15 mL). The combined organics were washed with brine (1×15 mL), dried (MgSO$_4$), filtered and concentrated under reduced pressure. The residue was purified via silica gel chromatography (5%-40% EtOAc in hexanes) to afford (R)-benzyl 3-methyl-1-(5-vinyl-1H-benzo[d]imidazol-2-yl)butylcarbamate (133 mg, 0.348 mmol, 29% yield) as a colorless oil. LC/MS (ESI) m/e 364.1 [(M+H)+, calcd for C22H26N3O2 364.2].

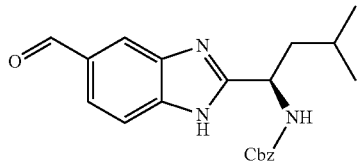 [SMILES: CC(C)C[C@@H](NC(=O)OCc1ccccc1)c1nc2cc(C=O)ccc2[nH]1]

Part B: (R)-benzyl (1-(5-formyl-1H-benzo[d]imidazol-2-yl)-3-methylbutyl)carbamate To a solution of (R)-benzyl 3-methyl-1-(5-vinyl-1H-benzo[d]imidazol-2-yl)butylcarbamate (133 mg, 0.366 mmol) in dioxane (4 mL) and water (1 mL) cooled to 0° C. was added 2,6-lutidine (85 µL, 0.732 mmol), osmium tetroxide (2.5% in 2-methyl-2-propanol) (91 µL, 7.32 µmol), and sodium periodate (313 mg, 1.146 mmol). The ice bath was removed and the solution stirred for 2.5 h while warming to room temperature. The residue was purified via silica gel chromatography (5%-80% EtOAc in hexanes) to afford (R)-benzyl 1-(5-formyl-1H-benzo[d]imidazol-2-yl)-3-methylbutylcarbamate (36 mg, 0.094 mmol, 26% yield) as a colorless film. LC/MS (ESI) m/e 366.1 [(M+H)+, calcd for C21H24N3O4 366.2].

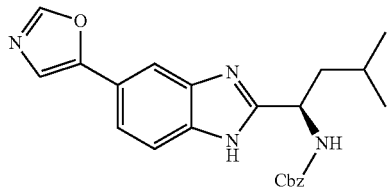 [SMILES: CC(C)C[C@@H](NC(=O)OCc1ccccc1)c1nc2cc(-c3cnco3)ccc2[nH]1]

Part C: (R)-benzyl (3-methyl-1-(5-(oxazol-5-yl)-1H-benzo[d]imidazol-2-yl)butyl)carbamate A solution of (R)-benzyl 1-(5-formyl-1H-benzo[d]imidazol-2-yl)-3-methylbutylcarbamate (50 mg, 0.137 mmol), tosylmethyl isocyanide (29.4 mg, 0.151 mmol) and potassium carbonate (22.69 mg, 0.164 mmol) in methanol (1368 µL) was heated to reflux for 3 h. The mixture was cooled to room temperature, quenched with saturated aqueous NaHCO$_3$ and extracted with EtOAc (3×5 mL). The combined organics were washed with brine (1×5 mL), dried (MgSO$_4$), and concentrated under reduced pressure. The crude (R)-benzyl 3-methyl-1-(5-(oxazol-5-yl)-1H-benzo[d]imidazol-2-yl)butylcarbamate (40 mg, 0.094 mmol, 68% yield, 95% purity) was carried on without purification. LC/MS (ESI) m/e 405.1 [(M+H)+, calcd for C23H25N4O3 405.2].

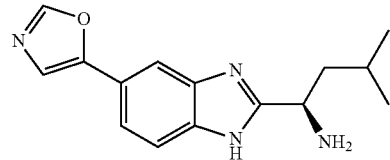 [SMILES: CC(C)C[C@@H](N)c1nc2cc(-c3cnco3)ccc2[nH]1]

Part D: (R)-3-methyl-1-(5-(oxazol-5-yl)-1H-benzo[d]imidazol-2-yl)butan-1-amine To a solution of (R)-benzyl 3-methyl-1-(5-(oxazol-5-yl)-1H-benzo[d]imidazol-2-yl)butylcarbamate (40 mg, 0.099 mmol) and anisole (23.65 µL, 0.218 mmol) in DCM (899 µL) was added methanesulfonic acid (225 µL, 3.46 mmol). The solution was stirred at room temperature for 12 h The crude material was purified by reverse phase HPLC (10%-70% MeOH/H$_2$O/0.1% TFA over 20 min). Fractions were free based by passing through an SCX cartridge, eluting with 2M ammonium in methanol. Obtained (R)-3-methyl-1-(5-(oxazol-5-yl)-1H-benzo[d]imidazol-2-yl)butan-1-amine (19 mg, 0.069 mmol, 70% yield) as a yellow oil. $^1$H NMR (400 MHz, MeOD) δ ppm 8.26 (s, 1H), 7.99 (s, 1H), 7.71 (d, J=1.3 Hz, 2H), 7.52 (s, 1H), 4.69 (dd, J=8.7, 6.7 Hz, 1H), 2.14 (ddd, J=13.7, 8.7, 6.5 Hz, 1H), 1.94 (ddd, J=13.9, 7.5, 6.5 Hz, 1H), 1.61 (sept, J=6.5 Hz, 1 H), 1.02 (d, J=6.8 Hz, 3H), 0.99 (d, J=6.5 Hz, 3H); LC/MS (ESI) m/e 271.1 [(M+H)+, calcd for C15H19N4O 271.2]; HPLC (method C): t$_R$=5.66 min; HPLC (method D): t$_R$=5.59 min.

Example 5

(S)-3-methyl-1-(5-(oxazol-5-yl)-1H-benzo[d]imidazol-2-yl)butan-1-amine

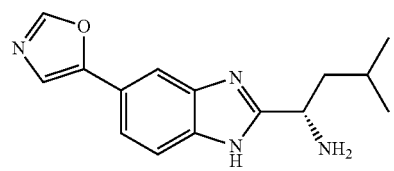 [SMILES: CC(C)C[C@H](N)c1nc2cc(-c3cnco3)ccc2[nH]1]

Prepared in a similar fashion as described in Example 4, using (S)-2-(benzyloxycarbonylamino)-4-methylpentanoic acid to give the title compound (0.056 g, 0.202 mmol, 53% yield) as a yellow amorphous solid. $^1$H NMR (400 MHz, METHANOL-d$_4$) δ 8.23 (s, 1H), 7.88 (s, 1H), 7.61 (d, J=1.3 Hz, 2H), 7.47 (s, 1H), 4.20 (t, J=7.4 Hz, 1H), 1.88-1.78 (m, 1H), 1.78-1.69 (m, 1H), 1.61 (tq, J=13.3, 6.7 Hz, 1H), 0.98 (d, J=6.5 Hz, 3H), 0.93 (d, J=6.5 Hz, 3H), LC/MS (ESI) m/e 271.2 [(M+H)+, calcd for C15H19N4O 271.2].

Example 6

(R)-1-(5-(1H-pyrrolo[2, 3-b]pyridin-4-yl)-1H-benzo[d]imidazol-2-yl)-3-methylbutan-1-amine

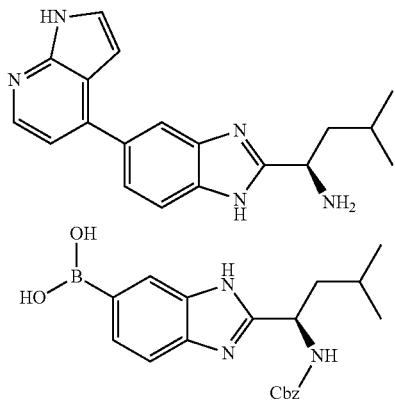

Part A: (R)-2-(1-(benzyloxycarbonylamino)-3-methylbutyl)-1H-benzo[d]imidazol-6-ylboronic acid To a solution of (R)-benzyl 1-(6-bromo-1H-benzo[d]imidazol-2-yl)-3-methylbutylcarbamate (2.8 g, 6.73 mmol), prepared as in Example 1, Part A, in dry THF (80 mL) at −78° C. under nitrogen was added N-butyllithium (4.62 mL, 7.40 mmol). The reaction mixture was stirred for 20 min then tiisopropylborate (1.72 mL, 7.40 mmol) was added slowly. The reaction mixture was allowed to warm to room temperature and stirred overnight (~12 h). The reaction mixture was quenched by addition of saturated ammonium chloride (30 mL) and extracted with ethyl acetate (3×100 mL). The combined organics were washed with water (50 mL), brine (50 mL) and dried (MgSO$_4$). The organic layer was concentrated under reduced pressure and the residue purified by reverse phase preparative HPLC (Methanol/water/0.1% TFA) to afford (R)-2-(1-(benzyloxycarbonylamino)-3-methylbutyl)-1H-benzo[d]imidazol-6-ylboronic acid (1.19 g, 3.12 mmol, 46% yield). $^1$H NMR (400 MHz, DMSO-d$_6$) δ 8.39-8.28 (m, 1H), 8.26-7.90 (m, 1H), 7.84-7.76 (m, 1H), 7.57-7.48 (m, 1H), 7.44-7.30 (m, 4H), 5.21-4.93 (m, 3H), 2.04-1.81 (m, 2H), 1.69 (d, J=6.3 Hz, 1H), 1.06-0.85 (m, 6H), LC/MS (ESI) m/e 382.0 [(M+H)+, calcd for C20H25BN3O4 382.2].

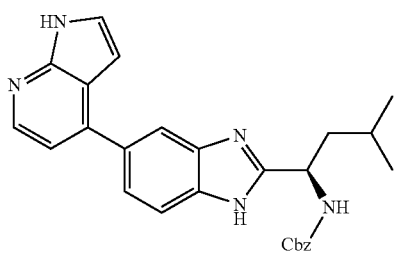 [SMILES: CC(C)C[C@@H](NC(=O)OCc1ccccc1)c1nc2cc(-c3ccnc4[nH]ccc34)ccc2[nH]1]

Part B: (R)-benzyl 1-(5-(1H-pyrrolo[2,3-b]pyridin-4-yl)-1H-benzo[d]imidazol-2-yl)-3-methylbutylcarbamate To a vial was added 4-bromo-1H-pyrrolo[2,3-b]pyridine (0.052 g, 0.262 mmol), tetrakis(triphenylphosphine)palladium(0) (0.030 g, 0.026 mmol), potassium carbonate (0.109 g, 0.787 mmol) and (R)-2-(1-(benzyloxycarbonylamino)-3-methylbutyl)-1H-benzo[d]imidazol-6-ylboronic acid (0.1 g, 0.262 mmol). The vial was sealed and purged with N$_2$ for 5 min. Dioxane (10 mL) and water (1.0 mL) were added and the vial purged with N$_2$ for 10 min. the reaction mixture was heated in an oil bath for 5 h. The cooled solution was filtered through a bed of diatomaceous earth (Celite®) and concentrated under reduced pressure. The residue was purified via silica gel chromatography (15%-100% EtOAc in hexanes). The required fractions were concentrated to obtain (R)-benzyl 1-(5-(1H-pyrrolo[2,3-b]pyridin-4-yl)-1H-benzo[d]imidazol-2-yl)-3-methylbutylcarbamate (0.065 g, 0.143 mmol, 55% yield). LC/MS (ESI) m/e 436.1 [(M+H)+, calcd for C27H26N5O 436.2].

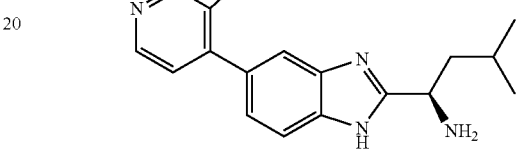

Part C: (R)-1-(5-(1H-pyrrolo[2,3-b]pyridin-4-yl)-1H-benzo[d]imidazol-2-yl)-3-methylbutan-1-amine To a solution of (R)-benzyl 1-(5-(1H-pyrrolo [2,3-b]pyridin-4-yl)-1H-benzo[d]imidazol-2-yl)-3-methylbutylcarbamate (0.065 g, 0.143 mmol) in dry MeOH (20 mL) under nitrogen was added Pd/C (5% by wt) (0.015 g, 0.143 mmol). The reaction flask was capped with a septum and flushed with hydrogen. The reaction mixture was stirred under a balloon of hydrogen for 12 h. The reaction mixture was filtered through a glass filter and the filtrate was concentrated under reduced pressure. The residue was purified by reverse phase preparative HPLC (5-80% 90% water, 10% Methanol, 0.1% TFA in 10% Water, 90% Methanol, 0.1% TFA). The required fractions were concentrated to obtain (R)-1-(5-(1H-pyrrolo[2,3-b]pyridin-4-yl)-1H-benzo[d]imidazol-2-yl)-3-methylbutan-1-amine, 2 TFA (0.0073 g, 0.013 mmol, 9% yield). $^1$H NMR (400 MHz, METHANOL-d$_4$) δ 8.45 (d, J=5.5 Hz, 1H), 8.22-8.15 (m, 1H), 7.92-7.82 (m, 2H), 7.78-7.68 (m, 2H), 7.05 (d, J=3.8 Hz, 1H), 4.74 (dd, J=8.5, 6.8 Hz, 1H), 2.16 (ddd, J=13.7, 8.4, 6.5 Hz, 1H), 1.96 (dt, J=13.9, 7.0 Hz, 1H), 1.64 (tq, J=13.7, 6.7 Hz, 1H), 1.05 (d, J=6.5 Hz, 3H), 1.02 (d, J=6.8 Hz, 3H), LC/MS (ESI) m/e 320.1 [(M+H)+, calcd for C19H22N5 320.2], HPLC (method G): t$_R$=5.90 min.

Example 7

(R)-1-(5-(1H-pyrazolo[3, 4-b]pyridin-4-yl)-1H-benzo[d]imidazol-2-yl)-3-methylbutan-1-amine

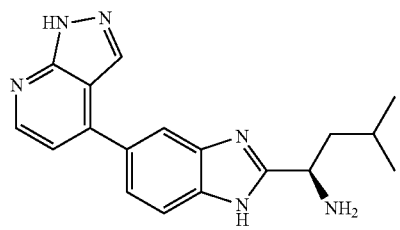

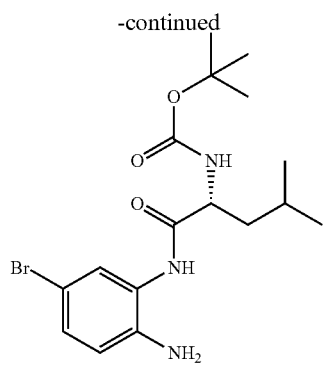

Part A: (R)-tert-butyl 1-(2-amino-5-bromophenylamino)-4-methyl-1-oxopentan-2-ylcarbamate To a solution of 4-bromobenzene-1,2-diamine (4.45 g, 23.78 mmol), (R)-2-(tert-butoxycarbonylamino)-4-methylpentanoic acid (5 g, 21.62 mmol) and HATU (12.33 g, 32.4 mmol) in DMF (20 mL) at 0° C. was added DIEA (11.33 ml, 64.9 mmol). The solution was stirred at 0° C. for 1.5 h. The solution was diluted with EtOAc (25 mL) and washed with saturated aqueous sodium bicarbonate (3×15 mL) then brine (3×15 mL). The organics were dried (MgSO4), filtered and concentrated under reduced pressure to obtain (R)-tert-butyl 1-(2-amino-5-bromophenylamino)-4-methyl-1-oxopentan-2-ylcarbamate (8.65 g, 21.61 mmol, 100% crude yield). The product was carried on without further purification. LC/MS (ESI) m/e 400.0 [(M+H)+, calcd for C17H27BrN3O3 400.1].

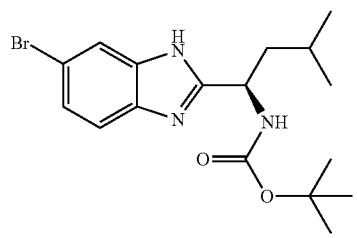 [SMILES: CC(C)C[C@@H](NC(=O)OC(C)(C)C)c1nc2ccc(Br)cc2[nH]1]

Part B: (R)-tert-butyl (1-(6-bromo-1H-benzo[d]imidazol-2-yl)-3-methylbutyl)carbamate A solution of (R)-tert-butyl (1-((2-amino-5-bromophenyl)amino)-4-methyl-1-oxopentan-2-yl)carbamate (8.65 g, 21.61 mmol) in acetic acid (80 mL) was heated at 65° C. overnight (~12 h). The reaction mixture was concentrated under reduced pressure and the residue purified by silica gel chromatography (0-60% EtOAc in hexanes). The required fractions were concentrated under reduced pressure to obtain (R)-tert-butyl (1-(6-bromo-1H-benzo[d]imidazol-2-yl)-3-methylbutyl)carbamate (6.11 g, 15.98 mmol, 74% yield) as a brown solid. LC/MS (ESI) m/e 382.0 [(M+H)+, calcd for C17H25BrN3O2 382.1].

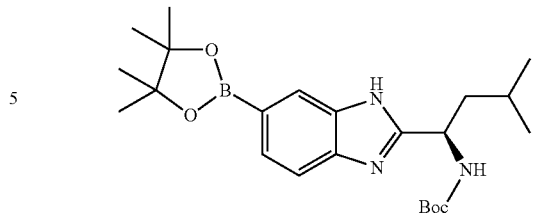

Part C: (R)-tert-butyl (3-methyl-1-(6-(4, 4, 5, 5-tetramethyl-1, 3, 2-dioxaborolan-2-yl)-1H-benzo[d]imidazol-2-yl)butyl)carbamate A solution containing (R)-tert-butyl (1-(6-bromo-1H-benzo[d]imidazol-2-yl)-3-methylbutyl)carbamate (5.01 g, 13.11 mmol), 4,4,4',4',5,5,5',5'-octamethyl-2,2'-bi(1,3,2-dioxaborolane) (8.32 g, 32.8 mmol) and potassium acetate (6.43 g, 65.5 mmol) in dry dioxane (131 mL) was stirred in a sealed tube and purged with N2 for 10 min. To the vial was added 1,1'-bis(diphenylphosphino)ferrocenepalladium(II) dichloride and toluene (0.863 g, 1.048 mmol). The vial was resealed and purged with N2 for 10 min. The reaction mixture was heated to 80° C. for 48 h. The reaction mixture was concentrated under reduced pressure and the residue purified by silica gel chromatography (0-25% EtOAc in hexanes). The required fractions were concentrated to obtain (R)-tert-butyl (3-methyl-1-(6-(4,4,5,5-tetramethyl-1,3,2-dioxaborolan-2-yl)-1H-benzo[d]imidazol-2-yl)butyl)carbamate (2.8 g, 6.52 mmol, 50% yield) as pale brown solid. LC/MS (ESI) m/e 430.2 [(M+H)+, calcd for C23H37BN3O4 430.3].

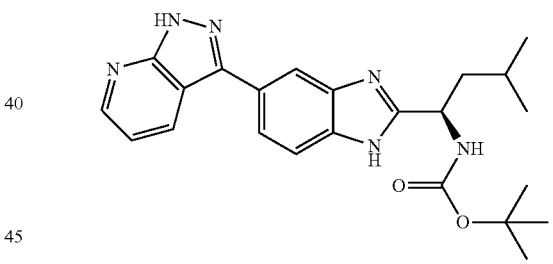

Part D: (R)-tert-butyl (1-(5-(1H-pyrazolo[3, 4-b]pyridin-3-yl)-1H-benzo[d]imidazol-2-yl)-3-methylbutyl)carbamate To a vial was added 3-bromo-1H-pyrazolo[3,4-b]pyridine (0.046 g, 0.233 mmol), tetrakis(triphenylphosphine)palladium(0) (0.027 g, 0.023 mmol), potassium carbonate (0.097 g, 0.699 mmol) and (R)-tert-butyl (3-methyl-1-(6-(4,4,5,5-tetramethyl-1,3,2-dioxaborolan-2-yl)-1H-benzo[d]imidazol-2-yl)butyl)carbamate (0.1 g, 0.233 mmol). The vial was sealed and purged with N2 for 5 min. Dioxane (10 mL) and water (1.0 mL) were added and the vial purged with N2 for 10 min. The reaction mixture was heated in an oil bath overnight (~14 h). The mixture was cooled to room temperature, filtered through diatomaceous earth (Celite®) and concentrated under reduced pressure. The residue was purified by reverse phase preparative HPLC (water/Methanol/ 0.1% TFA). The required fractions were concentrated to obtain (R)-tert-butyl (1-(5-(1H-pyrazolo[3,4-b]pyridin-3- yl)-1H-benzo[d]imidazol-2-yl)-3-methylbutyl)carbamate (0.071 g, 0.169 mmol, 73% yield). LC/MS (ESI) m/e 421.1 [(M+H)+, calcd for C23H29N6O2 421.2].

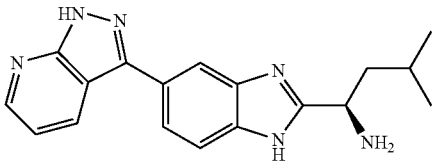 [SMILES: CC(C)C[C@@H](N)c1nc2cc(-c3n[nH]c4ncccc34)ccc2[nH]1]

Part E: (R)-1-(5-(1H-pyrazolo[3, 4-b]pyridin-3-yl)-1H-benzo[d]imidazol-2-yl)-3-methylbutan-1-amine To a solution of (R)-tert-butyl (1-(5-(1H-pyrazolo[3,4-b]pyridin-3-yl)-1H-benzo[d]imidazol-2-yl)-3-methylbutyl) carbamate (0.071 g, 0.169 mmol) in dry CH2Cl2 (20 mL) at room temperature under a nitrogen atmosphere was added TFA (0.052 mL, 0.675 mmol). The reaction mixture was stirred for 12 h at room temperature. The reaction mixture was concentrated under reduced pressure and the residue purified by reverse phase preparative HPLC (water/Methanol/0.1% TFA). The required fractions were concentrated under reduced pressure to obtain (R)-1-(5-(1H-pyrazolo[3,4-b]pyridin-3-yl)-1H-benzo[d]imidazol-2-yl)-3-methylbutan-1-amine, 2 TFA (0.0082 g, 0.015 mmol, 9% yield). $^1$H NMR (400 MHz, METHANOL-d4) δ 8.63 (dd, J=8.0, 1.5 Hz, 1H), 8.60 (d, J=4.5 Hz, 1H), 8.28-8.22 (m, 1H), 8.00 (dd, J=8.4, 1.6 Hz, 1H), 7.83 (dd, J=8.5, 0.5 Hz, 1H), 7.36 (dd, J=8.2, 4.6 Hz, 1H), 4.75 (dd, J=8.7, 6.7 Hz, 1H), 2.18 (ddd, J=13.7, 8.7, 6.4 Hz, 1H), 2.02-1.91 (m, 1H), 1.69-1.55 (m, 1H), 1.05 (d, J=6.5 Hz, 3H), 1.01 (d, J=6.5 Hz, 3H), LC/MS (ESI) m/e 321.1 [(M+H)+, calcd for C18H21N6 321.2], HPLC (method G): $t_R$=6.52 min.

Example 8

(R)-1-(5-(7H-pyrrolo[2, 3-d]pyrimidin-4-yl)-1H-benzo[d]imidazol-2-yl)-3-methylbutan-1-amine

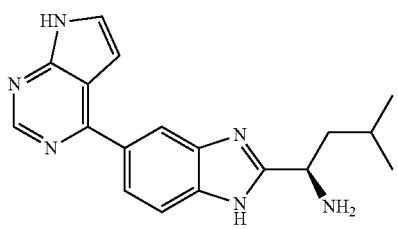

Prepared in a similar fashion as described in Example 7, Parts C and D using 4-bromo-7H-pyrrolo[2,3-d]pyrimidine in Part C to give the title compound as a bis TFA salt (0.068 g, 0.118 mmol, 72% yield) as a colorless amorphous solid. 1H NMR (400 MHz, METHANOL-d4) δ 9.06 (s, 1H), 8.42 (dd, J=1.8, 0.8 Hz, 1H), 8.04-7.94 (m, 3H), 7.23 (d, J=3.5 Hz, 1H), 4.81 (dd, J=8.4, 6.7 Hz, 1H), 2.17 (ddd, J=13.7, 8.4, 6.5 Hz, 1H), 2.04-1.93 (m, 1H), 1.64 (tq, J=13.7, 6.7 Hz, 1H), 1.04 (d, J=6.5 Hz, 3H), 1.00 (d, J=6.8 Hz, 3H). LC/MS (ESI) m/e 321.1 [(M+H)+, calcd for C18H21N6 321.2], HPLC (method G): $t_R$=3.84 min.

Example 9

(R)-3-methyl-1-(5-(quinolin-4-yl)-1H-benzo[d]imidazol-2-yl)butan-1-amine

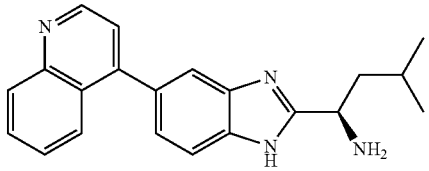 [SMILES: CC(C)C[C@@H](N)c1nc2cc(-c3ccnc4ccccc34)ccc2[nH]1]

Prepared in a similar fashion as described in Example 7, Parts C and D using 4-bromoquinoline in Part C to give the title compound as a bis TFA salt (0.067 g, 0.118 mmol, 67% yield) as a colorless amorphous solid. $^1$H NMR (400 MHz, METHANOL-d4) δ 9.22 (d, J=5.8 Hz, 1H), 8.39-8.31 (m, 2H), 8.20 (ddd, J=8.5, 7.1, 1.3 Hz, 1H), 8.10 (d, J=5.8 Hz, 1H), 8.03 (d, J=1.0 Hz, 1H), 8.00-7.91 (m, 2H), 7.66 (dd, J=8.4, 1.6 Hz, 1H), 4.81 (dd, J=8.8, 6.3 Hz, 1H), 2.20 (ddd, J=13.7, 8.7, 6.4 Hz, 1H), 2.00 (ddd, J=13.9, 7.6, 6.7 Hz, 1H), 1.71-1.55 (m, 1H), 1.05 (d, J=6.5 Hz, 3H), 1.01 (d, J=6.5 Hz, 3H), LC/MS (ESI) m/e 331.1 [(M+H)+, calcd for C21H23N4 331.2], HPLC (method G): $t_R$=4.55 min.

Example 10

(R)-1-(5-(3-fluoropyridin-4-yl)-1H-benzo[d]imidazol-2-yl)-3-methylbutan-1-amine

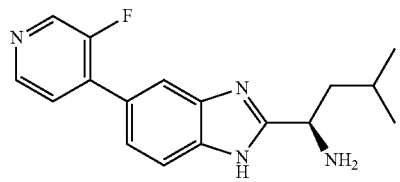 [SMILES: CC(C)C[C@@H](N)c1nc2cc(-c3ccncc3F)ccc2[nH]1]

Prepared in a similar fashion as described in Example 1, Parts B and C using 3-fluoropyridin-4-ylboronic acid in Part B to give the title compound 0.0037 g, 0.012 mmol, 12% yield) as a colorless amorphous solid. $^1$H NMR (400 MHz, METHANOL-d4) δ 8.53 (d, J=3.0 Hz, 1H), 8.44 (d, J=5.0 Hz, 1H), 7.89 (br. s., 1H), 7.74-7.65 (m, 2H), 7.57 (d, J=8.5 Hz, 1H), 4.30-4.18 (m, 1H), 1.91-1.81 (m, 1H), 1.81-1.70 (m, 1H), 1.62 (tt, J=13.3, 6.9 Hz, 1H), 1.00 (d, J=6.5 Hz, 3H), 0.95 (d, J=6.5 Hz, 3H), LC/MS (ESI) m/e 299.1 [(M+H)+, calcd for C17H20FN4 299.2], HPLC (method G): $t_R$=5.73 min.

Example 11

(R)-1-(5-(3-methoxypyridin-4-yl)-1H-benzo[d]imidazol-2-yl)-3-methylbutan-1-amine

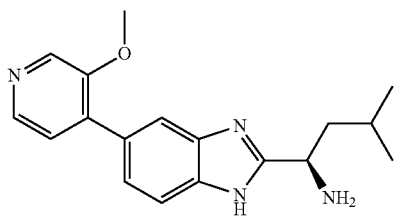 [SMILES: COc1cnccc1-c1ccc2[nH]c([C@H](N)CC(C)C)nc2c1]

Prepared in a similar fashion as described in Example 1, Parts B and C using 3-methoxypyridin-4-ylboronic acid in Part B to give the title compound (0.0652 g, 0.206 mmol, 54% yield) as a colorless amorphous solid. $^1$H NMR (400 MHz, METHANOL-$d_4$) δ 8.33 (s, 1H), 8.20 (d, J=5.0 Hz, 1H), 7.80 (d, J=1.0 Hz, 1H), 7.59 (d, J=8.3 Hz, 1H), 7.47-7.42 (m, 1H), 7.40 (d, J=4.8 Hz, 1H), 4.21 (s, 1H), 3.91 (s, 3H), 1.89-1.79 (m, 1H), 1.78-1.69 (m, 1H), 1.60 (tq, J=13.4, 6.7 Hz, 1H), 0.98 (d, J=6.5 Hz, 3H), 0.93 (d, J=6.5 Hz, 3H), LC/MS (ESI) m/e 311.2 [(M+H)+, calcd for C18H23N4O 311.2], HPLC (method G): $t_R$=5.44 min.

Example 12

(R)-1-(5-(2-fluoropyridin-4-yl)-1H-benzo[d]imidazol-2-yl)-3-methylbutan-1-amine

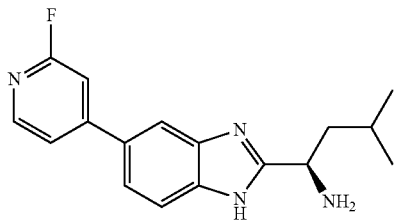 [SMILES: CC(C)C[C@@H](N)c1nc2cc(-c3ccnc(F)c3)ccc2[nH]1]

Prepared in a similar fashion as described in Example 1, Parts B and C using 2-fluoropyridin-4-ylboronic acid in Part B to give the title compound (0.0098 g, 0.032 mmol, 9% yield) as a colorless amorphous solid. $^1$H NMR (400 MHz, METHANOL-$d_4$) δ 8.24 (d, J=5.5 Hz, 1H), 7.97 (s, 1H), 7.74-7.61 (m, 3H), 7.41 (d, J=0.8 Hz, 1H), 4.33 (t, J=7.4 Hz, 1H), 1.97-1.85 (m, 1H), 1.84-1.73 (m, 1H), 1.68-1.55 (m, 1H), 1.01 (d, J=6.8 Hz, 3H), 0.96 (d, J=6.5 Hz, 3H), LC/MS (ESI) m/e 299.2 [(M+H)+, calcd for C17H20FN4 299.2], HPLC (method G): $t_R$=10.09 min.

Example 13

(R)-1-(5-(2-methoxypyridin-4-yl)-1H-benzo[d]imidazol-2-yl)-3-methylbutan-1-amine

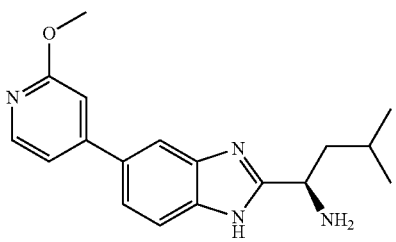 [SMILES: COc1cc(-c2ccc3[nH]c([C@H](N)CC(C)C)nc3c2)ccn1]

Prepared in a similar fashion as described in Example 1, Parts B and C using 2-methoxypyridin-4-ylboronic acid in Part B to give the title compound (0.0312 g, 0.092 mmol, 24% yield) as a colorless amorphous solid. $^1$H NMR (400 MHz, METHANOL-$d_4$) δ 8.18-8.12 (m, 1H), 7.93-7.82 (m, 1H), 7.73-7.62 (m, 1H), 7.62-7.54 (m, 1H), 7.31-7.25 (m, 1H), 7.12-7.05 (m, 1H), 3.96 (s, 3H), 3.92 (dd, J=9.0, 6.0 Hz, 1H), 1.91-1.80 (m, 1H), 1.80-1.69 (m, 1H), 1.55-1.40 (m, 1H), 0.98 (d, J=6.5 Hz, 3H), 0.90 (d, J=6.8 Hz, 3H), LC/MS (ESI) m/e 311.1 [(M+H)+, calcd for C18H23N4O 311.2], HPLC (method G): $t_R$=6.89 min.

Example 14

(R)-4-(2-(1-amino-3-methylbutyl)-1H-benzo[d]imidazol-5-yl)-N,N-dimethylpyrimidin-2-amine

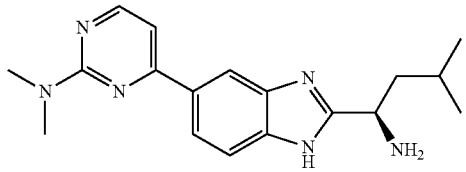 [SMILES: CC(C)C[C@@H](N)c1nc2cc(-c3ccnc(N(C)C)n3)ccc2[nH]1]

Prepared in a similar fashion as described in Example 7, Parts C and D using 4-bromo-N,N-dimethylpyrimidin-2-amine in Part C to give the title compound as a bis TFA salt (0.0556 g, 0.099 mmol, 56% yield) as a colorless amorphous solid. $^1$H NMR (400 MHz, METHANOL-$d_4$) δ 8.64 (d, J=1.0 Hz, 1H), 8.34-8.22 (m, 2H), 7.84-7.75 (m, 1H), 7.62 (d, J=6.8 Hz, 1H), 4.82-4.72 (m, 1H), 3.43 (br s, 6H), 2.15 (ddd, J=13.6, 8.5, 6.5 Hz, 1H), 1.97 (dt, J=13.7, 7.1 Hz, 1H), 1.62 (tq, J=13.7, 6.7 Hz, 1H), 1.03 (d, J=6.8 Hz, 3H), 0.99 (d, J=6.5 Hz, 3H), LC/MS (ESI) m/e 325.2 [(M+H)+, calcd for C18H25N6 325.2].

Example 15

(R)-4-(2-(1-amino-3-methylbutyl)-1H-benzo[d]imidazol-5-yl)picolinonitrile

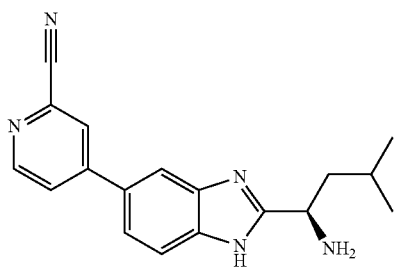 [SMILES: CC(C)C[C@@H](N)c1nc2cc(-c3ccnc(C#N)c3)ccc2[nH]1]

Prepared in a similar fashion as described in Example 1, Parts B and C using 4-(4,4,5,5-tetramethyl-1,3,2-dioxaborolan-2-yl)picolinonitrile in Part B to give the title compound (0.0304 g, 0.098 mmol, 54% yield) as a colorless oil. $^1$H NMR (400 MHz, METHANOL-$d_4$) δ 8.67 (dd, J=5.4, 0.6 Hz, 1H), 8.20 (dd, J=1.8, 0.8 Hz, 1H), 8.01-7.90 (m, 2H), 7.70-7.63 (m, 2H), 4.23 (t, J=7.4 Hz, 1H), 1.90-1.80 (m, 1H), 1.80-1.71 (m, 1H), 1.68-1.55 (m, 1H), 0.99 (d, J=6.5 Hz, 3H), 0.94 (d, J=6.8 Hz, 3H), LC/MS (ESI) m/e 306.2 [(M+H)+, calcd for C18H20N5 306.2].

Example 16

(R)-4-(2-(1-amino-3-methylbutyl)-1H-benzo[d]imidazol-5-yl)pyrimidin-2-amine

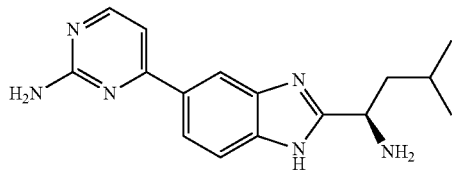

Prepared in a similar fashion as described in Example 7, Parts C and D using 4-bromopyrimidin-2-amine in Part C to give the title compound as a tri TFA (0.0209 g, 0.032 mmol, 16% yield) as a colorless amorphous solid. $^1$H NMR (400 MHz, METHANOL-$d_4$) δ 8.54 (dd, J=1.9, 0.6 Hz, 1H), 8.23-8.01 (m, 2H), 7.83 (dd, J=8.5, 0.5 Hz, 1H), 6.72 (d, J=7.3 Hz, 1H), 4.74 (dd, J=8.3, 6.8 Hz, 1H), 2.14 (ddd, J=13.7, 8.3, 6.8 Hz, 1H), 2.04-1.92 (m, 1H), 1.62 (tq, J=13.6, 6.7 Hz, 1H), 1.03 (d, J=6.5 Hz, 3H), 0.99 (d, J=6.5 Hz, 3H), LC/MS (ESI) m/e 297.1 [(M+H)+, calcd for C16H21N6 297.2].

Example 17

(R)-1-(5-(2,6-difluoropyridin-4-yl)-1H-benzo[d]imidazol-2-yl)-3-methylbutan-1-amine

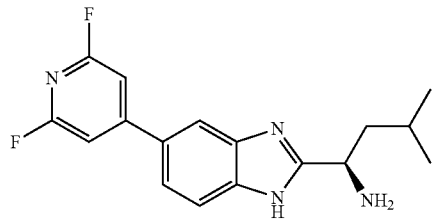 [SMILES: CC(C)C[C@@H](N)c1nc2cc(-c3cc(F)nc(F)c3)ccc2[nH]1]

Prepared in a similar fashion as described in Example 1, Parts B and C using 2,6-difluoropyridin-4-ylboronic acid in Part B to give the title compound (0.0531 g, 0.164 mmol, 57% yield) as a pale yellow amorphous solid. $^1$H NMR (400 MHz, METHANOL-$d_4$) δ 7.95-7.88 (m, 1H), 7.69-7.57 (m, 2H), 7.25 (s, 2H), 4.22 (t, J=7.4 Hz, 1H), 1.89-1.79 (m, 1H), 1.79-1.69 (m, 1H), 1.68-1.55 (m, 1H), 0.99 (d, J=6.5 Hz, 3H), 0.94 (d, J=6.5 Hz, 3H), LC/MS (ESI) m/e 317.2 [(M+H)+, calcd for C17H19F2N4 317.2].

Example 18

(R)-4-(2-(1-amino-3-methylbutyl)-1H-benzo[d]imidazol-5-yl)pyridin-2-amine

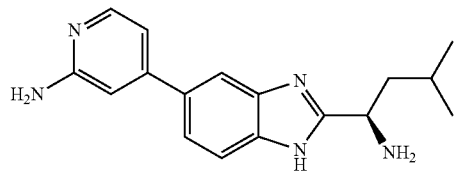 [SMILES: CC(C)C[C@@H](N)c1nc2cc(-c3ccnc(N)c3)ccc2[nH]1]

Prepared in a similar fashion as described in Example 7, Parts C and D using 4-bromopyridin-2-amine in Part C to give the title compound as a bis TFA salt (0.0634 g, 0.119 mmol, 59% yield) as a pale yellow amorphous solid. $^1$H NMR (400 MHz, METHANOL-$d_4$) δ 8.10 (d, J=1.0 Hz, 1H), 7.92-7.88 (m, 1H), 7.83-7.78 (m, 1H), 7.77-7.72 (m, 1H), 7.31-7.26 (m, 2H), 4.76 (dd, J=8.8, 6.5 Hz, 1H), 2.16 (ddd, J=13.7, 8.8, 6.4 Hz, 1H), 1.97 (ddd, J=13.9, 7.5, 6.7 Hz, 1H), 1.60 (tq, J=13.7, 6.7 Hz, 1H), 1.03 (d, J=6.5 Hz, 3H), 0.99 (d, J=6.5 Hz, 3H), LC/MS (ESI) m/e 296.3 [(M+H)+, calcd for C17H22N5 296.2].

Example 19

(R)-1-(5-(3,5-dimethyl-1H-pyrazol-4-yl)-1H-benzo[d]imidazol-2-yl)-3-methylbutan-1-amine

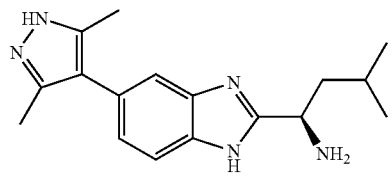 [SMILES: Cc1n[nH]c(C)c1-c1ccc2[nH]c([C@H](N)CC(C)C)nc2c1]

Prepared in a similar fashion as described in Example 1, Parts B and C using 3,5-dimethyl-4-(4,4,5,5-tetramethyl-1,3,2-dioxaborolan-2-yl)-1H-pyrazole in Part B to give the title compound (0.0238 g, 0.078 mmol, 17% yield) as a colorless amorphous solid. $^1$H NMR (400 MHz, METHANOL-d$_4$) δ 7.62-7.54 (m, 1H), 7.45-7.38 (m, 1H), 7.20-7.12 (m, 1H), 3.91 (dd, J=9.4, 5.9 Hz, 1H), 2.26 (s, 3H), 2.25 (s, 3H), 1.91-1.81 (m, 1H), 1.79-1.69 (m, 1H), 1.60 (tq, J=13.5, 6.7 Hz, 1H), 0.99 (d, J=6.8 Hz, 3H), 0.94 (d, J=6.5 Hz, 3H); LC/MS (ESI) m/e 298.2 [(M+H)+, calcd for C17H24N5 298.2].

Example 20

(R)-1-(5-(5-fluoro-2-methoxypyridin-4-yl)-1H-benzo[d]imidazol-2-yl)-3-methylbutan-1-amine

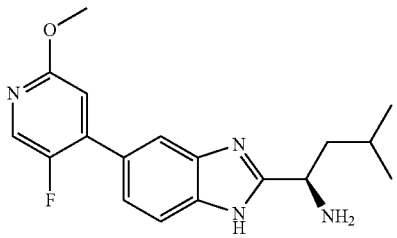 [SMILES: COc1cc(-c2ccc3[nH]c([C@H](N)CC(C)C)nc3c2)c(F)cn1]

Prepared in a similar fashion as described in Example 1, Parts B and C using 3,5-dimethyl-4-(4,4,5,5-tetramethyl-1,3,2-dioxaborolan-2-yl)-1H-pyrazole in Part B to give the title compound (0.0164 g, 0.046 mmol, 13% yield) as a colorless amorphous solid. $^1$H NMR (400 MHz, METHANOL-d$_4$) δ 8.10 (d, J=2.8 Hz, 1H), 7.92 (s, 1H), 7.76 (d, J=8.5 Hz, 1H), 7.59 (dt, J=8.5, 1.5 Hz, 1H), 6.97 (d, J=5.3 Hz, 1H), 4.72 (dd, J=8.5, 6.5 Hz, 1H), 3.93 (s, 3H), 2.15 (ddd, J=13.7, 8.5, 6.4 Hz, 1H), 2.01-1.91 (m, 1H), 1.62 (dquin, J=13.7, 6.7 Hz, 1H), 0.99 (d, J=6.5 Hz, 3H), 0.94 (d, J=6.5 Hz, 3H); LC/MS (ESI) m/e 329.2 [(M+H)+, calcd for C18H22FN4O 329.2].

Example 21

(R)-1-(7-methoxy-5-(oxazol-5-yl)-1H-benzo[d]imidazol-2-yl)-3-methylbutan-1-amine

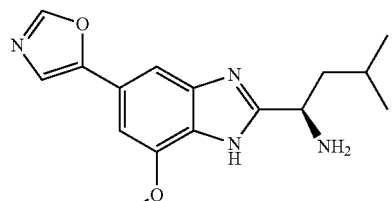

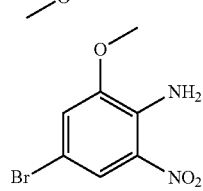

Part A: 4-bromo-2-methoxy-6-nitroaniline

To a solution of 2-methoxy-6-nitroaniline (2.8 g, 16.65 mmol) in dry DCM (90 mL) at room temperature under nitrogen was added NBS (3.85 g, 21.65 mmol).

The reaction mixture was stirred at room temperature overnight. The reaction mixture was concentrated under reduced pressure and purified by silica gel chromatography (0-100% ethyl acetate in hexanes) to obtain 4-bromo-2-methoxy-6-nitroaniline (4.01 g, 16.23 mmol, 97% yield). $^1$H NMR (400 MHz, CHLOROFORM-d) δ 7.91 (d, J=2.0 Hz, 1H), 6.95 (d, J=2.0 Hz, 1H), 6.47 (br. s., 2H), 3.94 (s, 3H); LC/MS (ESI) m/e 247.0, 249.0 Br pattern [(M+H)+, calcd for C7H8BrN2O3 247.0].

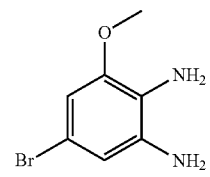

Part B: 5-bromo-3-methoxybenzene-1,2-diamine

To a solution of 4-bromo-2-methoxy-6-nitroaniline (4.01 g, 16.23 mmol) in EtOH (150 mL) at room temperature under nitrogen was added ammonium chloride (3.47 g, 64.9 mmol) and zinc powder (4.25 g, 64.9 mmol). The reaction mixture was heated to reflux for 12 h. The reaction mixture was cooled to room temperature and filtered through diatomaceous earth (Celite®). The filtrate was concentrated under reduced pressure to obtain 5-bromo-3-methoxybenzene-1,2-diamine (3.32 g, 15.30 mmol, 94% crude yield). Product was carried on without further purification. LC/MS (ESI) m/e 217.0, 219.0 Br pattern [(M+H)+, calcd for C7H10BrN2O 217.0].

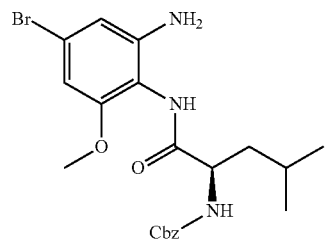 [SMILES: COc1cc(Br)cc(N)c1NC(=O)[C@@H](CC(C)C)NC(=O)OCc1ccccc1]

Part C: (R)-benzyl 1-(2-amino-4-bromo-6-methoxyphenylamino)-4-methyl-1-oxopentan-2-ylcarbamate To a solution of 5-bromo-3-methoxybenzene-1,2-diamine (3.32 g, 15.30 mmol), (R)-2-(benzyloxycarbonylamino)-4-methylpentanoic acid (4.06 g, 15.30 mmol) and HATU (8.72 g, 22.94 mmol) in DMF (60 mL) at 0° C. was added DIEA (13.36 mL, 76 mmol). The mixture was stirred at room temperature for 1.5 h. The reaction mixture was diluted with EtOAc (80 mL) and washed with saturated aqueous sodium bicarbonate (3×60 mL) and brine (3×60 mL). The solution was dried (MgSO$_4$), filtered and concentrated under reduced pressure to obtain (R)-benzyl 1-(2-amino-4-bromo-6-methoxyphenylamino)-4-methyl-1-oxopentan-2-ylcarbamate (6.5 g, 14.00 mmol, 92% crude yield). Carried on without further purification. LC/MS (ESI) m/e 464.0, 466.0 Br pattern [(M+H)+, calcd for C21H27BrN3O4 464.1].

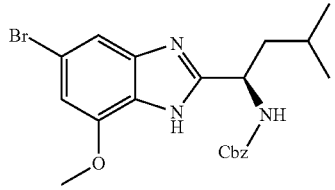 [SMILES: COc1cc(Br)cc2nc([C@@H](CC(C)C)NC(=O)OCc3ccccc3)[nH]c12]

Part D: (R)-benzyl 1-(5-bromo-7-methoxy-1H-benzo[d]imidazol-2-yl)-3-methylbutylcarbamate A solution of (R)-benzyl 1-(2-amino-4-bromo-6-methoxyphenylamino)-4-methyl-1-oxopentan-2-ylcarbamate (5.9 g, 12.71 mmol) in acetic acid (90 mL) was heated at 65° C. for 12 h under a nitrogen atmosphere. The reaction mixture was cooled to room temperature and concentrated under reduced pressure. The residue was purified by silica gel chromatography (0-70% ethyl acetate in hexanes) to obtain (R)-benzyl 1-(5-bromo-7-methoxy-1H-benzo[d]imidazol-2-yl)-3-methylbutylcarbamate (3.6 g, 8.07 mmol, 64% yield) as a brown solid. LC/MS (ESI) m/e 446.1, 448.1 Br pattern [(M+H)+, calcd for C21H25BrN3O3 446.1].

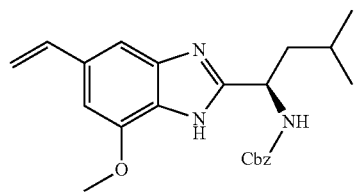 [SMILES: C=Cc1cc(OC)c2[nH]c([C@@H](CC(C)C)NC(=O)OCc3ccccc3)nc2c1]

Part E: (R)-benzyl 1-(7-methoxy-5-vinyl-1H-benzo[d]imidazol-2-yl)-3-methylbutylcarbamate A solution of (R)-benzyl 1-(5-bromo-7-methoxy-1H-benzo[d]imidazol-2-yl)-3-methylbutylcarbamate (200 mg, 0.448 mmol), potassium trifluoro(vinyl)borate (66.0 mg, 0.493 mmol) and DIEA (235 µL, 1.344 mmol) in 2-propanol (1867 µL) and water (934 µL) was sealed and purged with N2 for 10 min. 1,1'-Bis(diphenylphosphino)ferrocene palladium (II) chloride complex with dichloromethane (18.43 mg, 0.022 mmol) was added and the solution heated to 100° C. in an oil bath for 14 h. The mixture was cooled to room temperature, diluted with water (5 mL) and extracted with EtOAc (2×10 mL). The combined organics were washed with brine (1×10 mL), dried (MgSO4), filtered, and concentrated under reduced pressure. The residue was purified via silica gel chromatography (5%-60% EtOAc in hexanes) to afford (R)-benzyl 1-(7-methoxy-5-vinyl-1H-benzo[d]imidazol-2-yl)-3-methylbutylcarbamate (50 mg, 0.108 mmol, 24% yield) as a brown oil. $^1$H NMR (400 MHz, CHLOROFORM-d) δ 11.04 (br. s., 1H), 7.35-7.22 (m, 5H), 6.89-6.61 (m, 2H), 5.85-5.82 (m, 1H), 5.68 (d, J=17.3 Hz, 1H), 5.21-4.98 (m, 3H), 3.97-3.85 (m, 3H), 2.07-1.87 (m, 2H), 1.68 (dd, J=12.8, 6.5 Hz, 1H), 0.88 (m, 6H), LC/MS (ESI) m/e 394.1 [(M+H)+, calcd for C23H28N3O3 394.2].

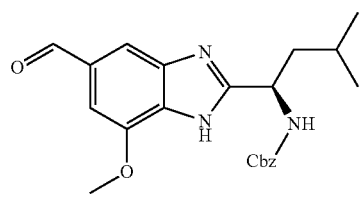 [SMILES: COc1cc(C=O)cc2nc([C@@H](CC(C)C)NC(=O)OCc3ccccc3)[nH]c12]

Part F: (R)-benzyl 1-(5-formyl-7-methoxy-1H-benzo[d]imidazol-2-yl)-3-methylbutylcarbamate To a solution of (R)-benzyl 3-methyl-1-(5-vinyl-1H-benzo[d]imidazol-2-yl)butylcarbamate (64 mg, 0.176 mmol) in dioxane (2012 µL) and water (503 µL) at 0° C. was added 2,6-lutidine (41.0 µL, 0.352 mmol), osmium tetroxide (2.5% in 2-methyl-2-propanol) (44.0 µL, 3.52 µmol), and sodium periodate (151 mg, 0.704 mmol). The ice bath was removed and the solution stirred for 2.5 h while warming to room temperature. The solution was diluted with water (5 mL) and extracted with EtOAc (3×5 mL). The combined organics were washed with brine (1×5 mL), dried (MgSO4), filtered and concentrated under reduced pressure. Obtained (R)-benzyl 1-(5-formyl-7-methoxy-1H-benzo[d]imidazol-2-yl)-3-methylbutylcarbamate (50.2 mg, 0.127 mmol, quantitative crude yield) as a brown oil. Carried on without further purification. LC/MS (ESI) m/e 396.1 [(M+H)+, calcd for C22H26N3O4 396.2].

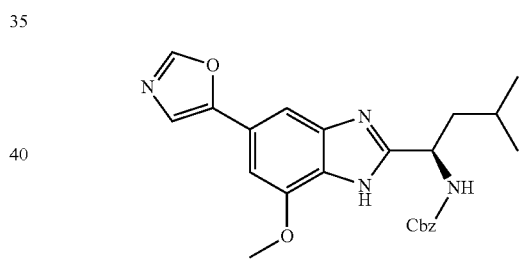

Part G: (R)-benzyl (1-(7-methoxy-5-(oxazol-5-yl)-1H-benzo[d]imidazol-2-yl)-3-methylbutyl)carbamate A solution of (R)-benzyl 1-(5-formyl-7-methoxy-1H-benzo[d]imidazol-2-yl)-3-methylbutylcarbamate (50.2 mg, 0.127 mmol), tosylmethyl isocyanide (24.80 mg, 0.127 mmol) and potassium carbonate (17.55 mg, 0.127 mmol) in methanol (1270 µL) was heated to reflux for 3.5 h. The reaction mixture was cooled to room temperature, quenched with saturated aqueous NaHCO3, and extracted with EtOAc (3×5 mL). The combined organics were washed with brine (1×5 mL), dried (MgSO4), filtered and concentrated under reduced pressure. The residue was purified via silica gel chromatography (5%-50% EtOAc in hexanes). Obtained (R)-benzyl (1-(7-methoxy-5-(oxazol-5-yl)-1H-benzo[d]imidazol-2-yl)-3-methylbutyl)carbamate (26 mg, 0.059 mmol, 46% yield) as a colorless solid. LC/MS (ESI) m/e 435.1 [(M+H)+, calcd for C24H27N4O4 435.2].

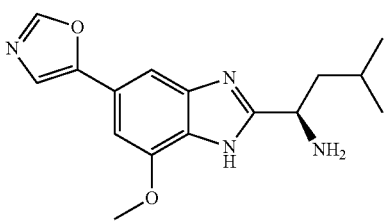 [SMILES: COc1cc(-c2cnco2)cc2nc([C@H](N)CC(C)C)[nH]c12]

Part H. (R)-3-methyl-1-(5-(oxazol-5-yl)-1H-benzo[d]imidazol-2-yl)butan-1-amine

A solution of (R)-benzyl 1-(7-methoxy-5-(oxazol-5-yl)-1H-benzo[d]imidazol-2-yl)-3-methylbutylcarbamate (24 mg, 0.055 mmol), anisole (13.27 μL, 0.122 mmol) and methanesulfonic acid (126 μL, 1.933 mmol) in DCM (502 μL) was stirred at room temperature for 1.5 h. The reaction mixture was concentrated under reduced pressure and the residue purified by reverse phase HPLC (10%-70% MeOH/H2O/0.1% TFA over 20 min). The product was free based by passing through an SCX cartridge, eluting with 2M ammonium in methanol. Obtained (R)-3-methyl-1-(5-(oxazol-5-yl)-1H-benzo[d]imidazol-2-yl)butan-1-amine (19 mg, 0.069 mmol, 70% yield) as a yellow amorphous solid. $^1$H NMR (400 MHz, CHLOROFORM-d) δ ppm 7.91 (s, 1H), 7.50 (br. s., 1 H), 7.32 (s, 1H), 6.96 (s, 1H), 4.38 (dd, J=8.9, 5.1 Hz, 1H), 4.04 (s, 3H), 1.88-2.02 (m, 1H), 1.72-1.86 (m, 1H), 1.66 (ddd, J=13.7, 8.7, 5.4 Hz, 1H), 0.99 (d, J=6.5 Hz, 3H), 0.96 (d, J=6.5 Hz, 3H), LC/MS (ESI) m/e 301.2 [(M+H)+, calcd for C16H21N4O2 301.2]; HPLC (method E): $t_R$=4.38 min; HPLC (method F): $t_R$=4.45 min.

Example 22

(R)-1-(7-methoxy-5-(pyridin-4-yl)-1H-benzo[d]imidazol-2-yl)-3-methylbutan-1-amine

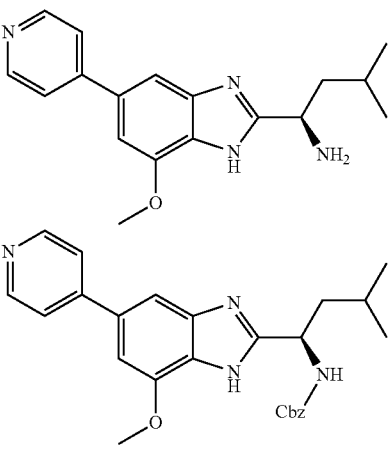

Part A: (R)-benzyl 1-(4-methoxy-6-(pyridin-4-yl)-1H-benzo[d]imidazol-2-yl)-3-methylbutylcarbamate To a sealable vial was added (R)-benzyl 1-(6-bromo-4-methoxy-1H-benzo[d]imidazol-2-yl)-3-methylbutylcarbamate (87 mg, 0.195 mmol) prepared as in Example 21, Part D, potassium carbonate (36.3 mg, 0.585 mmol), tetrakis(triphenylphosphine)palladium(0) (2.56 mg, 9.75 μmol) and 4-(4,4,5,5-tetramethyl-1,3,2-dioxaborolan-2-yl)pyridine (48.0 mg, 0.234 mmol). The vial was sealed and purged with N2 for 5 min. Dioxane (1671 μL) and water (278 μL) were added and the vial purged with N2 for 10 min. The reaction mixture was heated in an oil bath at 90° C. for 12 h. The mixture was cooled to room temperature, filtered through diatomaceous earth (Celite®) and concentrated under reduced pressure. The residue was purified via silica gel chromatography (10%-100% EtOAc in hexanes). Obtained (R)-benzyl 1-(4-methoxy-6-(pyridin-4-yl)-1H-benzo[d]imidazol-2-yl)-3-methylbutylcarbamate (52 mg, 0.111 mmol, 57% yield) as a colorless amorphous solid. LC/MS (ESI) m/e 445.2 [(M+H)+, calcd for C26H29N4O3 445.2].

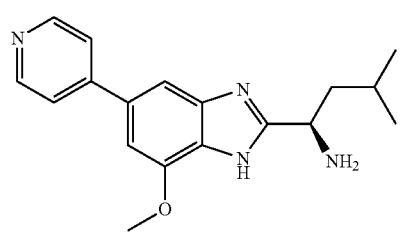 [SMILES: COc1cc(-c2ccncc2)cc2nc([C@H](N)CC(C)C)[nH]c12]

Part B: (R)-1-(7-methoxy-5-(pyridin-4-yl)-1H-benzo[d]imidazol-2-yl)-3-methylbutan-1-amine A solution of (R)-benzyl 1-(4-methoxy-6-(pyridin-4-yl)-1H-benzo[d]imidazol-2-yl)-3-methylbutylcarbamate (49.3 mg, 0.111 mmol), anisole (26.7 μl, 0.244 mmol), and methanesulfonic acid (252 μL, 3.89 mmol) in DCM (1009 μL) was stirred at room temperature for 1.5 h. The reaction mixture was concentrated under reduced pressure and the residue was purified by reverse phase HPLC (10%-70% MeOH/H2O/0.1% TFA). The product was free based by passing through an SCX cartridge, eluting with 2M ammonium in methanol to afford (R)-1-(4-methoxy-6-(pyridin-4-yl)-1H-benzo[d]imidazol-2-yl)-3-methylbutan-1-amine (32 mg, 0.101 mmol, 91% yield) as a pale yellow oil. $^1$H NMR (400 MHz, CHLOROFORM-d) δ ppm 8.64 (d, J=4.8 Hz, 2H), 7.54 (d, J=5.0 Hz, 2H), 7.46 (br. s., 1 H), 6.92 (s, 1H), 4.39 (dd, J=8.8, 5.3 Hz, 1H), 4.04 (s, 3H), 1.88-2.03 (m, 1H), 1.73-1.88 (m, 1H), 1.69 (ddd, J=13.5, 8.3, 5.8 Hz, 1H), 0.98 (d, J=6.5 Hz, 3H), 0.95 (d, J=5.5 Hz, 3H), LC/MS (ESI) m/e 311.2 [(M+H)+, calcd for C18H23N4O 311.2], HPLC (method E): $t_R$=2.93 min; HPLC (method F): $t_R$=2.94 min.

Example 23

(R)-1-(7-methoxy-5-(3-methoxypyridin-4-yl)-1H-benzo[d]imidazol-2-yl)-3-methylbutan-1-amine

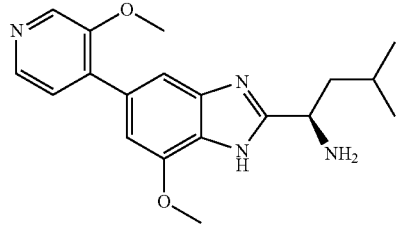 [SMILES: COc1cnccc1-c1cc(OC)c2[nH]c([C@H](N)CC(C)C)nc2c1]

Prepared in a similar fashion as described in Example 22, Parts A and B using 3-methoxypyridin-4-ylboronic acid in Part A to give the title compound (0.0638 g, 0.184 mmol, 57% yield) as a yellow amorphous solid. $^1$H NMR (400 MHz, METHANOL-$d_4$) δ 8.33 (s, 1H), 8.21 (d, J=5.0 Hz, 1H), 7.42 (d, J=5.0 Hz, 1H), 7.39 (d, J=1.3 Hz, 1H), 6.95 (d, J=1.3 Hz, 1H), 4.18 (t, J=7.5 Hz, 1H), 1.90-1.78 (m, 1H), 1.77-1.67 (m, 1H), 1.55 (tq, J=13.5, 6.7 Hz, 1H), 0.97 (d, J=6.5 Hz, 3H), 0.91 (d, J=6.5 Hz, 3H), LC/MS (ESI) m/e 341.2 [(M+H)+, calcd for C19H25N4O2 341.2].

Example 24

(R)-1-(7-methoxy-5-(2-methoxypyridin-4-yl)-1H-benzo[d]imidazol-2-yl)-3-methylbutan-1-amine

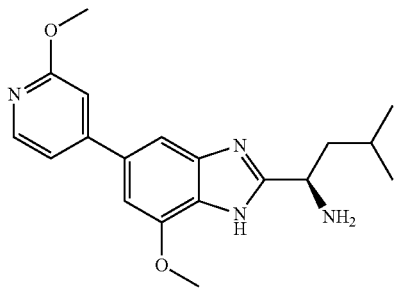 [SMILES: COc1cc(-c2cc(OC)c3[nH]c([C@H](N)CC(C)C)nc3c2)ccn1]

Prepared in a similar fashion as described in Example 22, Parts A and B using 2-methoxypyridin-4-ylboronic acid in Part A to give the title compound (0.0578 g, 0.165 mmol, 42% yield) as a colorless amorphous solid. $^1$H NMR (400 MHz, METHANOL-$d_4$) δ 8.14-8.09 (m, 1H), 7.43 (d, J=1.0 Hz, 1H), 7.23 (dd, J=5.5, 1.5 Hz, 1H), 7.04 (d, J=1.0 Hz, 1H), 7.00 (s, 1H), 4.18 (t, J=7.5 Hz, 1H), 4.03 (s, 3H), 3.94 (s, 3H), 1.88-1.78 (m, 1H), 1.77-1.67 (m, 1H), 1.56 (tq, J=13.4, 6.7 Hz, 1H), 0.97 (d, J=6.8 Hz, 3H), 0.91 (d, J=6.8 Hz, 3H), LC/MS (ESI) m/e 341.2 [(M+H)+, calcd for C19H25N4O2 341.2].

Example 25

2-isopentyl-4-methoxy-6-(pyridin-4-yl)-1H-benzo[d]imidazole

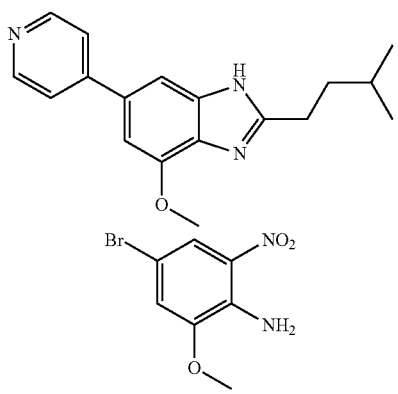

Part A: 4-bromo-2-methoxy-6-nitroaniline

To a solution of 2-methoxy-6-nitroaniline (3 g, 17.84 mmol) in dry CH$_2$Cl$_2$ (60 mL) at room temperature under nitrogen was added NBS (4.13 g, 23.19 mmol). The reaction mixture was stirred at room temperature overnight. The reaction mixture was concentrated under reduced pressure and purified by silica gel chromatography (EtOAc in hexanes) to obtain 4-bromo-2-methoxy-6-nitroaniline (2.5 g, 10.12 mmol, 57% yield) as reddish solid. LC/MS (ESI) m/e 247.0, 249.0 Br pattern [(M+H)+, calcd for C7H8BrN2O3 247.0].

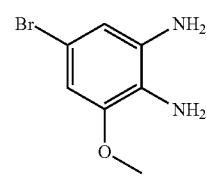

Part B: 5-bromo-3-methoxybenzene-1,2-diamine

To a solution of 4-bromo-2-methoxy-6-nitroaniline (1.2 g, 4.86 mmol) in ethanol (50 mL) at room temperature under nitrogen was added ammonium chloride (1.039 g, 19.43 mmol) and zinc powder (1.27 g, 19.43 mmol). The reaction mixture was stirred at room temperature for 12 h. The mixture was filtered through diatomaceous earth (Celite®) and concentrated under reduced pressure to obtain 5-bromo-3-methoxybenzene-1,2-diamine (0.98 g, 4.51 mmol, 93% crude yield). The product was carried on without further purification. LC/MS (ESI) m/e 217.0, 219.0 Br pattern [(M+H)+, calcd for C7H10BrN2O 217.0].

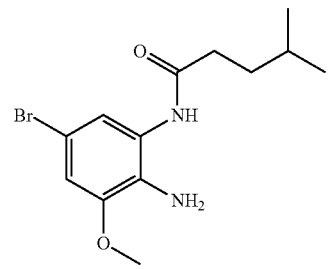 [SMILES: COc1cc(Br)cc(NC(=O)CCC(C)C)c1N]

Part C: N-(2-amino-5-bromo-3-methoxyphenyl)-4-methylpentanamide

To a solution of 5-bromo-3-methoxybenzene-1,2-diamine (0.98 g, 4.51 mmol), 4-methylpentanoic acid (0.577 g, 4.97 mmol) and HATU (2.58 g, 6.77 mmol) in DMF (40 mL) at 0° C. was added DIEA (1.577 mL, 9.03 mmol). The mixture was stirred at room temperature for 2 h. The reaction mixture was concentrated under reduced pressure and the residue purified by silica gel chromatography (97:3 DCM/MeOH) to obtain N-(2-amino-5-bromo-3-methoxyphenyl)-4-methyl-pentanamide (1.15 g, 3.65 mmol, 81% yield). LC/MS (ESI) m/e 315.0, 317.0 Br pattern [(M+H)+, calcd for C13H20BrN2O2 315.1].

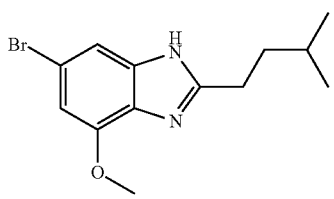 [SMILES: COc1cc(Br)cc2[nH]c(CCC(C)C)nc12]

Part D: 6-bromo-2-isopentyl-4-methoxy-1H-benzo[d]imidazole

A solution of N-(2-amino-5-bromo-3-methoxyphenyl)-4-methylpentanamide (1.15 g, 3.65 mmol) in acetic acid (50 mL) was heated at 65° C. under nitrogen atmosphere for 14 h. The reaction mixture was cooled to room temperature and concentrated under reduced pressure. The residue was purified by silica chromatography (0-70% EtOAc in hexanes). The required fractions were concentrated to obtain 6-bromo-2-isopentyl-4-methoxy-1H-benzo[d]imidazole (0.985 g, 3.31 mmol, 91% yield). LC/MS (ESI) m/e 297.0, 299.0 Br pattern [(M+H)+, calcd for C13H18N2O 297.1].

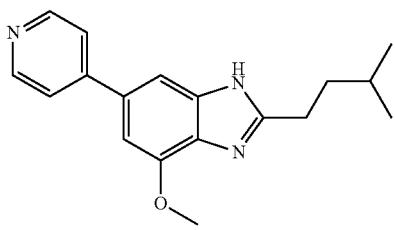 [SMILES: COc1cc(-c2ccncc2)cc2[nH]c(CCC(C)C)nc12]

Part E: 2-isopentyl-4-methoxy-6-(pyridin-4-yl)-1H-benzo[d]imidazole

To a vial was added 6-bromo-2-isopentyl-4-methoxy-1H-benzo[d]imidazole (0.3 g, 1.009 mmol), potassium carbonate (0.419 g, 3.03 mmol), tetrakis(triphenylphosphine)palladium(0) (0.233 g, 0.202 mmol) and pyridin-4-ylboronic acid (0.124 g, 1.009 mmol). The vial was sealed and purged with $N_2$ for 5 min. Dioxane (10 mL) and water (2.5 mL) were added and the vial purged with $N_2$ for 10 min. The reaction mixture was heated in an oil bath for 14 h. The mixture was cooled to room temperature, filtered through diatomaceous earth (Celite®) and concentrated under reduced pressure. The residue was purified via silica gel chromatography (15%-100% EtOAc in hexanes). Obtained 2-isopentyl-4-methoxy-6-(pyridin-4-yl)-1H-benzo[d]imidazole (0.1627 g, 0.540 mmol, 54% yield) as a colorless solid. $^1$H NMR (400 MHz, METHANOL-$d_4$) δ 8.93 (d, J=5.5 Hz, 2H), 8.49 (d, J=5.5 Hz, 2H), 7.94 (s, 1H), 7.59 (s, 1H), 4.20 (s, 3H), 3.27-3.15 (m, 2H), 1.90-1.78 (m, 2H), 1.69 (tq, J=13.2, 6.6 Hz, 1H), 1.02 (d, J=6.5 Hz, 6H), LC/MS (ESI) m/e 296.2 [(M+H)+, calcd for C13H18N2O 296.2].

Example 26

5-(2-isopentyl-4-methoxy-1H-benzo[d]imidazol-6-yl)oxazole

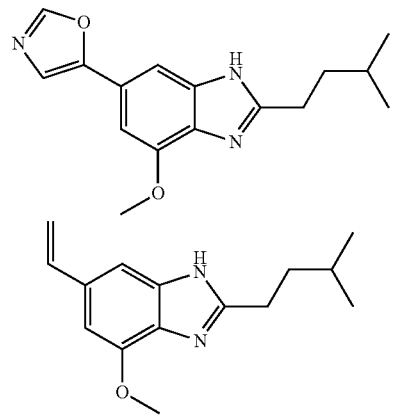

Part A: 2-isopentyl-4-methoxy-6-vinyl-1H-benzo[d]imidazole

A microwave vial was charged with 6-bromo-2-isopentyl-4-methoxy-1H-benzo[d]imidazole (0.301 g, 1.013 mmol) prepared as in Example 25, Part D, potassium trifluoro(vinyl)borate (0.149 g, 1.114 mmol) and 1,1'-bis(diphenylphosphino)ferrocenepalladium(II) dichloride, dichloromethane complex (0.083 g, 0.101 mmol) then sealed and purged with N2 for 5 min. 2-Propanol (8 mL), water (4.0 mL) and DIEA (0.531 mL, 3.04 mmol) were added and the vial purged with $N_2$ for 10 min. The mixture was heated to 90° C. overnight (~14 h) in an oil bath. The mixture was cooled to room temperature, filtered through diatomaceous earth (Celite®) and concentrated under reduced pressure. The residue was purified via silica gel chromatography (5%-40% EtOAc in hexanes) to obtain 2-isopentyl-4-methoxy-6-vinyl-1H-benzo[d]imidazole (0.196 g, 0.802 mmol, 79% yield). LC/MS (ESI) m/e 245.2 [(M+H)+, calcd for C15H21N2O 245.2].

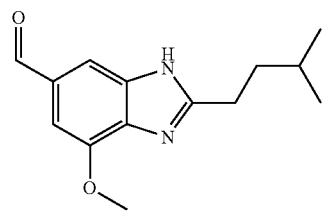 [SMILES: COc1cc(C=O)cc2[nH]c(CCC(C)C)nc12]

Part B: 2-isopentyl-4-methoxy-1H-benzo[d]imidazole-6-carbaldehyde

To a solution of 2-isopentyl-4-methoxy-6-vinyl-1H-benzo[d]imidazole (0.196 g, 0.802 mmol) in dioxane (15 mL) and water (3.75 mL) at 0° C. was added sodium periodate (0.686 g, 3.21 mmol), osmium(VIII) oxide (0.163 g, 0.016 mmol) (2.5% in 2-methyl-2-propanol), and 2,6-lutidine (0.187 mL, 1.604 mmol). The ice bath was removed and the solution stirred overnight while warming to room temperature. The residue was purified via silica gel chromatography (5%-80% EtOAc in hexanes) to obtain 2-isopentyl-4-methoxy-1H-benzo[d]imidazole-6-carbaldehyde (0.096 g, 0.390 mmol, 49% crude yield). The product was carried on without further purification. LC/MS (ESI) m/e 247.2 [(M+H)+, calcd for C14H19N2O2 247.2].

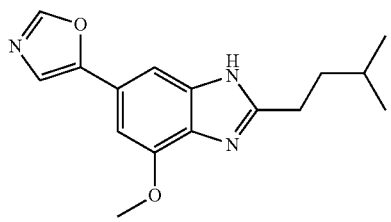 [SMILES: COc1cc(-c2cnco2)cc2[nH]c(CCC(C)C)nc12]

Part C: 5-(2-isopentyl-4-methoxy-1H-benzo[d]imidazol-6-yl)oxazole

To a solution of 2-isopentyl-4-methoxy-1H-benzo[d]imidazole-6-carbaldehyde (0.096 g, 0.390 mmol) in MeOH (20 mL) was added TosMIC (0.076 g, 0.390 mmol) and potassium carbonate (0.057 g, 0.409 mmol). The reaction mixture was heated at reflux for 3 h. The reaction mixture was cooled to room temperature and was transferred to a separatory funnel containing saturated aqueous NaHCO$_3$ solution (80 mL). The aqueous layer was extracted with EtOAc (3×75 mL). The combined organic layers were washed with brine (60 mL), dried over MgSO$_4$, filtered and concentrated under reduced pressure. The residue was purified by silica gel chromatography using (0-80% EtOAc in hexanes). The required fractions were concentrated under reduced pressure to afford 5-(2-isopentyl-4-methoxy-1H-benzo[d]imidazol-6-yl)oxazole (0.0513 g, 0.176 mmol, 45% yield) as an off-white amorphous solid. $^1$H NMR (400 MHz, METHANOL-d$_4$) δ 8.33 (s, 1H), 7.72 (s, 1H), 7.64 (d, J=1.0 Hz, 1H), 7.43 (d, J=1.3 Hz, 1H), 4.14 (s, 3H), 3.20-3.11 (m, 2H), 1.88-1.77 (m, 2H), 1.69 (tq, J=13.3, 6.6 Hz, 1H), 1.03 (d, J=6.5 Hz, 6H), LC/MS (ESI) m/e 286.2 [(M+H)+, calcd for C16H20N3O2 286.2].

Example 27

(R)-1-(6-methoxy-5-(3-methoxypyridin-4-yl)-1H-benzo[d]imidazol-2-yl)-3-methylbutan-1-amine

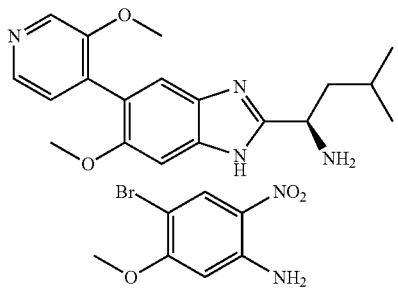

Part A: 4-bromo-5-methoxy-2-nitroaniline

To a solution of 5-methoxy-2-nitroaniline (1.99 g, 11.83 mmol) in dry CH$_2$Cl$_2$ (60 mL) at room temperature under nitrogen was added NBS (2.74 g, 15.39 mmol). The reaction mixture was stirred at room temperature for 12 h. The reaction mixture was concentrated under reduced pressure and purified by silica gel chromatography (0-100% EtOAc in hexanes). Obtained 4-bromo-5-methoxy-2-nitroaniline (1.4 g, 5.67 mmol, 48% yield) as yellow solid. $^1$H NMR (400 MHz, CHLOROFORM-d) δ 8.35 (s, 1H), 6.29 (br. s., 2H), 6.19 (s, 1H), 3.92 (s, 3H), LC/MS (ESI) m/e 247.1, 249.1 Br pattern [(M+H)+, calcd for C7H8BrN2O3 247.0].

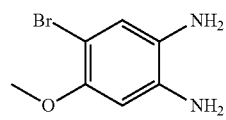

Part B: 4-bromo-5-methoxybenzene-1,2-diamine

To a solution of 4-bromo-5-methoxy-2-nitroaniline (1.4 g, 5.67 mmol) in ethanol (50 mL) at room temperature under nitrogen was added ammonium chloride (1.213 g, 22.67 mmol) and zinc powder (1.483 g, 22.67 mmol). The reaction mixture was stirred at room temperature for 12 h. The reaction mixture was filtered through diatomaceous earth (Celite®) and the filtrate was concentrated under reduced pressure to obtain 4-bromo-5-methoxybenzene-1,2-diamine (1.23 g, 5.67 mmol, 100% crude yield). The product was carried on without further purification. LC/MS (ESI) m/e 217.1, 219.1 Br pattern [(M+H)+, calcd for C7H10BrN2O 217.0].

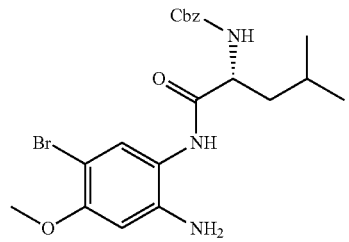 [SMILES: COc1cc(N)c(NC(=O)[C@@H](CC(C)C)NC(=O)OCc2ccccc2)cc1Br]

Part C: (R)-benzyl 1-(2-amino-5-bromo-4-methoxyphenylamino)-4-methyl-1-oxopentan-2-ylcarbamate To a solution of 4-bromo-5-methoxybenzene-1,2-diamine (5.6 g, 25.8 mmol), (R)-2-(benzyloxycarbonylamino)-4-methylpentanoic acid (7.53 g, 28.4 mmol) and HATU (14.71 g, 38.7 mmol) in DMF (100 mL) at 0° C. was added DIEA (9.01 mL, 51.6 mmol). The mixture was stirred at 0° C. for 1.5 h. The reaction mixture was diluted with EtOAc (100 mL) and washed with saturated aqueous sodium bicarbonate (3×50 mL) and brine (3×50 mL). The organics were dried (MgSO4), filtered and concentrated under reduced pressure to obtain (R)-benzyl 1-(2-amino-5-bromo-4-methoxyphenylamino)-4-methyl-1-oxopentan-2-ylcarbamate (11.98 g, 25.8 mmol, 100% crude yield). The product was carried on further purification. LC/MS (ESI) m/e 464.1, 466.1 Br pattern [(M+H)+, calcd for C21H27BrN3O4 464.0].

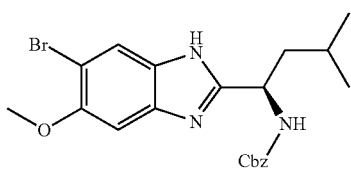 [SMILES: COc1cc2nc([C@@H](CC(C)C)NC(=O)OCc3ccccc3)[nH]c2cc1Br]

Part D: (R)-benzyl 1-(6-bromo-5-methoxy-1H-benzo[d]imidazol-2-yl)-3-methylbutylcarbamate A solution of (R)-benzyl 1-(2-amino-5-bromo-4-methoxyphenylamino)-4-methyl-1-oxopentan-2-ylcarbamate (11.98 g, 25.8 mmol) in acetic acid (150 mL) was heated at 65° C. over 2 days under nitrogen atmosphere. The reaction mixture was cooled to room temperature and concentrated under reduced pressure. The residue was purified by silica gel chromatography (0-70% EtOAc in hexanes) to obtain (R)-benzyl 1-(6-bromo-5-methoxy-1H-benzo[d]imidazol-2-yl)-3-methylbutylcarbamate (7.55 g, 16.92 mmol, 66% yield). LC/MS (ESI) m/e 446.0, 448.0 Br pattern [(M+H)+, calcd for C21H25BrN3O3 446.1].

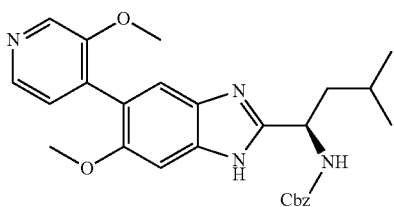 [SMILES: COc1cnccc1-c1cc2nc([C@@H](CC(C)C)NC(=O)OCc3ccccc3)[nH]c2cc1OC]

Part E: (R)-benzyl 1-(6-methoxy-5-(3-methoxypyridin-4-yl)-1H-benzo[d]imidazol-2-yl)-3-methylbutylcarbamate To a vial was added (R)-benzyl 1-(6-bromo-5-methoxy-1H-benzo[d]imidazol-2-yl)-3-methylbutylcarbamate (0.3 g, 0.672 mmol), potassium carbonate (0.279 g, 2.016 mmol), tetrakis(triphenylphosphine)palladium(0) (0.155 g, 0.134 mmol) and 3-methoxypyridin-4-ylboronic acid (0.103 g, 0.672 mmol). The vial was sealed and purged with $N_2$ for 5 min. Dioxane (10 mL) and water (2.5 mL) were added and the vial purged with $N_2$ for 10 min. The mixture was heated in an oil bath overnight for 14 h. The mixture was filtered and concentrated under reduced pressure. The residue was purified by silica gel chromatography (15-100% EtOAc in hexanes) to obtain (R)-benzyl 1-(6-methoxy-5-(3-methoxypyridin-4-yl)-1H-benzo[d]imidazol-2-yl)-3-methylbutylcarbamate (0.169 g, 0.356 mmol, 53% yield). LC/MS (ESI) m/e 475.2 [(M+H)+, calcd for C27H31N4O4 475.2].

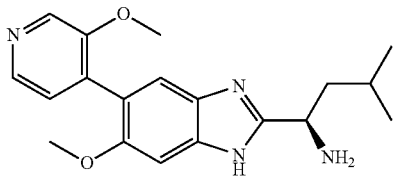 [SMILES: COc1cnccc1-c1cc2nc([C@H](N)CC(C)C)[nH]c2cc1OC]

Part F: (R)-1-(6-methoxy-5-(3-methoxypyridin-4-yl)-1H-benzo[d]imidazol-2-yl)-3-methylbutan-1-amine To a solution of (R)-benzyl 1-(6-methoxy-5-(3-methoxypyridin-4-yl)-1H-benzo[d]imidazol-2-yl)-3-methylbutylcarbamate (0.169 g, 0.356 mmol) in dichloromethane (10 mL) at room temperature under nitrogen was added anisole (0.085 g, 0.783 mmol) and methanesulfonic acid (1.198 g, 12.46 mmol). The reaction mixture was stirred overnight at room temperature under nitrogen. The reaction mixture was concentrated under reduced pressure and the residue purified by reverse phase preparative HPLC (water/Methanol/0.1% TFA) to obtain the product as a TFA salt. The material was passed through an ion exchange column (Strata-X-C-33 um Polymeric Strong Cation from Phenomenex) and washed with water (10 mL) then methanol (10 mL) followed by eluting the product with methanolic ammonia (10 ML, 2M in methanol). The solvent was concentrated to obtain (R)-1-(6-methoxy-5-(3-methoxypyridin-4-yl)-1H-benzo[d]imidazol-2-yl)-3-methylbutan-1-amine (0.056 g, 0.159 mmol, 45% yield) as a colorless amorphous solid. $^1$H NMR (400 MHz, METHANOL-$d_4$) δ 8.30 (s, 1H), 8.17 (d, J=4.8 Hz, 1H), 7.39 (s, 1H), 7.27 (d, J=4.8 Hz, 1H), 7.19 (s, 1H), 4.35 (t, J=7.5 Hz, 1H), 3.83 (s, 3H), 3.79 (s, 3H), 2.05-1.89 (m, 1H), 1.80 (dt, J=13.7, 7.1 Hz, 1H), 1.58 (tq, J=13.5, 6.7 Hz, 1H), 1.00 (d, J=6.5 Hz, 3H), 0.94 (d, J=6.5 Hz, 3H), LC/MS (ESI) m/e 341.2 [(M+H)+, calcd for C19H25N4O2 341.2].

Example 28

(R)-1-(6-methoxy-5-(2-methoxypyridin-4-yl)-1H-benzo[d]imidazol-2-yl)-3-methylbutan-1-amine

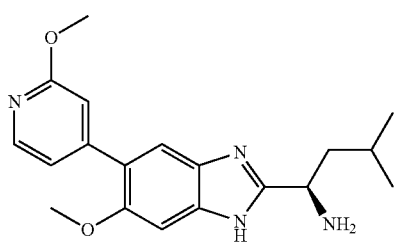 [SMILES: COc1cc(-c2cc3nc([C@H](N)CC(C)C)[nH]c3cc2OC)ccn1]

Prepared in a similar fashion as described in Example 27, using 3-methoxypyridin-4-ylboronic acid in Part E to give the title compound (0.0506 g, 0.146 mmol, 35% yield) as a colorless amorphous solid. $^1$H NMR (400 MHz, METHANOL-$d_4$) δ 8.05 (dd, J=5.4, 0.6 Hz, 1H), 7.47 (s, 1H), 7.16 (s, 1H), 7.08 (dd, J=5.5, 1.5 Hz, 1H), 6.92 (dd, J=1.5, 0.5 Hz, 1H), 4.17 (t, J=7.4 Hz, 1H), 3.90 (s, 3H), 3.81 (s, 3H), 1.88-1.78 (m, 1H), 1.77-1.67 (m, 1H), 1.59 (tq, J=13.4, 6.6 Hz, 1H), 0.97 (d, J=6.5 Hz, 3H), 0.91 (d, J=6.5 Hz, 3H). LC/MS (ESI) m/e 341.2 [(M+H)+, calcd for C19H25N4O2 341.2].

Example 29

(R)-1-(5-methoxy-6-(oxazol-5-yl)-1H-benzo[d]imidazol-2-yl)-3-methylbutan-1-amine

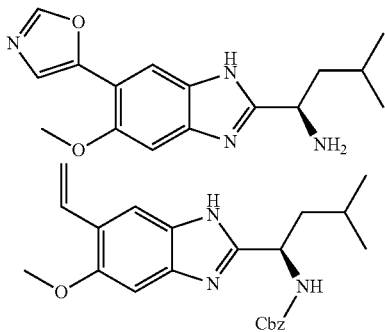

Part A: (S)-benzyl 3-methyl-1-(6-vinyl-1H-benzo[d]imidazol-2-yl)butylcarbamate A microwave vial was charged with (S)-benzyl 1-(6-bromo-1H-benzo[d]imidazol-2-yl)-3-methylbutylcarbamate (0.365 g, 0.877 mmol) prepared as in Example 26, Part D, potassium trifluoro(vinyl)borate (0.129 g, 0.964 mmol) and 1,1'-bis(diphenylphosphino)ferrocenepalladium(II) dichloride, dichloromethane complex (0.072 g, 0.088 mmol) then sealed and purged with N$_2$ for 5 min. 2-propanol (10 mL), water (5.0 mL) and DIEA (0.459 mL, 2.63 mmol) were added and the vial purged with N$_2$ for 10 min. The mixture was heated to 90° C. overnight in an oil bath. The mixture was cooled to room temperature, filtered through diatomaceous earth (Celite®) and concentrated under reduced pressure. The residue was purified via silica gel chromatography (5%-40% EtOAc in hexanes) to obtain (S)-benzyl 3-methyl-1-(6-vinyl-1H-benzo[d]imidazol-2-yl)butylcarbamate (0.23 g, 0.619 mmol, 71% yield). LC/MS (ESI) m/e 394.2 [(M+H)+, calcd for C23H28N3O3 394.2].

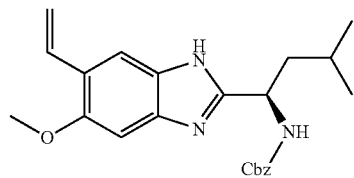 [SMILES: C=Cc1cc2[nH]c([C@@H](CC(C)C)NC(=O)OCc3ccccc3)nc2cc1OC]

Part B: (R)-benzyl 1-(6-formyl-5-methoxy-1H-benzo[d]imidazol-2-yl)-3-methylbutylcarbamate To a solution of (R)-benzyl 1-(5-methoxy-6-vinyl-1H-benzo[d]imidazol-2-yl)-3-methylbutylcarbamate (0.201 g, 0.511 mmol) in dioxane (15 mL) and water (3.75 mL) at 0° C. was added osmium(VIII) oxide (0.104 g, 10.22 µmol), (2.5% in 2-methyl-2-propanol), sodium periodate (0.437 g, 2.043 mmol) and 2,6-lutidine (0.119 mL, 1.022 mmol). The ice bath was removed and the solution stirred for 2.5 h while warming to room temperature. The concentrated residue was purified via silica gel chromatography (5%-80% EtOAc in hexanes) to obtain (R)-benzyl 1-(6-formyl-5-methoxy-1H-benzo[d]imidazol-2-yl)-3-methylbutylcarbamate (0.191 g, 0.483 mmol, 95% yield). LC/MS (ESI) m/e 396.2 [(M+H)+, calcd for C22H26N3O4 396.2].

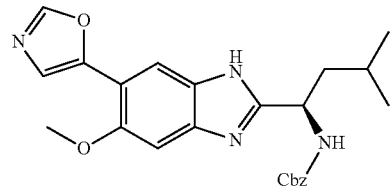 [SMILES: COc1cc2nc([C@@H](CC(C)C)NC(=O)OCc3ccccc3)[nH]c2cc1-c1cnco1]

Part C: (R)-benzyl 1-(5-methoxy-6-(oxazol-5-yl)-1H-benzo[d]imidazol-2-yl)-3-methylbutylcarbamate To a solution of (R)-benzyl 1-(6-formyl-5-methoxy-1H-benzo[d]imidazol-2-yl)-3-methylbutylcarbamate (0.191 g, 0.483 mmol) in MeOH (20 mL) was added TosMIC (0.094 g, 0.483 mmol) and potassium carbonate (0.070 g, 0.507 mmol). The reaction mixture was heated at reflux for 3 h, then cooled to room temperature. The mixture was transferred to a separatory funnel containing saturated aqueous NaHCO$_3$ solution (80 mL). The aqueous layer was extracted with EtOAc (3×75 mL). The combined organic layers were washed with brine (60 mL), dried over MgSO$_4$, filtered and concentrated under reduced pressure. The residue was purified by silica gel chromatography (0-80% EtOAc in hexanes) to afford (R)-benzyl 1-(5-methoxy-6-(oxazol-5-yl)-1H-benzo[d]imidazol-2-yl)-3-methylbutylcarbamate (0.159 g, 0.366 mmol, 76% yield). LC/MS (ESI) m/e 435.2 [(M+H)+, calcd for C24H27N4O4 435.2].

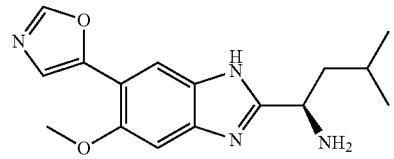

Part D: (R)-1-(5-methoxy-6-(oxazol-5-yl)-1H-benzo[d]imidazol-2-yl)-3-methylbutan-1-amine To a solution of (R)-benzyl 1-(5-methoxy-6-(oxazol-5-yl)-1H-benzo[d]imidazol-2-yl)-3-methylbutylcarbamate (0.159 g, 0.366 mmol) in dichloromethane (10 mL) at room temperature under nitrogen was added anisole (0.087 g, 0.805 mmol) and methanesulfonic acid (1.231 g, 12.81 mmol). The reaction mixture was stirred overnight at room temperature under nitrogen. The reaction mixture was concentrated under reduced pressure and the residue purified by reverse phase preparative HPLC (water/MeOH. 0.1% TFA) to obtain the product as TFA salt. The product was passed through an ion exchange column (Strata-X-C-33 um Polymeric Strong Cation from Phenomenex) and washed with water (10 mL) then methanol (10 mL) followed by eluting the product with methanolic ammonia (10 ML, 2M in methanol). The solvent was concentrated to obtain (R)-1-(5-methoxy-6-(oxazol-5-yl)-1H-benzo[d]imidazol-2-yl)-3-methylbutan-1-amine (0.0403 g, 0.131 mmol, 36% yield). $^1$H NMR (400 MHz, METHANOL-d$_4$) δ 8.21 (s, 1H), 7.91 (s, 1H), 7.49 (s, 1H), 7.18 (s, 1H), 4.17 (t, J=7.4 Hz, 1H), 3.99 (s, 3H), 1.88-1.78 (m, 1H), 1.77-1.68 (m, 1H), 1.60 (tq, J=13.4, 6.7 Hz, 1H), 0.98 (d, J=6.5 Hz, 3H), 0.93 (d, J=6.5 Hz, 3H), LC/MS (ESI) m/e 301.2 [(M+H)+, calcd for C16H21N4O2 301.2].

Example 30

(R)-1-(6-fluoro-5-(pyridin-4-yl)-1H-benzo[d]imidazol-2-yl)-3-methylbutan-1-amine

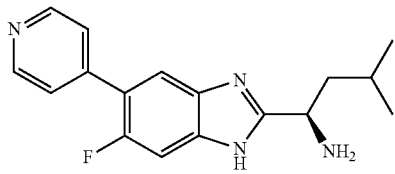 [SMILES: CC(C)C[C@@H](N)c1nc2cc(-c3ccncc3)c(F)cc2[nH]1]

Prepared in a similar fashion as described in Example 1, using 4-bromo-5-fluorobenzene-1,2-diamine in Part A to give the title compound (0.0889 g, 0.292 mmol, 93% yield) as a colorless amorphous solid. $^1$H NMR (400 MHz, METHANOL-$d_4$) δ 8.64-8.53 (m, 2H), 7.69 (d, J=6.8 Hz, 1H), 7.65-7.60 (m, 2H), 7.39 (d, J=11.0 Hz, 1H), 4.21 (t, J=7.4 Hz, 1H), 1.88-1.78 (m, 1H), 1.77-1.69 (m, 1H), 1.62 (tq, J=13.3, 6.7 Hz, 1H), 0.98 (d, J=6.5 Hz, 3H), 0.94 (d, J=6.5 Hz, 3H). LC/MS (ESI) m/e 299.2 [(M+H)+, calcd for C17H20FN4 299.2].

Example 31

(R)-1-(5-fluoro-6-(oxazol-5-yl)-1H-benzo[d]imidazol-2-yl)-3-methylbutan-1-amine

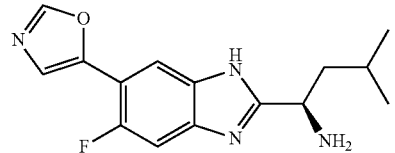 [SMILES: CC(C)C[C@@H](N)c1nc2cc(F)c(-c3cnco3)cc2[nH]1]

Prepared in a similar fashion as described in Example 4, to give the title compound (0.0108 g, 0.036 mmol, 8% yield) as a yellow amorphous solid. $^1$H NMR (400 MHz, METHANOL-$d_4$) δ 8.31 (s, 1H), 7.94 (d, J=6.3 Hz, 1H), 7.45 (d, J=4.5 Hz, 1H), 7.41 (d, J=11.3 Hz, 1H), 4.20 (t, J=7.5 Hz, 1H), 1.88-1.79 (m, 1H), 1.78-1.69 (m, 1H), 1.61 (tt, J=13.3, 6.7 Hz, 1H), 0.99 (d, J=6.5 Hz, 3H), 0.95 (d, J=6.5 Hz, 3H). LC/MS (ESI) m/e 289.2 [(M+H)+, calcd for C15H18FN4O 289.2].

Example 32

(R)-1-(1-ethyl-6-(oxazol-5-yl)-1H-benzo[d]imidazol-2-yl)-3-methylbutan-1-amine

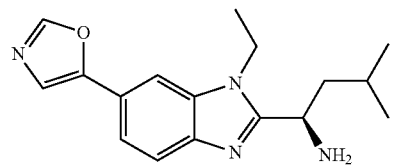

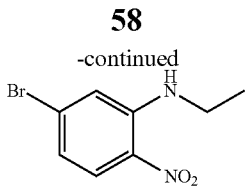

Part A: 5-bromo-N-ethyl-2-nitroaniline

A solution of 4-bromo-2-fluoro-1-nitrobenzene (5.1 g, 23.18 mmol), ethanamine, HCl (1.890 g, 23.18 mmol) and DIEA (8.10 mL, 46.4 mmol) in DMA (25.8 mL) was heated to 80° C. for 19 h The mixture was cooled to room temperature, diluted with water and extracted with EtOAc (3×20 mL). The combined organic layers were washed with brine (3×15 mL), dried over MgSO$_4$, filtered and concentrated under reduced pressure. Obtained 5-bromo-N-ethyl-2-nitroaniline (5.1 g, 19.77 mmol, 85% yield). Carried on without further purification. $^1$H NMR (400 MHz, CHLOROFORM-d) δ ppm 8.03 (d, J=9.0 Hz, 1H), 7.97 (br. S., 1H), 7.02 (d, J=1.8 Hz, 1H), 6.76 (dd, J=9.3, 2.0 Hz, 1H), 3.34 (qd, J=7.2, 5.0 Hz, 2H), 1.39 (t, J=7.3 Hz, 3H), LC/MS (ESI) m/e 245.0, 247.0 Br pattern [(M+H)+, calcd for C8H10BrN2O2 245.0].

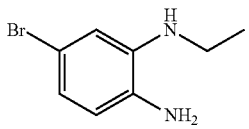

Part B: 5-bromo-N1-ethylbenzene-1,2-diamine

A solution of 5-bromo-N-ethyl-2-nitroaniline (4.85 g, 19.77 mmol), iron powder (4.77 g, 85 mmol) and calcium chloride (0.189 g, 1.700 mmol) in EtOH (198 mL) and water (49.4 mL) was heated to reflux for 12 h. The mixture was filtered through diatomaceous earth (Celite®) to remove iron, then quenched with water and extracted with EtOAc (3×75 mL). The combined organic layers were washed with brine (1×50 mL), dried over MgSO$_4$, filtered and concentrated under reduced pressure. Obtained 5-bromo-N1-ethylbenzene-1,2-diamine (4.25 g, 19.77 mmol, 100% crude yield) as a brown semi-solid. Carried on without further purification. $^1$H NMR (400 MHz, CHLOROFORM-d) δ ppm 6.76 (dd, J=8.0, 2.0 Hz, 1H), 6.74 (d, J=2.0 Hz, 1H), 6.58 (d, J=8.0 Hz, 1H), 3.30 (br. s., 3H), 3.13 (q, J=7.2 Hz, 2 H), 1.31 (t, J=7.2 Hz, 3H), LC/MS (ESI) m/e 215.0, 217.0 Br pattern [(M+H)+, calcd for C8H12BrN2 215.0].

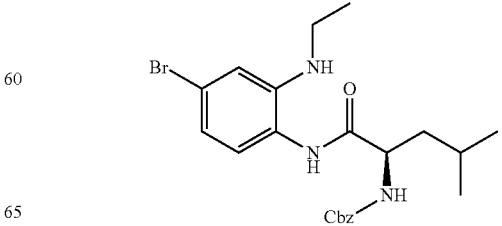

Part C: (R)-benzyl (1-((4-bromo-2-(ethylamino) phenyl)amino)-4-methyl-1-oxopentan-2-yl)carbamate To a solution of 5-bromo-N1-ethylbenzene-1,2-diamine (4.25 g, 19.77 mmol), (R)-2-(benzyloxycarbonylamino)-4-methylpentanoic acid (5.25 g, 19.77 mmol) and 2-(1H-benzo[d][1,2,3]triazol-1-yl)-1,1,3,3-tetramethyluronium hexafluorophosphate(V) (7.50 g, 19.77 mmol) in DMF (15.2 mL) at 0° C. was added DIEA (790 µL, 4.52 mmol) and the solution stirred at 0° C. for 12 h. The mixture was quenched with saturated aqueous sodium bicarbonate (15 mL) and extracted with EtOAc (3×15 mL). The combined organics were washed with saturated aqueous sodium bicarbonate (2×15 mL), brine (3×15 mL), dried over MgSO4, filtered and concentrated under reduced pressure. Obtained (R)-benzyl 1-(4-bromo-2-(ethylamino)phenylamino)-4-methyl-1-oxopentan-2-ylcarbamate (9.14 g, 11.86 mmol, 60% crude yield) as a brown semi-solid. Carried on without further purification. LC/MS (ESI) m/e 462.0 [(M+H)+, calcd for C22H29BrN3O3 462.1].

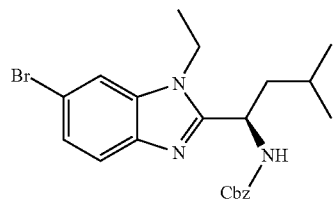 [SMILES: CCn1c([C@@H](CC(C)C)NC(=O)OCc2ccccc2)nc2ccc(Br)cc21]

Part D: (R)-benzyl 1-(6-bromo-1-ethyl-1H-benzo[d]imidazol-2-yl)-3-methylbutylcarbamate A solution of (R)-benzyl 1-(4-bromo-2-(ethylamino)phenylamino)-4-methyl-1-oxopentan-2-ylcarbamate (9 g, 19.46 mmol) in acetic acid (50 mL) was heated at 65° C. for 12 h under a nitrogen atmosphere. The reaction mixture was cooled to room temperature and concentrated under reduced pressure. The residue was purified by silica gel chromatography (0-70% EtOAc in hexanes). The required fractions were concentrated to obtain (R)-benzyl 1-(6-bromo-1-ethyl-1H-benzo[d]imidazol-2-yl)-3-methylbutylcarbamate (5.44 g, 12.24 mmol, 63% yield) as an off white solid. LC/MS (ESI) m/e 444.0, 446.0 Br pattern [(M+H)+, calcd for C22H27BrN3O2 444.1].

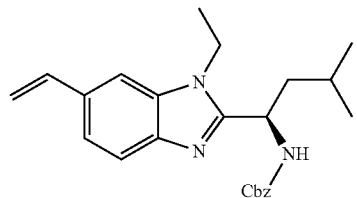 [SMILES: C=Cc1ccc2nc([C@@H](CC(C)C)NC(=O)OCc3ccccc3)n(CC)c2c1]

Part E: (R)-benzyl 1-(1-ethyl-6-vinyl-1H-benzo[d]imidazol-2-yl)-3-methylbutylcarbamate A solution of (R)-benzyl 1-(6-bromo-1-ethyl-1H-benzo[d]imidazol-2-yl)-3-methylbutylcarbamate (0.5 g, 1.125 mmol), 2,4,6-trivinylcyclotriboroxane pyridine complex (0.271 g, 1.125 mmol), and sodium bicarbonate (0.189 g, 2.25 mmol) in toluene (10 mL) and EtOH (2.5 mL) was sealed and purged with N2 for 10 min. Tetrakis(triphenylphosphine)palladium(0) (0.065 g, 0.056 mmol) was added and the solution heated to 95° C. for 2.5 h. The solution was cooled to room temperature and diluted with water. The mixture was extracted with EtOAc (2×10 mL). The combined organics were washed with saturated aqueous sodium bicarbonate (2×10 mL), brine (3×10 mL), dried over MgSO4, filtered and concentrated under reduced pressure. The residue was purified via silica gel chromatography (5%-40% EtOAc in hexanes). Obtained (R)-benzyl 1-(1-ethyl-6-vinyl-1H-benzo[d]imidazol-2-yl)-3-methylbutylcarbamate (0.311 g, 0.794 mmol, 71% yield) as a colorless solid. LC/MS (ESI) m/e 392.1 [(M+H)+, calcd for C24H30N3O2 392.2].

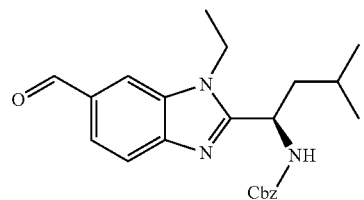 [SMILES: CCn1c([C@@H](CC(C)C)NC(=O)OCc2ccccc2)nc2ccc(C=O)cc21]

Part F: (R)-benzyl 1-(1-ethyl-6-formyl-1H-benzo[d]imidazol-2-yl)-3-methylbutylcarbamate To a solution of (R)-benzyl 1-(1-ethyl-6-vinyl-1H-benzo[d]imidazol-2-yl)-3-methylbutylcarbamate (0.311 g, 0.794 mmol) in dioxane (10 mL) and water (2.5 mL) at 0° C. was added 2,6-lutidine (0.185 mL, 1.589 mmol), osmium tetroxide (0.162 g, 0.016 mmol) (2.5% in 2-methyl-2-propanol), and sodium periodate (0.680 g, 3.18 mmol). The ice bath was removed and the solution stirred for 2.5 h while warming to room temperature. The residue was purified via silica gel chromatography (5%-80% EtOAc in hexane) to afford (R)-benzyl 1-(1-ethyl-6-formyl-1H-benzo[d]imidazol-2-yl)-3-methylbutylcarbamate (0.281 g, 0.714 mmol, 90% yield) as a colorless film. LC/MS (ESI) m/e 394.2 [(M+H)+, calcd for C23H28N3O3 394.2].

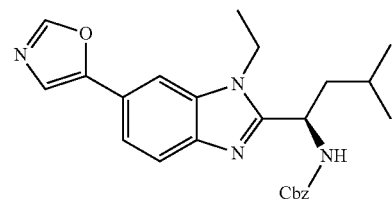 [SMILES: CCn1c([C@@H](CC(C)C)NC(=O)OCc2ccccc2)nc2ccc(-c3cnco3)cc21]

Part G: (R)-benzyl 1-(1-ethyl-6-(oxazol-5-yl)-1H-benzo[d]imidazol-2-yl)-3-methylbutylcarbamate To a solution of (R)-benzyl 1-(1-ethyl-6-formyl-1H-benzo[d]imidazol-2-yl)-3-methylbutylcarbamate (0.281 g, 0.714 mmol) in methanol (30 mL) was added TosMIC (0.139 g, 0.714 mmol) and potassium carbonate (0.104 g, 0.750 mmol). The reaction mixture was heated to reflux for 3 h. The reaction mixture was cooled to room temperature and transferred to a separatory funnel containing a saturated aqueous NaHCO3 solution (80 mL). The aqueous layer was extracted with EtOAc (3×20 mL). The combined organic layers were washed with brine (60 mL), dried over MgSO$_4$, filtered and concentrated under reduced pressure. The residue was purified by reverse phase preparative HPLC (Solvent A: 90% water, 10% Methanol, 0.1% TFA: Solvent B: 10% Water, 90% Methanol, 0.1% TFA). The required fractions were concentrated to obtain (R)-benzyl 1-(1-ethyl-6-(oxazol-5-yl)-1H-benzo[d]imidazol-2-yl)-3-methylbutylcarbamate (0.212 g, 0.490 mmol, 69% yield) as a colorless film. LC/MS (ESI) m/e 433.2 [(M+H)+, calcd for C25H29N4O3 433.2].

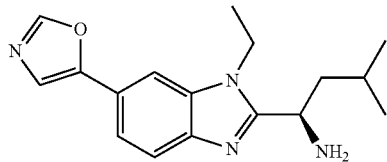 [SMILES: CCn1c([C@H](N)CC(C)C)nc2ccc(-c3cnco3)cc21]

Part H: (R)-1-(1-ethyl-6-(oxazol-5-yl)-1H-benzo[d]imidazol-2-yl)-3-methylbutan-1-amine To a solution of (R)-benzyl 1-(1-ethyl-6-(oxazol-5-yl)-1H-benzo[d]imidazol-2-yl)-3-methylbutylcarbamate (0.212 g, 0.490 mmol) in MeOH (40 mL) under nitrogen was added Pd/C (0.052 g, 0.490 mmol). The flask was purged with hydrogen and stirred under a balloon of hydrogen for 2 h. The reaction mixture was filtered through a glass filter. The filtrate was concentrated and the residue purified by reverse phase preparative HPLC (Solvent A: 90% water, 10% Methanol, 0.1% TFA: Solvent B: 10% Water, 90% Methanol, 0.1% TFA). The required fractions were concentrated to obtain (R)-1-(1-ethyl-6-(oxazol-5-yl)-1H-benzo[d]imidazol-2-yl)-3-methylbutan-1-amine, 2 TFA (0.031 g, 0.058 mmol, 12% yield). $^1$H NMR (400 MHz, METHANOL-d$_4$) δ 8.29 (s, 1H), 7.99 (d, J=1.0 Hz, 1H), 7.81-7.76 (m, 1H), 7.74-7.69 (m, 1H), 7.59 (s, 1H), 4.57-4.34 (m, 3H), 2.14-2.05 (m, 1H), 2.05-1.95 (m, 1H), 1.68 (tq, J=13.3, 6.7 Hz, 1H), 1.52 (t, J=7.2 Hz, 3H), 1.03 (d, J=5.5 Hz, 3H), 1.01 (d, J=5.5 Hz, 3H), LC/MS (ESI) m/e 299.2 [(M+H)+, calcd for C17H23N4O 299.2], HPLC (method G): t$_R$=7.38 min.

Example 33

(R)-1-(1-ethyl-6-(pyridin-4-yl)-1H-benzo[d]imidazol-2-yl)-3-methylbutan-1-amine

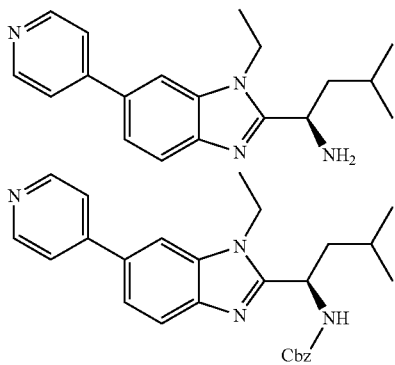

Part A: (R)-benzyl 1-(1-ethyl-6-(pyridin-4-yl)-1H-benzo[d]imidazol-2-yl)-3-methylbutylcarbamate To a microwave vial was added (R)-benzyl 1-(6-bromo-1-ethyl-1H-benzo[d]imidazol-2-yl)-3-methylbutylcarbamate (2.1 g, 4.73 mmol) prepared as in Example 32, Part D, potassium carbonate (0.879 g, 14.18 mmol), tetrakis(triphenylphosphine)palladium(0) (62 mg, 0.236 mmol) and 4-(4,4,5,5-tetramethyl-1,3,2-dioxaborolan-2-yl)pyridine (1.163 g, 5.67 mmol). The vial was sealed and purged with N$_2$ for 5 min. Dioxane (27 mL) and water (4.5 mL) were added and the vial purged with N$_2$ for 10 min. Heated in a microwave at 110° C. for 4 h. The mixture was cooled to room temperature and filtered through diatomaceous earth (Celite®). The concentrated residue was purified via silica gel chromatography (10%-100% EtOAc in hexanes) to obtain (R)-benzyl 1-(1-ethyl-6-(pyridin-4-yl)-1H-benzo[d]imidazol-2-yl)-3-methylbutylcarbamate (620 mg, 1.33 mmol, 28% yield) as an off-white amorphous solid. LC/MS (ESI) m/e 443.1 [(M+H)+, calcd for C27H31N4O2 443.2].

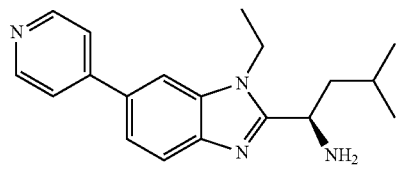

Part B: (R)-1-(1-ethyl-6-(pyridin-4-yl)-1H-benzo[d]imidazol-2-yl)-3-methylbutan-1-amine A solution of (R)-benzyl 1-(1-ethyl-6-(pyridin-4-yl)-1H-benzo[d]imidazol-2-yl)-3-methylbutylcarbamate (620 mg, 1.401 mmol), anisole (337 μl, 3.08 mmol), and methanesulfonic acid (5.46 mL, 84.0 mmol) in DCM (12.7 mL) was stirred at room temperature for 12 h. The crude material was purified by reverse phase HPLC (10%-70% MeOH/H$_2$O/0.1% TFA). The product was free based: quenched with saturated aqueous sodium bicarbonate (20 mL) and extracted with ethyl acetate (3×10 mL). The combined organics were washed with saturated aqueous sodium bicarbonate (2×15 mL) and brine (1×15 mL), dried (MgSO$_4$), filtered and concentrated under reduced pressure. Obtained (R)-1-(1-ethyl-6-(pyridin-4-yl)-1H-benzo[d]imidazol-2-yl)-3-methylbutan-1-amine (360 mg, 1.132 mmol, 81% yield) as an off-white amorphous solid. $^1$H NMR (400 MHz, CHLOROFORM-d) δ ppm 8.61-8.67 (m, 2 H), 7.81 (dd, J=8.3, 0.5 Hz, 1H), 7.57 (d, J=1.3 Hz, 1H), 7.53-7.56 (m, 2H), 7.52 (dd, J=8.3, 1.8 Hz, 1H), 4.25-4.42 (m, 2H), 4.21 (t, J=6.9 Hz, 1H), 1.77-1.89 (m, 3H), 1.73 (br. s., 2 H), 1.49 (t, J=7.3 Hz, 3H), 0.98 (d, J=2.8 Hz, 3H), 0.97 (d, J=2.8 Hz, 3H), LC/MS (ESI) m/e 309.1 [(M+H)+, calcd for C19H25N4 309.2], HPLC (method E): t$_R$=3.62 min; HPLC (method F): t$_R$=3.68 min.

Example 34

(R)-1-(1-ethyl-6-(1H-pyrazol-4-yl)-1H-benzo[d]imidazol-2-yl)-3-methylbutan-1-amine

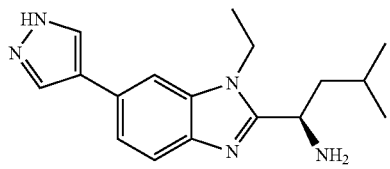 [SMILES: CCn1c([C@H](N)CC(C)C)nc2ccc(-c3cn[nH]c3)cc21]

Prepared in a similar fashion as described in Example 33, using 4-pyrazoleboronic acid in Part A to give the title compound (37 mg, 6.90 μmol, 3% yield) as a colorless amorphous solid. $^1$H NMR (400 MHz, METHANOL-$d_4$) δ 8.07 (m, 2H), 7.82 (d, J=0.8 Hz, 1H), 7.69 (d, J=8.0 Hz, 1H), 7.61-7.55 (m, 1H), 4.87-4.81 (m, 1H), 4.55-4.33 (m, 2H), 2.17-2.06 (m, 1H), 2.04-1.94 (m, 1H), 1.74-1.61 (m, 1H), 1.52 (t, J=7.2 Hz, 3H), 1.02 (app t, J=6.9 Hz, 6H); LC/MS (ESI) m/e 298.2 [(M+H)+, calcd for C17H24N5 298.2].

Example 35

(R)-1-(6-(3-methoxypyridin-4-yl)-1-(2,2,2-trifluoroethyl)-1H-benzo[d]imidazol-2-yl)-3-methylbutan-1-amine

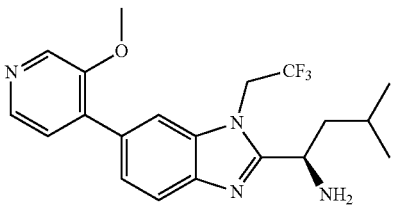 [SMILES: COc1cnccc1-c1ccc2nc([C@H](N)CC(C)C)n(CC(F)(F)F)c2c1]

Prepared in a similar fashion as described in Example 32, Parts A-D using 2,2,2-trifluoroethylamine in Part A and Example 33, Parts A and B using 3-methoxypyridin-4-ylboronic acid in Part A to give the title compound (0.0373 g, 0.093 mmol, 43% yield) as a pale brown amorphous solid: $^1$H NMR (400 MHz, METHANOL-$d_4$) δ 8.39 (s, 1H), 8.26 (d, J=4.8 Hz, 1H), 7.88 (s, 1H), 7.74 (d, J=8.3 Hz, 1H), 7.56 (dd, J=8.5, 1.5 Hz, 1H), 7.47 (d, J=4.8 Hz, 1H), 5.47-5.32 (m, 1H), 5.23 (dq, J=16.8, 8.6 Hz, 1H), 4.33 (t, J=7.0 Hz, 1H), 3.95 (s, 3H), 1.90 (dt, J=7.7, 5.8 Hz, 2H), 1.86-1.75 (m, 1H), 1.00 (app t, J=6.7 Hz, 6H), LC/MS (ESI) m/e 393.2 [(M+H)+, calcd for C20H24F3N4O 393.2].

Example 36

(R)-3-methyl-1-(6-(oxazol-5-yl)-1-(2,2,2-trifluoroethyl)-1H-benzo[d]imidazol-2-yl)butan-1-amine

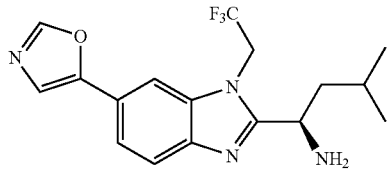 [SMILES: CC(C)C[C@@H](N)c1nc2ccc(-c3cnco3)cc2n1CC(F)(F)F]

Prepared in a similar fashion as described in Example 32 using 2,2,2-trifluoroethylamine in Part A to give the title compound (10 mg, 0.028 mmol, 90% yield) as a colorless amorphous solid: $^1$H NMR (400 MHz, CHLOROFORM-d) δ ppm 7.95 (s, 1H), 7.80 (d, J=8.5 Hz, 1H), 7.67 (s, 1H), 7.61 (dd, J=8.4, 1.6 Hz, 1 H), 7.39 (s, 1H), 5.30-5.45 (m, 1H), 4.78-4.93 (m, 1H), 4.20-4.27 (m, 1H), 1.95-2.06 (m, 1H), 1.81-1.91 (m, 2H), 1.74 (br. s., 2 H), 1.02 (d, J=6.5 Hz, 3H), 1.00 (d, J=6.3 Hz, 3H); $^{19}$F NMR (376 MHz, CHLOROFORM-d) δ ppm −69.63 (s, 3 F), LC/MS (ESI) m/e 353.2 [(M+H)+, calcd for C17H20F3N4O 353.2], HPLC (method E): $t_R$=5.92 min; HPLC (method F): $t_R$=5.88 min.

Example 37

(R)-3-methyl-1-(6-(pyridin-4-yl)-1-(2,2,2-trifluoroethyl)-1H-benzo[d]imidazol-2-yl)butan-1-amine

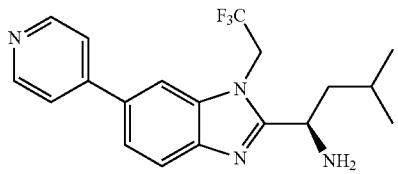 [SMILES: CC(C)C[C@@H](N)c1nc2ccc(-c3ccncc3)cc2n1CC(F)(F)F]

Prepared in a similar fashion as described in Example 32, Parts A-D using 2,2,2-trifluoroethylamine in Part A and Example 33, Parts A and B using pyridin-4-ylboronic acid in Part A to give the title compound (33 mg, 0.089 mmol, 63% yield) as a colorless amorphous solid: $^1$H NMR (400 MHz, CHLOROFORM-d) δ ppm 8.67 (dd, J=4.5, 1.5 Hz, 2H), 7.85 (d, J=8.3 Hz, 1H), 7.61 (s, 1H), 7.58 (dd, J=8.4, 1.6 Hz, 1H), 7.55 (dd, J=4.5, 1.5 Hz, 2H), 5.31-5.49 (m, 1H), 4.78-4.96 (m, 1H), 4.24 (dd, J=8.2, 5.6 Hz, 1H), 1.96-2.06 (m, 1H), 1.80-1.92 (m, 2H), 1.67 (br. s., 2 H), 1.01 (d, J=6.3 Hz, 3H), 0.99 (d, J=6.5 Hz, 3H), $^{19}$F NMR (376 MHz, CHLOROFORM-d) δ ppm −69.59 (s, 3 F), LC/MS (ESI) m/e 363.2 [(M+H)+, calcd for C19H22F3N4 363.2], HPLC (method E): $t_R$=4.02 min; HPLC (method F): $t_R$=4.01 min.

Example 38

(R)-1-(1-(2-methoxyethyl)-6-(pyridin-4-yl)-1H-benzo[d]imidazol-2-yl)-3-methylbutan-1-amine

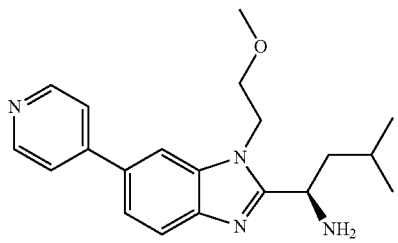

Prepared in a similar fashion as described in Example 32, Parts A-D using 2-methoxyethanamine in Part A and Example 33, Parts A and B using pyridin-4-ylboronic acid in Part A to give the title compound (56 mg, 0.162 mmol, 70% yield) as a colorless amorphous solid: $^1$H NMR (400 MHz, CHLOROFORM-d) δ ppm 8.61-8.69 (m, 2H), 7.83 (d, J=8.3 Hz, 1H), 7.50-7.61 (m, 4H), 4.39-4.56 (m, 2 H), 4.26

(t, J=7.0 Hz, 1H), 3.71-3.79 (m, 2H), 3.30 (s, 3H), 1.74-1.95 (m, 5H), 0.98 (d, J=1.3 Hz, 3H), 0.97 (d, J=1.0 Hz, 3H), LC/MS (ESI) m/e 339.1 [(M+H)+, calcd for C20H27N4O 339.2], HPLC (method E): $t_R$=3.72 min; HPLC (method F): $t_R$=3.90 min.

Example 39

(R)-1-(1-(2-methoxyethyl)-6-(oxazol-5-yl)-1H-benzo[d]imidazol-2-yl)-3-methylbutan-1-amine

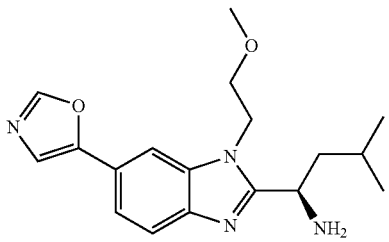 [SMILES: COCCn1c([C@H](N)CC(C)C)nc2ccc(-c3cnco3)cc21]

Prepared in a similar fashion as described in Example 32 using 2-methoxyethanamine in Part A to give the title compound (0.0647 g, 0.193 mmol, 94% yield) as a colorless amorphous solid. ¹H NMR (400 MHz, METHANOL-$d_4$) δ 8.26 (s, 1H), 7.94-7.88 (m, 1H), 7.74-7.61 (m, 2H), 7.56-7.52 (m, 1H), 4.64-4.48 (m, 2H), 4.34 (t, J=7.2 Hz, 1H), 3.77 (t, J=4.9 Hz, 2H), 3.29 (s, 3H), 1.94 (dt, J=13.7, 7.0 Hz, 1H), 1.85-1.63 (m, 2H), 0.98 (d, J=5.5 Hz, 3H), 0.96 (d, J=5.5 Hz, 3H), LC/MS (ESI) m/e 329.1 [(M+H)+, calcd for C18H25N4O2 329.2].

Example 40

(R)-2-(2-(1-amino-3-methylbutyl)-6-(pyridin-4-yl)-1H-benzo[d]imidazol-1-yl)ethanol

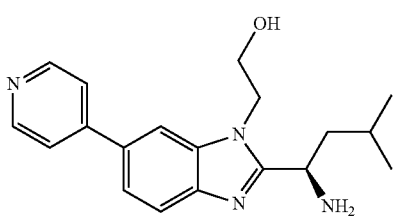 [SMILES: CC(C)C[C@@H](N)c1nc2ccc(-c3ccncc3)cc2n1CCO]

Prepared in a similar fashion as described in Example 32, Parts A-D using 2-aminoethanol in Part A and Example 33, Parts A and B using pyridin-4-ylboronic acid in Part A to give the title compound (59 mg, 0.167 mmol, 32% yield) as a colorless amorphous solid: ¹H NMR (400 MHz, CHLOROFORM-d) δ ppm 8.48-8.76 (m, 2H), 7.78-7.91 (m, 1H), 7.45-7.63 (m, 4H), 4.38-4.58 (m, 2H), 4.24 (t, J=7.2 Hz, 1H), 3.91-4.07 (m, 2H), 2.03-2.26 (m, 1H), 1.86-2.03 (m, 1H), 1.67-1.86 (m, 1H), 0.88-1.07 (m, 6H), LC/MS (ESI) m/e 325.1 [(M+H)+, calcd for C19H25N4O 325.2], HPLC (method E): $t_R$=4.07 min; HPLC (method F): $t_R$=4.29 min.

Example 41

(R)-2-(2-(1-amino-3-methylbutyl)-6-(oxazol-5-yl)-1H-benzo[d]imidazol-1-yl)ethanol

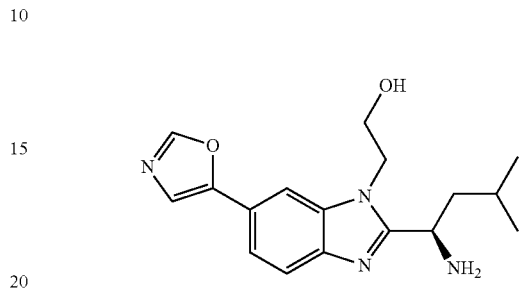

Prepared in a similar fashion as described in Example 32 using 2-aminoethanol in Part A to give the title compound (0.023 g, 0.072 mmol, 63% yield) as a colorless amorphous solid. ¹H NMR (400 MHz, METHANOL-$d_4$) δ 8.28 (s, 1H), 8.01 (s, 1H), 7.82-7.78 (m, 1H), 7.76-7.71 (m, 1H), 7.58 (s, 1H), 4.96 (t, J=7.4 Hz, 1H), 4.67-4.47 (m, 2H), 4.05-3.86 (m, 2H), 2.34-2.23 (m, 1H), 2.00 (dt, J=13.9, 7.0 Hz, 1H), 1.73 (dquin, J=13.4, 6.8 Hz, 1H), 1.04 (d, J=4.5 Hz, 3H), 1.02 (d, J=4.5 Hz, 3H); LC/MS (ESI) m/e 315.2 [(M+H)+, calcd for C17H23N4O 315.2].

Example 42

(R)-3-methyl-1-(1-methyl-6-(pyridin-4-yl)-1H-benzo[d]imidazol-2-yl)butan-1-amine

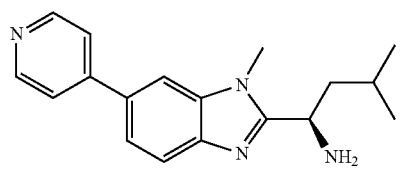

Prepared in a similar fashion as described in Example 32, Parts A-D using methyl amine in Part A and Example 33, Parts A and B using pyridin-4-ylboronic acid in Part A to give the title compound (30 mg, 0.097 mmol, 48% yield) as a colorless amorphous solid: ¹H NMR (400 MHz, CHLOROFORM-d) δ ppm 8.65-8.69 (m, 2H), 7.83 (d, J=8.8 Hz, 1H), 7.59 (d, J=1.5 Hz, 2H), 7.57-7.58 (m, 1H), 7.53-7.57 (m, 1H), 4.28 (t, J=6.9 Hz, 1H), 3.90 (s, 3H), 1.73-1.91 (m, 5H), 1.01 (d, J=4.0 Hz, 3H), 1.00 (d, J=4.0 Hz, 3H), LC/MS (ESI) m/e 295.2 [(M+H)+, calcd for C18H23N4 295.2], HPLC (method E): $t_R$=2.89 min; HPLC (method F): $t_R$=3.06 min.

Example 43

(R)-3-methyl-1-(1-propyl-6-(pyridin-4-yl)-1H-benzo[d]imidazol-2-yl)butan-1-amine

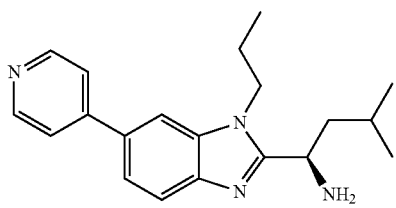 [SMILES: CCCn1c([C@H](N)CC(C)C)nc2ccc(-c3ccncc3)cc21]

Prepared in a similar fashion as described in Example 32, Parts A-D using N-propyl amine in Part A and Example 33, Parts A and B using pyridin-4-ylboronic acid in Part A to give the title compound (39 mg, 0.119 mmol, 71% yield) as a colorless amorphous solid: $^1$H NMR (400 MHz, CHLOROFORM-d) δ ppm 8.62-8.68 (m, 2H), 7.81 (d, J=8.3 Hz, 1H), 7.56 (d, J=1.8 Hz, 2H), 7.54-7.55 (m, 1H), 7.52 (dd, J=8.3, 1.8 Hz, 1H), 4.14-4.33 (m, 3H), 1.76-2.00 (m, 5H), 1.74 (br. s., 2 H), 1.04 (t, J=7.4 Hz, 3H), 0.99 (d, J=3.0 Hz, 3H), 0.98 (d, J=3.0 Hz, 3H), LC/MS (ESI) m/e 323.2 [(M+H)+, calcd for C20H27N4 323.2], HPLC (method E): $t_R$=3.73 min; HPLC (method F): $t_R$=3.83 min.

Example 44

(R)-1-(1-isopropyl-6-(pyridin-4-yl)-1H-benzo[d]imidazol-2-yl)-3-methylbutan-1-amine

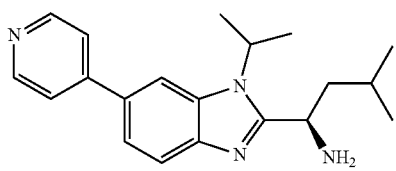 [SMILES: CC(C)C[C@@H](N)c1nc2ccc(-c3ccncc3)cc2n1C(C)C]

Prepared in a similar fashion as described in Example 32, Parts A-D using isopropylamine in Part A and Example 33, Parts A and B using pyridin-4-ylboronic acid in Part A to give the title compound (34 mg, 0.099 mmol, 63% yield) as a colorless amorphous solid: $^1$H NMR (400 MHz, CHLOROFORM-d) δ ppm 8.62-8.71 (m, 2H), 7.83 (d, J=8.3 Hz, 1H), 7.76 (d, J=1.0 Hz, 1H), 7.54-7.59 (m, 2H), 7.51 (dd, J=8.5, 1.8 Hz, 1H), 4.90-5.08 (m, 1H), 4.29 (t, J=6.9 Hz, 1H), 1.81-1.93 (m, 1H), 1.75-1.81 (m, 4H), 1.74 (d, J=3.8 Hz, 3H), 1.72 (d, J=3.5 Hz, 3H), 1.01 (d, J=5.5 Hz, 3H), 0.99 (d, J=5.5 Hz, 3H), LC/MS (ESI) m/e 323.2 [(M+H)+, calcd for C20H27N4 323.2], HPLC (method E): $t_R$=3.40 min; HPLC (method F): $t_R$=3.45 min.

Example 45

(R)-1-(1-ethyl-5-(pyridin-4-yl)-1H-benzo[d]imidazol-2-yl)-3-methylbutan-1-amine

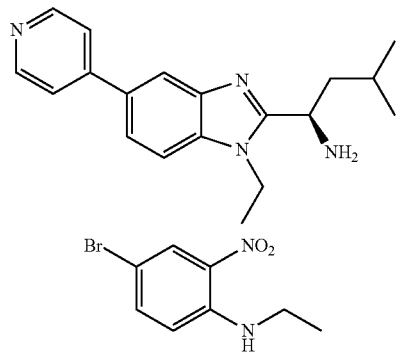

Part A: 4-bromo-N-ethyl-2-nitroaniline

A solution of 4-bromo-1-fluoro-2-nitrobenzene (0.560 ml, 4.55 mmol), ethanamine, HCl (0.371 g, 4.55 mmol) and DIEA (1.588 ml, 9.09 mmol) in DMA (5.05 ml) was heated to 80° C. for 12 h. The reaction mixture was cooled to room temperature, diluted with water (5 mL) and extracted with EtOAc (3×10 mL). The combined organics were washed with brine (1×10 mL), dried (MgSO$_4$), filtered and concentrated under reduced pressure. The crude material was carried on without further purification. Obtained 4-bromo-N-ethyl-2-nitroaniline (1115 mg, 4.55 mmol, 95% crude yield). LC/MS (ESI) m/e 245.0, 247.0 Br pattern [(M+H)+, calcd for C8H10BrN2O2 245.0].

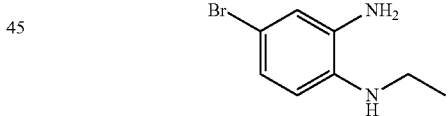

Part B: 4-bromo-N1-ethylbenzene-1,2-diamine

A solution of 4-bromo-N-ethyl-2-nitroaniline (1115 mg, 4.55 mmol) and tin(II) chloride dihydrate (6160 mg, 27.3 mmol) in hydrochloric acid, 37% (22.8 mL) was heated to 50° C. for 1.5 h. The reaction mixture was cooled to 0° C. and quenched with 10N NaOH. The solution was extracted with ethyl acetate (3×15 mL). The combined organics were washed with brine (1×10 mL), dried (MgSO$_4$), filtered and concentrated under reduced pressure. Obtained 4-bromo-N1-ethylbenzene-1,2-diamine (598 mg, 2.502 mmol, 55% crude yield, 90% purity) as an amorphous orange solid which was carried on without further purification. LC/MS (ESI) m/e 215.0, 217.0 [(M+H)+, calcd for C8H12BrN2 215.0].

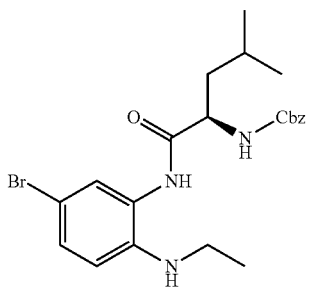 [SMILES: CCNc1ccc(Br)cc1NC(=O)[C@@H](CC(C)C)NC(=O)OCc1ccccc1]

Part C: (R)-benzyl 1-(5-bromo-2-(ethylamino)phenylamino)-4-methyl-1-oxopentan-2-ylcarbamate To a stirred solution of (R)-2-(benzyloxycarbonylamino)-4-methylpentanoic acid (1056 mg, 3.98 mmol), o-benzotriazol-1-yl-tetramethyluronium hexafluorophosphate (1510 mg, 3.98 mmol), and DIEA (2.09 mL, 11.94 mmol) in DMF (13.3 mL) was added N1-ethyl-4-methylbenzene-1,2-diamine (598 mg, 3.98 mmol). The mixture was stirred at room temperature for 14 h then quenched with water (10 mL) and extracted with EtOAc (3×20 mL). The combined organics were washed with brine (4×15 mL), dried (MgSO$_4$), filtered and concentrated under reduced pressure. Obtained (R)-benzyl 1-(5-bromo-2-(ethylamino)phenylamino)-4-methyl-1-oxopentan-2-ylcarbamate (1.8 g, 3.70 mmol, 93% crude yield, 95% purity) as a pale yellow amorphous solid. Carried on without further purification. LC/MS (ESI) m/e 462.0, 464.0 Br pattern [(M+H)+, calcd for C22H29BrN3O3 462.1].

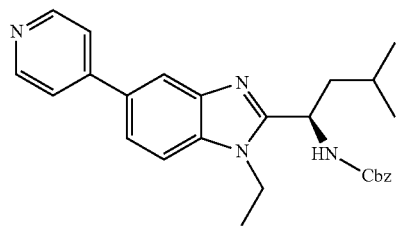

Part E: (R)-benzyl 1-(1-ethyl-5-(pyridin-4-yl)-1H-benzo[d]imidazol-2-yl)-3-methylbutylcarbamate To a vial was added (R)-benzyl 1-(5-bromo-1-ethyl-1H-benzo[d]imidazol-2-yl)-3-methylbutylcarbamate (154 mg, 0.347 mmol), potassium carbonate (64.5 mg, 1.040 mmol), tetrakis(triphenylphosphine)palladium(0) (4.54 mg, 0.017 mmol) and 4-(4,4,5,5-tetramethyl-1,3,2-dioxaborolan-2-yl)pyridine (85 mg, 0.416 mmol). The vial was sealed and purged with N$_2$ for 5 min. Dioxane (2971 μL) and water (495 μL) were added and the vial purged with N$_2$ for 10 min. The mixture was then heated in an oil bath for 5 h. After cooling to room temperature the solids were removed by filtering through a bed of diatomaceous earth (Celite®). The solution was concentrated under reduced pressure and the residue was purified via silica gel chromatography (15%-100% EtOAc in hexanes). Obtained (R)-benzyl 1-(1-ethyl-5-(pyridin-4-yl)-1H-benzo[d]imidazol-2-yl)-3-methylbutylcarbamate (129 mg, 0.277 mmol, 80% yield) as a colorless film. LC/MS (ESI) m/e 443.1 [(M+H)+, calcd for C27H31N4O2 443.1].

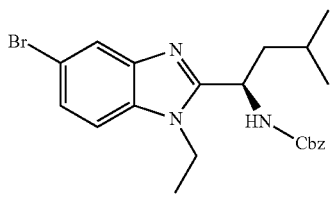 [SMILES: CCn1c([C@@H](CC(C)C)NC(=O)OCc2ccccc2)nc2cc(Br)ccc21]

Part D: (R)-benzyl 1-(5-bromo-1-ethyl-1H-benzo[d]imidazol-2-yl)-3-methylbutylcarbamate A solution of (R)-benzyl 1-(5-bromo-2-(ethylamino)phenylamino)-4-methyl-1-oxopentan-2-ylcarbamate (1711 mg, 3.70 mmol) in acetic acid (8473 μL, 148 mmol) was heated to 65° C. for 1.5 h. The mixture was cooled to room temperature and concentrated under reduced pressure. The residue was purified via silica gel chromatography (10%-60% EtOAc in hexanes). Obtained (R)-benzyl 1-(5-bromo-1-ethyl-1H-benzo[d]imidazol-2-yl)-3-methylbutylcarbamate (953 mg, 1.930 mmol, 52% yield) as a yellow orange oil. $^1$H NMR (400 MHz, CHLOROFORM-d) δ 7.86 (d, J=1.5 Hz, 1H), 7.38 (dd, J=8.5, 1.8 Hz, 1H), 7.35-7.30 (m, 5H), 7.23 (d, J=8.0 Hz, 1H), 5.41 (d, J=9.8 Hz, 1H), 5.19-5.08 (m, 3H), 4.44-4.32 (m, 1H), 4.30-4.17 (m, 1H), 1.98 (ddd, J=13.7, 9.0, 5.1 Hz, 1H), 1.86-1.69 (m, 2H), 1.42 (t, J=7.3 Hz, 3H), 1.02 (d, J=6.3 Hz, 3H), 0.98 (d, J=6.5 Hz, 3H), LC/MS (ESI) m/e 444.0, 446.0 [(M+H)+, calcd for C22H27BrN3O2 444.1].

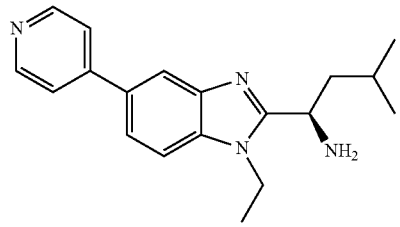 [SMILES: CCn1c([C@H](N)CC(C)C)nc2cc(-c3ccncc3)ccc21]

Part F: (R)-1-(1-ethyl-5-(pyridin-4-yl)-1H-benzo[d]imidazol-2-yl)-3-methylbutan-1-amine A solution of (R)-benzyl 1-(1-ethyl-5-(pyridin-4-yl)-1H-benzo[d]imidazol-2-yl)-3-methylbutylcarbamate (123 mg, 0.277 mmol), anisole (66.6 μl, 0.609 mmol) and methanesulfonic acid (630 μL, 9.70 mmol) in DCM (2518 μL) was stirred at room temperature for 1.5 h. The reaction mixture was concentrated under reduced pressure and the residue was purified by reverse phase HPLC (10%-70% MeOH/H$_2$O/0.1% TFA). The product was free based by passing through an SCX cartridge, eluting with 2M ammonium in methanol. Obtained (R)-1-(1-ethyl-5-(pyridin-4-yl)-1H-benzo[d]imidazol-2-yl)-3-methylbutan-1-amine (54 mg, 0.172 mmol, 62% yield) as a pale yellow oil. $^1$H NMR (400 MHz, CHLOROFORM-d) δ ppm 8.56-8.67 (m, 2H), 8.02 (d, J=1.0 Hz, 1H), 7.50-7.60 (m, 3H), 7.43 (d, J=8.3 Hz, 1H), 4.25-4.40 (m, 2H), 4.22 (t, J=6.8 Hz, 1H), 1.89-2.06 (m, 2H), 1.75-1.85 (m, 3H), 1.49 (t, J=7.2 Hz, 3H), 0.99 (d, J=2.5 Hz, 3H), 0.98 (d, J=2.5 Hz, 3H), LC/MS (ESI) m/e

Example 46

(R)-1-(1-ethyl-5-(oxazol-5-yl)-1H-benzo[d]imidazol-2-yl)-3-methylbutan-1-amine

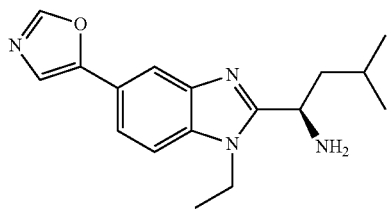 [SMILES: CCn1c([C@H](N)CC(C)C)nc2cc(-c3cnco3)ccc21]

Prepared in a similar fashion as described in Example 4, using (R)-benzyl 1-(5-bromo-1-ethyl-1H-benzo[d]imidazol-2-yl)-3-methylbutylcarbamate (prepared as in Example 45, Part D) in Part A to give the title compound (0.044 g, 0.145 mmol, 96% yield) as a pale yellow amorphous solid. $^1$H NMR (400 MHz, METHANOL-$d_4$) δ 8.30-8.22 (m, 1H), 8.03-7.94 (m, 1H), 7.71-7.65 (m, 1H), 7.65-7.57 (m, 1H), 7.53-7.44 (m, 1H), 4.50-4.32 (m, 2H), 4.29 (t, J=7.2 Hz, 1H), 1.91-1.75 (m, 2H), 1.71 (dt, J=13.6, 6.5 Hz, 1H), 1.47 (t, J=7.3 Hz, 3H), 0.99 (d, J=6.5 Hz, 3H), 0.97 (d, J=6.5 Hz, 3H). LC/MS (ESI) m/e 299.2 [(M+H)+, calcd for C17H23N4O 299.2].

Example 47

(R)-1-(5-methoxy-6-(pyridin-4-yl)-1H-benzo[d]imidazol-2-yl)-3-methylbutan-1-amine

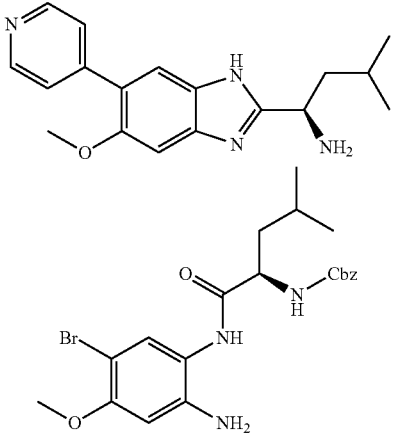

Part A: (R)-benzyl 1-(2-amino-5-bromo-4-methoxyphenylamino)-4-methyl-1-oxopentan-2-ylcarbamate To a stirred solution of (R)-2-(benzyloxycarbonylamino)-4-methylpentanoic acid (1.943 g, 7.33 mmol), 2-(1H-benzo[d][1,2,3]triazol-1-yl)-1,1,3,3-tetramethyluronium hexafluorophosphate(V) (2.78 g, 7.33 mmol) and DIEA (3.84 ml, 21.98 mmol) in DMF (24.42 mL) was added 4-bromo-5-methoxybenzene-1,2-diamine (1.59 g, 7.33 mmol). The mixture was stirred at room temperature for 1.5 h. The mixture was diluted with saturated aqueous sodium bicarbonate (15 mL) and extracted with ethyl acetate (3×15 mL). The combined organics were washed with saturated aqueous sodium bicarbonate (2×15 mL), 10% aqueous citric acid (3×15 mL) and brine (1×15 mL). The solution was dried (MgSO$_4$), filtered and concentrated under reduced pressure to yield (R)-benzyl 1-(2-amino-5-bromo-4-methoxyphenylamino)-4-methyl-1-oxopentan-2-ylcarbamate (3.40 g, 7.33 mmol, quantitative crude yield). Carried on without further purification. LC/MS (ESI) m/e 464.0, 468.0 Br pattern [(M+H)+, calcd for C21H27BrN3O4 464.1].

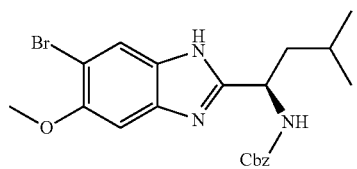

Part B: (R)-benzyl 1-(6-bromo-5-methoxy-1H-benzo[d]imidazol-2-yl)-3-methylbutylcarbamate A solution of (R)-benzyl 1-(2-amino-5-bromo-4-methoxyphenylamino)-4-methyl-1-oxopentan-2-ylcarbamate (3.40 g, 7.33 mmol) in acetic acid (16.78 mL, 293 mmol) was heated to 65° C. for 2 h. The mixture was cooled to room temperature and concentrated under reduced pressure. The residue was purified via silica gel chromatography (5%-40% EtOAc in hexanes). Obtained (R)-benzyl 1-(6-bromo-5-methoxy-1H-benzo[d]imidazol-2-yl)-3-methylbutylcarbamate (2.2 g, 4.44 mmol, 61% yield) as an amorphous yellow solid. LC/MS (ESI) m/e 446.0, 448.0 [(M+H)+, calcd for C21H25BrN3O3 446.1].

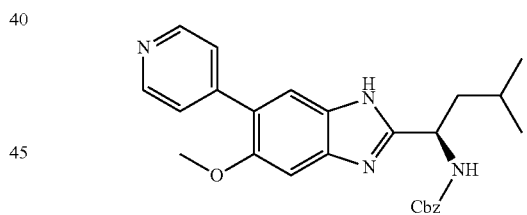

Part C: (R)-benzyl 1-(5-methoxy-6-(pyridin-4-yl)-1H-benzo[d]imidazol-2-yl)-3-methylbutylcarbamate To a vial was added (R)-benzyl 1-(6-bromo-5-methoxy-1H-benzo[d]imidazol-2-yl)-3-methylbutylcarbamate (370 mg, 0.829 mmol), potassium carbonate (154 mg, 2.487 mmol), tetrakis(triphenylphosphine)palladium(0) (10.87 mg, 0.041 mmol) and 4-(4,4,5,5-tetramethyl-1,3,2-dioxaborolan-2-yl)pyridine (204 mg, 0.995 mmol). The vial was sealed and purged with N$_2$ for 5 min. Dioxane (7105 μL) and water (1184 μL) were added and the vial purged with N$_2$ for 10 min. The mixture was heated in an oil bath for 5 h. The solution filtered through diatomaceous earth (Celite®) and concentrated under reduced pressure. The residue was purified via silica gel chromatography (15%-100% EtOAc in hexanes). Obtained (R)-benzyl 1-(5-methoxy-6-(pyridin-4-yl)-1H-benzo[d]imidazol-2-yl)-3-methylbutylcarbamate (50 mg, 0.107 mmol, 13% yield) as a yellow amorphous solid. LC/MS (ESI) m/e 445.1 [(M+H)+, calcd for C26H29N4O3 445.2].

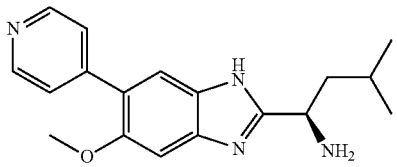 [SMILES: COc1cc2nc([C@H](N)CC(C)C)[nH]c2cc1-c1ccncc1]

Part D: (R)-1-(5-methoxy-6-(pyridin-4-yl)-1H-benzo[d]imidazol-2-yl)-3-methylbutan-1-amine A solution of (R)-benzyl 1-(5-methoxy-6-(pyridin-4-yl)-1H-benzo[d]imidazol-2-yl)-3-methylbutylcarbamate (47.6 mg, 0.107 mmol), anisole (25.7 µL, 0.235 mmol) and methanesulfonic acid (243 µL, 3.75 mmol) in DCM (973 µL) was stirred at room temperature for 1.5 h. LC/MS shows complete conversion. The reaction mixture was concentrated under reduced pressure and the residue was purified by reverse phase HPLC (10%-70% MeOH/H₂O/0.1% TFA). The product was free based by passing through an SCX cartridge, eluting with 2M ammonium in methanol. Obtained (R)-1-(5-methoxy-6-(pyridin-4-yl)-1H-benzo[d]imidazol-2-yl)-3-methylbutan-1-amine (19 mg, 0.060 mmol, 56% yield) as a pale yellow oil. 1H NMR (400 MHz, CHLOROFORM-d) δ ppm 8.55-8.67 (m, 2H), 7.50 (dd, J=4.5, 1.8 Hz, 3H), 7.16 (s, 1H), 4.26-4.40 (m, 1H), 3.83 (s, 3H), 1.84-1.98 (m, 1H), 1.71-1.84 (m, 1H), 1.66 (ddd, J=13.6, 8.3, 5.8 Hz, 1H), 0.99 (d, J=6.3 Hz, 3H), 0.95 (d, J=6.3 Hz, 3H), LC/MS (ESI) m/e 311.1 [(M+H)+, calcd for C18H23N4O 311.2].

Example 48

2-(2-methylcyclopropyl)-6-(pyridin-4-yl)-1H-benzo[d]imidazole

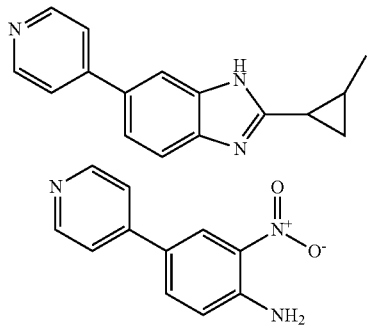

Part A: 2-nitro-4-(pyridin-4-yl)aniline

To a vial was added 4-bromo-2-nitroaniline (1.02 g, 4.70 mmol), potassium carbonate (1.77 g, 12.82 mmol), tetrakis(triphenylphosphine)palladium(0) (0.987 g, 0.855 mmol) and 4-(4,4,5,5-tetramethyl-1,3,2-dioxaborolan-2-yl)pyridine (0.876 g, 4.27 mmol). The vial was sealed and purged with N₂ for 5 min. Dioxane (20 mL) and water (5.0 mL) were added and the vial purged with N₂ for 10 min. The mixture was heated in an oil bath at 90° C. for 5 h, then cooled to room temperature. The solids were filtered off through diatomaceous earth (Celite®) and the filtrate concentrated under reduced pressure. The residue was diluted with ethyl acetate (25 mL) and washed with water (1×20 mL), brine (1×20 mL), dried (MgSO₄) and filtered. The solution was concentrated to obtain 2-nitro-4-(pyridin-4-yl)aniline (0.815 g, 3.79 mmol, 89% yield) which was carried on without further purification. LC/MS (ESI) m/e 216.1 [(M+H)+, calcd for C11H10N3O2 216.2].

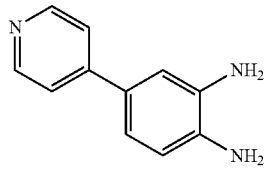 [SMILES: Nc1ccc(-c2ccncc2)cc1N]

Part B: 4-(pyridin-4-yl)benzene-1, 2-diamine

To a solution of 2-nitro-4-(pyridin-4-yl)aniline (0.815 g, 3.79 mmol) in ethanol (50 mL) at room temperature under nitrogen was added ammonium chloride (0.810 g, 15.15 mmol) and zinc powder (0.991 g, 15.15 mmol). The reaction mixture was stirred at room temperature for 12 h. The reaction mixture was filtered through diatomaceous earth (Celite®). The filtrate was concentrated to obtain 4-(pyridin-4-yl)benzene-1,2-diamine (0.701 g, 3.78 mmol, 100% crude yield). The product was carried on without further purification. LC/MS (ESI) m/e 186.1 [(M+H)+, calcd for C11H12N3 186.1].

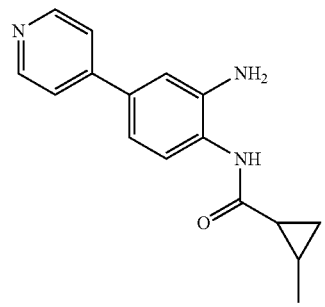 [SMILES: CC1CC1C(=O)Nc1ccc(-c2ccncc2)cc1N]

Part C: N-(2-amino-4-(pyridin-4-yl)phenyl)-2-methylcyclopropanecarboxamide

To a stirred solution of 2-methylcyclopropanecarboxylic acid (16.22 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µL, 0.486 mmol) in DMF (810 µL) was added 4-(pyridin-4-yl)benzene-1,2-diamine (30 mg, 0.162 mmol). The mixture was stirred at room temperature for 1.5 h. The reaction mixture was concentrated under reduced pressure and the residue was diluted with water (5 mL) and extracted with EtOAc (3×10 mL). The combined organics were washed with brine (3×10 mL), dried (MgSO₄), filtered and concentrated under reduced pressure. Obtained N-(2-amino-4-(pyridin-4-yl)phenyl)-2-methylcyclopropanecarboxamide (43.3 mg, 0.162 mmol, quantitative crude yield) as a yellow oil.

Carried on without further purification. LC/MS (ESI) m/e 268.1 [(M+H)+, calcd for C16H18N3O 268.1].

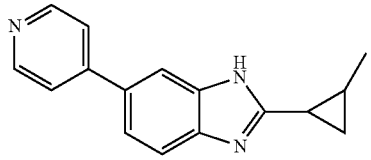 [SMILES: CC1CC1c1nc2ccc(-c3ccncc3)cc2[nH]1]

Part D: 2-(2-methylcyclopropyl)-6-(pyridin-4-yl)-1H-benzo[d]imidazole

A solution of N-(2-amino-4-(pyridin-4-yl)phenyl)-2-methylcyclopropanecarboxamide (43.3 mg, 0.162 mmol) in acetic acid (371 µL, 6.48 mmol) was heated to 65° C. for 24 h. The reaction mixture was cooled to room temperature and concentrated under reduced pressure. The residue was diluted with saturated aqueous sodium bicarbonate (5 mL) and extracted with EtOAc (3×10 mL).

The combined organics were washed with saturated aqueous sodium bicarbonate (2×5 mL) and brine (1×5 mL), dried (MgSO$_4$), filtered and concentrated under reduced pressure. The material was purified by reverse phase HPLC (10%-55% MeOH/H$_2$O/0.1% TFA). The product was free based by quenching with saturated aqueous sodium bicarbonate (5 mL) and extracting with ethyl acetate (3×10 mL). The combined organics were washed with saturated aqueous sodium bicarbonate (2×5 mL) and brine (1×5 mL), dried (MgSO$_4$), filtered and concentrated under reduced pressure. Obtained 2-(2-methylcyclopropyl)-6-(pyridin-4-yl)-1H-benzo[d]imidazole (17 mg, 0.067 mmol, 41% yield) as an off-white film. $^1$H NMR (400 MHz, CHLOROFORM-d) δ ppm 11.27 (br. s., 1 H), 8.65 (d, J=4.8 Hz, 2H), 7.79 (br. s., 1 H), 7.57 (d, J=6.0 Hz, 3H), 7.50 (dd, J=8.4, 1.6 Hz, 1H), 1.85 (ddd, J=8.7, 4.5, 4.4 Hz, 1H), 1.59-1.71 (m, 1H), 1.46 (ddd, J=8.8, 4.8, 4.5 Hz, 1H), 1.23 (d, J=5.8 Hz, 3H), 0.92-1.00 (m, 1H), LC/MS (ESI) m/e 250.1 [(M+H)+, calcd for C16H16N3 250.1], HPLC (method H): t$_R$=3.16 min; HPLC (method I): t$_R$=3.17 min.

Example 49

2-(2,2-dimethylcyclopropyl)-6-(pyridin-4-yl)-1H-benzo[d]imidazole

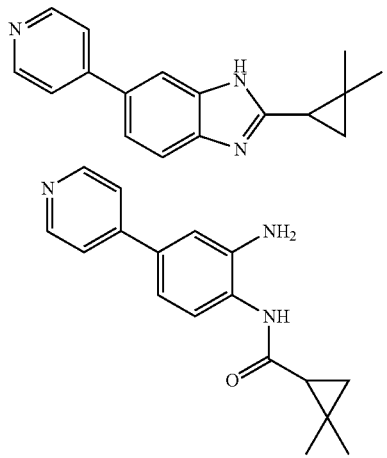

Part A: N-(2-amino-4-(pyridin-4-yl)phenyl)-2,2-dimethylcyclopropanecarboxamide

To a stirred solution of 2,2-dimethylcyclopropanecarboxylic acid (18.49 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µl, 0.486 mmol) in DMF (810 µL) was added 4-(pyridin-4-yl)benzene-1,2-diamine (30 mg, 0.162 mmol) prepared as in Example 48, Part B. The mixture was stirred at room temperature for 1.5 h. The reaction mixture was concentrated under reduced pressure and the residue was diluted with water (5 mL) and extracted with EtOAc (3×10 mL). The combined organics were washed with brine (3×10 mL), dried (MgSO$_4$), filtered and concentrated under reduced pressure. Obtained N-(2-amino-4-(pyridin-4-yl)phenyl)-2,2-dimethylcyclopropanecarboxamide (45.6 mg, 0.162 mmol, quantitative crude yield) as a yellow oil. Carried on without further purification. LC/MS (ESI) m/e 282.1 [(M+H)+, calcd for C17H20N3O 282.2].

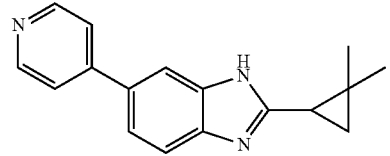 [SMILES: CC1(C)CC1c1nc2ccc(-c3ccncc3)cc2[nH]1]

Part B: 2-(2,2-dimethylcyclopropyl)-6-(pyridin-4-yl)-1H-benzo[d]imidazole

A solution of N-(2-amino-4-(pyridin-4-yl)phenyl)-2,2-dimethylcyclopropanecarboxamide (45.6 mg, 0.162 mmol) in acetic acid (371 µL, 6.48 mmol) was heated to 65° C. for 12 h. The reaction mixture was cooled to room temperature and concentrated under reduced pressure. The residue was diluted with saturated aqueous sodium bicarbonate (5 mL) and extracted with EtOAc (3×10 mL). The combined organics were washed with saturated aqueous sodium bicarbonate (2×5 mL) and brine (1×5 mL), dried (MgSO$_4$), filtered and concentrated under reduced pressure. The material was purified by reverse phase HPLC (5%-30% MeOH/H$_2$O/0.1% TFA). The product was treated with saturated aqueous sodium bicarbonate (10 mL) and extracted with ethyl acetate (3×10 mL). The combined organics were washed with saturated aqueous sodium bicarbonate (2×5 mL) and brine (1×5 mL), dried (MgSO$_4$), filtered and concentrated under reduced pressure. Obtained 2-(2,2-dimethylcyclopropyl)-6-(pyridin-4-yl)-1H-benzo[d]imidazole (15 mg, 0.056 mmol, 35% yield) as an off-white film. $^1$H NMR (400 MHz, CHLOROFORM-d) δ ppm 10.77 (br. s., 1 H), 8.65 (d, J=5.5 Hz, 2H), 7.83 (br. s., 1 H), 7.59-7.70 (m, 1H), 7.57 (dd, J=4.5, 1.5 Hz, 2H), 7.52 (dd, J=8.3, 1.8 Hz, 1H), 2.03 (dd, J=8.4, 5.6 Hz, 1H), 1.45 (t, J=5.1 Hz, 1H), 1.25 (s, 3H), 1.11 (s, 3H), 1.05-1.10 (m, 1H), LC/MS (ESI) m/e 264.1 [(M+H)+, calcd for C17H18N3 264.2], HPLC (method E): t$_R$=3.18 min; HPLC (method F): t$_R$=3.17 min.

Example 50

2-(3-(tert-butyl)-1-methyl-1H-pyrazol-5-yl)-6-(pyridin-4-yl)-1H-benzo[d]imidazole

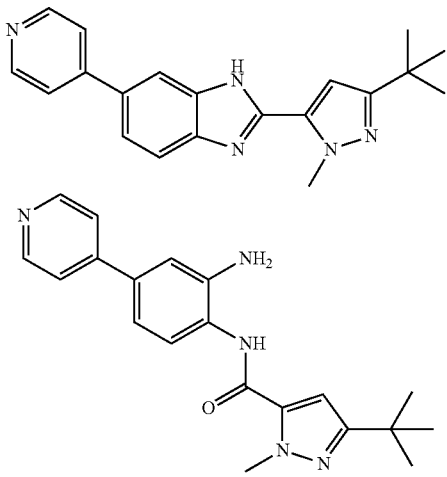

Part A: N-(2-amino-4-(pyridin-4-yl)phenyl)-3-tert-butyl-1-methyl-1H-pyrazole-5-carboxamide To a stirred solution of 3-(tert-butyl)-1-methyl-1H-pyrazole-5-carboxylic acid (29.5 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µl, 0.486 mmol) in DMF (810 µL) was added 4-(pyridin-4-yl)benzene-1,2-diamine (30 mg, 0.162 mmol) prepared as in Example 48, Part B. The mixture was stirred at room temperature for 1.5 h. The reaction mixture was cooled to room temperature and concentrated under reduced pressure. The residue was diluted with water (5 mL) and extracted with EtOAc (3×10 mL). The combined organics were washed with brine (3×10 mL), dried (MgSO4), filtered and concentrated under reduced pressure. Obtained N-(2-amino-4-(pyridin-4-yl)phenyl)-3-tert-butyl-1-methyl-1H-pyrazole-5-carboxamide (56.6 mg, 0.162 mmol, quantitative crude yield) as a yellow oil. Carried on without further purification. LC/MS (ESI) m/e 350.2 [(M+H)+, calcd for C20H24N5O 350.2].

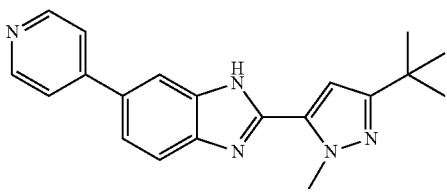 [SMILES: Cn1nc(C(C)(C)C)cc1-c1nc2ccc(-c3ccncc3)cc2[nH]1]

Part B: 2-(3-tert-butyl-1-methyl-1H-pyrazol-5-yl)-6-(pyridin-4-yl)-1H-benzo[d]imidazole A solution of N-(2-amino-4-(pyridin-4-yl)phenyl)-3-tert-butyl-1-methyl-1H-pyrazole-5-carboxamide (56.6 mg, 0.162 mmol) in acetic acid (371 µL, 6.48 mmol) was heated to 65° C. overnight. The crude material was purified by reverse phase HPLC (10%-50% MeOH/H2O/0.1% TFA). The product was treated with saturated aqueous sodium bicarbonate (10 mL) and extracted with ethyl acetate (3×10 mL). The combined organics were washed with saturated aqueous sodium bicarbonate (2×5 mL) and brine (1×5 mL), dried (MgSO4), filtered and concentrated under reduced pressure. Obtained 2-(3-tert-butyl-1-methyl-1H-pyrazol-5-yl)-6-(pyridin-4-yl)-1H-benzo[d]imidazole (21 mg, 0.06 mmol, 37% yield) as a colorless amorphous solid. $^1$H NMR (400 MHz, CHLOROFORM-d) δ ppm 11.16 (br. s., 0.5 H), 10.88 (br. s., 0.5 H), 8.70 (d, J=4.8 Hz, 2H), 8.15 (s, 0.5 H), 7.93 (d, J=8.5 Hz, 0.5 H), 7.52-7.74 (m, 4H), 6.63 (d, J=11.0 Hz, 1H), 4.39 (s, 3H), 1.34 (s, 9H)—rotomers seen, LC/MS (ESI) m/e 322.1 [(M+H)+, calcd for C20H22N5 322.2], HPLC (method E): $t_R$=5.43 min; HPLC (method F): $t_R$=5.46 min.

Example 51

1-isopropyl-4-(6-(pyridin-4-yl)-1H-benzo[d]imidazol-2-yl)pyrrolidin-2-one

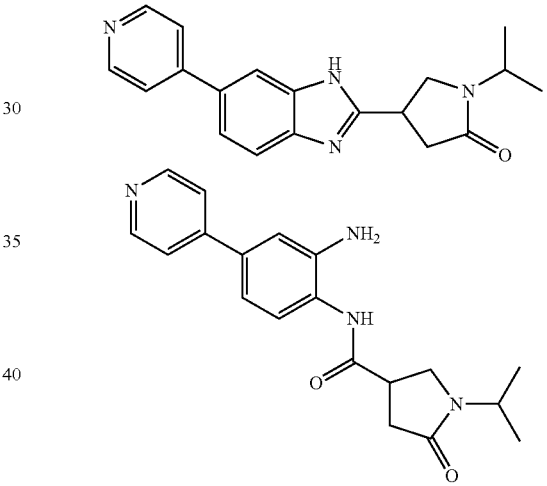

Part A: N-(2-amino-4-(pyridin-4-yl)phenyl)-1-isopropyl-5-oxopyrrolidine-3-carboxamide To a stirred solution of 1-isopropyl-5-oxo-pyrrolidine-3-carboxylic acid (27.7 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µL, 0.486 mmol) in DMF (810 µL) was added 4-(pyridin-4-yl)benzene-1,2-diamine (30 mg, 0.162 mmol) prepared as in Example 48, Part B. The mixture was stirred at room temperature for 1.5 h. The mixture was cooled to room temperature and concentrated under reduced pressure. The residue was diluted with water (5 mL) and extracted with EtOAc (3×10 mL). The combined organics were washed with brine (3×10 mL), dried (MgSO4), filtered and concentrated under reduced pressure. Obtained N-(2-amino-4-(pyridin-4-yl)phenyl)-1-isopropyl-5-oxopyrrolidine-3-carboxamide (54.8 mg, 0.162 mmol, quantitative yield) as a yellow oil. Carried on without further purification. LC/MS (ESI) m/e 339.1 [(M+H)+, calcd for C19H23N4O 339.2].

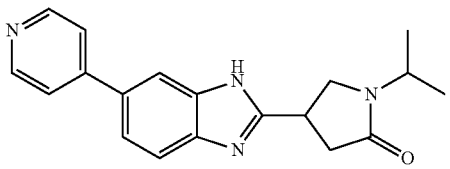 [SMILES: CC(C)N1CC(c2nc3ccc(-c4ccncc4)cc3[nH]2)CC1=O]

Part B: 1-isopropyl-4-(6-(pyridin-4-yl)-1H-benzo[d]imidazol-2-yl)pyrrolidin-2-one A solution of N-(2-amino-4-(pyridin-4-yl)phenyl)-1-isopropyl-5-oxopyrrolidine-3-carboxamide (54.8 mg, 0.162 mmol) in acetic acid (371 µL, 6.48 mmol) was heated to 65° C. overnight. The crude material was concentrated under reduced pressure and purified by reverse phase HPLC (5%-30% MeOH/H$_2$O/0.1% TFA). The product was free based by passing through a SCX cartridge eluting with 2N ammonia in methanol. Obtained 1-isopropyl-4-(6-(pyridin-4-yl)-1H-benzo[d]imidazol-2-yl)pyrrolidin-2-one (9 mg, 0.025 mmol, 16% yield) as an off-white film. $^1$H NMR (400 MHz, CHLOROFORM-d) δ ppm 11.12 (br. s., 1 H), 8.66 (d, J=5.5 Hz, 2H), 7.42-7.96 (m, 5H), 4.46 (spt, J=6.8 Hz, 1 H), 3.83-4.01 (m, 3H), 2.86-3.05 (m, 2H), 1.23 (d, J=6.8 Hz, 3H), 1.19 (d, J=6.8 Hz, 3H), LC/MS (ESI) m/e 321.1 [(M+H)+, calcd for C19H21N4O 321.2], HPLC (method E): $t_R$=2.42 min; HPLC (method F): $t_R$=2.52 min.

Example 52

3,3,3-trifluoro-2-methyl-1-(6-(pyridin-4-yl)-1H-benzo[d]imidazol-2-yl)propan-1-amine

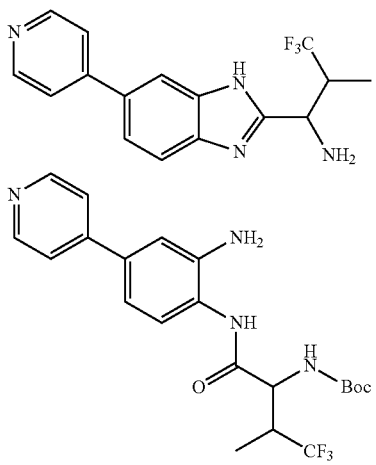

Part A: tert-butyl 1-(2-amino-4-(pyridin-4-yl)phenylamino)-4,4,4-trifluoro-3-methyl-1-oxobutan-2-ylcarbamate To a stirred solution of 4,4,4-trifluoro-DL-valine (44.3 mg, 0.259 mmol), 2-(1H-benzo[d][1,2,3]triazol-1-yl)-1,1,3,3-tetramethyluronium hexafluorophosphate(V) (98 mg, 0.259 mmol) and DIEA (136 µL, 0.777 mmol) in DMF (1296 µL) was added 4-(pyridin-4-yl)benzene-1,2-diamine (48 mg, 0.259 mmol) prepared as in Example 48, Part B. The mixture was stirred at room temperature for 1.5 h. The solution was diluted with water (10 mL) and extracted with EtOAc (3×10 mL). The combined organics were washed with brine (3×10 mL), dried (MgSO$_4$), filtered and concentrated under reduced pressure. Obtained tert-butyl 1-(2-amino-4-(pyridin-4-yl)phenylamino)-4,4,4-trifluoro-3-methyl-1-oxobutan-2-ylcarbamate (114 mg, 0.259 mmol, quantitative crude yield) as a yellow oil. Carried on without further purification. LC/MS (ESI) m/e 439.1 [(M+H)+, calcd for C21H26F3N4O3 439.2].

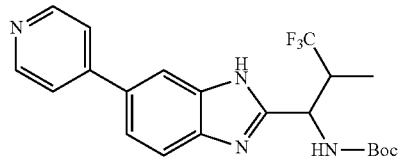 [SMILES: CC(C(NC(=O)OC(C)(C)C)c1nc2ccc(-c3ccncc3)cc2[nH]1)C(F)(F)F]

Part B: N-(2-amino-4-(pyridin-4-yl)phenyl)-1-isopropyl-5-oxopyrrolidine-3-carboxamide A solution of tert-butyl 1-(2-amino-4-(pyridin-4-yl)phenylamino)-4,4,4-trifluoro-3-methyl-1-oxobutan-2-ylcarbamate (114 mg, 0.259 mmol) in acetic acid (593 µL, 10.36 mmol) was heated to 65° C. for 24 h. The reaction mixture was cooled to room temperature and concentrated under reduced pressure. The residue was quenched with saturated aqueous sodium bicarbonate (5 mL) and extracted with EtOAc (3×10 mL). The combined organics were washed with brine (3×10 mL), dried (MgSO$_4$), filtered and concentrated under reduced pressure. The residue was purified by reverse phase HPLC (5%-30% MeOH/H$_2$O/0.1% TFA). Obtained a 50:50 mixture of diastereomers: (A): tert-butyl 3,3,3-trifluoro-2-methyl-1-(6-(pyridin-4-yl)-1H-benzo[d]imidazol-2-yl)propylcarbamate (12.0 mg, 0.029 mmol, 10% yield). LC/MS (ESI) m/e 421.1 [(M+H)+, calcd for C21H24F3N4O2 421.2] and (B): tert-butyl 3,3,3-trifluoro-2-methyl-1-(6-(pyridin-4-yl)-1H-benzo[d]imidazol-2-yl)propylcarbamate (12.0 mg, 0.029 mmol 10% yield), LC/MS (ESI) m/e 421.1 [(M+H)+, calcd for C21H24F3N4O2 421.2].

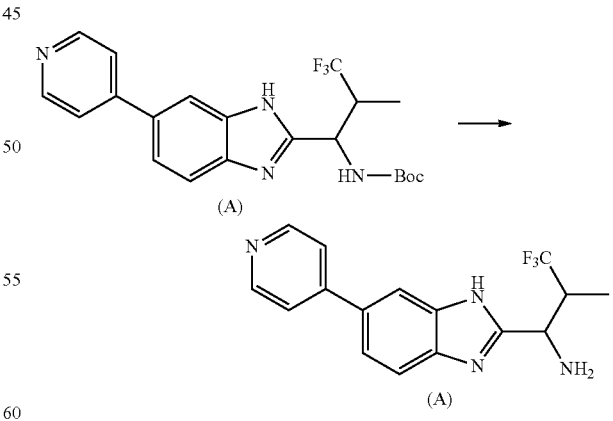

Part C: 3,3,3-trifluoro-2-methyl-1-(6-(pyridin-4-yl)-1H-benzo[d]imidazol-2-yl)propan-1-amine To diastereomer (A): tert-butyl 3,3,3-trifluoro-2-methyl-1-(6-(pyridin-4-yl)-1H-benzo[d]imidazol-2-yl)propylcarbamate (12 mg, 0.029 mmol) was added hydrogen chloride (2M in diethyl ether) (714 µL, 1.427 mmol). The solution was stirred at room temperature for 1.5 h, then concentrated under reduced pressure. The crude materials were purified by reverse phase HPLC (5%-25% MeOH/H₂O/0.1% TFA). The product was free based by running through an SCX cartridge eluting with 2 N ammonia in methanol. Obtained diastereomer (A): 3,3,3-trifluoro-2-methyl-1-(6-(pyridin-4-yl)-1H-benzo[d]imidazol-2-yl)propan-1-amine (7 mg, 0.021 mmol, 73% yield) as a yellow film. The absolute stereochemistry was not determined. ¹H NMR (400 MHz, MeOD) δ ppm 8.84 (d, J=6.8 Hz, 2H), 8.43 (d, J=6.8 Hz, 2H), 8.34 (d, J=1.5 Hz, 1H), 7.92-8.02 (m, 1H), 7.75-7.92 (m, 1H), 5.02 (d, J=6.5 Hz, 1H), 3.20-3.31 (m, 1H), 1.23 (d, J=7.0 Hz, 3H); ¹⁹F NMR (376 MHz, MeOD) ppm −71.37 (s, 3 F), −77.21 (s, 9 F), LC/MS (ESI) m/e 321.1 [(M+H)+, calcd for C16H16F3N4 321.2], HPLC (method E): t$_R$=4.26 min; HPLC (method F): t$_R$=4.14 min.

Example 53

3,3,3-trifluoro-2-methyl-1-(6-(pyridin-4-yl)-1H-benzo[d]imidazol-2-yl)propan-1-amine

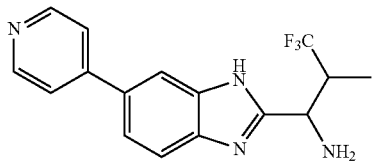 [SMILES: CC(C(N)c1nc2ccc(-c3ccncc3)cc2[nH]1)C(F)(F)F]

To diastereomer (B): tert-butyl 3,3,3-trifluoro-2-methyl-1-(6-(pyridin-4-yl)-1H-benzo[d]imidazol-2-yl)propylcarbamate (12 mg, 0.029 mmol) (from Example 52, Part B) was added hydrogen chloride (2M in diethyl ether) (714 µL, 1.427 mmol). The solution was stirred at room temperature for 1.5 h, then concentrated under reduced pressure. The crude materials were purified by reverse phase HPLC (5%-25% MeOH/H₂O/0.1% TFA). The product was free based by running through and SCX cartridge eluting with 2 N ammonia in methanol. Obtained diastereomer (B): 3,3,3-trifluoro-2-methyl-1-(6-(pyridin-4-yl)-1H-benzo[d]imidazol-2-yl)propan-1-amine (8 mg, 0.024 mmol, 83% yield) as an amorphous off-white solid. The absolute stereochemistry was not determined. ¹H NMR (400 MHz, MeOD) δ ppm 8.82 (d, J=6.8 Hz, 2H), 8.41 (d, J=6.8 Hz, 2H), 8.32 (d, J=1.3 Hz, 1H), 7.91-7.99 (m, 1H), 7.81-7.90 (m, 1H), 5.10 (d, J=5.3 Hz, 1H), 3.34-3.43 (m, 1H), 1.37 (d, J=7.0 Hz, 3H); ¹⁹F NMR (376 MHz, MeOD) ppm −71.63 (s, 3 F), −77.12 (s, 9 F), LC/MS (ESI) m/e 321.1 [(M+H)+, calcd for C16H16F3N4 321.2], HPLC (method E): t$_R$=4.17 min; HPLC (method F): t$_R$=4.10 min.

Example 54

2-(isopropoxymethyl)-6-(pyridin-4-yl)-1H-benzo[d]imidazole

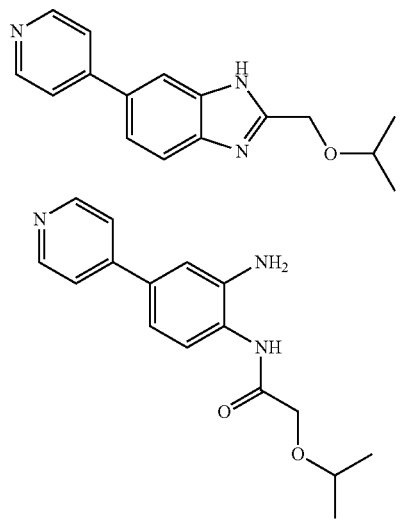

Part A: N-(2-amino-4-(pyridin-4-yl)phenyl)-2-isopropoxyacetamide

To a stirred solution of isopropoxyacetic acid (19.13 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µL, 0.486 mmol) in DMF (810 µL) was added 4-(pyridin-4-yl)benzene-1,2-diamine (30 mg, 0.162 mmol) prepared as in Example 48, Part B. The mixture was stirred at room temperature for 45 min. The mixture concentrated under reduced pressure and the residue was diluted with water (5 mL) and extracted with EtOAc (3×10 mL). The combined organics were washed with brine (3×10 mL), dried (MgSO₄), filtered and concentrated under reduced pressure. Obtained N-(2-amino-4-(pyridin-4-yl)phenyl)-2-isopropoxyacetamide (46.2 mg, 0.162 mmol, quantitative crude yield) as a yellow oil. Carried on without further purification. LC/MS (ESI) m/e 286.1 [(M+H)+, calcd for C16H20N3O2 286.2].

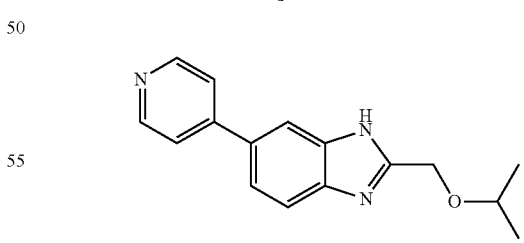

Part B: 2-(isopropoxymethyl)-6-(pyridin-4-yl)-1H-benzo[d]imidazole

A solution of N-(2-amino-4-(pyridin-4-yl)phenyl)-2-isopropoxyacetamide (46.2 mg, 0.162 mmol) in acetic acid (927 µL, 16.20 mmol) was heated to 70° C. overnight. The mixture was cooled to room temperature and concentrated under reduced pressure. The crude material was purified by reverse phase HPLC (5%-40% MeOH/H$_2$O/0.1% TF). The product was free based by quenching with saturated aqueous sodium bicarbonate (5 mL) and extracting with ethyl acetate (3×10 mL). The combined organics were washed with saturated aqueous sodium bicarbonate (2×10 mL) and brine (1×10 mL), dried (MgSO$_4$), filtered and concentrated under reduced pressure. Obtained 2-(isopropoxymethyl)-6-(pyridin-4-yl)-1H-benzo[d]imidazole (23 mg, 0.082 mmol, 51% yield) as an off-white film. $^1$H NMR (400 MHz, CHLOROFORM-d) δ ppm 10.46 (br. s., 1H), 8.67 (d, J=5.3 Hz, 2H), 7.63-8.19 (m, 2H), 7.52-7.64 (m, 3H), 4.86 (s, 2H), 3.73-3.89 (m, 1H), 1.27 (d, J=6.3 Hz, 6H), LC/MS (ESI) m/e 268.1 [(M+H)+, calcd for C16H18N3O 268.2], HPLC (method J): t$_R$=3.74 min; HPLC (method K): t$_R$=3.73 min.

Example 55

2-(tert-butoxymethyl)-6-(pyridin-4-yl)-1H-benzo[d]imidazole

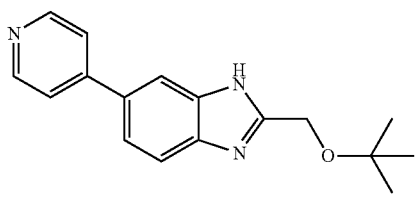

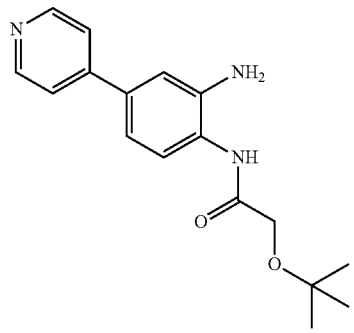

Part A: N-(2-amino-4-(pyridin-4-yl)phenyl)-2-(tert-butoxy)acetamide

To a stirred solution of 2-tert-butoxyacetic acid (21.40 mg, 0.162 mmol), 2-(1H-benzo[d][1,2,3]triazol-1-yl)-1,1,3,3-tetramethyluronium hexafluorophosphate(V) (61.4 mg, 0.162 mmol) and DIEA (85 µL, 0.486 mmol) in DMF (810 µL) was added 4-(pyridin-4-yl)benzene-1,2-diamine (30 mg, 0.162 mmol) prepared as in Example 48, Part B. The mixture was stirred at room temperature for 45 min. The mixture concentrated under reduced pressure and the residue was diluted with water (5 mL) and extracted with EtOAc (3×10 mL). The combined organics were washed with brine (3×10 mL), dried (MgSO$_4$), filtered and concentrated under reduced pressure. Obtained N-(2-amino-4-(pyridin-4-yl)phenyl)-2-tert-butoxyacetamide (21.40 mg, 0.162 mmol, quantitative crude yield) as a yellow oil. Carried on without further purification. LC/MS (ESI) m/e 300.1 [(M+H)+, calcd for C17H22N3O2 300.2].

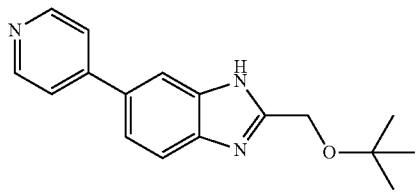 [SMILES: CC(C)(C)OCc1nc2ccc(-c3ccncc3)cc2[nH]1]

Part B: 2-(tert-butoxymethyl)-6-(pyridin-4-yl)-1H-benzo[d]imidazole

A solution of N-(2-amino-4-(pyridin-4-yl)phenyl)-2-tert-butoxyacetamide (48.5 mg, 0.162 mmol) in acetic acid (927 µL, 16.20 mmol) was heated to 70° C. overnight. The mixture was cooled to room temperature and concentrated under reduced pressure. The crude material was purified by reverse phase HPLC (5%-40% MeOH/H$_2$O/0.1% TFA). The product was free based by quenching with saturated aqueous sodium bicarbonate (5 mL) and extracting with ethyl acetate (3×10 mL). The combined organics were washed with saturated aqueous sodium bicarbonate (2×10 mL) and brine (1×10 mL), dried (MgSO$_4$), filtered and concentrated under reduced pressure. Obtained 2-(tert-butoxymethyl)-6-(pyridin-4-yl)-1H-benzo[d]imidazole (19 mg, 0.064 mmol, 40% yield) as an off-white amorphous solid. $^1$H NMR (400 MHz, CHLOROFORM-d) δ ppm 10.02 (br. s., 1 H), 8.67 (dd, J=4.5, 1.8 Hz, 2H), 7.60-8.18 (m, 2H), 7.51-7.60 (m, 3H), 4.82 (s, 2H), 1.33 (s, 9H), LC/MS (ESI) m/e 282.1 [(M+H)+, calcd for C17H20N3O 282.2].

Example 56

2-isopentyl-5-(3-methoxypyridin-4-yl)-1H-benzo[d]imidazole

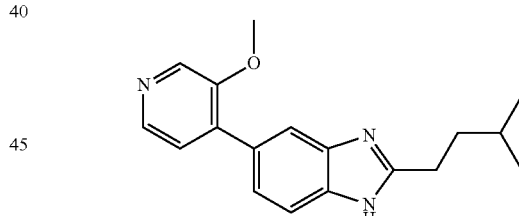

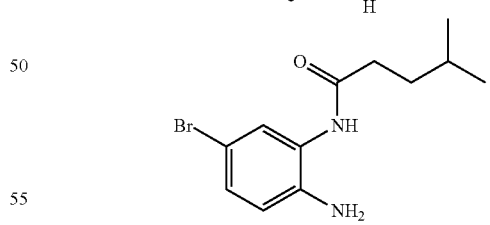

Part A:
N-(2-amino-5-bromophenyl)-4-methylpentanamide

To a solution of 4-bromobenzene-1,2-diamine (2 g, 10.69 mmol), 4-methylpentanoic acid (1.366 g, 11.76 mmol) and HATU (6.10 g, 16.04 mmol) in DMF (40 mL) at 0° C. was added DIEA (3.74 mL, 21.39 mmol). Stirred at room temperature for 2 h. The mixture was diluted with EtOAc (50 mL) and washed with saturated aqueous sodium bicarbonate (3×30 mL) and brine (3×30 mL). The solution was dried (MgSO$_4$), filtered and concentrated under reduced pressure to obtain N-(2-amino-5-bromophenyl)-4-methylpentanamide (3.05 g, 10.69 mmol, quantitative crude yield). The product was carried on without further purification. LC/MS (ESI) m/e 285.1 [(M+H)+, calcd for C12H18BrN2O 285.1].

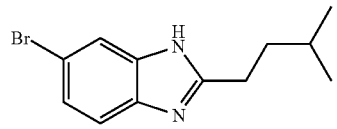

Part B: 6-bromo-2-isopentyl-1H-benzo[d]imidazole

A solution of N-(2-amino-5-bromophenyl)-4-methylpentanamide (1.7 g, 5.96 mmol) in acetic acid (150 mL) was heated at 65° C. over 3 days under nitrogen atmosphere. The reaction mixture was cooled to room temperature and concentrated under reduced pressure. The residue was purified by silica gel chromatography (0-70% EtOAc in hexanes). The required fractions were concentrated under reduced pressure to obtain 6-bromo-2-isopentyl-1H-benzo[d]imidazole (1.32 g, 4.94 mmol, 83% yield) as a pale yellow solid. LC/MS (ESI) m/e 267.2, 269.2 Br pattern [(M+H)+, calcd for C12H16BrN2 267.1].

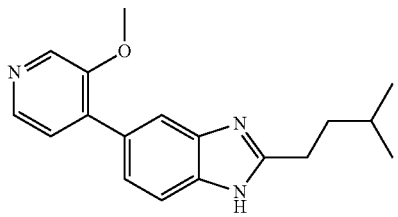 [SMILES: COc1cnccc1-c1ccc2[nH]c(CCC(C)C)nc2c1]

Part C: 2-isopentyl-5-(3-methoxypyridin-4-yl)-1H-benzo[d]imidazole

To a vial was added 6-bromo-2-isopentyl-1H-benzo[d]imidazole (0.265 g, 0.992 mmol), potassium carbonate (0.411 g, 2.98 mmol), tetrakis(triphenylphosphine)palladium(0) (0.229 g, 0.198 mmol) and 3-methoxypyridin-4-ylboronic acid (0.152 g, 0.992 mmol). The vial was purged with N$_2$ for 5 min. Dioxane (10 mL) and water (2.5 mL) were added and the vial purged with N$_2$ for 10 min. The mixture was heated in an oil bath overnight (~12 h). The reaction mixture was cooled to room temperature, then filtered through diatomaceous earth (Celite®) and the filtrate concentrated under reduced pressure. The residue was purified via silica gel chromatography (15%-100% EtOAc in hexanes) to obtain 2-isopentyl-5-(3-methoxypyridin-4-yl)-1H-benzo[d]imidazole (0.0759 g, 0.252 mmol, 25% yield) as a colorless oil. $^1$H NMR (400 MHz, METHANOL-d$_4$) δ 8.75 (s, 1H), 8.59 (d, J=5.8 Hz, 1H), 8.17 (t, J=1.1 Hz, 1H), 8.10 (d, J=6.0 Hz, 1H), 7.95-7.89 (m, 2H), 4.11 (s, 3H), 3.29-3.21 (m, 2H), 1.92-1.81 (m, 2H), 1.72 (tq, J=13.3, 6.7 Hz, 1H), 1.04 (d, J=6.5 Hz, 6H), LC/MS (ESI) m/e 296.2 [(M+H)+, calcd for C18H22N3O 296.2].

Example 57

2-isopentyl-5-(2-methoxypyridin-4-yl)-1H-benzo[d]imidazole

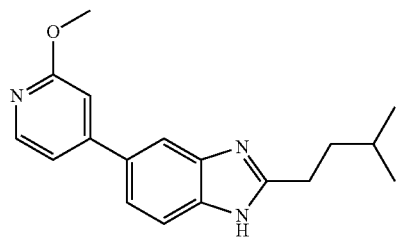 [SMILES: COc1cc(-c2ccc3[nH]c(CCC(C)C)nc3c2)ccn1]

Prepared in a similar fashion as described in Example 56, using 2-methoxypyridin-4-ylboronic acid in Part C to give the title compound (0.0624 g, 0.207 mmol, 22% yield) as a colorless amorphous solid. $^1$H NMR (400 MHz, METHANOL-d$_4$) δ 8.24 (d, J=5.5 Hz, 1H), 8.07 (dd, J=1.5, 0.8 Hz, 1H), 7.95-7.89 (m, 1H), 7.88-7.83 (m, 1H), 7.36 (dd, J=5.5, 1.5 Hz, 1H), 7.19 (d, J=1.0 Hz, 1H), 4.01 (s, 3H), 3.27-3.17 (m, 2H), 1.90-1.80 (m, 2H), 1.71 (tq, J=13.3, 6.7 Hz, 1H), 1.04 (d, J=6.8 Hz, 6H). LC/MS (ESI) m/e 296.2 [(M+H)+, calcd for C18H22N3O 296.2].

Example 58

2-(4-methylpentan-2-yl)-5-(pyridin-4-yl)-1H-benzo[d]imidazole

Prepared in a similar fashion as described in Example 56, using 2,4-dimethylpentanoic acid in Part A and pyridin-4-ylboronic acid in Part C and to give the title compound (20 mg, 0.072 mmol, 5% yield) as a colorless amorphous solid. $^1$H NMR (400 MHz, METHANOL-d$_4$) δ 8.65 (d, J=6.0 Hz, 2H), 8.01 (d, J=1.2 Hz, 1H), 7.91 (dd, J=4.8, 1.6 Hz, 2H), 7.79-7.72 (m, 2H), 1.90-1.83 (m, 1H), 1.67-1.62 (m, 2H), 1.56 (quin, J=6.8 Hz, 1H), 1.46 (d, J=6.8 Hz, 3H), 0.98 (d, J=6.8 Hz, 3H), 0.93 (d, J=6.8 Hz, 3H); LC/MS (ESI) m/e 279.9 [(M+H)+, calcd for C18H22N3 280.2].

Example 59

(R)-4-(2-(3-methyl-1-(methylamino)butyl)-1H-benzo[d]imidazol-5-yl)pyridin-2-amine

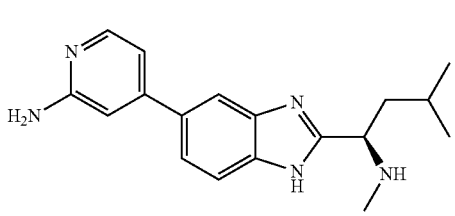

-continued

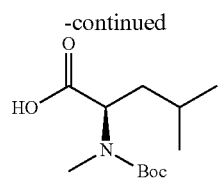

Part A. (R)-2-(tert-butoxycarbonyl(methyl)amino)-4-methylpentanoic acid

To a solution of Boc-D-leucine (10 g, 0.043 mol) and methyl iodide (27.9 mL, 0.432 mol) in THF (500 mL) cooled to 0° C. was added sodium hydride (10.46 g, 0.432 mol) in portions. The resulting mixture was stirred at room temperature overnight. The reaction mixture was carefully quenched with water (50 mL) and ethyl acetate (100 mL). The solvents were removed by concentration under reduced pressure. The reaction mixture was diluted with water (100 mL). The aqueous layer was washed with ethyl acetate (100 mL) and acidified to pH 4 using 5% citric acid solution. The aqueous layer was then extracted with ethyl acetate (3×100 mL). The combined ethyl acetate layers were dried over $Na_2SO_4$, filtered and concentrated under reduced pressure to afford the title compound (10.5 g, 0.043 mmol, 99% yield) as an oil. The crude product was taken to the next step without purification. $^1$H NMR (400 MHz, DMSO-$d_6$) δ 12.56 (s, 1H), 4.39-4.64 (m, 1H), 2.69 (s, 3H), 1.54-1.72 (m, 2H), 1.30-1.50 (m, 10H), 0.85-0.95 (m, 6H) ppm; LCMS (ESI) m/e 244.2 [(M–H)$^-$, calcd for $C_{12}H_{22}NO_4$, 244.16]; LC/MS retention time (method F): $t_R$=1.73 min.

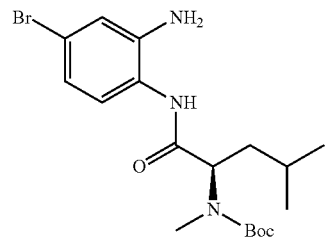 [SMILES: CC(C)C[C@H](C(=O)Nc1ccc(Br)cc1N)N(C)C(=O)OC(C)(C)C]

Part B. (R)-tert-butyl 1-(2-amino-4-bromophenylamino)-4-methyl-1-oxopentan-2-yl(methyl)carbamate To the solution of 4-bromobenzene-1,2-diamine (9.0 g, 0.066 mmol) in DMF (90 mL), (R)-2-(tert-butoxycarbonyl (methyl)amino)-4-methylpentanoic acid (12.3 g, 0.05 mmol), HATU (16. 97 g, 0.045 mmol) and diisopropyl ethyl amine (30.8 mL, 0.18 mmol) were added at 0° C. The reaction mixture was allowed to stir at RT for 3 h. The reaction mixture was diluted with water (100 mL). The aqueous layer was extracted with ethyl acetate (3×200 mL). Combined organic layer was washed with brine (150 mL). The organic layer was dried over $Na_2SO_4$, filtered and concentrated under reduced pressure to afford the title compound (12 g, 0.029 mmol, 58.1% yield) as an oil. LCMS (ESI) m/e 412.0[(M–H)$^-$, calcd for $C_{18}H_{27}BrN_3O_3$, 412.13]; LC/MS retention time (method F): $t_R$=2.07 min.

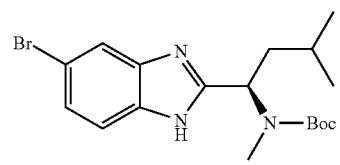 [SMILES: CC(C)C[C@H](c1nc2cc(Br)ccc2[nH]1)N(C)C(=O)OC(C)(C)C]

Part C. (R)-tert-butyl 1-(5-bromo-1H-benzo[d]imidazol-2-yl)-3-methylbutyl(methyl)carbamate A solution of (R)-tert-butyl 1-(2-amino-4-bromophenylamino)-4-methyl-1-oxopentan-2-yl(methyl)carbamate (5.0 g, 0.012 mmol) in acetic acid (50 mL) was refluxed at 65° C. for 2 h. The reaction mixture was cooled to room temperature. The acetic acid was removed under reduced pressure. The residue was diluted with water (50 mL). The aqueous layer was extracted with ethyl acetate (3×50 mL). The combined organic layers were washed with brine (50 mL), dried over $Na_2SO_4$, filtered and concentrated under reduced pressure. The crude product was purified by silica gel chromatography (pet ether:ethyl acetate) to afford the title compound (5.0 g, 0.012 mmol, quantitative yield). LCMS (ESI) m/e 396.2 [(M+H)$^+$, calcd for $C_{18}H_{27}BrN_3O_2$, 396.12]; LC/MS retention time (method F): $t_R$=2.11 min.

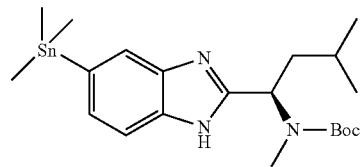 [SMILES: CC(C)C[C@H](c1nc2c[c]([Sn]([CH3])([CH3])[CH3])ccc2[nH]1)N(C)C(=O)OC(C)(C)C]

Part D. (R)-tert-butyl methyl(3-methyl-1-(5-(trimethylstannyl)-1H-benzo[d]imidazol-2-yl)butyl)carbamate To a suspension of (R)-tert-butyl 1-(5-bromo-1H-benzo[d]imidazol-2-yl)-3-methylbutyl (methyl) carbamate (1 g, 2.52 mmol) in dioxane (10 mL), hexamethylditin (1.65 g, 5.04 mmol) was added. Nitrogen gas was bubbled through the stirred solution for 5 min. Pd(PPh$_3$)$_2$Cl$_2$ (0.265 g, 0.378 mmol) was added and nitrogen gas was bubbled through the solution for another 5 min. The reaction mixture was then heated at 80° C. for 12 h. The reaction mixture was cooled to room temperature, concentrated under reduced pressure to remove solvents and diluted with water (50 mL). The aqueous layer was extracted with ethyl acetate (3×100 mL). The combined organic layers were washed with brine (50 mL). The organic layer was dried over $Na_2SO_4$, filtered and concentrated under reduced pressure to afford the title compound (1.1 g, 2.29 mmol, 91% yield) as a black solid. The compound was pure enough to be taken to the next step without further purification. LCMS (ESI) m/e 482.2 [(M+H)$^+$, calcd for $C_{21}H_{36}N_3O_2Sn$, 482.18]; LC/MS retention time (method F): $t_R$=2.38 min.

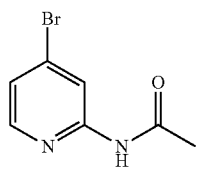

Part E. N-(4-bromopyridin-2-yl) acetamide

To a solution of 4-bromopyridin-2-amine (5.0 g, 29.07 mmol) in dichloromethane (50 mL) cooled to 0° C. was added pyridine (3.5 mL, 43.4 mmol) and the solution was stirred for 10 min. Acetyl chloride (2.1 mL, 29.5 mmol) was added. The reaction mixture was allowed to stir at 0° C. for 30 min. Then the reaction mixture was allowed to warm to RT and stirred for 1 h. The reaction mixture was diluted with brine (50 mL). The aqueous layer was extracted with dichloromethane (3×200 mL). The organic layer was dried over $Na_2SO_4$, filtered and concentrated under reduced to afford the title compound (4.1 g, 19.2 mmol, 66% yield) as a light yellow solid. LCMS (ESI) m/e 215.0 [(M+H)$^+$, calcd for $C_7H_8BrN_2O$, 215.0]; LC/MS retention time (method F): $t_R$=1.53 min.

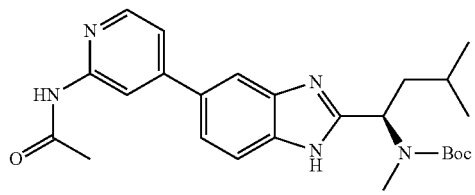 [SMILES: CC(=O)Nc1cc(-c2ccc3[nH]c([C@@H](CC(C)C)N(C)C(=O)OC(C)(C)C)nc3c2)ccn1]

Part F. (R)-tert-butyl 1-(5-(2-acetamidopyridin-4-yl)-1H-benzo[d]imidazol-2-yl)-3-methylbutyl (methyl)carbamate To the solution of (R)-tert-butyl methyl(3-methyl-1-(5-(trimethylstannyl)-1H-benzo[d]imidazol-2-yl)butyl)carbamate (600 mg, 1.25 mmol) in DMF (6 mL), N-(4-bromopyridin-2-yl)acetamide (284 mg, 1.32 mmol), TBAB (530 mg, 1.65 mmol) and $K_2CO_3$ (430 mg, 3.11 mmol) were added. Nitrogen gas was bubbled through the stirred solution for 5 min. Pd $(PPh_3)_2Cl_2$ (73 mg, 0.378 mmol) was added and nitrogen purging through the solution was continued for another 5 min. The reaction mixture was then heated at 90° C. for overnight. The reaction mixture was cooled to room temperature, concentrated under reduced pressure to remove solvents and diluted with water. The aqueous layer was extracted with ethyl acetate (3×100 mL). The combined organic layers were washed with brine (50 mL). The organic layer was dried over $Na_2SO_4$, filtered and concentrated under reduced pressure to afford the title compound (330 mg, 0.73 mmol, 59% yield) as solid. LCMS (ESI) m/e 450.2[(M−H)$^−$, calcd for $C_{25}H_{32}N_5O_3$, 450.26]; LC/MS retention time (method C): $t_R$=1.71 min.

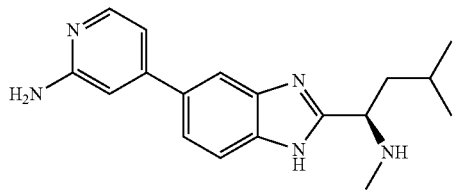 [SMILES: CN[C@H](CC(C)C)c1nc2cc(-c3ccnc(N)c3)ccc2[nH]1]

Part G. (R)-4-(2-(3-methyl-1-(methylamino)butyl)-1H-benzo[d]imidazol-5-yl)pyridin-2-amine To the solution of (R)-tert-butyl 1-(5-(2-acetamidopyridin-4-yl)-1H-benzo[d]imidazol-2-yl)-3-methylbutyl (methyl)carbamate (140 mg, 0.31 mmol) in MeOH (2 mL) and water (2 mL), KOH (90 mg, 1.58 mmol) was added. The reaction mixture was then heated at 100° C. and stirred overnight. The reaction mixture was cooled to room temperature and concentrated under reduced pressure. The crude product was purified by preparative HPLC (0.05% TFA in water and acetonitrile) to afford the title compound (14 mg, 0.045 mmol, 15% yield) as a solid which was isolated as TFA salt. $^1$H NMR (400 MHz, CD$_3$OD) δ 8.12 (s, 1H) 7.91-7.93 (m, 1H) 7.84 (d, J=8.4 Hz, 1H) 7.77 (dd, J=8.8, 2.0 Hz, 1H) 7.31-7.33 (m, 2H) 4.64-4.69 (m, 1H) 2.71 (d, J=1.2 Hz, 3H) 2.24-2.28 (m, 1H) 1.95-2.01 (m, 1H) 1.47-1.51 (m, 3H) 1.03 (d, J=6.4 Hz, 3H) 0.96 (dd, J=6.4, 0.8 Hz, 3H) ppm; LCMS (ESI) m/e 310.0 [(M+H)$^+$, calcd for $C_{18}H_{24}N_5$, 310.20]; LC/MS retention time (method C): $t_R$=1.51 min; HPLC retention time (method S): $t_R$=7.38 min; HPLC retention time (method T): $t_R$=7.71 min; Chiral SFC retention time (method B): $t_R$=2.13 min.

Example 60

(R)-1-Cyclohexyl-N-methyl-1-(5-(pyridin-4-yl)-1H-benzo[d]imidazol-2-yl)methanamine

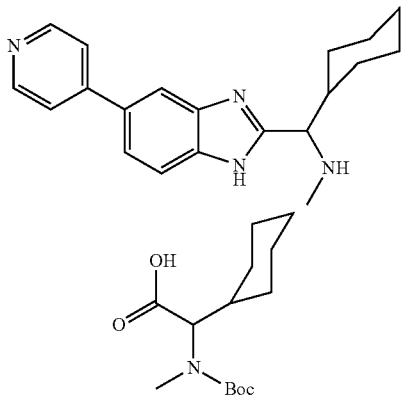

Part A. 2-(Tert-butoxycarbonyl(methyl)amino)-2-cyclohexylacetic acid

To a solution of 2-(tert-butoxycarbonylamino)-2-cyclohexylacetic acid (0.5 g, 1.94 mmol) and methyl iodide (1.21 mL, 19 mmol) in THF (25 mL) cooled to 0° C. was added sodium hydride (0.47 g, 19.6 mmol) in portions. The resulting mixture was stirred at room temperature for 24 h. The reaction mixture was quenched with water (25 mL) and ethyl acetate (25 mL). The solvents were removed by concentration under reduced pressure. The reaction mixture was diluted with water (100 mL) and washed with ethyl acetate (50 mL). The aqueous layer was acidified to pH 4 using 5% citric acid solution and extracted with ethyl acetate (3×100 mL). The combined ethyl acetate layers were dried over $Na_2SO_4$, filtered and concentrated under reduced pressure to afford the title compound (0.43 g, 1.58 mmol, 82% yield). The crude product was taken to the next step without purification. LCMS (ESI) m/e 270.2 [(M−H)$^−$, calcd for $C_{14}H_{24}NO_4$, 270.18]; LC/MS retention time (method F): $t_R$=1.82 min.

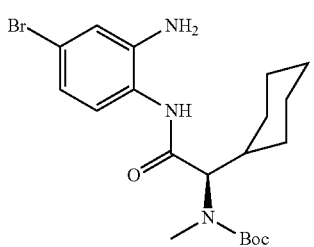 [SMILES: CN(C(=O)OC(C)(C)C)[C@@H](C(=O)Nc1ccc(Br)cc1N)C1CCCCC1]

Part B. (R)-tert-butyl 2-(2-amino-4-bromophenylamino)-1-cyclohexyl-2-oxoethyl (methyl)carbamate Prepared in a similar fashion as described in Example 59, Part B using 4-bromobenzene-1,2-diamine (300 mg, 1.6 mmol) and (R)-2-(tert-butoxycarbonyl (methyl)amino)-2-cyclohexylacetic acid (434 mg, 1.6 mmol) to afford the title compound (600 mg, 1.36 mmol, 85% yield). LCMS (ESI) m/e 440.1 [(M+H)$^+$, calcd for $C_{20}H_{31}BrN_3O_3$, 440.2]; LC/MS retention time (method D): $t_R$=1.12 min.

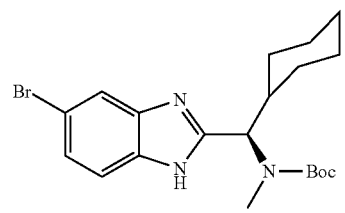 [SMILES: CN(C(=O)OC(C)(C)C)[C@@H](c1nc2cc(Br)ccc2[nH]1)C1CCCCC1]

Part C. (R)-tert-butyl (5-bromo-1H-benzo[d]imidazol-2-yl) (cyclohexyl)methyl(methyl) carbamate Prepared in a similar fashion as described in Example 59, Part C using (R)-tert-butyl 2-(2-amino-4-bromophenylamino)-1-cyclohexyl-2-oxoethyl(methyl)carbamate. The crude product was purified by silica gel chromatography (2:3 ethyl acetate and pet ether) to afford the title compound (420 mg, 0.997 mmol, 73% yield). LCMS (ESI) m/e 422.2 [(M+H)$^+$, calcd for $C_{20}H_{29}BrN_3O_2$, 422.14]; LC/MS retention time (method A): $t_R$=2.36 min.

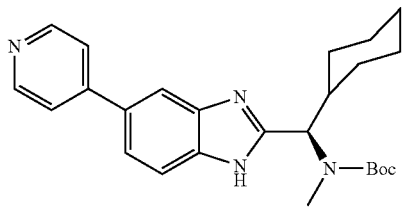 [SMILES: CN(C(=O)OC(C)(C)C)[C@@H](c1nc2cc(-c3ccncc3)ccc2[nH]1)C1CCCCC1]

Part D. (R)-tert-butyl cyclohexyl(5-(pyridin-4-yl)-1H-benzo[d]imidazol-2-yl)methyl(methyl)carbamate To the solution of (R)-tert-butyl (5-bromo-1H-benzo[d]imidazol-2-yl)(cyclohexyl)methyl(methyl)carbamate (420 mg, 0.99 mmol) in dioxane (6 mL) and water (3 mL) was added pyridine-4-boronic acid (245 mg, 1.99 mmol) and $Cs_2CO_3$ (975 mg, 2.98 mmol). Nitrogen gas was bubbled through the stirred suspension for 5 min. Pd (PPh$_3$)$_4$ (57 mg, 0.049 mmol) was added and nitrogen bubbling was continued through the stirred suspension for another 5 min. The reaction mixture was then heated at 110° C. for 4 h in microwave. The reaction mixture was cooled to room temperature and diluted with water (20 mL). The aqueous layer was extracted with ethyl acetate (3×50 mL). The combined organic layers were washed with brine (50 mL). The organic layer was dried over $Na_2SO_4$, filtered and concentrated under reduced pressure. The crude product was purified by preparative TLC on silica gel using 80% ethyl acetate in pet ether mobile phase to afford the title compound (100 mg, 0.24 mmol, 24% yield). LCMS (ESI) m/e 421.2 [(M+H)$^+$, calcd for $C_{25}H_{33}N_4O_2$, 421.3]; LC/MS retention time (method A): $t_R$=2.06 min.

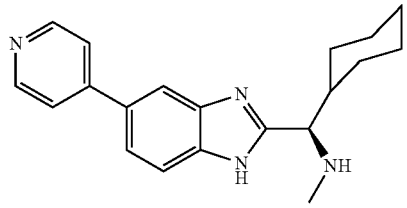 [SMILES: CN[C@@H](c1nc2cc(-c3ccncc3)ccc2[nH]1)C1CCCCC1]

Part E. (R)-1-cyclohexyl-N-methyl-1-(5-(pyridin-4-yl)-1H-benzo[d]imidazol-2-yl)methanamine To a solution of (R)-tert-butyl cyclohexyl (5-(pyridin-4-yl)-1H-benzo[d]imidazol-2-yl) methyl (methyl)carbamate (100 mg, 0.24 mmol) in methanol (1 mL) cooled to 0° C. was added 2M HCl in ether (5 mL, 10 mmol) slowly over a period of 5 min. The reaction mixture was stirred at 0° C. for 5 min then was warmed to room temperature and allowed to stir for 2 h. The solvents were removed by concentration under reduced pressure. The crude product was purified by preparative HPLC (0.1% HCl in water and acetonitrile) to afford the title compound (30 mg, 0.093 mmol, 39% yield) as a pale yellow solid which was isolated as HCl salt. 1H NMR (400 MHz, CD$_3$OD) δ 8.86-8.91 (m, 2H), 8.50 (d, J=6.8 Hz, 2H), 8.38 (d, J=1.2 Hz, 1H), 8.01 (dd, J=8.4, 1.6 Hz, 1H), 7.92 (d, J=8.8 Hz, 1H), 4.54 (d, J=6.8 Hz, 1H) 2.73 (s, 3H), 2.27-2.29 (m, 1H), 2.02-2.05 (m, 1H), 1.87-1.90 (m, 1H), 1.70-1.81 (m, 2H), 1.61-1.64 (m, 1H), 1.29-1.43 (m, 2H), 1.12-1.21 (m, 3H) ppm; LCMS (ESI) m/e 321.2 [(M+H)$^+$, calcd for $C_{20}H_{25}N_4$, 321.20]; LC/MS retention time (method A): $t_R$=1.36 min; HPLC retention time (method S): $t_R$=7.38 min; HPLC retention time (method T): $t_R$=8.02 min.

Example 61

(R)-N-methyl-4-(2-(3-methyl-1-(methylamino)butyl)-1H-benzo[d]imidazol-5-yl) pyridin-2-amine

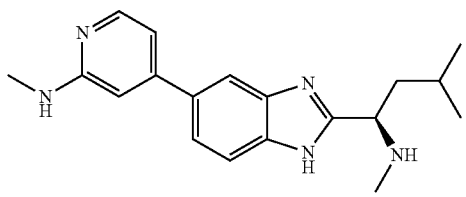

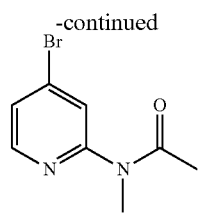

Part A.
N-(4-bromopyridin-2-yl)-N-methylacetamide

To a solution of N-(4-bromopyridin-2-yl) acetamide (250 mg, 1.16 mmol) and methyl iodide (0.094 mL, 1.51 mmol) in THF (4 mL) cooled to 0° C., sodium hydride (67 mg, 2.8 mmol) was added. The resulting mixture was stirred at room temperature overnight. The reaction mixture was quenched with water (5 mL) and ethyl acetate (5 mL). The solvents were removed by concentration under reduced pressure. The reaction mixture was diluted with water (20 mL) and extracted with ethyl acetate (3×20 mL). The combined ethyl acetate layers were dried over $Na_2SO_4$, filtered and concentrated under reduced pressure to afford the title compound (284 mg, 1.24 mmol, 69% yield). LCMS (ESI) m/e 229.0 (Bromo pattern) [(M+H)$^+$, calcd for $C_8H_{10}BrN_2O$, 228.99]; LC/MS retention time (method F): $t_R$=1.50 min.

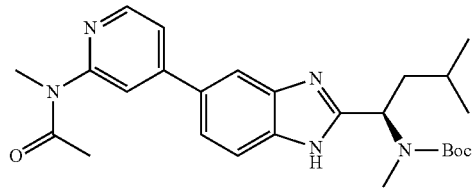 [SMILES: CC(=O)N(C)c1cc(-c2ccc3[nH]c([C@@H](CC(C)C)N(C)C(=O)OC(C)(C)C)nc3c2)ccn1]

Part B. (R)-tert-butyl methyl(3-methyl-1-(5-(2-(N-methylacetamido)pyridin-4-yl)-1H-benzo[d]imidazol-2-yl)butyl)carbamate Prepared in a similar fashion as described in Example 59, Part F using (R)-tert-butyl methyl(3-methyl-1-(5-(trimethylstannyl)-1H-benzo[d]imidazol-2-yl)butyl)carbamate (prepared in Example 59, Part D) (500 mg, 1.04 mmol) and N-(4-bromopyridin-2-yl)-N-methylacetamide (284 mg, 1.24 mmol) to afford the title compound (290 mg, 0.62 mmol, 56% yield) as a solid. LCMS (ESI) m/e 466.2[(M+H)$^+$, calcd for $C_{26}H_{36}N_5O_3$, 466.3]; LC/MS retention time (method C): $t_R$=1.71 min.

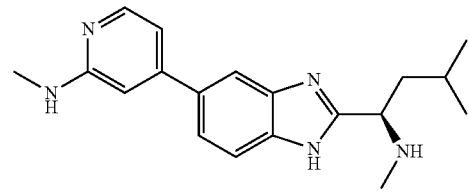 [SMILES: CNc1cc(-c2ccc3[nH]c([C@@H](CC(C)C)NC)nc3c2)ccn1]

Part C. (R)-N-methyl-4-(2-(3-methyl-1-(methylamino)butyl)-1H-benzo[d]imidazol-5-yl)pyridin-2-amine Prepared in a similar fashion as described in Example 59, Part G using (R)-tert-butyl methyl(3-methyl-1-(5-(2-(N-methylacetamido)pyridin-4-yl)-1H-benzo[d]imidazol-2-yl)butyl)carbamate. The crude product was purified by preparative HPLC (0.05% TFA in water and acetonitrile) to afford the title compound (18 mg, 0.056 mmol, 9% yield) as a yellow oil which was isolated as TFA salt. $^1$H NMR (400 MHz, CD$_3$OD) δ 8.12 (s, 1H) 7.91 (d, J=6.8 Hz, 1H) 7.83 (d, J=8.8 Hz, 1H) 7.77 (dd, J=8.8, 1.6 Hz, 1H) 7.29-7.31 (m, 2H) 4.63-4.66 (m, 1H) 3.11 (s, 3H) 2.71 (d, J=3.2 Hz, 3H) 2.24-2.29 (m, 1H) 1.94-2.01 (m, 1H) 1.48 (m, 1H) 1.02 (d, J=6.4 Hz, 3H) 0.96 (d, J=6.8 Hz, 3H) ppm; LCMS (ESI) m/e 324.2 [(M+H)$^+$, calcd for $C_{19}H_{26}N_5$, 324.2]; LC/MS retention time (method B): $t_R$=1.20 min; HPLC retention time (method T): $t_R$=8.19 min; HPLC retention time (method S): $t_R$=7.62 min.

Example 62

N,3-dimethyl-1-(5-(pyridin-4-yl)-1H-benzo[d]imidazol-2-yl) butan-1-amine

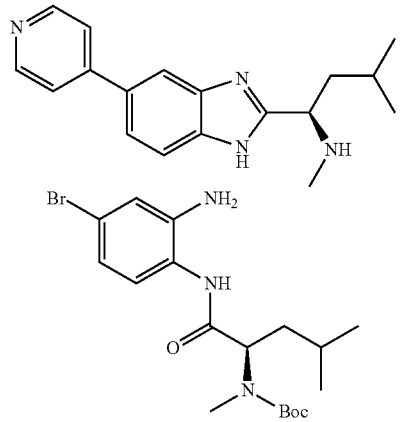

Part A. (R)-tert-butyl 1-(2-amino-4-bromophenylamino)-4-methyl-1-oxopentan-2-yl (methyl)carbamate Prepared in a similar fashion as described in Example 59, Part B using 4-bromobenzene-1,2-diamine (700 mg, 3.74 mmol), (R)-2-(tert-butoxycarbonyl(methyl)amino)-4-methylpentanoic acid (1.6 g, 6.5 mmol) to afford the title compound (1.1 g, 2.7 mmol, 71% yield) as an oil. LCMS (ESI) m/e 414.2 (Bromo pattern) [(M+H)$^+$, calcd for $C_{18}H_{29}BrN_3O_3$, 414.13]; LC/MS retention time (method A): $t_R$=2.14 min.

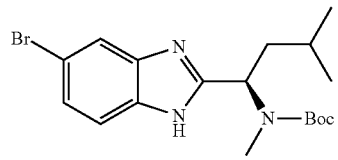 [SMILES: CC(C)C[C@H](c1nc2cc(Br)ccc2[nH]1)N(C)C(=O)OC(C)(C)C]

Part B. (R)-tert-butyl 1-(5-bromo-1H-benzo[d]imidazol-2-yl)-3-methylbutyl(methyl)carbamate Prepared in a similar fashion as described in Example 59, Part C using (R)-tert-butyl 1-(2-amino-4-bromophenylamino)-4-methyl-1-oxopentan-2-yl(methyl)carbamate (1.1 g, 2.7 mmol). The crude product was purified by column chromatography on silica gel (using 3:7 ethyl acetate and pet ether as eluent) to afford the title compound (850 mg, 2.15 mmol, 80% yield) as an oil. LCMS (ESI) m/e 398.2 [(M+H)$^+$, calcd for $C_{18}H_{27}BrN_3O_2$, 396.1]; LC/MS retention time (method A): $t_R$=2.23 min.

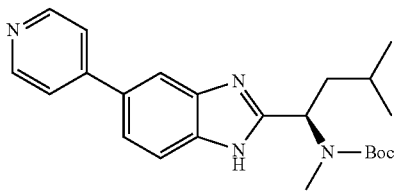 [SMILES: CC(C)C[C@H](c1nc2cc(-c3ccncc3)ccc2[nH]1)N(C)C(=O)OC(C)(C)C]

Part C. (R)-tert-butyl methyl(3-methyl-1-(5-(pyridin-4-yl)-1H-benzo[d]imidazol-2-yl)butyl)carbamate To a suspension of tert-butyl 1-(5-bromo-1H-benzo[d]imidazol-2-yl)-3-methylbutyl(methyl)carbamate (850 mg, 2.15 mmol) in dioxane (10 mL) and water (2 mL), pyridine-4-boronic acid (520 mg, 4.2 mmol) and $Cs_2CO_3$ (2.0 g, 6.15 mmol) were added. Nitrogen gas was bubbled through the stirred suspension for 5 min. Pd(PPh$_3$)$_4$ (198 mg, 0.17 mmol) was added and nitrogen gas was bubbled through the stirred suspension for another 5 min. The reaction mixture was then heated at 90° C. overnight. The reaction mixture was cooled to RT and diluted with water (20 mL). The aqueous layer was extracted with ethyl acetate (3×20 mL). The combined organic layers were washed with brine (20 mL). The organic layer was dried over $Na_2SO_4$, filtered and concentrated under reduced pressure to afford the title compound (450 mg, 1.14 mmol, 53.1% yield) as a white solid. LCMS (ESI) m/e 395.2 [(M+H)$^+$, calcd for $C_{23}H_{31}N_4O_2$, 395.24]; LC/MS retention time (method A): $t_R$=1.93 min.

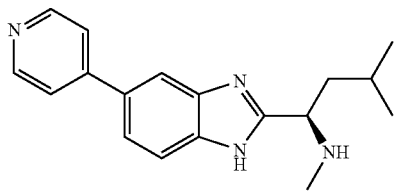 [SMILES: CN[C@H](CC(C)C)c1nc2cc(-c3ccncc3)ccc2[nH]1]

Part D. (R)-N,3-dimethyl-1-(5-(pyridin-4-yl)-1H-benzo[d]imidazol-2-yl)butan-1-amine To the solution of tert-butyl methyl(3-methyl-1-(5-(pyridin-4-yl)-1H-benzo[d]imidazol-2-yl)butyl)carbamate (450 mg, 1.14 mmol) in dichloromethane (5.0 mL) cooled to 0° C. was added TFA (1 mL, 13 mmol) slowly over a period of 5 min. The reaction mixture was stirred at 0° C. for 5 min then was warmed to room temperature and allowed to stir for 2 h. The volatiles were removed by concentration under reduced pressure. The crude product was purified by preparative HPLC (0.05% TFA in water and acetonitrile) to afford the title compound (40 mg, 0.14 mmol, 12% yield) as a white solid which was isolated as TFA salt. $^1$H NMR (400 MHz, CD$_3$OD) δ 8.86 (dd, J=6.0, 1.2 Hz, 2H) 8.46-8.48 (m, 2H) 8.35 (d, J=1.2 Hz, 1H) 7.98 (dd, J=8.4, 1.6 Hz, 1H) 7.90 (d, J=8.4 Hz, 1H) 4.64-4.68 (m, 1H) 2.74 (s, 3H) 2.22-2.30 (m, 1H) 1.96-2.03 (m, 1H) 1.47-1.54 (m, 1H) 0.95-1.05 (m, 6H) ppm; LCMS (ESI) m/e 295.2 [(M+H)$^+$, calcd for $C_{18}H_{23}N_4$, 295.2]; LC/MS retention time (method F): $t_R$=1.51 min; HPLC retention time (method S): $t_R$=6.88 min; HPLC retention time (method T): $t_R$=7.35 min.

Example 63

(R)-N-(4-(2-(3-methyl-1-(methylamino)butyl)-1H-benzo[d]imidazol-5-yl)pyridin-2-yl)acetamide

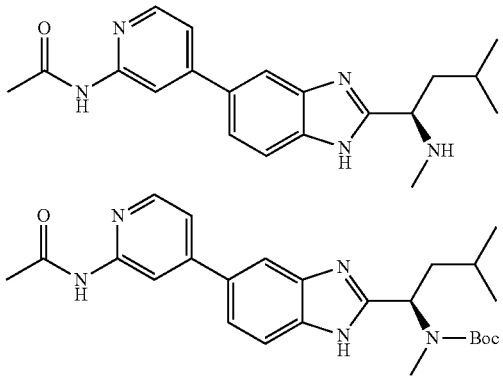

Part A. (R)-tert-butyl 1-(5-(2-acetamidopyridin-4-yl)-1H-benzo[d]imidazol-2-yl)-3-methylbutyl (methyl)carbamate Prepared in a similar fashion as described in Example 59, Part F using (R)-tert-butyl methyl(3-methyl-1-(5-(trimethylstannyl)-1H-benzo[d]imidazol-2-yl)butyl)carbamate (500 mg, 1.04 mmol) and N-(4-bromopyridin-2-yl)acetamide (267 mg, 1.24 mmol) to afford the title compound (350 mg, 0.77 mmol, 74% yield) as a solid. LCMS (ESI) m/e 450.3 [(M−H)$^−$, calcd for $C_{25}H_{32}N_5O_3$, 450.3]; LC/MS retention time (method C): $t_R$=1.69 min.

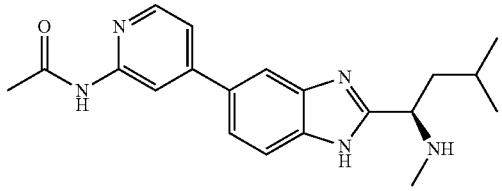 [SMILES: CN[C@H](CC(C)C)c1nc2cc(-c3ccnc(NC(C)=O)c3)ccc2[nH]1]

Part B. (R)-N-(4-(2-(3-methyl-1-(methylamino)butyl)-1H-benzo[d]imidazol-5-yl)pyridin-2-yl)acetamide To a solution of (R)-tert-butyl 1-(5-(2-acetamidopyridin-4-yl)-1H-benzo[d]imidazol-2-yl)-3-methylbutyl(methyl)carbamate (160 mg, 0.35 mmol) in dichloromethane (2 mL) cooled to 0° C. was added 4M HCl in dioxane (2 mL) slowly over a period of 5 min. The reaction mixture was stirred at 0° C. for 5 min then was warmed to room temperature and allowed to stir for 1 h. The solvents were removed by concentration under reduced pressure. The crude product was purified by preparative HPLC (0.1% HCl in water and acetonitrile) to afford the title compound (30 mg, 0.085 mmol, 24% yield) as an off-white solid which was isolated as a HCl salt. $^1$H NMR (400 MHz, CD$_3$OD) δ 8.41 (d, J=6.4 Hz, 1H) 8.28 (d, J=9.2 Hz, 1H) 8.01 (d, J=6.8 Hz, 1H) 7.90-7.93 (m, 2H) 7.75 (d, J=8.4 Hz, 1H) 4.68-4.77 (m, 1H) 2.75 (d, J=1.6 Hz, 3H) 2.40 (s, 3H) 2.28-2.31 (m, 1H) 2.01-2.06 (m, 1H) 1.48-1.53 (m, 1H) 1.04 (d, J=6.4 Hz, 3H) 0.98 (d, J=6.8 Hz, 3H) ppm; LCMS (ESI) m/e 350.2 [(M–H)$^-$, calcd for C$_{20}$H$_{24}$N$_5$O, 350.21]; LC/MS retention time (method C): t$_R$=1.51 min; HPLC retention time (method S): t$_R$=8.74 min; HPLC retention time (method T): t$_R$=9.45 min; Chiral SFC retention time (method A): t$_R$=4.1 min.

Example 64

(R)-cyclohexyl(6-methoxy-5-(oxazol-5-yl)-1H-benzo[d]imidazol-2-yl)methanamine

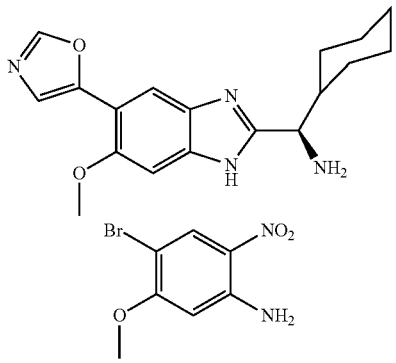

Part A. 4-bromo-5-methoxy-2-nitroaniline

To a solution of 5-methoxy-2-nitroaniline (4.0 g, 23 mmol) in acetonitrile (80 mL) was added N-bromosuccinimide (4.21 g, 23 mmol). The reaction mixture was heated to reflux overnight. The reaction mixture was cooled to R.T. Acetonitrile was evaporated under reduced pressure. The reaction mixture was diluted with water (100 mL). The aqueous layer was extracted with ethyl acetate (3×100 mL). The combined organic layers were washed with brine (50 mL). The organic layer was dried over Na$_2$SO$_4$, filtered and concentrated under reduced pressure to afford the title compound (5.6 g, 22.8 mmol, 99% yield) as a yellow solid. The crude product was taken to next step without further purification. LCMS (ESI) m/e 245.0 (Bromo pattern) [(M–H)$^-$, calcd for C$_7$H$_6$BrN$_2$O$_3$, 245.0]; LC/MS retention time (method A): t$_R$=1.68 min.

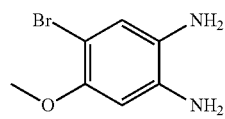

Part B. 4-bromo-5-methoxybenzene-1,2-diamine

To a solution of 4-bromo-5-methoxy-2-nitroaniline (5.6 g, 22.7 mmol) in THF (120 mL) was added Raney nickel (2.8 g, 100 mmol) in a autoclave. The reaction mixture was stirred at room temperature for overnight under 45 psi of hydrogen pressure. The reaction mixture was filtered through diatomaceous earth (Celite®) and the bed was washed with methanol. The combined filtrate was concentrated under reduced pressure to afford the title compound (4 g, 18.5 mmol, 82% yield) as a black solid. The crude product was taken to next step without further purification. LCMS (ESI) m/e 217.0 (Bromo pattern) [(M+H)$^+$, calcd for C$_7$H$_{10}$BrN$_2$O, 217.0]; LC/MS retention time (method B): t$_R$=0.76 min.

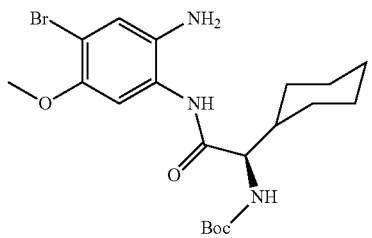 [SMILES: COc1cc(NC(=O)[C@H](NC(=O)OC(C)(C)C)C2CCCCC2)c(N)cc1Br]

Part C. (R)-tert-butyl 2-(2-amino-4-bromo-5-methoxyphenylamino)-1-cyclohexyl-2-oxoethylcarbamate Prepared in a similar fashion as described in Example 59, Part B using 4-bromo-5-methoxybenzene-1,2-diamine (922 mg, 4.26 mmol) and (R)-2-(tert-butoxycarbonylamino)-2-cyclohexylacetic acid (1.1 g, 4.28 mmol) to afford the title compound (1 g, 2.2 mmol, 52% yield). The crude product was taken to next step without purification. LCMS (ESI) m/e 456.2 [(M+H)$^+$, calcd for C$_{20}$H$_{31}$BrN$_3$O$_4$, 456.1]; LC/MS retention time (method A): t$_R$=1.98 min.

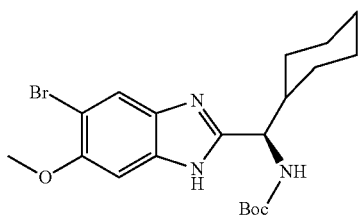 [SMILES: COc1cc2[nH]c([C@H](NC(=O)OC(C)(C)C)C3CCCCC3)nc2cc1Br]

Part D. (R)-tert-butyl (5-bromo-6-methoxy-1H-benzo[d]imidazol-2-yl) (cyclohexyl)methylcarbamate Prepared in a similar fashion as described in Example 59, Part C using ((R)-tert-butyl 2-(2-amino-4-bromo-5-methoxyphenylamino)-1-cyclohexyl-2-oxoethylcarbamate. The crude product was purified by column chromatography on silica gel using gradient of ethyl acetate and hexane as mobile phase to afford the title compound (1 g, 2.29 mmol, 52% yield). LCMS (ESI) m/e 438.2 [(M+H)$^+$, calcd for C$_{20}$H$_{29}$BrN$_3$O$_3$, 438.1]; LC/MS retention time (method A): t$_R$=2.00 min.

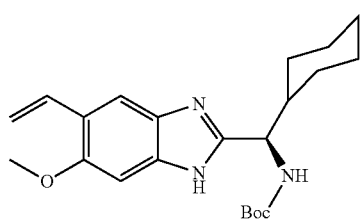 [SMILES: C=Cc1cc2nc([C@H](NC(=O)OC(C)(C)C)C3CCCCC3)[nH]c2cc1OC]

Part E. (R)-tert-butyl cyclohexyl(6-methoxy-5-vinyl-1H-benzo[d]imidazol-2-yl)methylcarbamate Prepared in a similar fashion as described in Example 4, Part A using (R)-tert-butyl (5-bromo-6-methoxy-1H-benzo[d]imidazol-2-yl)(cyclohexyl)methylcarbamate. The crude product was purified by column chromatography on silica gel using gradient of hexane:ethyl acetate as mobile phase to afford the title compound (400 mg, 1.04 mmol, 91% yield). LCMS (ESI) m/e 386.2 [(M+H)$^+$, calcd for $C_{22}H_{32}N_3O_3$, 386.2]; LC/MS retention time (method A): $t_R$=2.03 min.

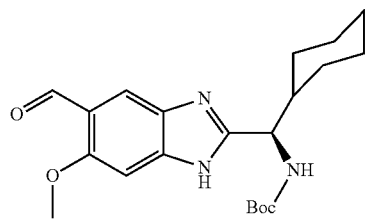 [SMILES: COc1cc2[nH]c([C@H](NC(=O)OC(C)(C)C)C3CCCCC3)nc2cc1C=O]

Part F. (R)-tert-butyl cyclohexyl(5-formyl-6-methoxy-1H-benzo[d]imidazol-2-yl)methylcarbamate Prepared in a similar fashion as described in Example 4, Part B using (R)-tert-butyl cyclohexyl(6-methoxy-5-vinyl-1H-benzo[d]imidazol-2-yl)methylcarbamate. The crude product was purified by column chromatography on silica gel using pet ether:ethyl acetate as mobile phase to afford the title compound (320 mg, 0.83 mmol, 80% yield). LCMS (ESI) m/e 388.2 [(M+H)$^+$, calcd for $C_{21}H_{30}N_3O_4$, 388.2]; LC/MS retention time (method A): $t_R$=1.78 min.

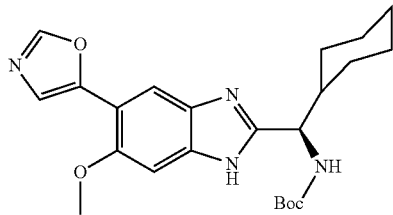 [SMILES: COc1cc2[nH]c([C@H](NC(=O)OC(C)(C)C)C3CCCCC3)nc2cc1-c1cnco1]

Part G. (R)-tert-butyl cyclohexyl(6-methoxy-5-(oxazol-5-yl)-1H-benzo[d]imidazol-2-yl)methylcarbamate Prepared in a similar fashion as described in Example 4, Part C using (R)-tert-butyl cyclohexyl(5-formyl-6-methoxy-1H-benzo[d]imidazol-2-yl)methylcarbamate to afford the title compound (74 mg, 0.17 mmol, 21% yield). LCMS (ESI) m/e 425.2 [(M–H)$^-$, calcd for $C_{23}H_{29}N_4O_4$, 425.2]; LC/MS retention time (method A): $t_R$=1.81 min.

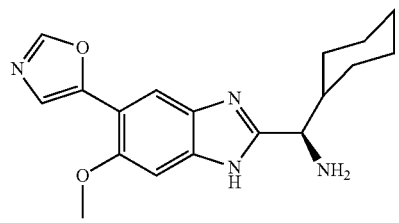 [SMILES: COc1cc2[nH]c([C@H](N)C3CCCCC3)nc2cc1-c1cnco1]

Part H. (R)-cyclohexyl(6-methoxy-5-(oxazol-5-yl)-1H-benzo[d]imidazol-2-yl)methanamine To a solution of (R)-tert-butyl cyclohexyl(6-methoxy-5-(oxazol-5-yl)-1H-benzo[d]imidazol-2-yl)methylcarbamate (24 mg, 0.056 mmol) in methanol (2 mL) cooled to 0° C. was added a 2 M solution of HCl in diethyl ether (2 mL, 4 mmol) slowly over a period of 5 min. The reaction mixture was stirred at 0° C. for 5 min then was warmed to room temperature and allowed to stir for 2 h. The solvents were removed by concentration under reduced pressure. The crude product was purified by preparative HPLC (0.1% HCl in water and acetonitrile) to afford the title compound (6.8 mg, 0.021 mmol, 37% yield) as a pale yellow solid which was isolated as a HCl salt. $^1$H NMR (400 MHz, CD$_3$OD) δ 8.46 (s, 1H) 8.15 (s, 1H) 7.78 (d, J=4.0 Hz, 1H) 7.42 (s, 1H) 4.51 (d, J=8.4 Hz, 1H) 4.10 (s, 3H) 2.22-2.25 (m, 1H) 1.88-1.93 (m, 1H) 1.73-1.81 (m, 2H) 1.46-1.53 (m, 1H) 1.22-1.43 (m, 6H) ppm; LCMS (ESI) m/e 327.2 [(M+H)$^+$, calcd for $C_{18}H_{23}N_4O_2$, 327.2]; LC/MS retention time (method B): $t_R$=1.56 min; HPLC retention time (method U): $t_R$=5.55 min; HPLC retention time (method V): $t_R$=5.88 min.

Example 65

4-methyl-2-(5-(oxazol-5-yl)-1H-benzo[d]imidazol-2-yl)pentan-1-amine

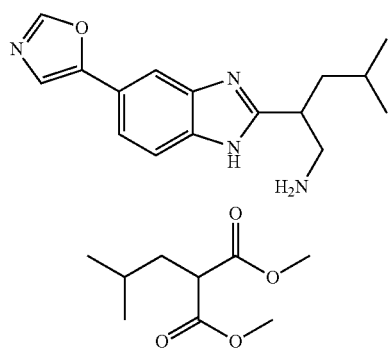

Part A. dimethyl 2-isobutylmalonate

To methanol (25 mL) was added sodium metal (624 mg, 27 mmol) in portions. After complete dissolution of the sodium, dimethyl malonate (3.10 mL, 27 mmol) and 1-iodo-2-methylpropane (3.16 mL, 27 mmol) were added. The reaction mixture was refluxed at 65° C. for 2.5 h. The reaction mixture was cooled to RT and quenched with water (15 mL). The aqueous layer was extracted with hexane (3×50 mL). The combined organic layers were washed with brine (50 mL). The organic layer was dried over $Na_2SO_4$, filtered and concentrated under reduced pressure to afford the title compound (3.1 g, 16.5 mmol, 61% yield). The crude product was taken to next step without further purification. LCMS (ESI) m/e 188.7 [(M+H)$^+$, calcd for $C_9H_{17}O_4$, 189.1]; LC/MS retention time (method C): $t_R$=1.67 min.

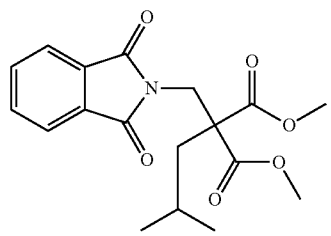 [SMILES: COC(=O)C(CC(C)C)(CN1C(=O)c2ccccc2C1=O)C(=O)OC]

Part B. dimethyl 2-((1,3-dioxoisoindolin-2-yl)methyl)-2-isobutylmalonate

To a stirred suspension of sodium hydride (60% dispersion in mineral oil, 0.997 g, 24.9 mmol) in diethyl ether (100 mL) was added dimethyl 2-isobutylmalonate (3.13 g, 16.6 mmol) dropwise. The resulting mixture was stirred at RT for 3 h. The reaction mixture was cooled to 0° C. N-chloromethyl phthalimide (3.24 g, 16.6 mmol) was added in one portion. The reaction mixture was stirred at RT overnight followed by heating to reflux for 1 h. The reaction mixture was cooled to RT and cold 1.5 N HCl (100 mL) was added. The organic layer was separated. The aqueous layer was extracted with diethyl ether (2×50 mL). The combined ether layers were dried over $Na_2SO_4$, filtered and concentrated under reduced pressure to afford the title compound (5.3 g, 15.2 mmol, 92% yield). The crude product was taken to next step without further purification. LCMS (ESI) m/e 347.9 [(M+H)$^+$, calcd for $C_{18}H_{22}NO_6$, 348.1]; LC/MS retention time (method C): $t_R$=1.95 min.

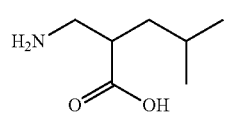

Part C. 2-(aminomethyl)-4-methylpentanoic acid

To dimethyl 2-((1,3-dioxoisoindolin-2-yl)methyl)-2-isobutylmalonate (5.3 g, 15.2 mmol) was added 6N HCl (150 mL) and the mixture was heated to reflux for 40 h. The reaction mixture was cooled to 0° C., filtered and the filtrate was concentrated under reduced pressure to afford the title compound (2.2 g, 15.2 mmol, 57% yield) which was obtained as a HCl salt. The crude product was taken to next step without further purification. LCMS (ESI) m/e 145.8 [(M+H)$^+$, calcd for $C_7H_{16}NO_2$, 146.1]; LC/MS retention time (method C): $t_R$=0.17 min.

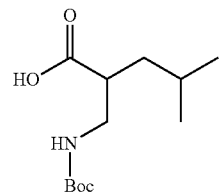 [SMILES: CC(C)CC(CNC(=O)OC(C)(C)C)C(=O)O]

Part D. 2-((tert-butoxycarbonylamino)methyl)-4-methylpentanoic acid

To a solution of 2-(aminomethyl)-4-methylpentanoic acid (2.2 g, 15.2 mmol) in THF (200 mL) and water (10 mL) was added di-tert-butyl dicarbonate (3.64 g, 16.69 mmol) and potassium carbonate (6.29 g, 45.52 mmol). The reaction mixture was allowed to stir at RT for 16 h. The solvent was removed by concentration under reduced pressure and diluted with water. The aqueous layer was washed with ethyl acetate (3×50 mL). The aqueous layer was acidified with 10% aqueous citric acid and extracted with ethyl acetate (3×150 mL). The combined organic layers were washed with brine (50 mL). The organic layer was dried over $Na_2SO_4$, filtered and concentrated under reduced pressure to afford the title compound (2.5 g, 10.2 mmol, 67% yield). The crude product was taken to next step without further purification. LCMS (ESI) m/e 244.2 [(M–H)$^-$, calcd for $C_{12}H_{22}NO_4$, 244.2]; LC/MS retention time (method F): $t_R$=1.69 min.

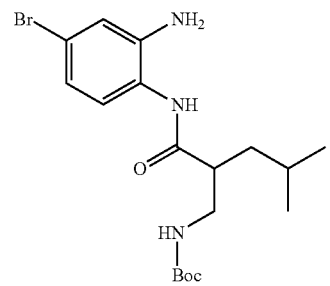 [SMILES: CC(C)CC(CNC(=O)OC(C)(C)C)C(=O)Nc1ccc(Br)cc1N]

Part E. tert-butyl 2-(2-amino-4-bromophenylcarbamoyl)-4-methylpentylcarbamate

Prepared in a similar fashion as described in Example 59, Part B using 4-bromobenzene-1,2-diamine (1.3 g, 6.9 mmol) and 2-((tert-butoxycarbonylamino)methyl)-4-methylpentanoic acid (3.4 g, 13.9 mmol) to afford the title compound (2.5 g, 6.05 mmol) as a brown oil. The crude product was taken to the next step without purification. LCMS (ESI) m/e 416.0 [(M+H)$^+$, calcd for $C_{18}H_{29}BrN_3O_3$, 414.1]; LC/MS retention time (method B): $t_R$=1.95 min.

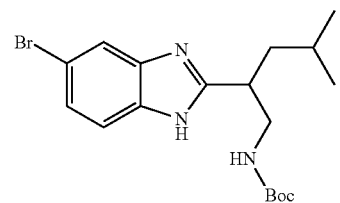

Part F. tert-butyl 2-(5-bromo-1H-benzo[d]imidazol-2-yl)-4-methylpentylcarbamate Prepared in a similar fashion as described in Example 59, Part C using tert-butyl 2-(2-amino-4-bromophenylcarbamoyl)-4-methylpentylcarbamate to afford the title compound (2.5 g, 6.3 mmol, 77% yield). The crude product was taken for next step without purification. LCMS (ESI) m/e 396.0 (Bromo pattern) [(M+H)$^+$, calcd for $C_{18}H_{27}BrN_3O_2$, 396.1]; LC/MS retention time (method B): $t_R$=1.66 min.

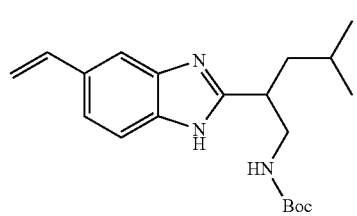 [SMILES: C=Cc1ccc2[nH]c(C(CNC(=O)OC(C)(C)C)CC(C)C)nc2c1]

Part G. tert-butyl 4-methyl-2-(5-vinyl-1H-benzo[d]imidazol-2-yl)pentylcarbamate To a solution of tert-butyl 2-(5-bromo-1H-benzo[d]imidazol-2-yl)-4-methylpentylcarbamate (2.0 g, 5.0 mmol) in 2-propanol (15 mL) and water (3 mL) was added potassium vinyl trifluoroborate (1.4 g, 10.6 mmol) and diisopropyl ethyl amine (7.8 mL, 15 mmol). Nitrogen gas was bubbled through the stirred solution for 5 min. PdCl$_2$(dppf) (408 mg, 0.5 mmol) was added nitrogen bubbling was continued for another 5 min. The reaction mixture was then heated at 95° C. overnight. The reaction mixture was cooled to room temperature, concentrated under reduced pressure to remove volatiles and diluted with water (50 mL). The aqueous layer was extracted with ethyl acetate (3×100 mL). The combined organic layers were washed with brine (50 mL). The organic layer was dried over Na$_2$SO$_4$, filtered and concentrated under reduced pressure to afford the title compound (400 mg, 1.17 mmol, 23% crude yield). This was taken to the next step without purification. LCMS (ESI) m/e 344.3 [(M+H)$^+$, calcd for $C_{20}H_{30}N_3O_2$, 343.2]; LC/MS retention time (method A): $t_R$=1.89 min.

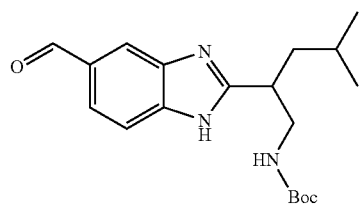 [SMILES: CC(C)CC(CNC(=O)OC(C)(C)C)c1nc2cc(C=O)ccc2[nH]1]

Part H. tert-butyl 2-(5-formyl-1H-benzo[d]imidazol-2-yl)-4-methylpentylcarbamate Prepared in a similar fashion as described in Example 4, Part B_tert-butyl 4-methyl-2-(5-vinyl-1H-benzo[d]imidazol-2-yl) pentylcarbamate. The crude product was purified by column chromatography on silica gel using a gradient of pet ether: ethyl acetate as mobile phase to afford the title compound (200 mg, 0.58 mmol, 38% yield). LCMS (ESI) m/e 346.2 [(M+H)$^+$, calcd for $C_{19}H_{28}N_3O_3$, 346.21]; LC/MS retention time (method A): $t_R$=1.65 min.

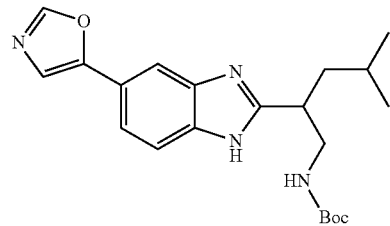 [SMILES: CC(C)CC(CNC(=O)OC(C)(C)C)c1nc2cc(-c3cnco3)ccc2[nH]1]

Part I. tert-butyl 4-methyl-2-(5-(oxazol-5-yl)-1H-benzo[d]imidazol-2-yl)pentylcarbamate Prepared in a similar fashion as described in Example 4, Part C using tert-butyl 2-(5-formyl-1H-benzo[d]imidazol-2-yl)-4-methylpentylcarbamate to afford crude product which was purified by column chromatography on silica gel using a gradient of hexane:ethyl acetate as mobile phase to afford the title compound (130 mg, 0.34 mmol, 63% yield). LCMS (ESI) m/e 385.2 [(M+H)$^+$, calcd for $C_{21}H_{29}N_4O_3$, 385.2]; LC/MS retention time (method A): $t_R$=1.66 min.

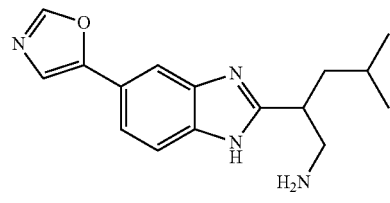 [SMILES: CC(C)CC(CN)c1nc2cc(-c3cnco3)ccc2[nH]1]

Part J. 4-methyl-2-(5-(oxazol-5-yl)-1H-benzo[d]imidazol-2-yl)pentan-1-amine

To a solution of tert-butyl 4-methyl-2-(5-(oxazol-5-yl)-1H-benzo[d]imidazol-2-yl)pentylcarbamate (130 mg, 0.34 mmol) in methanol (1 mL) cooled to 0° C. was added 2 M HCl in diethyl ether (5 mL, 10 mmol) and the reaction mixture was stirred at room temperature for 2 h. The volatiles were removed under reduced pressure to afford crude product which was purified by preparative HPLC (0.1% HCl in water and acetonitrile) to afford the title compound (15 mg, 0.053 mmol, 16% yield) which was isolated as HCl salt. $^1$H NMR (400 MHz, CD$_3$OD) δ 8.37 (s, 1H), 8.17 (s, 1H), 8.04 (dd, J=8.8, 1.2 Hz, 1H), 7.93 (d, J=8.4 Hz, 1H), 7.74 (s, 1H), 3.84-3.89 (m, 1H), 3.50-3.62 (m, 2H), 1.83-2.00 (m, 2H), 1.40-1.45 (m, 1H), 1.05 (d, J=6.4 Hz, 3H), 0.97 (d, J=6.8 Hz, 3H) ppm; LCMS (ESI) m/e 283.2 [(M-H)$^-$, calcd for $C_{16}H_{19}N_4O$, 283.2]; LC/MS retention time (method A): $t_R$=1.11 min; HPLC retention time (method S): $t_R$=8.25 min; HPLC retention time (method T): $t_R$=8.66 min.

Example 66

3-methyl-1-(5-(pyridin-4-yl)-1H-benzo[d]imidazol-2-yl)-N-(2,2,2-trifluoroethyl)butan-1-amine

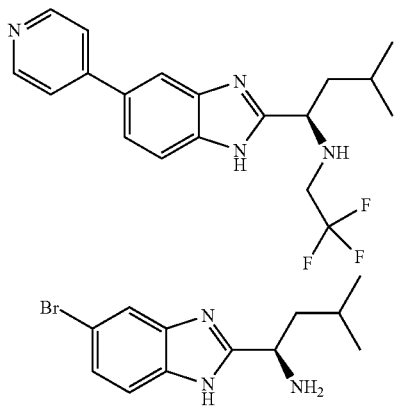

Part A. (R)-1-(5-bromo-1H-benzo[d]imidazol-2-yl)-3-methylbutan-1-amine

To a stirred solution of (R)-tert-butyl 1-(5-bromo-1H-benzo[d]imidazol-2-yl)-3-methylbutylcarbamate (preparation described in Example 7, Part C) in dichloromethane (25 mL) was added TFA and the reaction mixture was stirred at RT for 6 h. Later the organic volatiles were evaporated to dryness to afford the title compound (300 mg, 1.07 mmol, 56% yield). The crude product was taken to next step without purification. LCMS (ESI) m/e 284.7 (Bromo pattern) [(M+H)$^+$, calcd for $C_{12}H_{17}BrN_3$, 282.05]; LC/MS retention time (method D): $t_R$=0.68 min.

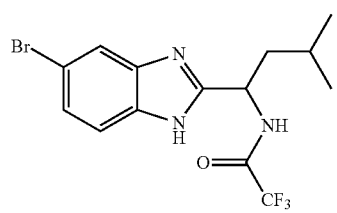 [SMILES: CC(C)CC(NC(=O)C(F)(F)F)c1nc2cc(Br)ccc2[nH]1]

Part B. (R)-N-(1-(5-bromo-1H-benzo[d]imidazol-2-yl)-3-methylbutyl)-2,2,2-trifluoroacetamide To a solution of (R)-1-(5-bromo-1H-benzo[d]imidazol-2-yl)-3-methylbutan-1-amine-TFA (300 mg, 1.0 mmol) in dichloromethane (15 mL) at 0° C. was added diisopropyl ethyl amine (530 mg, 3.0 mmol) and stirred for 15 min. Later trifluoroacetic anhydride (330 mg, 1.5 mmol) was added slowly and the reaction mixture was stirred at room temperature for 12 h. The reaction mixture was quenched with water (15 mL). The aqueous layer was extracted with dichloromethane (2×20 mL). The combined organic layers were dried over Na$_2$SO$_4$, filtered and concentrated under reduced pressure to afford the title compound (380 mg, 1.01 mmol, quantitative yield). LCMS (ESI) m/e 378.0 (Bromo pattern) [(M+H)$^+$, calcd for $C_{14}H_{16}BrF_3N_3O$, 378.0]; LC/MS retention time (method A): $t_R$=1.84 min.

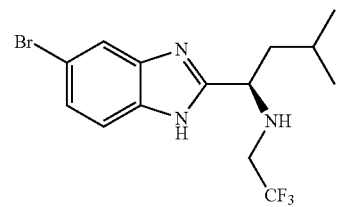

Part C. (R)-1-(5-bromo-1H-benzo[d]imidazol-2-yl)-3-methyl-N-(2,2,2-trifluoroethyl)butan-1-amine To a solution of (R)-N-(1-(5-bromo-1H-benzo[d]imidazol-2-yl)-3-methylbutyl)-2,2,2-trifluoroacetamide (200 mg, 0.52 mmol) in THF (25 mL), borane in THF (10 mL) was added dropwise at RT, later the reaction mixture was heated to 80° C. and stirred for 10 h. The reaction mixture was cooled to RT and quenched with methanol (50 mL) and stirred for 1.5 h. The organic volatiles were evaporated to dryness. To the residue was added water (25 mL). The aqueous layer was extracted with ethyl acetate (2×30 mL). The combined organic layers were dried over Na$_2$SO$_4$, filtered and concentrated under reduced pressure to afford the title compound (200 mg, 0.5 mmol, quantitative yield). LCMS (ESI) m/e 364.0 [(M+H)$^+$, calcd for $C_{14}H_{18}BrF_3N_3$, 364.1]; LC/MS retention time (method A): $t_R$=1.96 min.

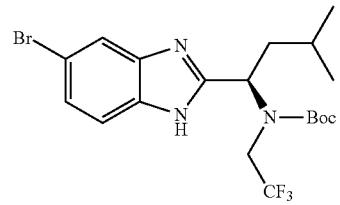 [SMILES: CC(C)C[C@H](c1nc2cc(Br)ccc2[nH]1)N(CC(F)(F)F)C(=O)OC(C)(C)C]

Part D. (R)-tert-butyl 1-(5-bromo-1H-benzo[d]imidazol-2-yl)-3-methylbutyl(2,2,2-trifluoroethyl)carbamate To a solution of (R)-1-(5-bromo-1H-benzo[d]imidazol-2-yl)-3-methyl-N-(2,2,2-trifluoroethyl)butan-1-amine (150 mg, 0.41 mmol) in THF (10 mL), diisopropyl ethyl amine (0.4 mL, 2.2 mmol) was added at RT followed by addition of DMAP (0.6 mg, 0.05 mmol). The reaction mixture was stirred at RT for 5 min. Boc-anhydride (360 mg, 0.56 mmol) was added and the reaction mixture was stirred at RT overnight. The reaction mixture was diluted with water (25 mL). The aqueous layer was extracted with ethyl acetate (2×30 mL). The combined organic layers were dried over Na$_2$SO$_4$, filtered and concentrated under reduced pressure to afford the title compound (210 mg, 0.4 mmol, quantitative yield). The crude product was taken to next step without purification. LCMS (ESI) m/e 464.2 [(M+H)$^+$, calcd for $C_{19}H_{26}BrF_3N_3O_2$, 464.11]; LC/MS retention time (method A): $t_R$=2.67 min.

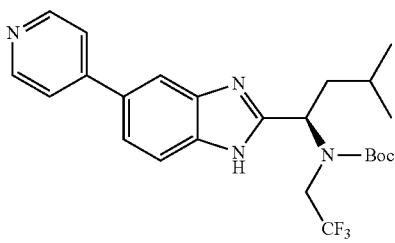 [SMILES: CC(C)C[C@H](c1nc2cc(-c3ccncc3)ccc2[nH]1)N(CC(F)(F)F)C(=O)OC(C)(C)C]

Part E. (R)-tert-butyl 3-methyl-1-(5-(pyridin-4-yl)-1H-benzo[d]imidazol-2-yl) butyl (2,2,2-trifluoroethyl)carbamate Prepared in a similar fashion as described in Example 1, Part B using (R)-tert-butyl 1-(5-bromo-1H-benzo[d]imidazol-2-yl)-3-methylbutyl(2,2,2-trifluoroethyl)carbamate and pyridine-4-boronic acid. The crude product was purified by column chromatography on silica gel using gradient ethyl acetate in hexane mobile phase to afford the title compound (120 mg, 0.33 mmol, 60% yield). LCMS (ESI) m/e 463.2 [(M+H)$^+$, calcd for $C_{24}H_{30}F_3N_4O_2$ 463.2]; LC/MS retention time (method A): $t_R$ 1.64 min.

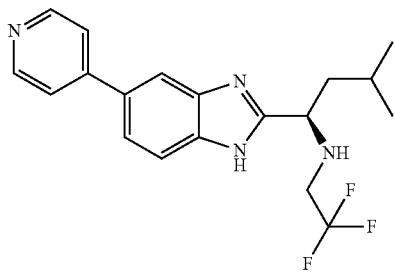 [SMILES: CC(C)C[C@@H](NCC(F)(F)F)c1nc2cc(-c3ccncc3)ccc2[nH]1]

Part F. 3-methyl-1-(5-(pyridin-4-yl)-1H-benzo[d]imidazol-2-yl)-N-(2,2,2-trifluoroethyl)butan-1-amine Prepared in a similar fashion as described in Example 64, Part H using tert-butyl 3-methyl-1-(5-(pyridin-4-yl)-1H-benzo[d]imidazol-2-yl)butyl(2,2,2-trifluoroethyl)carbamate. The crude compound was purified by Preparative HPLC (0.05% TFA in water and acetonitrile) to afford the title compound (18 mg, 0.05 mmol, 28% yield) as a yellow solid which was isolated as TFA salt. $^1$H NMR (400 MHz, CD$_3$OD) δ 8.86-8.90 (m, 2H) 8.38 (d, J=6.8 Hz, 2H) 8.31 (d, J=1.2 Hz, 1H) 8.06 (dd, J=8.4, 1.6 Hz, 1H) 7.94 (d, J=8.8 Hz, 1H) 4.39-4.43 (m, 1H) 3.35-3.41 (m, 1H) 3.25-3.31 (m, 1H) 1.80-1.94 (m, 1H) 1.72-1.79 (m, 2H) 1.00-1.05 (m, 6H) ppm; LCMS (ESI) m/e 363.2 [(M+H)$^+$, calcd for $C_{19}H_{22}F_3N_4$, 363.17]; LC/MS retention time (method B): $t_R$=1.19 min; HPLC retention time (method S): $t_R$=9.18 min; HPLC retention time (method T): $t_R$=10.19 min.

Example 67

4-methyl-2-(5-(pyridin-4-yl)-1H-benzo[d]imidazol-2-yl) pentan-1-amine

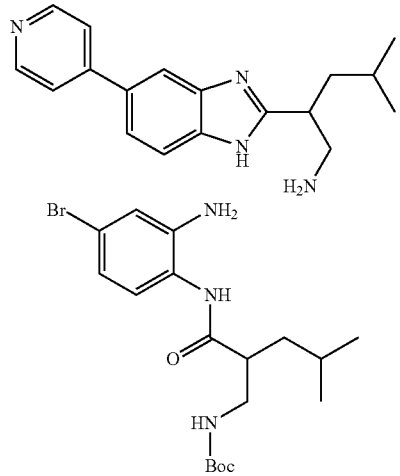

Part A. tert-butyl 2-(2-amino-4-bromophenylcarbamoyl)-4-methylpentylcarbamate

To a solution of 4-bromobenzene-1,2-diamine (0.5 g, 2.67 mmol) in DMF (10 mL), 2-((tert-butoxycarbonylamino)methyl)-4-methylpentanoic acid (0.785 g, 3.207 mmol), HATU (1.219 g, 3.207 mmol) and diisopropyl ethyl amine (1.906 mL, 10.69 mmol) were added at 0° C. The reaction mixture was allowed to stir at RT for 2 h. The reaction mixture was diluted with water (50 mL). The aqueous layer was extracted with ethyl acetate (3×50 mL). The combined organic layers were washed with brine (50 mL). The organic layer was dried over Na$_2$SO$_4$, filtered and concentrated under reduced pressure. The crude product was recrystallized from dichloromethane and hexane to afford the title compound (0.8 g, 1.94 mmol, 72% yield). LCMS (ESI) m/e 414.2 [(M+H)$^+$, calcd for $C_{18}H_{29}BrN_3O_3$, 414.1]; LC/MS retention time (method A): $t_R$=1.93 min.

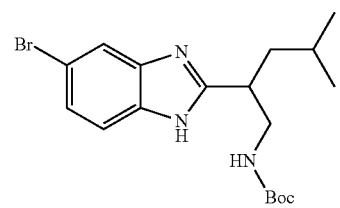 [SMILES: CC(C)CC(CNC(=O)OC(C)(C)C)c1nc2cc(Br)ccc2[nH]1]

Part B. tert-butyl 2-(5-bromo-1H-benzo[d]imidazol-2-yl)-4-methylpentylcarbamate

A suspension of tert-butyl 2-(2-amino-4-bromophenylcarbamoyl)-4-methylpentylcarbamate (0.8 g, 1.93 mmol) in acetic acid (16 mL) was refluxed at 95° C. for 2 h. The reaction mixture was cooled to RT. The acetic acid was removed under reduced pressure. The residue was diluted with water (50 mL). The aqueous layer was extracted with ethyl acetate (3×50 mL). The combined organic layers were washed with brine (50 mL), dried over Na$_2$SO$_4$, filtered and concentrated under reduced pressure. The crude product was washed with 10% dichloromethane in hexane to afford the title compound (0.5 g, 1.26 mmol, 65% yield). LCMS (ESI) m/e 396.2 [(M+H)$^+$, calcd for C$_{18}$H$_{27}$BrN$_3$O$_2$, 396.1]; LC/MS retention time (method A): t$_R$=1.95 min.

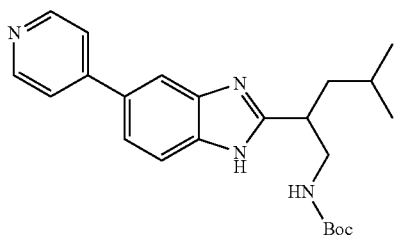 [SMILES: CC(C)CC(CNC(=O)OC(C)(C)C)c1nc2cc(-c3ccncc3)ccc2[nH]1]

Part C. tert-butyl 4-methyl-2-(5-(pyridin-4-yl)-1H-benzo[d]imidazol-2-yl) pentylcarbamate To a suspension of tert-butyl 2-(5-bromo-1H-benzo[d]imidazol-2-yl)-4-methylpentylcarbamate (250 mg, 0.630 mmol) in dioxane (4 mL) and water (1 mL) pyridine-4-boronic acid (77 mg, 1.261 mmol) and Cs$_2$CO$_3$ 616 mg, 1.892 mmol) were added in microwave vial. Nitrogen gas was bubbled through the stirred suspension for 5 min. Pd(PPh$_3$)$_4$ (36 mg, 0.031 mmol) was added. Nitrogen gas was bubbled through the stirred suspension for 5 min. The reaction mixture was then heated at 110° C. for 4 h in a microwave. The reaction mixture was cooled to room temperature and diluted with water. The aqueous layer was extracted with ethyl acetate (3×50 mL). The combined organic layers were washed with brine (50 mL). The organic layer was dried over Na$_2$SO$_4$, filtered and concentrated under reduced pressure. The crude product was purified by preparative TLC on silica gel using 80% ethyl acetate in pet ether mobile phase to afford the title compound (50 mg, 0.13 mmol, 20% yield). LCMS (ESI) m/e 395.2 [(M+H)$^+$, calcd for C$_{23}$H$_{31}$N$_4$O$_2$, 395.2]; LC/MS retention time (method A): t$_R$=1.68 min.

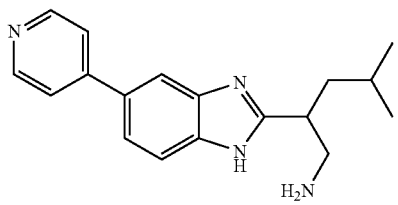 [SMILES: CC(C)CC(CN)c1nc2cc(-c3ccncc3)ccc2[nH]1]

Part D. 4-methyl-2-(5-(pyridin-4-yl)-1H-benzo[d]imidazol-2-yl)pentan-1-amine

Prepared in a similar fashion as described in Example 64, Part H using tert-butyl 4-methyl-2-(5-(pyridin-4-yl)-1H-benzo[d]imidazol-2-yl)pentylcarbamate. The crude product was purified by preparative HPLC (0.05% TFA in water and methanol) to afford the title compound (30 mg, 0.1 mmol, 45% yield) as a brownish yellow oil which was isolated as TFA salt. $^1$H NMR (400 MHz, CD3OD) δ 8.84 (d, J=6.0 Hz, 2H), 8.43-8.45 (m, 2H), 8.27 (d, J=1.6 Hz, 1H), 7.96 (dd, J=8.4, 1.6 Hz, 1H), 7.84 (d, J=8.8 Hz, 1H), 3.49-3.55 (m, 1H), 3.38-3.46 (m, 2H), 1.87-1.93 (m, 1H), 1.68-1.75 (m, 1H), 1.48-1.52 (m, 1H), 1.02 (d, J=6.8 Hz, 3H), 0.96 (d, J=6.8 Hz, 3H) ppm; LCMS (ESI) m/e 295.2 [(M+H)$^+$, calcd for C$_{18}$H$_{23}$N$_4$, 295.2]; LC/MS retention time (method B): t$_R$=1.01 min; HPLC retention time (method S): t$_R$=6.62 min; HPLC retention time (method T): t$_R$=7.25 min.

Example 68

(R)-cyclopentyl (6-methoxy-5-(oxazol-5-yl)-1H-benzo[d]imidazol-2-yl) methanamine

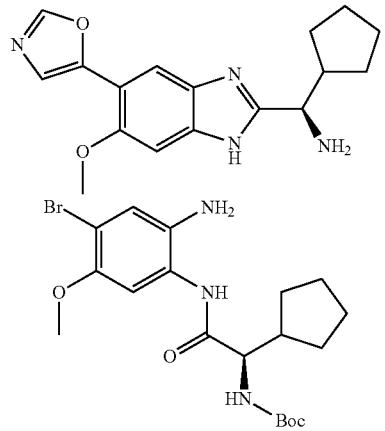

Part A. (R)-tert-butyl-(2-amino-4-bromo-5-methoxyphenylamino)-1-cyclopentyl-2-oxoethylcarbamate Prepared in a similar fashion as described in Example 59, Part B using 4-bromo-5-methoxybenzene-1,2-diamine and (R)-2-(tert-butoxycarbonylamino)-2-cyclopentylacetic acid to afford the title compound (3 g, 1.83 mmol, 33% yield) as a crude solid. This was taken to the next step without purification. LCMS (ESI) m/e 442.2 [(M+H)$^+$, calcd for C$_{19}$H$_{29}$BrN$_3$O$_4$, 442.1]; LC/MS retention time (method A): t$_R$=1.88 min.

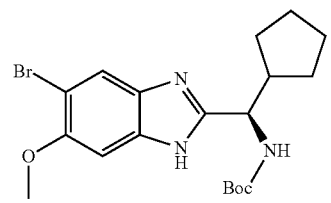 [SMILES: COc1cc2[nH]c([C@H](NC(=O)OC(C)(C)C)C3CCCC3)nc2cc1Br]

Part B. (R)-tert-butyl (5-bromo-6-methoxy-1H-benzo[d]imidazol-2-yl) (cyclopentyl)methylcarbamate Prepared in a similar fashion as described in Example 59, Part C using (R)-tert-butyl-(2-amino-4-bromo-5-methoxyphenylamino)-1-cyclopentyl-2-oxoethylcarbamate to afford title compound (1.1 g, 2.6 mmol, 38% yield) after purification by column chromatography on silica gel (using gradient of ethyl acetate and pet ether). LCMS (ESI) m/e 426.2 (Bromo pattern) [(M+H)$^+$, calcd for C$_{19}$H$_{27}$BrN$_3$O$_3$, 424.1]; LC/MS retention time (method A): t$_R$=1.91 min.

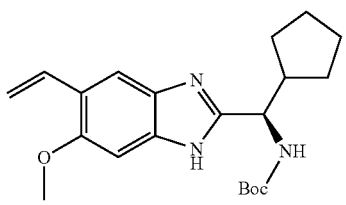 [SMILES: C=Cc1cc2nc([C@H](NC(=O)OC(C)(C)C)C3CCCC3)[nH]c2cc1OC]

Part C. (R)-tert-butyl cyclopentyl(6-methoxy-5-vinyl-1H-benzo[d]imidazol-2-yl) methylcarbamate Prepared in a similar fashion as described in Example 21, Part E using (R)-tert-butyl (5-bromo-6-methoxy-1H-benzo[d]imidazol-2-yl)(cyclopentyl)methylcarbamate to afford crude product which was purified by column chromatography on silica gel using hexane:ethyl acetate as mobile phase to afford the title compound (620 mg, 1.25 mmol, 76% yield). LCMS (ESI) m/e 372.2 [(M+H)$^+$, calcd for $C_{21}H_{30}N_3O_3$, 372.2]; LC/MS retention time (method A): $t_R$=1.94 min.

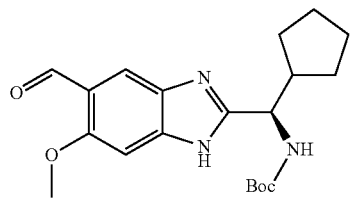 [SMILES: COc1cc2[nH]c([C@H](NC(=O)OC(C)(C)C)C3CCCC3)nc2cc1C=O]

Part D. (R)-tert-butyl cyclopentyl(5-formyl-6-methoxy-1H-benzo[d]imidazol-2-yl)methylcarbamate Prepared in a similar fashion as described in Example 4, Part B using (R)-tert-butyl cyclopentyl(6-methoxy-5-vinyl-1H-benzo[d]imidazol-2-yl)methylcarbamate to afford crude product which was purified by column chromatography on silica gel using hexane:ethyl acetate as mobile phase to afford the title compound (230 mg, 0.61 mmol, 38% yield). LCMS (ESI) m/e 374.2 [(M+H)$^+$, calcd for $C_{20}H_{28}N_3O_4$, 374.2]; LC/MS retention time (method A): $t_R$=1.69 min.

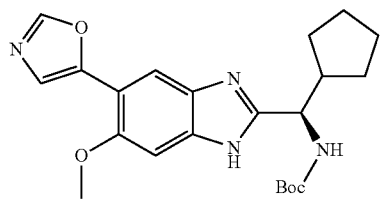 [SMILES: COc1cc2[nH]c([C@H](NC(=O)OC(C)(C)C)C3CCCC3)nc2cc1-c1cnco1]

Part E. (R)-tert-butyl cyclopentyl(6-methoxy-5-(oxazol-5-yl)-1H-benzo[d]imidazol-2-yl)methylcarbamate Prepared in a similar fashion as described in Example 4, Part C using (R)-tert-butyl cyclopentyl(5-formyl-6-methoxy-1H-benzo[d]imidazol-2-yl)methylcarbamate to afford crude product which was purified by column chromatography on silica gel using hexane:ethyl acetate as mobile phase to afford the title compound (150 mg, 0.36 mmol, 61% yield). LCMS (ESI) m/e 413.9 [(M+H)$^+$, calcd for $C_{22}H_{29}N_4O_4$, 413.2]; LC/MS retention time (method D): $t_R$=0.75 min.

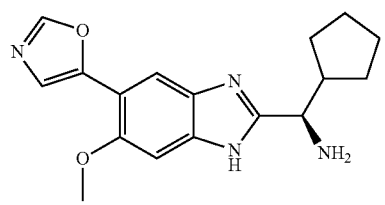 [SMILES: COc1cc2[nH]c([C@H](N)C3CCCC3)nc2cc1-c1cnco1]

Part F. (R)-cyclopentyl(6-methoxy-5-(oxazol-5-yl)-1H-benzo[d]imidazol-2-yl)methanamine Prepared in a similar fashion as described in Example 64. Part H using (R)-tert-butyl cyclopentyl(6-methoxy-5-(oxazol-5-yl)-1H-benzo[d]imidazol-2-yl)methylcarbamate.

The crude was purified by preparative HPLC (0.1% HCl in water and acetonitrile) to afford the title compound (50 mg, 0.16 mmol, 55% yield) as a yellow solid which was isolated as HCl salt. $^1$H NMR (400 MHz, CD$_3$OD) δ 8.44 (s, 1H), 8.19 (s, 1H), 7.72 (s, 1H), 7.47 (s, 1H), 4.64 (d, J=6.4 Hz, 1H), 4.13 (s, 3H), 2.73-2.79 (m, 1H), 2.12-2.17 (m, 1H), 1.69-1.88 (m, 5H), 1.57-1.64 (m, 1H), 1.31-1.38 (m, 1H) ppm; LCMS (ESI) m/e 313.2 [(M+H)$^+$, calcd for $C_{17}H_{21}N_4O_2$, 313.2]; LC/MS retention time (method A): $t_R$=1.21 min; HPLC retention time (method V): $t_R$=5.50 min; HPLC retention time (method U): $t_R$=5.04 min; Chiral SFC retention time (method B): $t_R$=2.2 min.

Example 69

5-(2-(cyclopentylmethyl)-6-methoxy-1H-benzo[d]imidazol-5-yl) oxazole

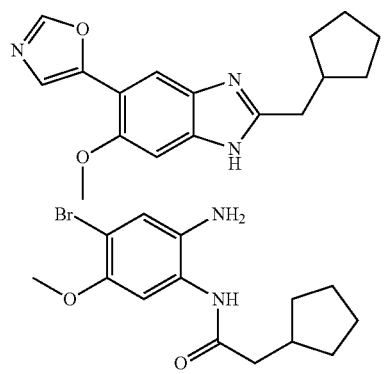

Part A. N-(2-amino-4-bromo-5-methoxyphenyl)-2-cyclopentylacetamide

Prepared in a similar fashion as described in Example 59, Part B using 4-bromo-5-methoxybenzene-1,2-diamine and 2-cyclopentylacetic acid to afford the title compound (1.3 g, 3.99 mmol, 87% yield). The crude was taken to the next step without purification. LCMS (ESI) m/e 327.0 [(M+H)+, calcd for $C_{14}H_{20}BrN_2O_2$, 327.1]; LC/MS retention time (method A): $t_R$=1.69 min.

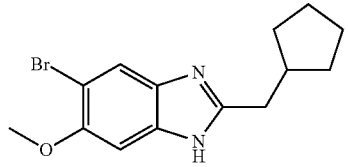 [SMILES: COc1cc2[nH]c(CC3CCCC3)nc2cc1Br]

Part B. 5-bromo-2-(cyclopentylmethyl)-6-methoxy-1H-benzo[d]imidazole

Prepared in a similar fashion as described in Example 59, Part C using N-(2-amino-4-bromo-5-methoxyphenyl)-2-cyclopentylacetamide to afford the title compound (800 mg, 2.59 mmol, 65% yield). LCMS (ESI) m/e 309.2 [(M+H)+, calcd for $C_{14}H_{18}BrN_2O$, 309.1]; LC/MS retention time (method A): $t_R$=1.75 min.

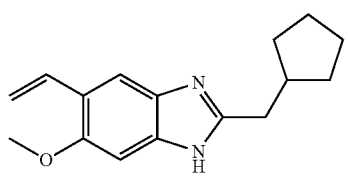 [SMILES: C=Cc1cc2nc(CC3CCCC3)[nH]c2cc1OC]

Part C. 2-(cyclopentylmethyl)-6-methoxy-5-vinyl-1H-benzo[d]imidazole

Prepared in a similar fashion as described in Example 4, Part A using 5-bromo-2-(cyclopentylmethyl)-6-methoxy-1H-benzo[d]imidazole to afford the title compound (350 mg, 1.37 mmol, 70.6% yield). $^1$H NMR (400 MHz, DMSO-$d_6$) δ 7.01 (m, 2H), 5.75 (m, 1H), 5.15 (d, J=12.4 Hz, 1H), 5 (m, 1H), 3.8 (s, 3H), 2.75 (d, J=7.6 Hz, 2H), 2.3 (m, 1H), 1.5-1.8 (m, 6H), 1.2 (m, 2H) ppm. LCMS (ESI) m/e 257.2 [(M+H)+, calcd for $C_{16}H_{21}N_2O$, 257.2]; LC/MS retention time (method A): $t_R$=1.78 min.

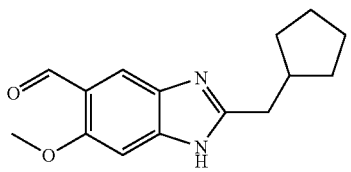 [SMILES: COc1cc2[nH]c(CC3CCCC3)nc2cc1C=O]

Part D. 2-(cyclopentylmethyl)-6-methoxy-1H-benzo[d]imidazole-5-carbaldehyde

Prepared in a similar fashion as described in Example 4, Part B using 2-(cyclopentylmethyl)-6-methoxy-5-vinyl-1H-benzo[d]imidazole to afford the title compound (320 mg, 1.24 mmol, 91% yield) after purification by column chromatography on silica gel (using gradient of ethyl acetate and pet ether). $^1$H NMR (400 MHz, CDCl$_3$) δ 10.5 (s, 1H), 7.9 (s, 1H), 7.1 (s, 1H), 3.9 (s, 3H), 2.9 (d, J=6.8 Hz, 2H), 2.35 (m, 1H), 1.5-1.9 (m, 6H), 1.2 (m, 2H) ppm.

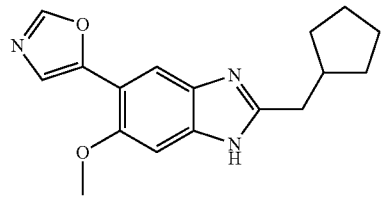 [SMILES: COc1cc2[nH]c(CC3CCCC3)nc2cc1-c1cnco1]

Part E. 5-(2-(cyclopentylmethyl)-6-methoxy-1H-benzo[d]imidazol-5-yl) oxazole

Prepared in a similar fashion as described in Example 4, Part C using 2-(cyclopentylmethyl)-6-methoxy-1H-benzo[d]imidazole-5-carbaldehyde to afford the title compound (100 mg, 0.34 mmol, 59% yield) as an off white solid after purification by column chromatography on silica gel (using gradient of ethyl acetate and pet ether. $^1$H NMR (400 MHz, CD$_3$OD) δ 8.25 (s, 1H), 7.93 (s, 1H), 7.54 (s, 1H), 7.22 (s, 1H), 4.04 (s, 3H), 2.91 (d, J=7.6 Hz, 2H), 2.41-2.45 (m, 1H), 1.80-1.85 (m, 2H), 1.72-1.75 (m, 2H), 1.62-1.65 (m, 2H), 1.32-1.37 (m, 2H) ppm; LCMS (ESI) m/e 298.2 [(M+H)+, calcd for $C_{17}H_{20}N_3O_2$, 298.2]; LC/MS retention time (method A): $t_R$=1.56 min; HPLC retention time (method U): $t_R$=5.43 min; HPLC retention time (method V): $t_R$=6.53 min; Chiral SFC retention time (method B): $t_R$=2.2 min.

Example 70

(R)-2-cyclopropyl-1-(5-(pyridin-4-yl)-1H-benzo[d]imidazol-2-yl) ethanamine

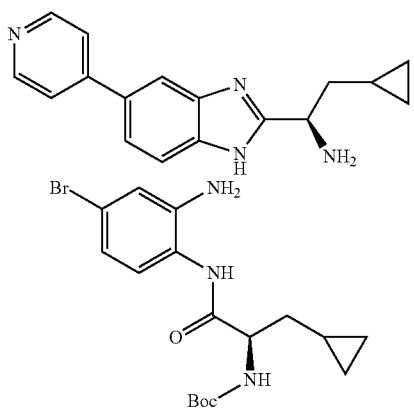

Part A. (R)-tert-butyl 1-(2-amino-4-bromophenylamino)-3-cyclopropyl-1-oxopropan-2-ylcarbamate Prepared in a similar fashion as described in Example 59, Part B using 4-bromobenzene-1,2-diamine and (R)-2-(tert-butoxycarbonylamino)-3-cyclopropylpropanoic acid to afford the title compound (1.3 g, 3.29 mmol, 99% yield) as oily liquid. The crude product was taken to next step without purification. LCMS (ESI) m/e 396.0 [(M–H)−, calcd for $C_{17}H_{23}BrN_3O_3$, 396.1]; LC/MS retention time (method A): $t_R$=1.84 min.

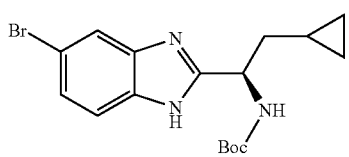

Part B. (R)-tert-butyl 1-(5-bromo-1H-benzo[d]imidazol-2-yl)-2-cyclopropylethylcarbamate Prepared in a similar fashion as described in Example 59, Part C using (R)-tert-butyl 1-(2-amino-4-bromophenylamino)-3-cyclopropyl-1-oxopropan-2-ylcarbamate. The crude product was purified by column chromatography on silica gel using pet ether:ethyl acetate mobile phase to afford the title compound (600 mg, 1.56 mmol, 32% yield) as an off white solid. $^1$H NMR (400 MHz, DMSO-$d_6$) δ 12.37 (m, 1H), 7.63-7.73 (m, 1H), 7.42-7.43 (m, 1H), 7.30-7.33 (m, 2H), 4.80-4.82 (m, 1H), 1.74-1.91 (m, 2H), 1.40 (s, 9H), 0.72-0.97 (m, 1H), 0.32-0.40 (m, 2H), 0.24-0.12 (m, 2H) ppm.

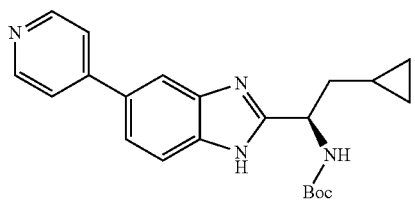 [SMILES: CC(C)(C)OC(=O)N[C@H](CC1CC1)c1nc2cc(-c3ccncc3)ccc2[nH]1]

Part C. (R)-tert-butyl 2-cyclopropyl-1-(5-(pyridin-4-yl)-1H-benzo[d]imidazol-2-yl) ethylcarbamate Prepared in a similar fashion as described in Example 1, Part B using (R)-tert-butyl 1-(5-bromo-1H-benzo[d]imidazol-2-yl)-2-cyclopropylethylcarbamate and pyridine-4-boronic acid to afford the title compound (170 mg, 0.45 mmol, 34% yield) as an off white solid. LCMS (ESI) m/e 379.2 [(M+H)$^+$, calcd for $C_{22}H_{27}N_4O_2$, 379.2]; LC/MS retention time (method A): $t_R$=1.65 min.

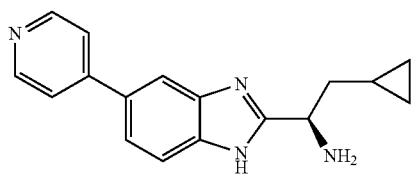 [SMILES: N[C@H](CC1CC1)c1nc2cc(-c3ccncc3)ccc2[nH]1]

Part D. (R)-2-cyclopropyl-1-(5-(pyridin-4-yl)-1H-benzo[d]imidazol-2-yl)ethanamine Prepared in a similar fashion as described in Example 7, Part E using (R)-tert-butyl 2-cyclopropyl-1-(5-(pyridin-4-yl)-1H-benzo[d]imidazol-2-yl) ethylcarbamate to afford the title compound (50 mg, 0.18 mmol, 40% yield) as light yellow solid. $^1$H NMR (400 MHz, CD3OD) δ 8.58-8.60 (m, 2H) 7.96 (s, 1H) 7.78-7.79 (m, 2H) 7.66-7.71 (m, 2H) 4.30-4.33 (m, 1H) 1.84-1.89 (m, 2H) 0.73-0.75 (m, 1H) 0.40-0.50 (m, 2H) 0.09-0.13 (m, 1H), 0.03 (m, 1H) ppm; LCMS (ESI) m/e 279.2 [(M+H)$^+$, calcd for $C_{17}H_{19}N_4$, 279.2]; LC/MS retention time (method A): $t_R$=1.13 min; HPLC retention time (method T): $t_R$=7.05 min; HPLC retention time (method S): $t_R$=6.28 min; Chiral HPLC retention time (method B): $t_R$=3.55 min.

Example 71

2-cyclopentyl-1-(6-methoxy-5-(oxazol-5-yl)-1H-benzo[d]imidazol-2-yl)ethanamine

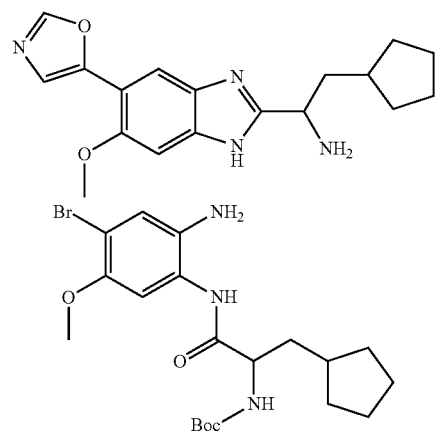

Part A. tert-butyl 1-(2-amino-4-bromo-5-methoxyphenylamino)-3-cyclopentyl-1-oxopropan-2-ylcarbamate Prepared in a similar fashion as described in Example 59, Part B using 4-bromo-5-methoxybenzene-1,2-diamine (1.0 g, 4.60 mmol) and N-Boc-DL-cyclopentylalanine to afford the title compound (3 g, 6.59 mmol, 87% yield). The crude product was taken for next step without purification. LCMS (ESI) m/e 456.0 [(M+H)$^+$, calcd for $C_{20}H_{31}BrN_3O_4$, 456.1]; LC/MS retention time (method F): $t_R$=1.99 min.

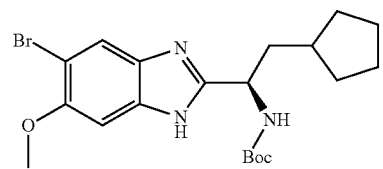 [SMILES: COc1cc2[nH]c([C@@H](CC3CCCC3)NC(=O)OC(C)(C)C)nc2cc1Br]

Part B. tert-butyl 1-(5-bromo-6-methoxy-1H-benzo[d]imidazol-2-yl)-2-cyclopentylethylcarbamate Prepared in a similar fashion as described in Example 59, Part C using tert-butyl 1-(2-amino-4-bromo-5-methoxyphenylamino)-3-cyclopentyl-1-oxopropan-2-ylcarbamate. The crude product was purified by column chromatography using pet ether:ethyl acetate mobile phase to afford the title compound (0.70 g, 1.60 mmol, 27% yield). LCMS (ESI) m/e 438.2 [(M+H)$^+$, calcd for $C_{20}H_{29}BrN_3O_3$, 438.1]; LC/MS retention time (method A): $t_R$=2.03 min.

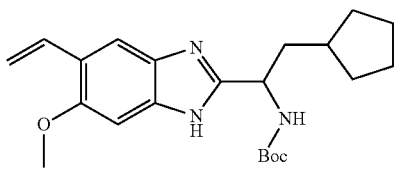 [SMILES: C=Cc1cc2nc(C(CC3CCCC3)NC(=O)OC(C)(C)C)[nH]c2cc1OC]

Part C. tert-butyl 2-cyclopentyl-1-(6-methoxy-5-vinyl-1H-benzo[d]imidazol-2-yl) ethylcarbamate Prepared in a similar fashion as described in Example 4, Part A using tert-butyl 1-(5-bromo-6-methoxy-1H-benzo[d]imidazol-2-yl)-2-cyclopentylethylcarbamate to afford the title compound (0.20 g, 0.52 mmol, 28% yield) after purification by column chromatography using pet ether:ethyl acetate mobile phase. LCMS (ESI) m/e 386.2 [(M+H)$^+$, calcd for $C_{22}H_{32}N_3O_3$, 386.2]; LC/MS retention time (method A): $t_R$=2.02 min.

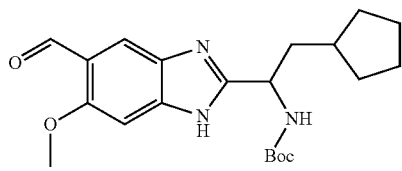 [SMILES: COc1cc2[nH]c(C(CC3CCCC3)NC(=O)OC(C)(C)C)nc2cc1C=O]

Part D. tert-butyl 2-cyclopentyl-1-(5-formyl-6-methoxy-1H-benzo[d]imidazol-2-yl) ethylcarbamate Prepared in a similar fashion as described in Example 4, Part B using tert-butyl 2-cyclopentyl-1-(6-methoxy-5-vinyl-1H-benzo[d]imidazol-2-yl)ethylcarbamate to afford the title compound (0.20 g, 0.52 mmol, 49% yield). The crude product was taken to next step without purification. LCMS (ESI) m/e 388.2 [(M+H)$^+$, calcd for $C_{21}H_{30}N_3O_4$, 388.2]; LC/MS retention time (method A): $t_R$=1.84 min.

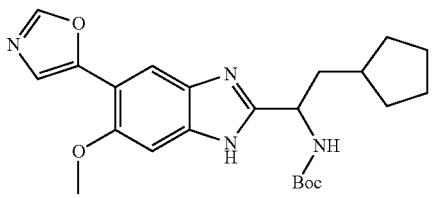 [SMILES: COc1cc2[nH]c(C(CC3CCCC3)NC(=O)OC(C)(C)C)nc2cc1-c1cnco1]

Part E. tert-butyl 2-cyclopentyl-1-(6-methoxy-5-(oxazol-5-yl)-1H-benzo[d]imidazol-2-yl) ethylcarbamate Prepared in a similar fashion as described in Example 4, Part C using tert-butyl 2-cyclopentyl-1-(5-formyl-6-methoxy-1H-benzo[d]imidazol-2-yl)ethylcarbamate. The crude product was purified by preparative TLC on silica gel using 60% ethyl acetate in hexane to afford the title compound (35 mg, 0.08 mmol, 40% yield). LCMS (ESI) m/e 425.2 [(M−H)$^-$, calcd for $C_{23}H_{29}N_4O_4$, 425.2]; LC/MS retention time (method A): $t_R$=1.85 min.

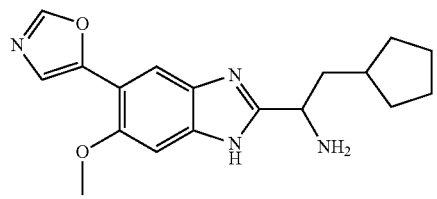 [SMILES: COc1cc2[nH]c(C(N)CC3CCCC3)nc2cc1-c1cnco1]

Part F. 2-cyclopentyl-1-(6-methoxy-5-(oxazol-5-yl)-1H-benzo[d]imidazol-2-yl) ethanamine Prepared in a similar fashion as described in Example 64, Part H using tert-butyl 2-cyclopentyl-1-(6-methoxy-5-(oxazol-5-yl)-1H-benzo[d]imidazol-2-yl)ethylcarbamate to afford the title compound (25 mg, 0.07 mmol, 84% yield) as an off white solid which was isolated as HCl salt. $^1$H NMR (400 MHz, CD$_3$OD) δ 8.37 (s, 1H) 8.12 (s, 1H) 7.66 (s, 1H) 7.39 (s, 1H) 4.69-4.73 (m, 1H) 4.10 (s, 3H) 2.32-2.35 (m, 1H) 2.13-2.16 (m, 1H) 1.84-1.91 (m, 1H) 1.64-1.82 (m, 4H) 1.62 (m, 2H) 1.19-1.31 (m, 2H) ppm; LCMS (ESI) m/e 327.2 [(M+H)$^+$, calcd for $C_{18}H_{23}N_4O_2$, 327.2]; LC/MS retention time (method A): $t_R$=1.39 min; HPLC retention time (method U): $t_R$=5.64 min; HPLC retention time (method V): $t_R$=6.09 min.

Example 72

2-(cyclohexylmethyl)-5-(pyridin-4-yl)-1H-benzo[d]imidazole

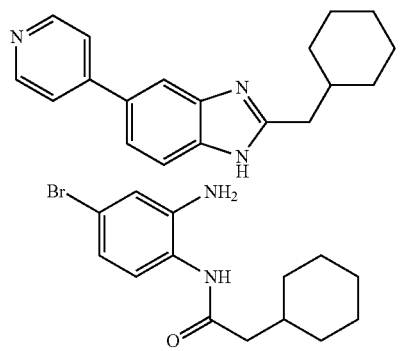

Part A.
N-(2-amino-4-bromophenyl)-2-cyclohexylacetamide

Prepared in a similar fashion as described in Example 59, Part B using 4-bromobenzene-1,2-diamine and 2-cyclohexylacetic acid to afford the title compound (500 mg, 1.61 mmol, 59% yield). The crude product was taken to next step without purification. LCMS (ESI) m/e 311.7 [(M+H)$^+$, calcd for $C_{14}H_{20}BrN_2O$, 311.1]; LC/MS retention time (method D): $t_R$=0.92 min.

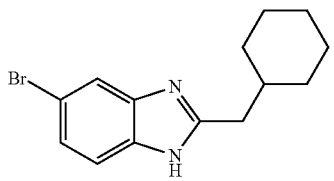 [SMILES: Brc1ccc2[nH]c(CC3CCCCC3)nc2c1]

Part B. 5-bromo-2-(cyclohexylmethyl)-1H-benzo[d]imidazole

Prepared in a similar fashion as described in Example 59, Part C to afford the title compound (250 mg, 0.86 mmol, 77% yield) as a brown solid. $^1$H NMR (400 MHz, CDCl$_3$): δ 7.69 (s, 1H), 7.40 (d, J=8.4 Hz, 1H) 7.32 (dd, J=8.4, 2.0 Hz, 1H) 2.77 (d, J=7.2 Hz, 2H) 1.83-1.89 (m, 1H) 1.64-1.75 (m, 5H) 1.05-1.26 (m, 5H) ppm; LCMS (ESI) m/e 293.7 [(M+H)$^+$, calcd for C$_{14}$H$_{18}$BrN$_2$, 293.1]; LC/MS retention time (method D): $t_R$=0.75 min.

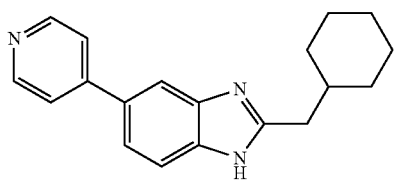 [SMILES: c1cc(-c2ccc3[nH]c(CC4CCCCC4)nc3c2)ccn1]

Part C. 2-(cyclohexylmethyl)-5-(pyridin-4-yl)-1H-benzo[d]imidazole

Prepared in a similar fashion as described in Example 1, Part B using N-(2-amino-4-bromophenyl)-2-cyclohexylacetamide and pyridine-4-boronic acid. The crude product was purified by column chromatography on silica gel using 40% ethyl acetate in hexane mobile phase to afford the title compound (100 mg, 0.34 mmol, 55% yield) as an off-white solid. $^1$H NMR (400 MHz, CD$_3$OD): δ 8.58 (d, J=6.00 Hz, 2H), 7.91 (s, 1H), 7.77-7.81 (m, 2H), 7.64 (s, 2H), 2.82 (d, J=7.20 Hz, 2H), 1.91-1.95 (m, 1H), 1.69-1.76 (m, 5H), 1.22-1.35 (m, 3H), 1.10-1.15 (m, 2H) ppm; LCMS (ESI) m/e 292.2 [(M+H)$^+$, calcd for C$_{19}$H$_{22}$N$_3$, 292.2]; LC/MS retention time (method B): $t_R$=1.21 min; HPLC retention time (method S): $t_R$=8.32 min; HPLC retention time (method T): $t_R$=9.28 min.

Example 73

1-(6-methoxy-5-(pyridin-4-yl)-1H-benzo[d]imidazol-2-yl)-N,3-dimethylbutan-1-amine

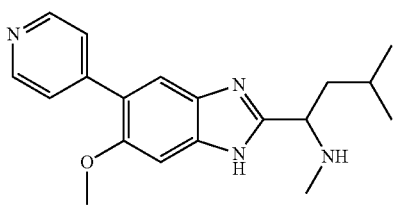

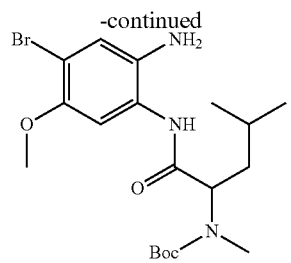

Part A. tert-butyl 1-(2-amino-4-bromo-5-methoxyphenylamino)-4-methyl-1-oxopentan-2-yl(methyl)carbamate Prepared in a similar fashion as described in Example 59, Part B using tert-butyl 1-(6-methoxy-5-(oxazol-5-yl)-1H-benzo[d]imidazol-2-yl)-3-methylbutyl(methyl)carbamate to afford the title compound (1.3 g, 2.93 mmol, 64% yield). LCMS (ESI) m/e 446.2 (Bromo pattern) [(M+H)$^+$, calcd for C$_{19}$H$_{31}$BrN$_3$O$_4$, 444.1]; LC/MS retention time (method A): $t_R$=2.08 min.

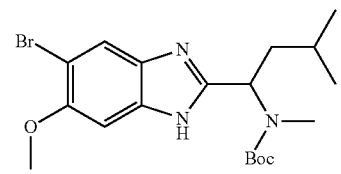 [SMILES: COc1cc2[nH]c(C(CC(C)C)N(C)C(=O)OC(C)(C)C)nc2cc1Br]

Part B. tert-butyl 1-(5-bromo-6-methoxy-1H-benzo[d]imidazol-2-yl)-3-methylbutyl(methyl)carbamate Prepared in a similar fashion as described in Example 59, Part C using tert-butyl 1-(2-amino-4-bromo-5-methoxyphenylamino)-4-methyl-1-oxopentan-2-yl(methyl)carbamate to afford the title compound (1.02 g, 2.35 mmol, 80% yield) as a white solid. LCMS (ESI) m/e 426.2 [(M+H)$^+$, calcd for C$_{19}$H$_{29}$BrN$_3$O$_3$, 426.1]; LC/MS retention time (method A): $t_R$=2.14 min.

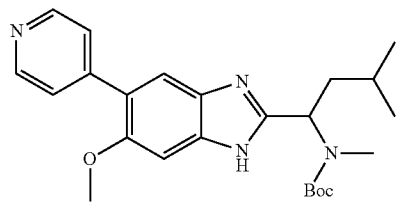 [SMILES: COc1cc2[nH]c(C(CC(C)C)N(C)C(=O)OC(C)(C)C)nc2cc1-c1ccncc1]

Part C. tert-butyl 1-(6-methoxy-5-(pyridin-4-yl)-1H-benzo[d]imidazol-2-yl)-3-methylbutyl (methyl)carbamate Prepared in a similar fashion as described in Example 1, Part B using tert-butyl 1-(5-bromo-6-methoxy-1H-benzo[d]imidazol-2-yl)-3-methylbutyl(methyl)carbamate to afford the title compound (100 mg, 0.23 mmol, 66% yield). The crude product was taken to next step without purification. LCMS (ESI) m/e 425.3 [(M+H)$^+$, calcd for C$_{24}$H$_{33}$N$_4$O$_3$, 425.5]; LC/MS retention time (method D): $t_R$=1.92 min.

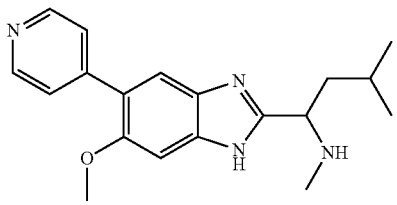

Part D. 1-(6-methoxy-5-(pyridin-4-yl)-1H-benzo[d]imidazol-2-yl)-N,3-dimethylbutan-1-amine Prepared in a similar fashion as described in Example 66, Part H using tert-butyl 1-(6-methoxy-5-(pyridin-4-yl)-1H-benzo[d]imidazol-2-yl)-3-methylbutyl(methyl)carbamate to afford the title compound (30 mg, 0.093 mmol, 36% yield) as a yellow oil which was isolated as HCl salt. $^1$H NMR (400 MHz, CD$_3$OD): δ 8.88 (d, J=6.80 Hz, 2H), 8.39 (d, J=6.80 Hz, 2H), 8.04 (s, 1H), 7.52 (s, 1H), 4.78-4.82 (m, 1H), 4.03 (s, 3H), 2.77 (s, 3H), 2.33-2.40 (m, 1H), 2.03-2.10 (m, 1H), 1.51-1.56 (m, 1H), 0.95-1.05 (m, 6H) ppm; LCMS (ESI) m/e 325.2 [(M+H)$^+$, calcd for C$_{19}$H$_{25}$N$_4$O, 325.2]; LC/MS retention time (method A): t$_R$=1.23 min; HPLC retention time (method S): t$_R$=6.83 min; HPLC retention time (method T): t$_R$=8.34 min.

Example 74

(R)-cyclopropyl (5-(pyridin-4-yl)-1H-benzo[d]imidazol-2-yl)methanamine

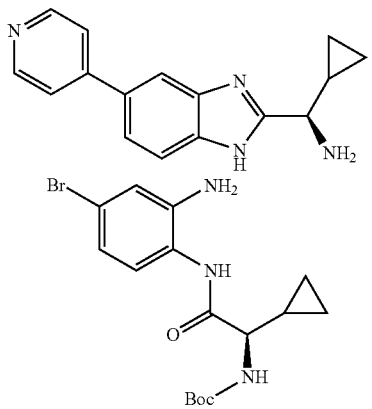

Part A. (R)-tert-butyl 2-(2-amino-4-bromophenylamino)-1-cyclopropyl-2-oxoethylcarbamate Prepared in a similar fashion as described in Example 59, Part B using 4-bromobenzene-1,2-diamine and N-Boc-D-cyclopropylglycine to afford the title compound (350 mg, 0.91 mmol, 86% yield). The crude product was taken for next step without purification. LCMS (ESI) m/e 384.0 [(M+H)$^+$, calcd for C$_{16}$H$_{23}$BrN$_3$O$_3$, 384.3]; LC/MS retention time (method A): t$_R$=1.72 min.

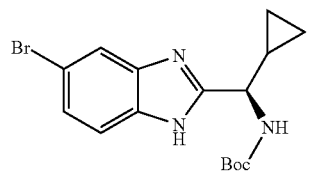 [SMILES: CC(C)(C)OC(=O)N[C@@H](c1nc2cc(Br)ccc2[nH]1)C1CC1]

Part B. (R)-tert-butyl (5-bromo-1H-benzo[d]imidazol-2-yl)(cyclopropyl)methylcarbamate A solution of crude (R)-tert-butyl 2-(2-amino-4-bromophenylamino)-1-cyclopropyl-2-oxoethylcarbamate (0.35 g, 0.91 mmol) in acetic acid (7 mL) was refluxed at 65° C. for 2 h. The reaction mixture was cooled to RT. The acetic acid was removed under reduced pressure. The residue was diluted with water. The aqueous layer was extracted with ethyl acetate (3×50 mL). The combined organic layers were washed with brine (50 mL), dried over Na$_2$SO$_4$, filtered and concentrated under reduced pressure. The crude product was purified by silica gel chromatography using gradient of pet ether:ethyl acetate mobile phase to afford the title compound (0.37 g, 1.01 mmol, 90% yield over 2 steps). LCMS (ESI) m/e 366.0 (Bromo pattern) [(M+H)$^+$, calcd for C$_{16}$H$_{21}$BrN$_3$O$_2$, 366.1]; LC/MS retention time (method E): t$_R$=1.58 min.

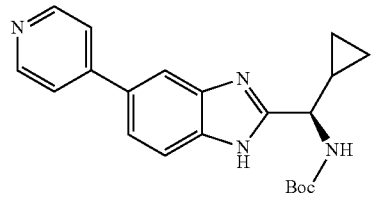 [SMILES: CC(C)(C)OC(=O)N[C@@H](c1nc2cc(-c3ccncc3)ccc2[nH]1)C1CC1]

Part C. (R)-tert-butyl cyclopropyl(5-(pyridin-4-yl)-1H-benzo[d]imidazol-2-yl)methylcarbamate Prepared in a similar fashion as described in Example 1, Part B using (R)-tert-butyl (5-bromo-1H-benzo[d]imidazol-2-yl)(cyclopropyl)methylcarbamate and pyridine-4-boronic acid. The crude product was purified by column chromatography on silica gel using chloroform and methanol as the mobile phase to afford the title compound (130 mg, 0.36 mmol, 23% yield). LCMS (ESI) m/e 365.2 [(M+H)$^+$, calcd for C$_{21}$H$_{25}$N$_4$O$_2$, 365.2]; LC/MS retention time (method A): t$_R$=1.50 min.

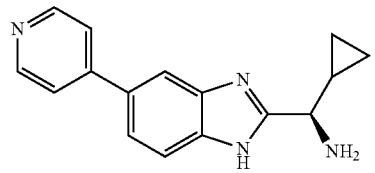 [SMILES: N[C@@H](c1nc2cc(-c3ccncc3)ccc2[nH]1)C1CC1]

Part D. (R)-cyclopropyl(5-(pyridin-4-yl)-1H-benzo[d]imidazol-2-yl)methanamine Prepared in a similar fashion as described in Example 64, Part H from (R)-tert-butyl cyclopropyl(5-(pyridin-4-yl)-1H- benzo[d]imidazol-2-yl)methylcarbamate. The crude product was purified by preparative HPLC using 0.05% TFA in water and ACN mobile phase to afford the title compound (60 mg, 0.23 mmol, 31% yield) as an off-white sticky solid which was isolated as TFA salt. $^1$H NMR (400 MHz, CD$_3$OD): δ 8.82 (d, J=6.00 Hz, 2H), 8.37 (d, J=6.80 Hz, 2H), 8.29 (d, J=1.60 Hz, 1H), 7.93 (dd, J=8.60, 2.00 Hz, 1H), 7.86 (dd, J=8.60, 0.40 Hz, 1H), 4.08 (d, J=10.00 Hz, 1H), 1.44-1.48 (m, 1H), 0.90-0.95 (m, 2H), 0.83-0.88 (m, 1H), 0.70-0.74 (m, 1H) ppm; LCMS (ESI) m/e 263.0 [(M−H)$^−$, calcd for C$_{16}$H$_{15}$N$_4$, 263.1]; LC/MS retention time (method F): t$_R$=1.41 min; HPLC retention time (method S): t$_R$=5.13 min; HPLC retention time (method T): t$_R$=5.55 min; Chiral SFC retention time (method B): t$_R$=2.42 min.

Example 75

(R)-N,N-dimethyl-4-(2-(3-methyl-1-(methylamino) butyl)-1H-benzo[d]imidazol-5-yl) pyridin-2-amine

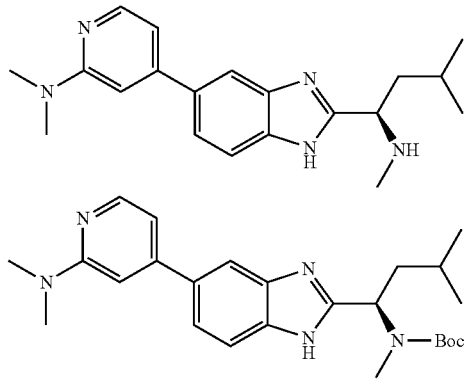

Part A. (R)-tert-butyl 1-(5-(2-(dimethylamino) pyridin-4-yl)-1H-benzo[d]imidazol-2-yl)-3-methylbutyl (methyl) carbamate Prepared in a similar fashion as described in Example 59, Part F using (R)-tert-butyl methyl(3-methyl-1-(5-(trimethylstannyl)-1H-benzo[d]imidazol-2-yl)butyl)carbamate (preparation described in Example 59, Part D) to afford the title compound (480 mg, 1.097 mmol, 88% yield). LCMS (ESI) m/e 438.2 [(M+H)$^+$, calcd for C$_{25}$H$_{36}$N$_5$O$_2$, 438.3]; LC/MS retention time (method F): t$_R$=2.05 min.

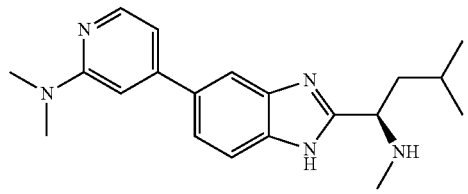 [SMILES: CN[C@H](CC(C)C)c1nc2cc(-c3ccnc(N(C)C)c3)ccc2[nH]1]

Part B. (R)-N,N-dimethyl-4-(2-(3-methyl-1-(methylamino)butyl)-1H-benzo[d]imidazol-5-yl)pyridin-2-amine Prepared in a similar fashion as described in Example 64, Part H using (R)-tert-butyl 1-(5-(2-(dimethylamino)pyridin-4-yl)-1H-benzo[d]imidazol-2-yl)-3-methylbutyl(methyl) carbamate. The crude product was purified by preparative HPLC (0.05% TFA in water and acetonitrile) to afford the title compound (25 mg, 0.073 mmol, 7% yield) as a light yellow oil which was isolated as TFA salt. 1H NMR (400 MHz, CD$_3$OD): δ 8.18 (d, J=1.20 Hz, 1H), 7.97 (d, J=6.80 Hz, 1H), 7.84 (d, J=0.80 Hz, 2H), 7.42 (d, J=1.20 Hz, 1H), 7.34-7.36 (m, 1H), 4.63-4.67 (m, 1H), 3.38 (d, J=8.00 Hz, 6H), 2.71 (s, 3H), 2.23-2.30 (m, 1H), 1.95-2.01 (m, 1H), 1.49-1.50 (m, 1H), 0.95-1.05 (m, 6H) ppm; LCMS (ESI) m/e 336.2 [(M−H)$^−$, calcd for C$_{20}$H$_{26}$N$_5$, 336.2]; LC/MS retention time (method A): t$_R$=1.41 min; HPLC retention time (method S): t$_R$=7.97 min; HPLC retention time (method T): t$_R$=8.64 min.

Example 76

3-fluoro-3-methyl-1-(5-(pyridin-4-yl)-1H-benzo[d] imidazol-2-yl)butan-1-amine

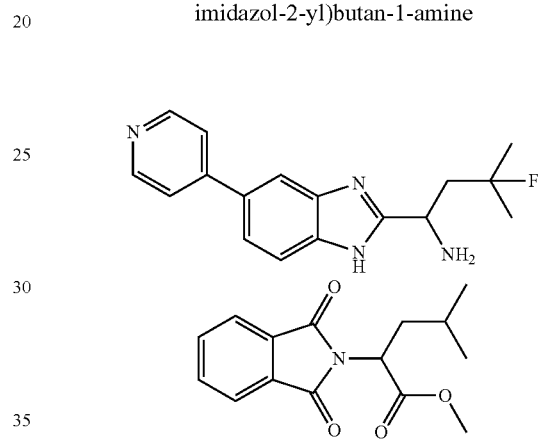

Part A. methyl 2-(1,3-dioxoisoindolin-2-yl)-4-methylpentanoate

To a solution of 2-(1,3-dioxoisoindolin-2-yl)-4-methylpentanoic acid (20 g, 76.54 mmol) in methanol (200 mL) cooled to 0° C. was added thionyl chloride (17 mL, 229 mmol) dropwise. The reaction mixture was stirred at RT for overnight. The solvents were removed by concentration under reduced pressure. The residue was dissolved in water, basified with 10% NaHCO$_3$ solution. The aqueous layer was extracted with ethyl acetate (3×250 mL). The combined organic layers were washed with brine (100 mL), dried over Na$_2$SO$_4$, filtered and concentrated under reduced pressure. The crude product was purified by column chromatography on silica gel using a gradient of pet ether:ethyl acetate mobile phase to afford the title compound (20 g, 72.7 mmol, 94% yield). LCMS (ESI) m/e 276.2 [(M+H)$^+$, calcd for C$_{15}$H$_{18}$NO$_4$, 276.1]; LC/MS retention time (method A): t$_R$=1.96 min.

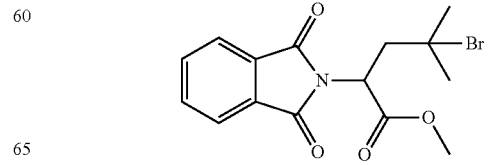

Part B. methyl 4-bromo-2-(1,3-dioxoisoindolin-2-yl)-4-methylpentanoate

To the solution of methyl 2-(1,3-dioxoisoindolin-2-yl)-4-methylpentanoate (20 g, 72 mmol) in carbon tetrachloride (500 mL), N-bromosuccinimide (14.24 g, 79 mmol) was added in portions. The reaction mixture was irradiated with 200 W bulb for 5 h. The reaction mixture was brought to room temperature, filtered and the residue was washed with dichloromethane (100 mL). The filtrate was concentrated under reduced pressure. The crude product was purified by column chromatography on silica gel using gradient of pet ether:ethyl acetate as mobile phase to afford the title compound (10 g, 28 mmol, 39% yield). LCMS (ESI) m/e 356.0 (Bromo pattern) [(M+H)$^+$, calcd for $C_{15}H_{17}BrNO_4$, 354.0]; LC/MS retention time (method A): $t_R$=1.91 min.

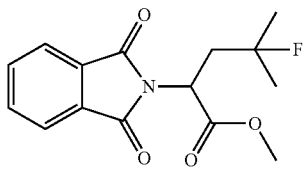

Part C. methyl 2-(1,3-dioxoisoindolin-2-yl)-4-fluoro-4-methylpentanoate

To the solution of methyl 4-bromo-2-(1,3-dioxoisoindolin-2-yl)-4-methylpentanoate (10 g, 28.24 mmol) in acetonitrile (150 mL), silver fluoride (35.8 g, 282.4 mmol) was added. The reaction mixture was stirred at RT for overnight. The reaction mixture was filtered through diatomaceous earth (Celite®) and the bed was washed with ethyl acetate (50 mL). Combined filtrate was concentrated under reduced pressure to afford crude product which was purified by column chromatography on silica gel using gradient of pet ether:ethyl acetate mobile phase to afford the title compound (1.7 g, 5.8 mmol, 20% yield). $^1$H NMR (400 MHz, CDCl$_3$): δ 7.84-7.88 (m, 2H) 7.72-7.75 (m, 2H) 5.13-5.17 (m, 1H) 3.74 (s, 3H) 2.73-2.83 (m, 1H) 2.43-2.55 (m, 1H) 1.33-1.47 (m, 6H) ppm; $^1$H NMR (400 MHz, CDCl$_3$): δ 143.17 (s, 1F) ppm.

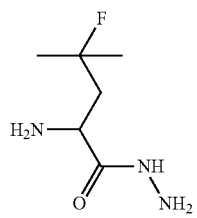

Part D. 2-amino-4-fluoro-4-methylpentanehydrazide

To a solution of methyl 2-(1,3-dioxoisoindolin-2-yl)-4-fluoro-4-methylpentanoate (1.6 g, 5.46 mmol) in ethanol (25.0 mL) hydrazine hydrate (2.30 mL, 47.50 mmol) was added slowly. The reaction mixture was refluxed at 85° C. for 1 h. The reaction mixture was cooled to R.T. filtered, and washed with ethyl acetate. The filtrate was concentrated under reduced pressure to afford the title compound (0.85 g, 5.21 mmol, 94% yield). LCMS (ESI) m/e 164.2 [(M+H)$^+$, calcd for $C_6H_{15}FN_3O$, 164.1]; LC/MS retention time (method G): $t_R$=0.72 min.

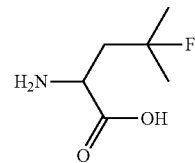

Part E. 2-amino-4-fluoro-4-methylpentanoic acid

To the vigorously stirred solution of N-bromosuccinimide (2.62 g, 14.72 mmol) in water (5.0 mL) 2-amino-4-fluoro-4-methylpentanehydrazide (1.2 g, 7.36 mmol) in water (5.0 mL) was added dropwise over 1 h. The reaction mixture was stirred at room temperature for 30 min and taken to the next step. LCMS (ESI) m/e 150.2 [(M+H)$^+$, calcd for $C_6H_{13}FNO_2$, 150.09]; LC/MS retention time (method G): $t_R$=0.83 min.

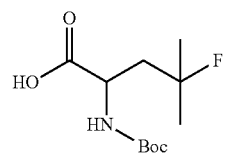

Part F. 2-(tert-butoxycarbonylamino)-4-fluoro-4-methylpentanoic acid

To a solution of 2-amino-4-fluoro-4-methylpentanoic acid (1.2 g, 8.05 mmol) in dioxane (10 mL) and water (10 mL) were added di-tert-butyl dicarbonate (5.26 g, 24.16 mmol) and potassium carbonate (3.33 g, 24.16 mmol). The reaction mixture was allowed to stir at RT overnight. The solvent was removed by concentration under reduced pressure and the residue diluted with water. The aqueous layer was washed with ethyl acetate (3×50 mL). The aqueous layer was acidified with 10% aqueous citric acid and extracted with ethyl acetate (3×150 mL). The combined organic layers were washed with brine (50 mL). The organic layer was dried over Na$_2$SO$_4$, filtered and concentrated under reduced pressure to afford the title compound (0.8 g, 3.21 mmol, 72% yield over 2 steps). LCMS (ESI) m/e 248.2 [(M–H)$^-$, calcd for $C_{11}H_{19}FNO_4$, 248.14]; LC/MS retention time (method F): $t_R$=1.49 min.

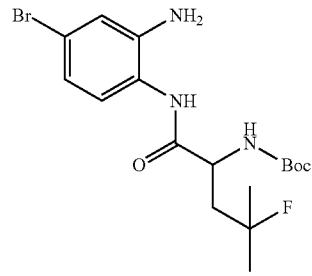 [SMILES: CC(C)(F)CC(NC(=O)OC(C)(C)C)C(=O)Nc1ccc(Br)cc1N]

Part G. tert-butyl 1-(2-amino-4-bromophenylamino)-4-fluoro-4-methyl-1-oxopentan-2-ylcarbamate Prepared in a similar fashion as described in Example 59, Part B using 4-bromobenzene-1,2-diamine and 2-(tert-butoxycarbonylamino)-4-fluoro-4-methylpentanoic acid to afford the title compound (300 mg, 0.72 mmol, 44% yield). The crude product was taken for next step without purification. LCMS (ESI) m/e 418.2 [(M+H)$^+$, calcd for $C_{17}H_{26}BrFN_3O_3$, 418.1]; LC/MS retention time (method A): $t_R$=1.84 min.

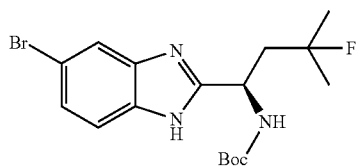 [SMILES: CC(C)(F)C[C@@H](NC(=O)OC(C)(C)C)c1nc2cc(Br)ccc2[nH]1]

Part H. tert-butyl 1-(5-bromo-1H-benzo[d]imidazol-2-yl)-3-fluoro-3-methylbutylcarbamate A solution of tert-butyl 1-(2-amino-4-bromophenylamino)-4-fluoro-4-methyl-1-oxopentan-2-ylcarbamate (300 mg) in acetic acid (9 mL) was refluxed at 65° C. overnight. The reaction mixture was cooled to RT and the acetic acid was removed under reduced pressure. The residue was diluted with water and basified with 10% NaHCO$_3$. The aqueous layer was extracted with ethyl acetate (3×50 mL). The combined organic layers were washed with brine (50 mL), dried over Na$_2$SO$_4$, filtered and concentrated under reduced pressure. The crude product was purified by silica gel chromatography using pet ether:ethyl acetate mobile phase to afford the title compound (230 mg, 0.57 mmol, 80% yield). LCMS (ESI) m/e 400.0 [(M+H)$^+$, calcd for $C_{17}H_{24}BrFN_3O_2$, 400.1]; LC/MS retention time (method F): $t_R$=1.94 min.

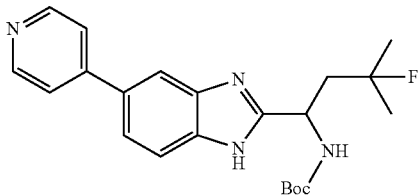 [SMILES: CC(C)(F)CC(NC(=O)OC(C)(C)C)c1nc2cc(-c3ccncc3)ccc2[nH]1]

Part I. tert-butyl 3-fluoro-3-methyl-1-(5-(pyridin-4-yl)-1H-benzo[d]imidazol-2-yl)butylcarbamate Prepared in a similar fashion as described in Example 1, Part B using tert-butyl 1-(5-bromo-1H-benzo[d]imidazol-2-yl)-3-fluoro-3-methylbutylcarbamate and pyridine-4-boronic acid. The crude product was purified by preparative TLC on silica gel using 60% ethyl acetate in pet ether as mobile phase to afford the title compound (40 mg, 0.1 mmol, 18% yield). LCMS (ESI) m/e 399.2 [(M+H)$^+$, calcd for $C_{22}H_{28}FN_4O_2$, 399.2]; LC/MS retention time (method A): $t_R$=1.61 min.

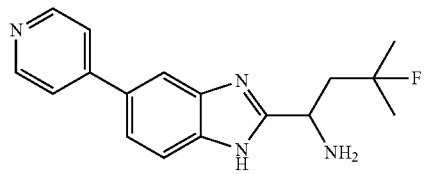 [SMILES: CC(C)(F)CC(N)c1nc2cc(-c3ccncc3)ccc2[nH]1]

Part J. 3-fluoro-3-methyl-1-(5-(pyridin-4-yl)-1H-benzo[d]imidazol-2-yl)butan-1-amine Prepared in a similar fashion as described in Example 64, Part H using tert-butyl 3-fluoro-3-methyl-1-(5-(pyridin-4-yl)-1H-benzo[d]imidazol-2-yl)butylcarbamate (40 mg) to afford crude product which was purified by preparative HPLC (0.1% HCl in water and acetonitrile) to afford the title compound (35 mg, 0.12 mmol, 94% yield) as an off-white sticky solid which was isolated as HCl salt. 1H NMR (400 MHz, CD$_3$OD): δ 8.86 (d, J=6.80 Hz, 2H), 8.48 (d, J=6.80 Hz, 2H), 8.35 (s, 1H), 7.97 (d, J=8.80 Hz, 1H), 7.88 (d, J=8.40 Hz, 1H), 5.00-5.03 (m, 1H), 2.48-2.68 (m, 2H), 1.48-1.55 (m, 6H) ppm; LCMS (ESI) m/e 299.2 [(M+H)$^+$, calcd for C17H20FN$_4$, 299.2]; LC/MS retention time (method A): $t_R$=1.17 min; HPLC retention time (method T): $t_R$=6.28 min; HPLC retention time (method S): $t_R$=5.87 min; Chiral SFC retention time (method D): $t_R$=2.61, 4.32 min.

Example 77

(R)-(5-(pyridin-4-yl)-1H-benzo[d]imidazol-2-yl)(tetrahydro-2H-pyran-4-yl) methanamine

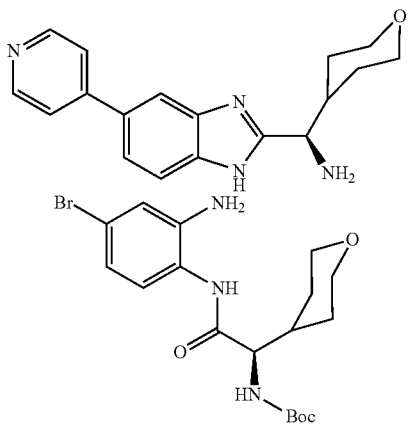

Part A. (R)-tert-butyl 2-(2-amino-4-bromophenylamino)-2-oxo-1-(tetrahydro-2H-pyran-4-yl) ethylcarbamate Prepared in a similar fashion as described in Example 59, Part B using 4-bromobenzene-1,2-diamine and (R)-2-(tert-butoxycarbonylamino)-2-(tetrahydro-2H-pyran-4-yl)acetic acid to afford the title compound (800 mg, 1.87 mmol, 70% yield). The crude product was taken to next step without purification. LCMS (ESI) m/e 428.0 [(M+H)$^+$, calcd for $C_{18}H_{27}BrN_3O_4$, 428.1]; LC/MS retention time (method A): $t_R$=1.62 min.

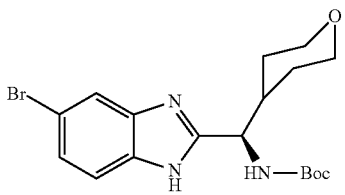 [SMILES: CC(C)(C)OC(=O)N[C@@H](c1nc2cc(Br)ccc2[nH]1)C1CCOCC1]

Part B. (R)-tert-butyl (5-bromo-1H-benzo[d]imidazol-2-yl) (tetrahydro-2H-pyran-4-yl)methylcarbamate Prepared in a similar fashion as described in Example 59, Part C using (R)-tert-butyl 2-(2-amino-4-bromophenylamino)-2-oxo-1-(tetrahydro-2H-pyran-4-yl)ethylcarbamate. The crude product was purified by silica gel chromatography using hexane:ethyl acetate mobile phase to afford the title compound (400 mg, 0.98 mmol, 55% yield). LCMS (ESI) m/e 410.0 [(M+H)$^+$, calcd for $C_{18}H_{25}BrN_3O_3$, 410.1]; LC/MS retention time (method A): $t_R$=1.66 min.

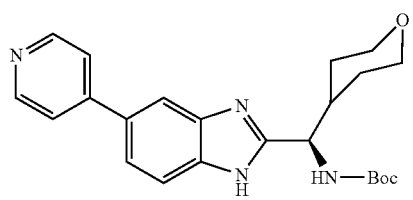 [SMILES: CC(C)(C)OC(=O)N[C@@H](c1nc2cc(-c3ccncc3)ccc2[nH]1)C1CCOCC1]

Part C. (R)-tert-butyl (5-(pyridin-4-yl)-1H-benzo[d]imidazol-2-yl) (tetrahydro-2H-pyran-4-yl) methylcarbamate Prepared in a similar fashion as described in Example 1, Part B using 6-bromo-2-(3-methylcyclohexyl)-1H-benzo[d]imidazole (200 mg, 0.48 mmol) and pyridine-4-boronic acid (90 mg, 0.73 mmol) to afford the title compound (200 mg, 0.49 mmol, 32% yield). LCMS (ESI) m/e 409.2 [(M+H)$^+$, calcd for $C_{23}H_{29}N_4O_3$, 409.2]; LC/MS retention time (method A): $t_R$=1.41 min.

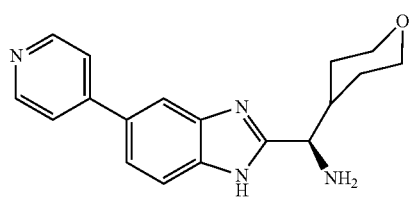 [SMILES: N[C@@H](c1nc2cc(-c3ccncc3)ccc2[nH]1)C1CCOCC1]

Part D. (R)-(5-(pyridin-4-yl)-1H-benzo[d]imidazol-2-yl) (tetrahydro-2H-pyran-4-yl)methanamine Prepared in a similar fashion as described in Example 64, Part H using (R)-tert-butyl (5-(pyridin-4-yl)-1H-benzo[d]imidazol-2-yl)(tetrahydro-2H-pyran-4-yl)methylcarbamate to afford the title compound (22 mg, 0.07 mmol, 11% yield) as a light yellow solid which was isolated as HCl salt. $^1$H NMR (400 MHz, CD$_3$OD): δ 8.87 (d, J=7.20 Hz, 2H), 8.49 (d, J=6.80 Hz, 2H), 8.37 (d, J=1.20 Hz, 1H), 7.99 (dd, J=8.80, 1.60 Hz, 1H), 7.90 (d, J=8.40 Hz, 1H), 4.54 (d, J=7.60 Hz, 1H), 4.04-4.08 (m, 1H), 3.95-3.99 (m, 1H), 3.37-3.51 (m, 2H), 2.44-2.46 (m, 1H), 1.82-1.85 (m, 1H), 1.43-1.58 (m, 3H) ppm; LCMS (ESI) m/e 309.2 [(M+H)$^+$, calcd for $C_{18}H_{21}N_4O$, 309.2]; LC/MS retention time (method A): $t_R$=1.02 min; HPLC retention time (method Y): $t_R$=6.22 min; HPLC retention time (method T): $t_R$=5.44 min.

Example 78

(R)-1-(5-(3,5-dimethylisoxazol-4-yl)-1H-benzo[d]imidazol-2-yl)-3-methylbutan-1-amine

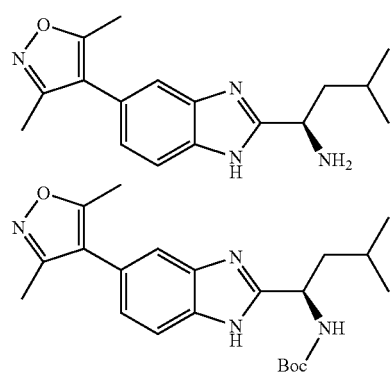

Part A. (R)-tert-butyl 1-(5-(3,5-dimethylisoxazol-4-yl)-1H-benzo[d]imidazol-2-yl)-3-methylbutylcarbamate Prepared in a similar fashion as described in Example 1, Part B using (R)-tert-butyl 1-(5-bromo-1H-benzo[d]imidazol-2-yl)-3-methylbutylcarbamate and 3,5-dimethyl isoxazole-4-boronic acid pinacol ester. The crude product was purified by preparative TLC on silica gel using 5% methanol in dichloromethane as the mobile phase to afford the title compound (80 mg, 0.20 mmol, 35% yield). LCMS (ESI) m/e 399.2 [(M+H)$^+$, calcd for $C_{22}H_{31}N_4O_3$, 399.2]; LC/MS retention time (method A): $t_R$=1.83 min.

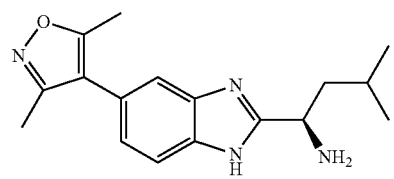 [SMILES: Cc1noc(C)c1-c1ccc2[nH]c([C@H](N)CC(C)C)nc2c1]

Part B. (R)-1-(5-(3,5-dimethylisoxazol-4-yl)-1H-benzo[d]imidazol-2-yl)-3-methylbutan-1-amine To a solution of (R)-tert-butyl 1-(5-(3,5-dimethylisoxazol-4-yl)-1H-benzo[d]imidazol-2-yl)-3-methylbutylcarbamate (80 mg) in diethyl ether (2.0 mL) and methanol (0.1 mL) cooled to 0° C. was added 2M HCl in ether (2 mL) slowly over a period of 5 min. The reaction mixture was stirred at 0° C. for 5 min then was warmed to room temperature and allowed to stir for 2 h. The solvents were removed by concentration under reduced pressure. The crude product was purified by preparative HPLC using 0.1%

HCl in water and acetonitrile mobile phase to afford the title compound (40 mg, 0.13 mmol, 58% yield) as a pale yellow solid which was isolated as HCl salt. $^1$H NMR (400 MHz, CD$_3$OD): δ 7.92 (d, J=8.40 Hz, 1H), 7.78 (s, 1H), 7.54 (d, J=8.40 Hz, 1H), 4.93-4.97 (m, 1H), 2.46 (s, 3H), 2.25-2.30 (m, 4H), 2.06-2.13 (m, 1H), 1.61-1.66 (m, 1H), 1.03-1.08 (m, 6H) ppm; LCMS (ESI) m/e 299.2 [(M+H)$^+$, calcd for C$_{17}$H$_{23}$N$_4$O, 299.2]; LC/MS retention time (method A): t$_R$=1.33 min; HPLC retention time (method V): t$_R$=6.18 min; HPLC retention time (method S): t$_R$=11.04 min; Chiral SFC retention time (method C): t$_R$=3.29 min.

Example 79

4-(1-(5-bromo-1H-benzo[d]imidazol-2-yl) ethyl) morpholine

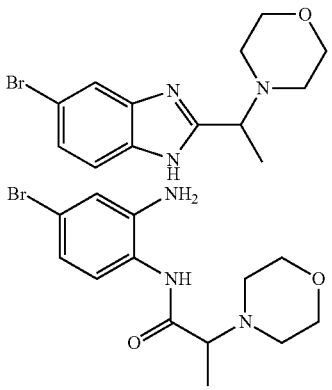

Part A.
N-(2-amino-4-bromophenyl)-2-morpholinopropanamide

Prepared in a similar fashion as described in Example 59, Part B using 4-bromobenzene-1,2-diamine and 2-morpholinopropanoic acid to afford the title compound (180 mg, 0.55 mmol, 96% yield). The crude product was taken to next step without purification. LCMS (ESI) m/e 327.7 [(M+H)$^+$, calcd for C$_{13}$H$_{19}$BrN$_3$O$_2$, 328.1]; LC/MS retention time (method C): t$_R$=1.56 min.

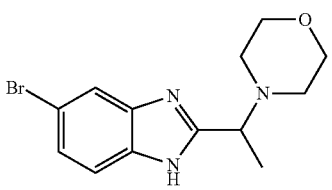 [SMILES: CC(c1nc2cc(Br)ccc2[nH]1)N1CCOCC1]

Part B. 4-(1-(5-bromo-1H-benzo[d]imidazol-2-yl) ethyl)morpholine

Prepared in a similar fashion as described in Example 59, Part C using N-(2-amino-4-bromophenyl)-2-morpholinopropanamide. The crude product was purified by column chromatography on silica gel using hexane:ethyl acetate as a mobile phase to afford the title compound (700 mg, 2.26 mmol, 86% yield). LCMS (ESI) m/e 312.7 (Bromo pattern) [(M+H)$^+$, calcd for C$_{13}$H$_{17}$BrN$_3$O, 310.1]; LC/MS retention time (method D): t$_R$=0.62 min.

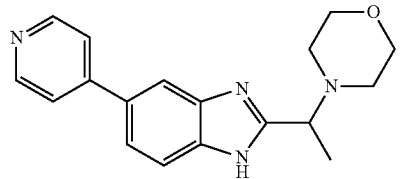 [SMILES: CC(c1nc2cc(-c3ccncc3)ccc2[nH]1)N1CCOCC1]

Part C. 4-(1-(5-(pyridin-4-yl)-1H-benzo[d]imidazol-2-yl) ethyl)morpholine

Prepared in a similar fashion as described in Example 1, Part B using 4-(1-(5-bromo-1H-benzo[d]imidazol-2-yl) ethyl)morpholine and pyridine-4-boronic acid to afford the title compound (24 mg, 0.077 mmol, 13% yield) as a white solid. LCMS (ESI) m/e 309.2 [(M+H)$^+$, calcd for C$_{18}$H$_{21}$N$_4$O, 309.2]; $^1$H NMR (400 MHz, CD$_3$OD): δ 8.60 (dd, J=4.40, 1.60 Hz, 2H), 7.90-8.00 (m, 1H), 7.79-7.80 (m, 2H), 7.69 (s, 2H), 3.92-3.97 (m, 1H), 3.74-3.77 (m, 4H), 2.60-2.65 (m, 2H), 2.50-2.55 (m, 2H), 1.58 (d, J=6.80 Hz, 3H) ppm; LC/MS retention time (method A): t$_R$=1.21 min; HPLC retention time (method W): t$_R$=10.41 min; HPLC retention time (method X): t$_R$=5.61 min.

Example 80

(R)-2,2,2-trifluoro-N-(3-methyl-1-(5-(pyridin-4-yl)-1H-benzo[d]imidazol-2-yl)butyl)acetamide

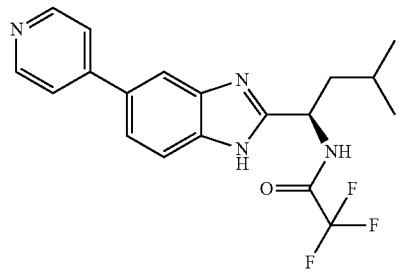

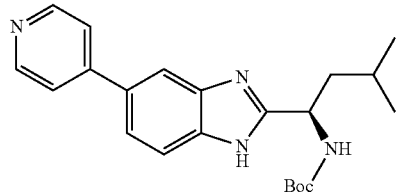

Part A. (R)-tert-butyl 3-methyl-1-(5-(pyridin-4-yl)-1H-benzo[d]imidazol-2-yl) butylcarbamate Prepared in a similar fashion as described in Example 1, Part B using (R)-tert-butyl 1-(5-bromo-1H-benzo[d]imidazol-2-yl)-3-methylbutylcarbamate (preparation described in Example 7, Part C) and pyridine-4-boronic acid. The crude product was purified by column chromatography on silica gel using 0-60% ethyl acetate in hexane mobile phase to afford the title compound (210 mg, 055 mmol, 14% yield).

LCMS (ESI) m/e 381.9 [(M+H)$^+$, calcd for $C_{22}H_{29}N_4O_2$, 381.2]; LC/MS retention time (method D): $t_R$=0.64 min.

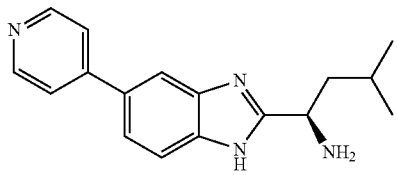 [SMILES: CC(C)C[C@@H](N)c1nc2cc(-c3ccncc3)ccc2[nH]1]

Part B. (R)-3-methyl-1-(5-(pyridin-4-yl)-1H-benzo[d]imidazol-2-yl) butan-1-amine The solution of (R)-tert-butyl 3-methyl-1-(5-(pyridin-4-yl)-1H-benzo[d]imidazol-2-yl) butylcarbamate in methanolic HCl was stirred at R.T. for 8 h. Later the volatiles were evaporated to dryness to afford the title compound (130 mg, 0.46 mmol, 84% yield). The crude product was taken to next step without purification. LCMS (ESI) m/e 281.0 [(M+H)$^+$, calcd for $C_{17}H_{21}N_4$, 281.2]; LC/MS retention time (method D): $t_R$=0.64 min.

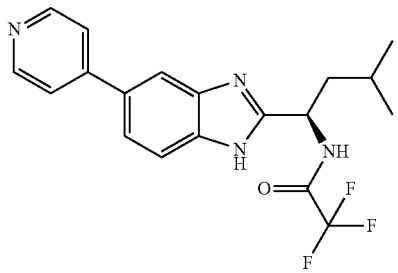 [SMILES: CC(C)C[C@@H](NC(=O)C(F)(F)F)c1nc2cc(-c3ccncc3)ccc2[nH]1]

Part C. (R)-2,2,2-trifluoro-N-(3-methyl-1-(5-(pyridin-4-yl)-1H-benzo[d]imidazol-2-yl)butyl)acetamide To a solution of (R)-3-methyl-1-(5-(pyridin-4-yl)-1H-benzo[d]imidazol-2-yl)butan-1-amine.HCl (100 mg, 0.35 mmol) in dichloromethane (15 mL) at 0° C. was added diisopropyl ethyl amine (0.096 mL, 0.53 mmol) and stirred for 15 min. Later trifluoroacetic anhydride (0.098 mL, 0.46 mmol) was added slowly and the reaction mixture was stirred at room temperature for 12 h. The reaction mixture was quenched with water (15 mL). The aqueous layer was extracted with dichloromethane (2×20 mL). Combined organic layer was dried over Na$_2$SO$_4$, filtered and concentrated under reduced pressure to afford the title compound (80 mg, 0.21 mmol, 60% yield) as a white solid. $^1$H NMR (400 MHz, CD$_3$OD): δ 8.83 (d, J=6.80 Hz, 2H), 8.41 (d, J=6.80 Hz, 2H), 8.25 (d, J=1.20 Hz, 1H), 7.95 (dd, J=8.40, 1.60 Hz, 1H), 7.83 (d, J=8.40 Hz, 1H), 5.38-5.42 (m, 1H), 2.05-2.10 (m, 2H), 1.68-1.75 (m, 1H), 1.03-1.08 (m, 6H) ppm; LCMS (ESI) m/e 377.2 [(M+H)$^+$, calcd for $C_{19}H_{20}F_3N_4O$, 377.2]; LC/MS retention time (method B): $t_R$=1.27 min; HPLC retention time (method V): $t_R$=5.93 min; HPLC retention time (method U): $t_R$=5.31 min.

Example 81

2-(3-methylcyclohexyl)-6-(pyridin-4-yl)-1H-benzo[d]imidazole

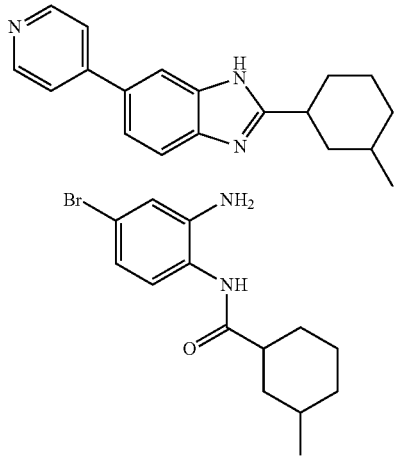

Part A. N-(2-amino-4-bromophenyl)-3-methylcyclohexanecarboxamide

Prepared in a similar fashion as described in Example 59, Part B using 4-bromobenzene-1,2-diamine and 3-methylcyclohexanecarboxylic acid to afford the title compound (900 mg, 2.90 mmol, 79% yield). The crude product was taken to next step without purification. LCMS (ESI) m/e 313.0 [(M+H)$^+$, calcd for $C_{14}H_{20}BrN_2O$, 311.1]; LC/MS retention time (method E): $t_R$=1.64 min.

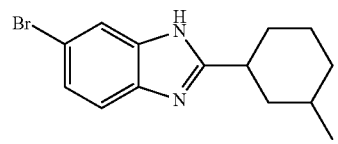 [SMILES: CC1CCCC(c2nc3ccc(Br)cc3[nH]2)C1]

Part B. 6-bromo-2-(3-methylcyclohexyl)-1H-benzo[d]imidazole

Prepared in a similar fashion as described in Example 59, Part C using N-(2-amino-4-bromophenyl)-3-methylcyclohexanecarboxamide. The crude product was purified by column chromatography on silica gel using gradient of ethyl acetate and pet ether as mobile phase to afford the title compound (450 mg, 1.54 mmol, 63% yield). LCMS (ESI) m/e 291.0 [(M−H)$^-$, calcd for $C_{14}H_{16}BrN_2$, 291.06]; LC/MS retention time (method E): $t_R$=1.63 min.

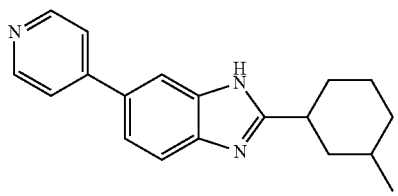 [SMILES: CC1CCCC(c2nc3ccc(-c4ccncc4)cc3[nH]2)C1]

Part C. 2-(3-methylcyclohexyl)-6-(pyridin-4-yl)-1H-benzo[d]imidazole

Prepared in a similar fashion as described in Example 1, Part B using 6-bromo-2-(3-methylcyclohexyl)-1H-benzo[d]imidazole and pyridine-4-boronic acid. The crude product was purified by preparative HPLC (10 mM ammonium acetate in water and acetonitrile) to afford the title compound (60 mg, 0.21 mmol, 15% yield) as a white solid. $^1$H NMR (400 MHz, CD$_3$OD): δ 8.81 (s, 2H), 8.20-8.22 (m, 3H), 8.05 (dd, J=8.80, 1.60 Hz, 1H), 7.91 (d, J=8.40 Hz, 1H), 3.27-3.30 (m, 1H), 2.21-2.24 (m, 2H), 2.00-2.04 (m, 1H), 1.87-1.90 (m, 1H), 1.59-1.72 (m, 3H), 1.37-1.46 (m, 1H), 1.06-1.12 (m, 4H) ppm; LCMS (ESI) m/e 292.2 [(M+H)$^+$, calcd for C$_{19}$H$_{22}$N$_3$, 292.2]; LC/MS retention time (method A): $t_R$=1.66 min; HPLC retention time (method S): $t_R$=8.43 min; HPLC retention time (method T): $t_R$=9.77 min.

Example 82

(R)-cyclopentyl(6-methoxy-5-(pyridin-4-yl)-1H-benzo[d]imidazol-2-yl)methanamine

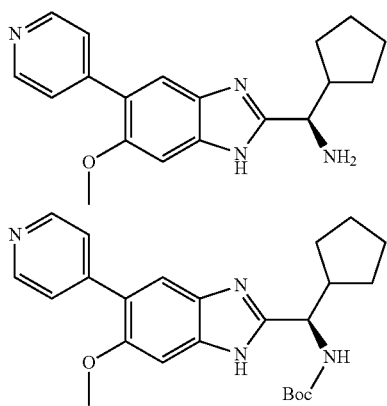

Part A. (R)-tert-butyl cyclopentyl(6-methoxy-5-(pyridin-4-yl)-1H-benzo[d]imidazol-2-yl)methylcarbamate Prepared in a similar fashion as described in Example 1, Part B using (R)-tert-butyl (5-bromo-6-methoxy-1H-benzo[d]imidazol-2-yl)(cyclopentyl)methylcarbamate (preparation described in Example 68, Part B) to afford the title compound (110 mg, 0.26 mmol, 50% yield) in crude form which was taken to the next step without purification. LCMS (ESI) m/e 423.2 [(M+H)$^+$, calcd for C$_{24}$H$_{31}$N$_4$O$_3$, 423.2]; LC/MS retention time (method E): $t_R$=1.73 min.

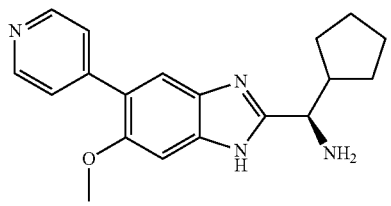 [SMILES: COc1cc2[nH]c([C@H](N)C3CCCC3)nc2cc1-c1ccncc1]

Part B. (R)-cyclopentyl(6-methoxy-5-(pyridin-4-yl)-1H-benzo[d]imidazol-2-yl)methanamine Prepared in a similar fashion as described in Example 64, Part H using to afford the title compound (12 mg, 0.037 mmol, 14% yield) as a yellow solid which was isolated as a HCl salt. $^1$H NMR (400 MHz, CD$_3$OD): δ 8.88 (d, J=6.40 Hz, 2H), 8.39 (d, J=6.80 Hz, 2H), 8.03 (s, 1H), 7.51 (s, 1H), 4.62 (d, J=10.00 Hz, 1H), 4.02 (s, 3H), 2.73-2.77 (m, 1H), 2.10-2.13 (m, 1H), 1.59-1.85 (m, 6H), 1.35-1.45 (m, 1H) ppm; LCMS (ESI) m/e 323.2 [(M+H)$^+$, calcd for C$_{19}$H$_{23}$N$_4$O, 323.2]; LC/MS retention time (method A): $t_R$=1.22 min; HPLC retention time (method T): $t_R$=7.61 min; HPLC retention time (method S): $t_R$=7.10 min; Chiral SFC retention time (method A): $t_R$=5.11 min.

Example 83

3-methyl-1-(5-(pyridin-4-yl)benzo[d]oxazol-2-yl)butan-1-amine

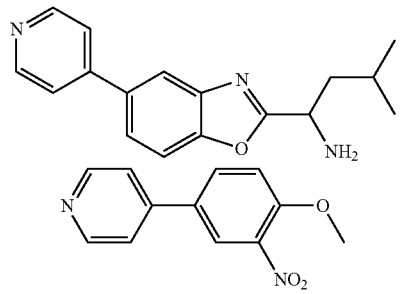

Part A: 4-(4-methoxy-3-nitrophenyl)pyridine

To a stirred mixture of 4-(4-methoxyphenyl)pyridine (2.7 g, 14.58 mmol) in acetic acid (42.5 ml, 742 mmol) was added fuming HNO$_3$ (0.655 mL, 15.60 mmol). The resultant mixture was heated to reflux for 1 h. The mixture was cooled to room temperature and sodium hydroxide (15.6 g, 390 mmol) in H$_2$O (20 mL) was added carefully to neutralized the mixture. The solid formed was collected by vacuum filtration and air dried to obtain 4-(4-methoxy-3-nitrophenyl)pyridine (3.2 g, 13.90 mmol, 95% yield) as a light yellow solid. $^1$H NMR (500 MHz, CHLOROFORM-d) δ 8.80-8.63 (m, 2H), 8.18 (d, J=2.4 Hz, 1H), 7.86 (dd, J=8.9, 2.4 Hz, 1H), 7.55-7.45 (m, 2H), 7.25 (d, J=8.5 Hz, 1H), 4.06 (s, 3H); LC/MS (ESI) m/e 231.2 [(M+H)+, calcd for C12H11N2O3 231.1].

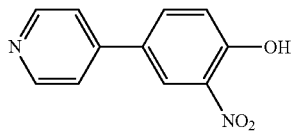

Part B: 2-nitro-4-(pyridin-4-yl)phenol

To a solution of 4-(4-methoxy-3-nitrophenyl)pyridine (500 mg, 2.172 mmol) in dry CH$_2$Cl$_2$ (40 mL) at room temperature under nitrogen was added BBr$_3$, 1M solution in CH$_2$Cl$_2$ (4.34 mL, 4.34 mmol). The reaction mixture was stirred at room temperature overnight. The mixture was concentrated under reduced pressure and the residue was dissolved in MeOH and coevaporated w/ MeOH (3×). The residue was purified via silica gel chromatography (DICHLOROMETHANE/MeOH) to obtain 2-nitro-4-(pyridin-4-yl)phenol (245 mg, 1.13 mmol, 52% yield) as a light yellow solid. $^1$H NMR (500 MHz, DMSO-d$_6$) δ 8.95 (d, J=6.1 Hz, 2H), 8.60 (d, J=1.8 Hz, 1H), 8.40 (d, J=6.1 Hz, 2H), 8.32-8.22 (m, 1H), 7.36 (d, J=8.9 Hz, 1H); LC/MS (ESI) m/e 217.1 [(M+H)+, calcd for C11H9N2O3 217.1].

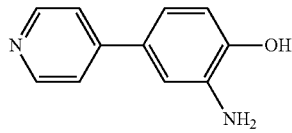 [SMILES: Nc1cc(-c2ccncc2)ccc1O]

Part C: 2-amino-4-(pyridin-4-yl)phenol

A solution of 2-nitro-4-(pyridin-4-yl)phenol (245 mg, 1.13 mmol) and palladium on carbon (50 mg, 0.047 mmol) in MeOH (50 mL) was shaken under H2 at 15 psi for 2 h. The mixture was filtered through diatomaceous earth (Celite®) and the filtrate concentrated under reduced pressure. The material was carried forward without further purification. Obtained 2-amino-4-(pyridin-4-yl)phenol (226 mg, 1.092 mmol, 96% crude yield) as a light green solid. $^1$H NMR (500 MHz, DMSO-d$_6$) δ 8.78 (d, J=6.7 Hz, 2H), 8.05 (d, J=6.7 Hz, 2H), 7.40 (d, J=2.4 Hz, 1H), 7.35 (dd, J=8.4, 2.3 Hz, 1H), 6.95 (d, J=8.5 Hz, 1H); LC/MS (ESI) m/e 187.1 [(M+H)+, calcd for C11H11N2O 187.1].

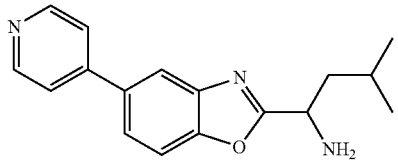 [SMILES: CC(C)CC(N)c1nc2cc(-c3ccncc3)ccc2o1]

Part D: 3-methyl-1-(5-(pyridin-4-yl)benzo[d]oxazol-2-yl)butan-1-amine

A solution of 2-amino-4-(pyridin-4-yl)phenol (183 mg, 0.983 mmol), 2-amino-4-methylpentanoic acid (159 mg, 1.214 mmol) and polyphosphoric acid (115% as H$_3$PO$_4$) (1.007 g, 4.20 mmol) in sulfolane (2 mL) was stirred in sealed vial at 80° C. for 14 h. The solution was cooled to room temperature and quenched with NH$_4$OH until pH=10. The neutralized mixture was extracted with EtOAc, (4×50 mL). The combined organics were washed with brine (1×50 mL), dried (MgSO4), filtered, and concentrated under reduced pressure. The residue was purified via silica gel chromatography (MeOH/DICHLOROMETHANE) to obtain 3-methyl-1-(5-(pyridin-4-yl)benzo[d]oxazol-2-yl)butan-1-amine (16.6 mg, 0.055 mmol, 6% yield) as a colorless solid. $^1$H NMR (500 MHz, CHLOROFORM-d) δ 8.70 (d, J=4.9 Hz, 2H), 7.97 (s, 1H), 7.63 (s, 2H), 7.58-7.53 (m, 2H), 4.30 (t, J=7.2 Hz, 1H), 1.95-1.86 (m, 1H), 1.86-1.72 (m, 2H), 1.03 (d, J=6.4 Hz, 3H), 1.00 (d, J=6.4 Hz, 3H); LC/MS (ESI) m/e 282.2 [(M+H)+, calcd for C17H20N3O 282.2]; HPLC (method L): t$_R$=9.25 min; HPLC (method M): t$_R$=9.40 min.

Example 84

3-methyl-1-(6-(pyridin-4-yl)benzo[d]oxazol-2-yl)butan-1-amine

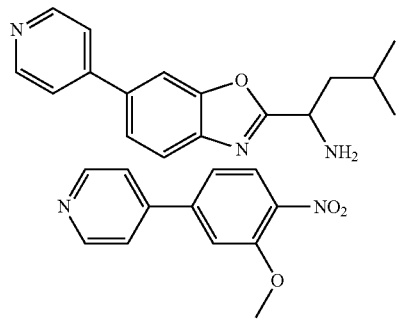

Part A: 4-(3-methoxy-4-nitrophenyl)pyridine

To a microwave vial was added 4-chloro-2-methoxy-1-nitrobenzene (580 mg, 3.09 mmol), bis(triphenylphosphine)palladium(II) chloride (43.4 mg, 0.062 mmol), pyridin-4-ylboronic acid (475 mg, 3.86 mmol) and Na$_2$CO$_3$ (983 mg, 9.27 mmol) in DME (15 mL), ethanol (2 mL), and water (3 mL). The reaction vial was sealed and heated in a microwave for 40 min at 125° C. The mixture was cooled to room temperature and concentrated under reduced pressure. Water (50 mL) was added and the mixture was extracted with EtOAc (120 mL). The organic layer was washed with water (3×70 mL) followed by brine (70 mL). The solution was dried with Na2SO4, filtered and concentrated under reduced pressure. The residue was purified via silica gel chromatography (DMC/EtOAc) to give 4-(3-methoxy-4-nitrophenyl)pyridine (471 mg, 2.025 mmol, 66% yield) as a pale yellow solid. $^1$H NMR (500 MHz, CHLOROFORM-d) δ 8.81-8.73 (m, 2H), 8.00 (d, J=8.8 Hz, 1H), 7.55-7.48 (m, 2H), 7.31-7.29 (m, 2H), 4.08 (s, 3H); LC/MS (ESI) m/e 231.1 [(M+H)+, calcd for C12H11N2O3 231.1].

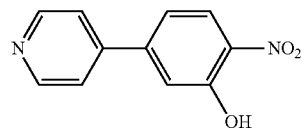 [SMILES: O=[N+]([O-])c1ccc(-c2ccncc2)cc1O]

Part B: 2-nitro-5-(pyridin-4-yl)phenol

To a solution of 4-(3-methoxy-4-nitrophenyl)pyridine (471 mg, 2.046 mmol) in dry CH$_2$Cl$_2$ (40 mL) under nitrogen cooled to 0° C. was added BBr$_3$ (1M solution in CH$_2$Cl$_2$) (4.09 mL, 4.09 mmol). The reaction mixture was stirred at room temperature overnight. The reaction mixture was concentrated under reduced pressure. The residue was dissolved in EtOAc (80 mL) and water (30 mL). The pH was adjusted to ~7-8 with concentrated ammonia (~15 drops) and solid NaCl was added. The solution was extracted with EtOAc (4×50 mL). The organic layer was dried (MgSO$_4$), filtered and concentrated under reduced pressure. The residue was purified via silica gel chromatography (MeOH/DMC) to afford 2-nitro-5-(pyridin-4-yl)phenol (400 mg, 1.850 mmol, 90% yield) as a yellow solid. ¹H NMR (500 MHz, CHLOROFORM-d) δ 10.71 (s, 1H), 8.81-8.75 (m, 2H), 8.26 (d, J=8.9 Hz, 1H), 7.55-7.53 (m, 2H), 7.45 (d, J=2.1 Hz, 1H), 7.28-7.26 (m, 1H); LC/MS (ESI) m/e 217.1 [(M+H)+, calcd for C11H9N2O3 217.1].

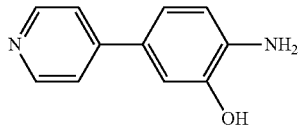

Part C: 2-amino-5-(pyridin-4-yl)phenol

A solution of 2-nitro-5-(pyridin-4-yl)phenol (400 mg, 1.850 mmol) and palladium on carbon (109 mg, 0.1023 mmol) in MeOH (50 mL) was shaken under hydrogen gas at 15 psi for 2 h. The mixture was filtered through glass wool and concentrated. The residue was purified via reverse phase HPLC (MeCN/H₂O/NH₄OAc) to give 2-amino-5-(pyridin-4-yl)phenol (320 mg, 1.117 mmol, 60% yield) as a pale brown solid. ¹H NMR (500 MHz, DMSO-d₆) δ 8.49 (d, J=5.2 Hz, 2H), 7.48 (d, J=5.2 Hz, 2H), 7.12-7.07 (m, 2H), 6.69 (d, J=8.2 Hz, 1H); LC/MS (ESI) m/e 187.1 [(M+H)+, calcd for C11H11N2O 187.1].

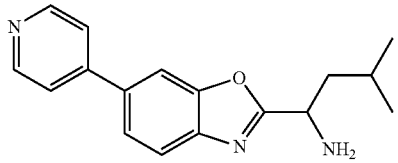 [SMILES: CC(C)CC(N)c1nc2ccc(-c3ccncc3)cc2o1]

Part D: 3-methyl-1-(6-(pyridin-4-yl)benzo[d]oxazol-2-yl)butan-1-amine

A solution of 2-amino-5-(pyridin-4-yl)phenol (255 mg, 1.369 mmol), 2-amino-4-methylpentanoic acid (222 mg, 1.691 mmol) and polyphosphoric acid (115% as H₃PO₄) (1401 mg, 5.84 mmol) in sulfolane (3 mL) was heated in a sealed vial at 80° C. for 14 h. The solution was cooled to room temperature and quenched with NH₄OH until pH=10. The neutralized mixture was extracted with EtOAc (4×50 mL). The combined organics were washed with brine (1×50 mL), dried (MgSO₄), filtered, and concentrated under reduced pressure. The residue was purified reverse phase HPLC (methanol/water/0.1% TFA) to obtain 3-methyl-1-(6-(pyridin-4-yl)benzo[d]oxazol-2-yl)butan-1-amine (3.8 mg, 0.013 mmol, 1% yield) as a pale yellow solid. ¹H NMR (500 MHz, CHLOROFORM-d) δ 8.75-8.67 (m, 1H), 7.84-7.77 (m, 1H), 7.64 (dd, J=8.2, 1.8 Hz, 1H), 7.58-7.53 (m, 2H), 7.29 (s, 2H), 4.30 (t, J=7.0 Hz, 1H), 1.95-1.86 (m, 1H), 1.86-1.77 (m, 2H), 1.03 (d, J=6.1 Hz, 3H), 1.00 (d, J=6.4 Hz, 3H); LC/MS (ESI) m/e 282.1 [(M+H)+, calcd for C17H20N3O 282.2]; HPLC (method L): t$_R$=3.01 min; HPLC (method M): t$_R$=3.20 min.

Example 85

2-isopentyl-6-(pyridin-4-yl)benzo[d]oxazole

Prepared in a similar fashion as described in Example 84 using 4-methylpentanoic acid in Part D to give the title compound (9.1 mg, 0.033 mmol, 10% yield) as a colorless amorphous solid: ¹H NMR (500 MHz, CHLOROFORM-d) δ 8.73-8.66 (m, 2H), 7.81-7.73 (m, 2H), 7.61 (dd, J=8.1, 1.7 Hz, 1H), 7.57-7.52 (m, 2H), 3.03-2.95 (m, 2H), 1.88-1.79 (m, 2H), 1.72 (tq, J=13.2, 6.7 Hz, 1H), 1.01 (d, J=6.7 Hz, 6H); LC/MS (ESI) m/e 267.2 [(M+H)+, calcd for C17H19N2O 267.2], HPLC (method L): t$_R$=5.30 min; HPLC (method M): t$_R$=5.76 min.

Example 86

(E)-2-(4-methylpent-2-en-2-yl)-5-(pyridin-4-yl)benzo[d]oxazole

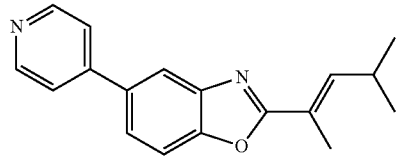 [SMILES: C/C(=C\C(C)C)c1nc2cc(-c3ccncc3)ccc2o1]

Prepared in a similar fashion as described in Example 83 using (E)-2,4-dimethylpent-2-enoic acid in Part D to give the title compound as a TFA salt (19.0 mg, 0.048 mmol, 24% yield) as a colorless solid: ¹H NMR (500 MHz, METHANOL-d₄) δ 8.89 (d, J=6.7 Hz, 2H), 8.50-8.42 (m, 2H), 8.30 (d, J=1.5 Hz, 1H), 8.02 (dd, J=8.5, 1.8 Hz, 1H), 7.85 (d, J=8.5 Hz, 1H), 6.87-6.79 (m, 1H), 2.98-2.82 (m, 1H), 2.24 (d, J=1.5 Hz, 3H), 1.17 (d, J=6.4 Hz, 6H); LC/MS (ESI) m/e 279.2 [(M+H)+, calcd for C18H19N2O 279.2], HPLC (method L): t$_R$=5.61 min; HPLC (method M): t$_R$=5.93 min.

Example 87

2-(4-methylpentan-2-yl)-6-(pyridin-4-yl)benzo[d]oxazole

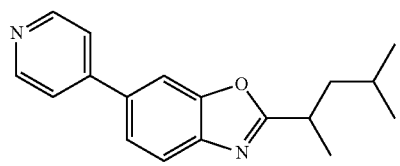 [SMILES: CC(C)CC(C)c1nc2ccc(-c3ccncc3)cc2o1]

Prepared in a similar fashion as described in Example 84 using 2,4-dimethylpentanoic acid in Part D to give the title compound (19.9 mg, 0.070 mmol, 20% yield) as a colorless solid: ¹H NMR (500 MHz, CHLOROFORM-d) δ 8.74-8.68 (m, 2H), 7.81-7.77 (m, 2H), 7.64-7.59 (m, 1H), 7.57-7.53 (m, 2H), 3.32-3.18 (m, 1H), 1.90 (ddd, J=13.2, 8.0, 6.6 Hz, 1H), 1.70-1.61 (m, 1H), 1.61-1.54 (m, 1H), 1.46 (d, J=7.0 Hz, 3H), 0.99 (d, J=6.4 Hz, 3H), 0.94 (d, J=6.4 Hz, 3H); LC/MS (ESI) m/e 281.1 [(M+H)+, calcd for C18H21N2O 281.2], HPLC (method N): $t_R$=7.15 min; HPLC (method O): $t_R$=11.39 min.

Example 88

2-(4-methylpentan-2-yl)-5-(pyridin-4-yl)benzo[d]oxazole

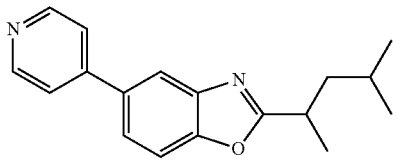 [SMILES: CC(C)CC(C)c1nc2cc(-c3ccncc3)ccc2o1]

Prepared in a similar fashion as described in Example 83 using 2,4-dimethylpentanoic acid in Part D to give the title compound (24.4 mg, 0.086 mmol, 25% yield) as a colorless solid: ¹H NMR (500 MHz, CHLOROFORM-d) δ 8.73-8.65 (m, 2H), 7.99-7.92 (m, 1H), 7.59 (t, J=1.4 Hz, 2H), 7.56-7.51 (m, 2H), 3.35-3.19 (m, 1H), 1.89 (ddd, J=13.2, 8.0, 6.6 Hz, 1H), 1.69-1.60 (m, 1H), 1.60-1.53 (m, 1H), 1.46 (d, J=7.0 Hz, 3H), 0.99 (d, J=6.4 Hz, 3H), 0.93 (d, J=6.4 Hz, 3H); LC/MS (ESI) m/e 281.1 [(M+H)+, calcd for C18H21N2O 281.2], HPLC (method L): $t_R$=4.93 min; HPLC (method M): $t_R$=5.16 min.

Example 89

2-isopentyl-5-(pyridin-4-yl)benzo[d]oxazole

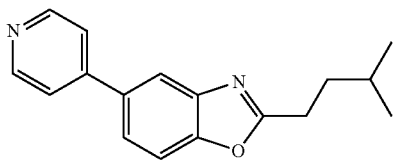 [SMILES: CC(C)CCc1nc2cc(-c3ccncc3)ccc2o1]

Prepared in a similar fashion as described in Example 83 using 4-methylpentanoic acid in Part D to give the title compound (16.8 mg, 0.061 mmol, 17% yield) as a colorless solid: ¹H NMR (500 MHz, CHLOROFORM-d) δ 8.72-8.67 (m, 2H), 7.94 (t, J=1.2 Hz, 1H), 7.60 (d, J=1.2 Hz, 2H), 7.56-7.53 (m, 2H), 3.00 (dd, J=8.4, 7.5 Hz, 2H), 1.87-1.80 (m, 2H), 1.75-1.67 (m, 1H), 1.01 (d, J=6.7 Hz, 6H); LC/MS (ESI) m/e 267.3 [(M+H)+, calcd for C17H19N2O 267.2], HPLC (method L): $t_R$=4.58 min; HPLC (method M): $t_R$=4.76 min.

Example 90

2-(cyclopentylmethyl)-5-(pyridin-4-yl)benzo[d]oxazole

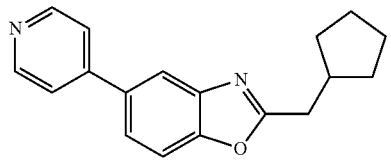 [SMILES: c1cc(-c2ccc3oc(CC4CCCC4)nc3c2)ccn1]

Prepared in a similar fashion as described in Example 83 using 2-cyclopentylacetic acid in Part D to give the title compound (58 mg, 0.206 mmol, 59% yield) as a colorless solid: ¹H NMR (500 MHz, CHLOROFORM-d) δ 8.67 (d, J=5.5 Hz, 2H), 7.93 (s, 1H), 7.58 (s, 2H), 7.53 (d, J=5.8 Hz, 2H), 2.97 (d, J=7.6 Hz, 2H), 2.48 (spt, J=7.7 Hz, 1H), 1.95-1.85 (m, 2H), 1.76-1.65 (m, 2H), 1.65-1.54 (m, 2H), 1.40-1.26 (m, 2H); LC/MS (ESI) m/e 279.1 [(M+H)+, calcd for C18H19N2O 279.2], HPLC (method L): $t_R$=5.40 min; HPLC (method M): $t_R$=5.81 min.

Example 91

4,4,4-trifluoro-1-(5-(pyridin-4-yl)benzo[d]oxazol-2-yl)-3-(trifluoromethyl)butan-1-amine

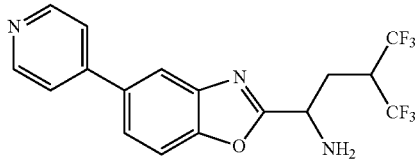 [SMILES: NC(CC(C(F)(F)F)C(F)(F)F)c1nc2cc(-c3ccncc3)ccc2o1]

Prepared in a similar fashion as described in Example 83 using hexafluoro-DL-leucine in Part D to give the title compound (5 mg, 0.012 mmol, 3% yield) as a colorless solid: ¹H NMR (500 MHz, METHANOL-d₄) δ 8.90 (d, J=7.0 Hz, 2H), 8.51-8.47 (m, 1H), 8.45-8.39 (m, 2H), 8.14 (dd, J=8.5, 1.8 Hz, 1H), 8.00 (d, J=8.2 Hz, 1H), 5.12 (dd, J=9.5, 5.2 Hz, 1H), 4.14-4.02 (m, 1H), 2.95-2.80 (m, 1H), 2.69 (ddd, J=15.3, 7.6, 5.2 Hz, 1H); LC/MS (ESI) m/e 390.0 [(M+H)+, calcd for C17H14F6N3O 390.1], HPLC (method L): $t_R$=5.97 min; HPLC (method M): $t_R$=6.40 min.

Example 92

2-(2-cyclopentylethyl)-5-(pyridin-4-yl)benzo[d]oxazole

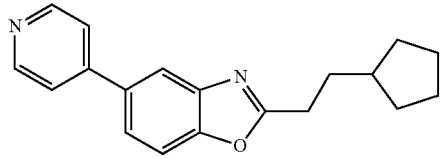 [SMILES: c1cc(-c2ccc3oc(CCC4CCCC4)nc3c2)ccn1]

Prepared in a similar fashion as described in Example 83 using 3-cyclopentylpropanoic acid in Part D to give the title compound (32 mg, 0.108 mmol, 31% yield) as a colorless solid: ¹H NMR (500 MHz, CHLOROFORM-d) δ 8.69 (d, J=5.8 Hz, 2H), 7.94 (s, 1H), 7.59 (s, 2H), 7.54 (d, J=5.8 Hz, 2H), 3.00 (t, J=7.6 Hz, 2H), 2.01-1.80 (m, 5H), 1.71-1.62 (m, 2H), 1.61-1.48 (m, 2H), 1.26-1.12 (m, 2H); LC/MS (ESI) m/e 293.3 [(M+H)+, calcd for C19H21N2O 293.2], HPLC (method L): $t_R$=11.66 min; HPLC (method M): $t_R$=11.19 min.

Example 93

4,4,4-trifluoro-1-(5-(pyridin-4-yl)benzo[d]oxazol-2-yl)butan-1-amine

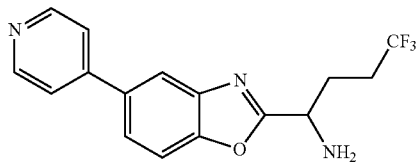 [SMILES: NC(CCC(F)(F)F)c1nc2cc(-c3ccncc3)ccc2o1]

Prepared in a similar fashion as described in Example 83 using 2-amino-5,5,5-trifluoropentanoic acid in Part D to give the title compound (2.3 mg, 6.66 μmol, 2% yield) as a colorless solid: ¹H NMR (500 MHz, CHLOROFORM-d) δ 8.74-8.70 (m, 2H), 7.99 (t, J=1.2 Hz, 1H), 7.66 (d, J=1.2 Hz, 2H), 7.58-7.53 (m, 2H), 4.27 (dd, J=8.1, 5.3 Hz, 1H), 2.55-2.30 (m, 3H), 2.19-2.05 (m, 1H); LC/MS (ESI) m/e 322.2 [(M+H)+, calcd for C16H15F3N3O 322.1], HPLC (method P): $t_R$=8.87 min; HPLC (method O): $t_R$=9.16 min.

Example 94

1-(5-(3-methoxypyridin-4-yl)benzo[d]oxazol-2-yl)-3-methylbutan-1-amine

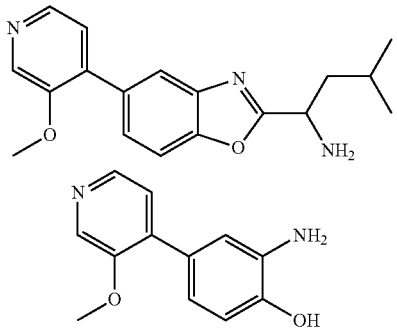

Part A: 2-amino-4-(3-methoxypyridin-4-yl)phenol

To a mixture of 5-bromobenzo[d]oxazole (192 mg, 0.972 mmol), 3-methoxypyridin-4-ylboronic acid (223 mg, 1.458 mmol), phosphoric acid, potassium salt (516 mg, 2.430 mmol), palladium(II) acetate (19.64 mg, 0.087 mmol), and 2-dicyclohexylphosphino-2',6'-dimethoxy-1,1'-biphenyl (44 mg, 0.107 mmol) in a round bottom flask under nitrogen was added n-butanol (6 mL). The reaction mixture was heated at 100° C. for 14 h. The mixture was cooled to room temperature, filtered through diatomaceous earth (Celite®) and the filtrate concentrated under reduced pressure. Water was added to the residue and it was extracted with EtOAc (3×20 mL). The organic layer was concentrated under reduced pressure. The residue was dissolved in EtOH (5 mL) and 1N NaOH (5 mL) and heated to 50 C° C. for 14 h. The solution was concentrated under reduced pressure. Water was added and the residue was extracted with EtOAc (3×20 mL). The combined organics were washed with brine (1×20 mL), dried over sodium sulfate, filtered, and concentrated under reduced pressure. The residue was carried on without further purification to give 2-amino-4-(3-methoxypyridin-4-yl)phenol (84 mg, 0.388 mmol, 40% crude yield) as a green solid. ¹H NMR (500 MHz, CHLOROFORM-d) δ 8.34 (s, 1H), 8.29 (d, J=4.6 Hz, 1H), 7.27 (d, J=4.9 Hz, 1H), 7.04 (d, J=1.8 Hz, 1H), 6.96-6.90 (m, 1H), 6.88-6.82 (m, 1H), 3.94 (s, 3H); LC/MS (ESI) m/e 217.2 [(M+H)+, calcd for C12H13N2O2 217.1].

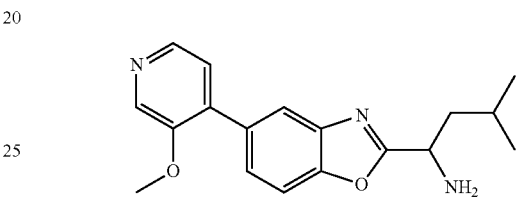

Part B: 1-(5-(3-methoxypyridin-4-yl)benzo[d]oxazol-2-yl)-3-methylbutan-1-amine

A solution of 2-amino-4-(3-methoxypyridin-4-yl)phenol (74 mg, 0.342 mmol), leucine (55.4 mg, 0.423 mmol) and polyphosphoric acid (115% as H₃PO₄) (588 mg, 2.45 mmol) in sulfolane (4 mL) was heated in a sealed vial at 85° C. for 14 h. The solution was cooled to room temperature and quenched with NaOH until pH=10. The neutralized mixture was extracted with EtOAc (3×60 mL). The combined organics were washed with brine (1×60 mL), dried (MgSO4), filtered, and concentrated under reduced pressure. The residue was purified via silica gel chromatography (DICHLOROMETHANE/MeOH) to obtain 1-(5-(3-methoxypyridin-4-yl)benzo[d]oxazol-2-yl)-3-methylbutan-1-amine (4.8 mg, 0.01 mmol, 3% yield) as a colorless solid. ¹H NMR (500 MHz, CHLOROFORM-d) δ 8.41 (s, 1H), 8.36 (d, J=4.6 Hz, 1H), 8.00-7.91 (m, 1H), 7.62-7.57 (m, 1H), 7.57-7.51 (m, 1H), 7.30 (d, J=4.6 Hz, 1H), 4.28 (t, J=7.2 Hz, 1H), 3.95 (s, 3H), 1.94-1.86 (m, 1H), 1.86-1.72 (m, 2H), 1.02 (d, J=6.4 Hz, 3H), 1.00 (d, J=6.4 Hz, 3H); LC/MS (ESI) m/e 312.1 [(M+H)+, calcd for C18H22N3O2 312.2]; HPLC (method L): $t_R$=2.81 min; HPLC (method M): $t_R$=3.00 min.

Example 95

3-methyl-1-(5-(pyridin-4-yl)benzo[d]thiazol-2-yl)butan-1-amine

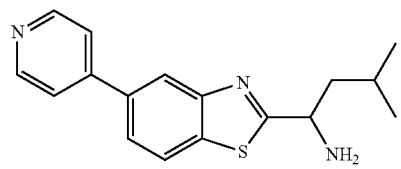

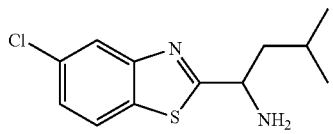

Part A: 1-(5-chlorobenzo[d]thiazol-2-yl)-3-methylbutan-1-amine

A mixture of 2-amino-4-chlorobenzenethiol, HCl (0.55 g, 2.80 mmol), (R)-2-amino-4-methylpentanoic acid (0.902 g, 6.88 mmol), and polyphosphoric acid (115% as $H_3PO_4$) (1.6 g, 6.67 mmol) in sulfolane (10 mL) was stirred in sealed vial at 80° C. for 2 h. The reaction mixture was cooled to room temperature and a solution of concentrated aqueous ammonia (10 mL) in ice water (20 mL) was added. The cloudy aqueous suspension was extracted with ethyl acetate (2×75 mL) until the layers were no longer cloudy. The organic layer was washed water (3×50 mL). The EtOAc layer was dried ($Na_2SO_4$) and concentrated under reduced pressure. The residue was purified via silica gel chromatography (10% MeOH in DICHLOROMETHANE) to afford (R)-1-(5-chlorobenzo[d]thiazol-2-yl)-3-methylbutan-1-amine (341 mg, 1.231 mmol, 44% yield) as a pale yellow solid. $^1$H NMR (500 MHz, CHLOROFORM-d) δ 7.96 (d, J=1.5 Hz, 1H), 7.80 (d, J=8.5 Hz, 1H), 7.35 (dd, J=8.5, 1.8 Hz, 1H), 2.28-2.21 (m, 1H), 1.89-1.78 (m, 1H), 1.76-1.64 (m, 2H), 1.02 (d, J=6.4 Hz, 3H), 1.01 (d, J=6.4 Hz, 3H); LC/MS (ESI) m/e 255.1 [(M+H)+, calcd for C12H16ClN2S 255.1].

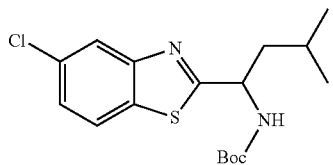 [SMILES: CC(C)CC(NC(=O)OC(C)(C)C)c1nc2cc(Cl)ccc2s1]

Part B: tert-butyl (1-(5-chlorobenzo[d]thiazol-2-yl)-3-methylbutyl)carbamate

A solution of 1-(5-chlorobenzo[d]thiazol-2-yl)-3-methylbutan-1-amine (330 mg, 1.295 mmol) in acetonitrile (6.5 mL) was treated with triethyl amine (364 µl, 2.61 mmol) then $BOC_2O$ (543 µl, 2.337 mmol) in portions. The mixture was stirred at room temperature for 1 h. Water (10 mL) was added and the mixture stirred for 5 min. The solution was concentrated under reduced pressure to afford tert-butyl 1-(5-chlorobenzo[d]thiazol-2-yl)-3-methylbutylcarbamate (0.46 g, 1.296 mmol, 100% crude yield) as a pale yellow solid which was carried on without further purification. LC/MS (ESI) m/e 355.2 [(M+H)+, calcd for C17H24ClN2O2S 355.1].

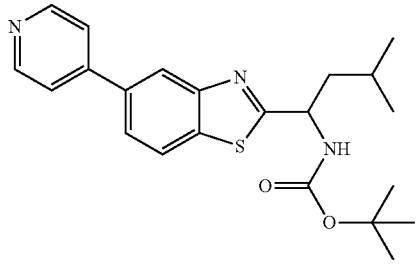 [SMILES: CC(C)CC(NC(=O)OC(C)(C)C)c1nc2cc(-c3ccncc3)ccc2s1]

Part C: tert-butyl (3-methyl-1-(5-(pyridin-4-yl)benzo[d]thiazol-2-yl)butyl)carbamate In a microwave vial was added tert-butyl 1-(5-chlorobenzo[d]thiazol-2-yl)-3-methylbutylcarbamate (120 mg, 0.338 mmol), pyridin-4-ylboronic acid (47 mg, 0.382 mmol), bis(triphenylphosphine)palladium(II) chloride (4.5 mg, 6.41 µmol), sodium carbonate (97 mg, 0.915 mmol), DME (1.5 mL), ethanol (0.20 mL) and water (0.3 mL). The reaction was sealed and heated in the microwave for 2.5 h at 125° C. The mixture was cooled to room temperature and extracted with ethyl acetate (3×10). The combined organics and washed with brine (1×10), dried (MgSO4), filtered and concentrated under reduced pressure. The residue was purified via silica gel chromatography (MeOH in DICHLOROMETHANE) to afford tert-butyl 3-methyl-1-(5-(pyridin-4-yl)benzo[d]thiazol-2-yl)butylcarbamate (10 mg, 0.023 mmol, 7% yield) as a pale yellow solid. LC/MS (ESI) m/e 398.3 [(M+H)+, calcd for C22H28N3O2S 398.2].

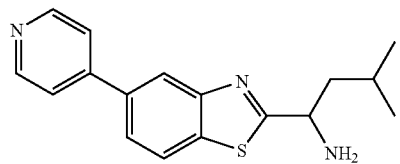

Part D: 3-methyl-1-(5-(pyridin-4-yl)benzo[d]thiazol-2-yl)butan-1-amine

A solution of tert-butyl 3-methyl-1-(5-(pyridin-4-yl)benzo[d]thiazol-2-yl)butylcarbamate (10 mg, 0.023 mmol) in dichloromethane (0.9 mL) was treated with TFA (100 µl, 1.298 mmol) and was maintained at ambient temperature for 3 h. The volatiles were evaporated under reduced pressure. The residue was taken up in MeOH (1 mL) and was treated with NH4OH (0.2 mL) then evaporated under reduced pressure. The residue was purified via silica gel chromatography (DICHLOROMETHANE/MeOH) to obtain 3-methyl-1-(5-(pyridin-4-yl)benzo[d]thiazol-2-yl)butan-1-amine (4.5 mg, 0.014 mmol, 64% yield) as a colorless solid. $^1$H NMR (500 MHz, MeOD) δ ppm 8.61-8.66 (m, 2H), 8.31 (d, J=1.2 Hz, 1H), 8.13 (d, J=8.9 Hz, 1H), 7.80-7.86 (m, 3H), 4.43 (t, J=7.0 Hz, 1H), 1.71-1.89 (m, 3H), 1.03 (d, J=6.3 Hz, 3H), 1.00 (d, J=6.3 Hz, 3H); LC/MS (ESI) m/e 298.1 [(M+H)+, calcd for C17H20N3S 298.2]; HPLC (method L): $t_R$=3.35 min; HPLC (method M): $t_R$=3.62 min.

Example 96 and 97

(R)-3-methyl-1-(5-(pyridin-4-yl)benzo[d]thiazol-2-yl)butan-1-amine and (S)-3-methyl-1-(5-(pyridin-4-yl)benzo[d]thiazol-2-yl) butan-1-amine

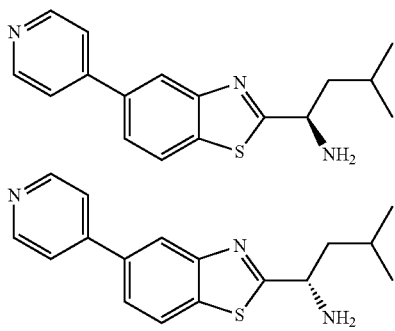

A mixture of 3-methyl-1-(5-(pyridin-4-yl)benzo[d]thiazol-2-yl)butan-1-amine (3.8 mg, 3.013 mmol), was separated via reverse phase SFC (Chiralcel OD-H column, using 15% methanol with 0.1% DEA as the modifier) to afford two enantiomers (absolute stereochemistry is unassigned). Enantiomer 1 (first eluting): 1-(5-chlorobenzo[d]thiazol-2-yl)-3-methylbutan-1-amine (1.5 mg, 4.54 umol, 36% yield) as a colorless film. $^1$H NMR (500 MHz, MeOD) δ ppm 8.61-8.66 (m, 2H), 8.31 (d, J=1.2 Hz, 1H), 8.13 (d, J=8.9 Hz, 1H), 7.80-7.86 (m, 3H), 4.43 (t, J=7.0 Hz, 1H), 1.71-1.89 (m, 3H), 1.03 (d, J=6.3 Hz, 3H), 1.00 (d, J=6.3 Hz, 3H); LC/MS (ESI) m/e 298.1 [(M+H)+, calcd for C17H20N3S 298.2]; Chiral HPLC (method A): $t_R$=11.77 min. Enantiomer 2 (second eluting): 1-(5-chlorobenzo[d]thiazol-2-yl)-3-methylbutan-1-amine (1.6 mg, 4.84 umol, 38% yield) as a colorless film. $^1$H NMR (500 MHz, MeOD) δ ppm 8.61-8.66 (m, 2H), 8.31 (d, J=1.2 Hz, 1H), 8.13 (d, J=8.9 Hz, 1H), 7.80-7.86 (m, 3H), 4.43 (t, J=7.0 Hz, 1H), 1.71-1.89 (m, 3H), 1.03 (d, J=6.3 Hz, 3H), 1.00 (d, J=6.3 Hz, 3H); LC/MS (ESI) m/e 298.1 [(M+H)+, calcd for C17H20N3S 298.2]; Chiral HPLC (method A): $t_R$=14.08 min.

Example 98

3-methyl-1-(6-(pyridin-4-yl)benzo[d]thiazol-2-yl)butan-1-amine

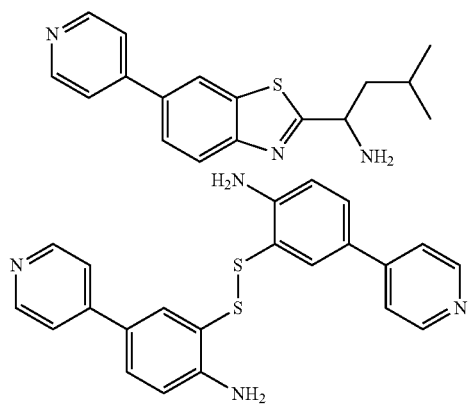

Part A: 1 2,2'-disulfanediylbis(4-(pyridin-4-yl)aniline)

To a sealable vial was added 6-bromobenzo[d]thiazole (214 mg, 1 mmol), pyridin-4-ylboronic acid (369 mg, 3.00 mmol), tetrakis(triphenylphosphine)palladium(0) (116 mg, 0.100 mmol), saturated aqueous potassium carbonate (5 mL, 1.00 mmol), and DMF (5 mL). The vial was sealed and purged with N$_2$ gas for 5 min. The mixture was then heated to 130° C. for 18 h. The mixture was cooled to room temperature and concentrated under reduced pressure. The residue was partitioned between EtOAc (50 mL) and water (50 mL). The aqueous layer was extracted with EtOAc (2×30 mL). The combined organics were washed with brine (1×50 mL), dried (MgSO$_4$), filtered and concentrated under reduced pressure. The residue was purified by silica gel chromatography (methanol in DICHLOROMETHANE) to obtain 2,2'-disulfanediylbis(4-(pyridin-4-yl)aniline) (123 mg, 0.306 mmol, 31% yield) as an off-white solid. $^1$H NMR (500 MHz, METHANOL-d$_4$) δ 8.31-8.24 (m, 4H), 7.49-7.44 (m, 2H), 7.27 (d, J=2.4 Hz, 2H), 7.20-7.14 (m, 4H), 6.87 (d, J=8.5 Hz, 2H); LC/MS (ESI) m/e 403.2 [(M+H)+, calcd for C22H19N4S2 403.1].

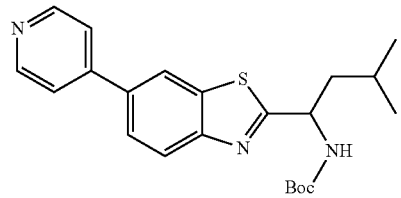 [SMILES: CC(C)CC(NC(=O)OC(C)(C)C)c1nc2ccc(-c3ccncc3)cc2s1]

Part B: tert-butyl (3-methyl-1-(6-(pyridin-4-yl)benzo[d]thiazol-2-yl)butyl)carbamate A solution of 2,2'-disulfanediylbis(4-(pyridin-4-yl)aniline) (32 mg, 0.079 mmol) and lithium borohydride (13 mg, 0.597 mmol) in THF (1 mL) under N$_2$ was stirred at room temperature for 1 h. MeOH (1 mL) was added and the solution was stirred for 1 h to quench the reaction. The red solution was treated with AcOH (0.01 mL) and concentrated under reduced pressure. DICHLOROMETHANE (1 mL) was added and the solution concentrated under reduced pressure (2×) to remove excess AcOH. DMSO (1 mL) was added and the solution was heat to 130° C. under N$_2$ for 18 h. The reaction mixture was cooled to ambient temperature, diluted to 4 mL volume with MeOH and purified by reverse phase HPLC (MeOH/H$_2$O/0.1% TFA) to afford tert-butyl 3-methyl-1-(6-(pyridin-4-yl)benzo[d]thiazol-2-yl)butylcarbamate, TFA (11 mg, 0.022 mmol, 27% crude yield) as a brown gum which was carried on without further purification. LC/MS (ESI) m/e 398.3 [(M+H)+, calcd for C22H28N3O2S 398.2].

Part C: tert3-methyl-1-(6-(pyridin-4-yl)benzo[d]thiazol-2-yl)butan-1-amine

A solution of tert-butyl 3-methyl-1-(6-(pyridin-4-yl)benzo[d]thiazol-2-yl)butylcarbamate, TFA (11 mg, 0.022 mmol) in 20% TFA in DCM (1 mL) was stirred at room temperature for 3 h. The solution was quenched saturated aqueous sodium bicarbonate (10 drops) and concentrated under reduced pressure. The residue was purified via reverse phase HPLC (MeOH/H$_2$O/0.1% TFA) to obtain 3-methyl-1-(6-(pyridin-4-yl)benzo[d]thiazol-2-yl)butan-1-amine, TFA (1.2 mg, 2.77 umol, 13% yield) as a colorless solid. $^1$H NMR (500 MHz, METHANOL-d$_4$) δ 8.87 (d, J=6.7 Hz, 2H), 8.74 (d, J=1.5 Hz, 1H), 8.40-8.34 (m, 2H), 8.30 (d, J=8.5 Hz, 1H), 8.16 (dd, J=8.7, 2.0 Hz, 1H), 5.01 (t, J=7.3 Hz, 1H), 2.15-2.06 (m, 1H), 1.99 (dt, J=14.0, 7.2 Hz, 1H), 1.78 (tq, J=13.5, 6.7 Hz, 1H), 1.09 (d, J=6.4 Hz, 3H), 1.05 (d, J=6.7 Hz, 3H); LC/MS (ESI) m/e 298.2 [(M+H)+, calcd for C17H20N3S 298.1]; HPLC (method P): t$_R$=12.81 min; HPLC (method Q): t$_R$=13.05 min.

Example 99

2-(cyclopentylmethyl)-5-(pyridin-4-yl)-1H-benzo[d]imidazole

Prepared in a similar fashion as described in Example 56 to afford 2-(cyclopentylmethyl)-5-(pyridin-4-yl)-1H-benzo[d]imidazole (25 mg, 0.09 mmol, 13% yield) as a white solid. $^1$H NMR (400 MHz, CDCl$_3$): δ 8.64-8.65 (m, 2H), 7.84 (br s, 1H), 7.65 (d, J=8.00 Hz, 1H), 7.52-7.57 (m, 3H), 2.97 (d, J=7.60 Hz, 2H), 2.41-2.43 (m, 1H), 1.85-1.89 (m, 2H), 1.67-1.71 (m, 2H), 1.57-1.59 (m, 2H), 1.28-1.34 (m, 2H) ppm; LCMS (ESI) m/e 278.2 [(M+H)$^+$, calcd for C$_{18}$H$_{20}$N$_3$, 278.16]; LC/MS retention time (method B): t$_R$=1.04 min; HPLC retention time (method A): t$_R$=7.34 min; HPLC retention time (method B): t$_R$=8.38 min.

Example 100

2-isopentyl-6-(oxazol-5-yl)benzo[d]oxazole

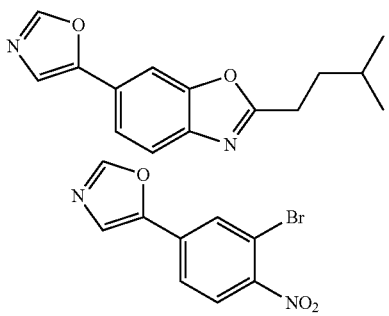

Part A: 5-(3-bromo-4-nitrophenyl)oxazole

Prepared in a similar fashion as described in Example 4, Part C using 3-bromo-4-nitrobenzaldehyde to afford the title compound (7.3 g, 27.14 mmol, 91% yield) as a brown solid. LCMS (ESI) m/e 268.7, 270.7 (Br pattern) [(M+H)$^+$, calcd for C$_9$H$_6$BrN$_2$O$_3$, 268.96]; LC/MS retention time (method C): t$_R$=1.75 min.

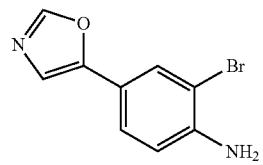

Part B: 2-bromo-4-(oxazol-5-yl)aniline

To a solution of 5-(3-bromo-4-nitrophenyl)oxazole (1.0 g, 3.73 mmol) in ethanol (35 mL) at room temperature under nitrogen was added ammonium chloride (2.34 g, 44.2 mmol) and zinc powder (3.37 g, 51.54 mmol). The reaction mixture was stirred at 70° C. for 16 h. The reaction mixture was allowed to cool to room temperature and was filtered through a diatomaceous earth (Celite®) plug. The filtrate was concentrated under reduced pressure to obtain 2-bromo-4-(oxazol-5-yl)aniline (370 mg, 1.55 mmol, 42% yield) as a brown solid. The product was carried on without further purification. LCMS (ESI) m/e 239.0, 241.0 Br pattern [(M+H)$^+$, calcd for C$_9$H$_8$BrN$_2$O, 238.97]; LC/MS retention time (method B): t$_R$=1.49 min.

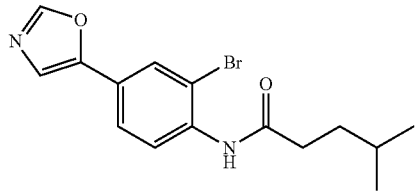 [SMILES: CC(C)CCC(=O)Nc1ccc(-c2cnco2)cc1Br]

Part C: N-(2-bromo-4-(oxazol-5-yl)phenyl)-4-methylpentanamide

A solution of 4-methylpentanoic acid (2.5 g, 21.52 mmol) in thionyl chloride (6.4 g, 53.8 mmol) under nitrogen atmosphere was heated at 60° C. for 3 h. The reaction mixture was cooled and the volatile organics were removed under reduced pressure. The oily residue so obtained was subjected to fractional distillation under atmospheric pressure. The distillation afforded a fraction at 155° C., 4-methylpentanoyl chloride (1 g, 7.43 mmol) as a colorless oil.

To a solution of 2-bromo-4-(oxazol-5-yl)aniline (900 mg, 3.76 mmol) in dichloroethane (30 mL) cooled to 0° C. under a nitrogen atmosphere was added DIPEA (1.45 g, 11.28 mmol). To this solution, 4-methylpentanoyl chloride (606 mg, 4.512 mmol) was added dropwise and stirring continued for 16 h at rt. The reaction was quenched by addition of saturated aqueous ammonium chloride (25 mL). The mixture was extracted with ethyl acetate (3×50 mL). The combined organic extracts were washed with brine (50 mL), dried over sodium sulfate and concentrated under reduced pressure. The residue was purified by silica gel column chromatography using a gradient of ethyl acetate in hexanes to afford N-(2-bromo-4-(oxazol-5-yl)phenyl)-4-methylpentanamide (350 mg, 1.042 mmol, 28% yield) as a light brown solid. LCMS (ESI) m/e 337.0, 339.0 (Br pattern) [(M+H)$^+$, calcd for $C_{15}H_{18}BrN_2O_2$, 337.05]; LC/MS retention time (method B): $t_R$=1.90 min.

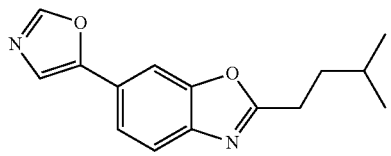 [SMILES: CC(C)CCc1nc2ccc(-c3cnco3)cc2o1]

Part D: 2-isopentyl-6-(oxazol-5-yl)benzo[d]oxazole

A suspension of N-(2-bromo-4-(oxazol-5-yl)phenyl)-4-methylpentanamide (800 mg, 2.374 mmol), 1,10-phenanthroline (42 mg, 0.23 mmol), copper iodide (22 mg, 0.11 mmol), cesium carbonate (5.4 g, 16.6 mmol), in dimethoxy ethane (7.5 mL) was charged in a screw capped vial and was purged with nitrogen for 5 min. The mixture was then heated at 140° C. overnight (~14 h). The reaction mixture was allowed to cool to room temperature and carefully quenched by addition of water (20 mL). The product was extracted with ethyl acetate (3×25 mL).The combined organic extracts were washed with brine (25 mL), dried over sodium sulfate and concentrated under reduced pressure. The residue was purified by preparative HPLC (10 mM ammonium acetate in water and acetonitrile) to afford 2-isopentyl-6-(oxazol-5-yl)benzo[d]oxazole (200 mg, 0.781 mmol, 33% yield) as a yellow solid. $^1$H NMR (400 MHz, CDCl$_3$) δ 7.93 (s, 1H), 7.77 (d, J=1.20 Hz, 1H), 7.69 (d, J=8.40 Hz, 1H), 7.61 (dd, J=8.20, 1.20 Hz, 1H), 7.38 (s, 1H), 2.94-2.98 (m, 2H), 1.78-1.83 (m, 2H), 1.66-1.74 (m, 1H), 0.99 (d, J=6.40 Hz, 6H) ppm; LCMS (ESI) m/e 257.2 [(M+H)$^+$, calcd for $C_{15}H_{17}N_2O_2$, 257.12]; LC/MS retention time (method B): $t_R$=2.06 min; HPLC retention time (method C): $t_R$=11.82 min; HPLC retention time (method D): $t_R$=9.97 min.

Example 101

(R)-N,3-dimethyl-1-(6-(oxazol-5-yl)-1H-benzo[d]imidazol-2-yl) butan-1-amine

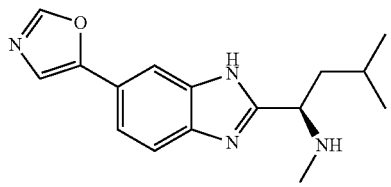 [SMILES: CN[C@H](CC(C)C)c1nc2ccc(-c3cnco3)cc2[nH]1]

To a solution of (R)-3-methyl-1-(6-(oxazol-5-yl)-1H-benzo[d]imidazol-2-yl)butan-1-amine (0.1 g, 0.37 mmol), prepared as described in Example 4, in dichloromethane (5 mL) was added triethyl amine (0.112 g, 1.11 mmol) followed by methyl iodide (0.053 g, 0.37 mmol). The reaction mixture was stirred at room temperature overnight (~14 h). The reaction mixture was cooled in an ice bath and quenched with water (10 mL). The product was extracted with ethyl acetate (3×10 mL). The combined organic extracts were washed with brine (15 mL), dried over sodium sulfate and concentrated under reduced pressure. The residue was purified by preparative HPLC (0.1% HCl in water and acetonitrile) to afford (R)-N,3-dimethyl-1-(6-(oxazol-5-yl)-1H-benzo[d]imidazol-2-yl)butan-1-amine (15 mg, 0.053 mmol, 14% yield) as a light brown solid. $^1$H NMR (400 MHz, CDCl$_3$) δ 7.91 (s, 1H), 7.88 (br s, 1H), 7.63 (d, J=8.4 Hz, 1H), 7.55 (dd, J=8.4, 1.6 Hz, 1H), 7.33 (s, 1H), 4.08-4.12 (m, 1H), 2.42 (s, 3H), 1.79-1.90 (m, 1H), 1.60-1.70 (m, 2H), 1.00 (d, J=6.4 Hz, 3H), 0.93 (d, J=6.4 Hz, 3H) ppm; LCMS (ESI) m/e 285.2 [(M+H)$^+$, calcd for $C_{16}H_{21}N_4O$, 285.16]; LC/MS retention time (method A): $t_R$=1.21 min; HPLC retention time (method A): $t_R$=9.55 min; HPLC retention time (method B): $t_R$=10.09 min.

Example 102

(R)-N-(2-methoxyethyl)-3-methyl-1-(5-(oxazol-5-yl)-1H-benzo[d]imidazol-2-yl)butan-1-amine

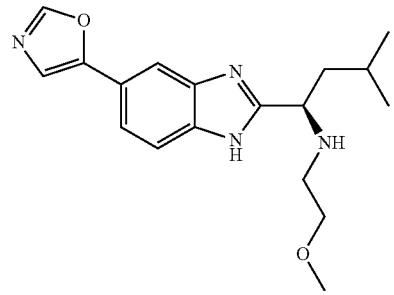 [SMILES: COCCN[C@H](CC(C)C)c1nc2cc(-c3cnco3)ccc2[nH]1]

To a solution of (R)-3-methyl-1-(5-(oxazol-5-yl)-1H-benzo[d]imidazol-2-yl)butan-1-amine hydrochloride (0.6 g, 1.89 mmol), prepared as described in Example 4, Part D, in methylene dichloride (6 mL) at 0° C. was added triethylamine (0.75 mL, 5.7 mmol) followed by bromomethoxy ethane (0.27 mL, 2.8 mmol) and the reaction mixture was heated at 50° C. overnight. The reaction mixture was cooled to room temperature, diluted with water (10 mL) and extracted with ethyl acetate (2×10 mL). The combined organic layers were dried over sodium sulfate, filtered and concentrated under reduced pressure. The crude product was purified by silica gel chromatography using a gradient of ethyl acetate and hexane to afford the title product (53 mg, 0.16 mmol, 9% yield) as a light yellow solid. $^1$H NMR (400 MHz, CD$_3$OD): δ 8.26 (s, 1H), 7.92 (s, 1H), 7.65 (d, J=1.60 Hz, 2H), 7.51 (s, 1H), 4.05-4.08 (m, 1H), 3.48-3.51 (m, 1H), 3.41-3.45 (m, 1H), 3.34 (s, 3H), 2.60-2.72 (m, 2H), 1.78-1.84 (m, 2H), 1.50-1.53 (m, 1H), 1.00 (d, J=6.80 Hz, 3H), 0.92 (d, J=6.80 Hz, 3H) ppm; LCMS (ESI) m/e 329.2 [(M+H)$^+$, calcd for $C_{18}H_{25}N_4O_2$, 329.19]; LC/MS retention time (method A): $t_R$=1.34 min; HPLC retention time (method D): $t_R$=5.68 min; HPLC retention time (method C): $t_R$=5.18 min; Chiral HPLC retention time (method B3): $t_R$=5.27 min.

Example 103

4-methyl-2-(6-(oxazol-5-yl)-1H-benzo[d]imidazol-2-yl)pentan-2-amine

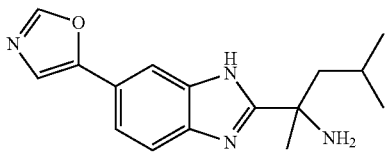 [SMILES: CC(C)CC(C)(N)c1nc2ccc(-c3cnco3)cc2[nH]1]

Prepared a similar fashion as described in Example 4 to afford 4-methyl-2-(6-(oxazol-5-yl)-1H-benzo[d]imidazol-2-yl)pentan-2-amine (20 mg, 0.07 mmol) as a white solid. $^1$H NMR (400 MHz, CD$_3$OD): δ 8.27 (s, 1H), 7.97 (s, 1H), 7.70 (d, J=1.20 Hz, 2H), 7.53 (s, 1H), 2.03-2.16 (m, 2H), 1.85 (s, 3H), 1.76-1.83 (m, 1H), 0.87 (d, J=6.80 Hz, 3H), 0.64 (d, J=6.80 Hz, 3H) ppm; LCMS (ESI) m/e 285.2 [(M+H)$^+$, calcd for C$_{16}$H$_{21}$N$_4$O, 285.16]; LC/MS retention time (method B): t$_R$=1.35 min; HPLC retention time (method A): t$_R$=9.16 min; HPLC retention time (method B): t$_R$=10.40 min.

Example 104

4,4,4-trifluoro-1-(6-(oxazol-5-yl)-1H-benzo[d]imidazol-2-yl)-3-(trifluoromethyl)butan-1-amine

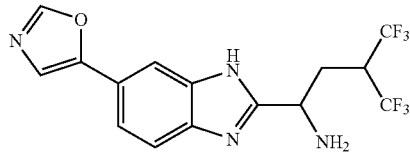

Prepared a similar fashion as described in Example 4 to afford 4,4,4-trifluoro-1-(6-(oxazol-5-yl)-1H-benzo[d]imidazol-2-yl)-3-(trifluoromethyl)butan-1-amine (15 mg, 0.039 mmol) as a pale yellow solid. $^1$H NMR (400 MHz, CD$_3$OD): δ 8.40 (s, 1H), 8.08 (s, 1H), 7.79 (s, 2H), 7.63 (s, 1H), 4.93-4.96 (m, 1H), 3.69-3.76 (m, 1H), 2.89-2.96 (m, 1H), 2.66-2.73 (m, 1H) ppm; LCMS (ESI) m/e 379.0 [(M+H)$^+$, calcd for C$_{15}$H$_{13}$F$_6$N$_4$O, 379.09]; LC/MS retention time (method B): t$_R$=1.52 min; HPLC retention time (method C): t$_R$=5.73 min; HPLC retention time (method D): t$_R$=6.63 min.

Example 105

4,4,4-trifluoro-1-(6-(oxazol-5-yl)-1H-benzo[d]imidazol-2-yl)butan-1-amine

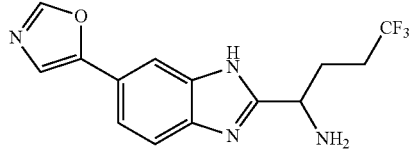 [SMILES: NC(CCC(F)(F)F)c1nc2ccc(-c3cnco3)cc2[nH]1]

Prepared a similar fashion as described in Example 4 to afford 4,4,4-trifluoro-1-(6-(oxazol-5-yl)-1H-benzo[d]imidazol-2-yl)butan-1-amine (16 mg, 0.051 mmol, 61% yield) as a white solid. $^1$H NMR (400 MHz, CD$_3$OD): δ 8.37 (s, 1H), 8.05 (s, 1H), 7.78 (d, J=1.20 Hz, 2H), 7.61 (s, 1H), 4.83-4.85 (m, 1H, obscured with solvent), 2.32-2.55 (m, 4H) ppm; LCMS (ESI) m/e 311.0 [(M+H)$^+$, calcd for C$_{14}$H$_{14}$F$_3$N$_4$O, 311.10]; LC/MS retention time (method B): t$_R$=1.32 min; HPLC retention time (method A): t$_R$=9.36 min; HPLC retention time (method D): t$_R$=5.35 min.

Example 106

2-isopentyl-6-(pyridin-4-yl)-1H-benzo[d]imidazole

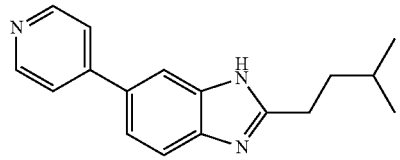 [SMILES: CC(C)CCc1nc2ccc(-c3ccncc3)cc2[nH]1]

Prepared a similar fashion as described in Example 1 to afford 2-isopentyl-6-(pyridin-4-yl)-1H-benzo[d]imidazole (200 mg, 0.753 mmol, 57% yield) as a white solid. $^1$H NMR (400 MHz, CD$_3$OD): δ 8.86 (d, J=6.80 Hz, 2H), 8.28-8.32 (m, 3H), 8.10 (dd, J=8.8, 1.6 Hz, 1H), 7.94 (d, J=8.80 Hz, 1H), 3.21-3.25 (m, 2H), 1.84-1.90 (m, 2H), 1.71-1.77 (m, 1H), 1.06 (d, J=6.80 Hz, 6H) ppm; LCMS (ESI) m/e 266.2 [(M+H)$^+$, calcd for C$_{17}$H$_{20}$N$_3$, 266.16]; LC/MS retention time (method A): t$_R$=1.52 min; HPLC retention time (method B): t$_R$=7.89 min; HPLC retention time (method A): t$_R$=7.13 min.

Example 107

1-(6-methoxy-5-(oxazol-5-yl)-1H-benzo[d]imidazol-2-yl)-N,3-dimethylbutan-1-amine

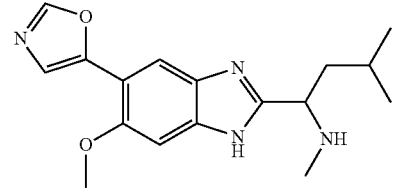 [SMILES: CNC(CC(C)C)c1nc2cc(-c3cnco3)c(OC)cc2[nH]1]

Prepared a similar fashion as described in Example 64 and (N-methylation described in Example 59 part A) to afford 1-(6-methoxy-5-(oxazol-5-yl)-1H-benzo[d]imidazol-2-yl)-N,3-dimethylbutan-1-amine (50 mg, 0.16 mmol, 47.3% yield) yellow solid. $^1$H NMR (400 MHz, CD$_3$OD) δ 8.28 (s, 1H) 8.07 (s, 1H) 7.59 (s, 1H) 7.73 (s, 1H) 4.54-4.58 (m, 1H) 4.07 (s, 3H) 2.70 (s, 3H) 2.22-2.29 (m, 1H) 1.91-1.98 (m, 1H) 1.49-1.53 (m, 1H) 0.95-1.05 (m, 6H) ppm; LCMS (ESI) m/e 315.2 [(M+H)$^+$, calcd for C$_{17}$H$_{23}$N$_4$O$_2$, 315.17]; LC/MS retention time (method A): t$_R$=1.23 min; HPLC retention time (method D): t$_R$=5.63 min; HPLC retention time (method C): t$_R$=5.26 min.

Example 108

2-(6-methoxy-5-(oxazol-5-yl)-1H-benzo[d]imidazol-2-yl)-4-methylpentan-2-amine

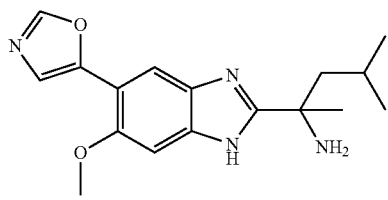 [SMILES: COc1cc2[nH]c(C(C)(N)CC(C)C)nc2cc1-c1cnco1]

Prepared a similar fashion as described in Example 64 to afford 2-(6-methoxy-5-(oxazol-5-yl)-1H-benzo[d]imidazol-2-yl)-4-methylpentan-2-amine (9 mg, 0.029 mmol, 79.6% yield) as a white solid. $^1$H NMR (400 MHz, CD$_3$OD) δ 8.49 (s, 1H) 7.09 (s, 1H) 7.69 (s, 1H) 7.34 (s, 1H) 4.08 (s, 3H) 2.18-2.23 (m, 1H) 2.06-2.11 (m, 1H) 1.90 (s, 3H) 1.79-1.82 (m, 1H) 0.83 (d, J=6.4 Hz, 3H) 0.73 (d, J=6.4 Hz, 3H) ppm; LCMS (ESI) m/e 313.0 [(M–H)$^-$, calcd for C$_{17}$H$_{21}$N$_4$O$_2$, 313.17]; LC/MS retention time (method F): $t_R$=1.54 min; HPLC retention time (method D): $t_R$=5.50 min; HPLC retention time (method C): $t_R$=5.01 min.

Example 109

(R)-N,3-dimethyl-1-(5-(pyridazin-4-yl)-1H-benzo[d]imidazol-2-yl)butan-1-amine

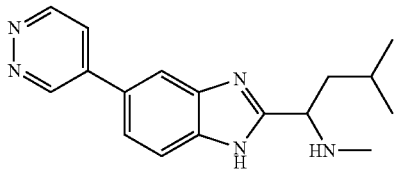 [SMILES: CNC(CC(C)C)c1nc2cc(-c3ccnnc3)ccc2[nH]1]

Prepared a similar fashion as described in Example 59 to afford (R)-N,3-dimethyl-1-(5-(pyridazin-4-yl)-1H-benzo[d]imidazol-2-yl)butan-1-amine (60 mg, 0.203 mmol, 30% yield) as a brown solid which was isolated as TFA salt. $^1$H NMR (400 MHz, CD$_3$OD): δ 9.76 (br s, 1H), 9.34 (br s, 1H), 8.33 (br s, 1H), 8.28 (s, 1H), 7.87-7.93 (m, 2H), 4.63-4.66 (m, 1H), 2.73 (s, 3H), 2.22-2.30 (m, 1H), 1.95-2.02 (m, 1H), 1.45-1.54 (m, 1H), 0.95-1.05 (m, 6H) ppm; LCMS (ESI) m/e 295.9 [(M+H)$^+$, calcd for C$_{17}$H$_{22}$N$_5$, 296.12]; LC/MS retention time (method C): $t_R$=1.42 min; HPLC retention time (method G): $t_R$=5.34 min; HPLC retention time (method A): $t_R$=8.01 min; Chiral SFC retention time (method A2): $t_R$=5.93 min.

BIOLOGICAL DATA

Methods

AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-NH2, 1.5 μM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis. Results are shown in Table 1.

TABLE 1

| Example | AAK1 IC$_{50}$ (nM) |
| --- | --- |
| 1 | 37 |
| 2 | 53 |
| 3 | 56 |
| 4 | 52 |
| 5 | 93 |
| 6 | 5 |
| 7 | 10 |
| 8 | 4 |
| 9 | 13 |
| 10 | 44 |
| 11 | 93 |
| 12 | 148 |
| 13 | 171 |
| 14 | 198 |
| 15 | 289 |
| 16 | 202 |
| 17 | 3940 |
| 18 | 19 |
| 19 | 41 |
| 20 | 489 |
| 21 | 33 |
| 22 | 52 |
| 23 | 553 |
| 24 | 1594 |
| 25 | 380 |
| 26 | 217 |
| 27 | 2000 |
| 28 | 2000 |
| 29 | 12 |
| 30 | 88 |
| 31 | 32 |
| 32 | 450 |
| 33 | 108 |
| 34 | 98 |
| 35 | 25 |
| 36 | 172 |
| 37 | 19 |
| 38 | 531 |
| 39 | 6740 |
| 40 | 271 |
| 41 | 559 |
| 42 | 159 |
| 43 | 103 |
| 44 | 124 |
| 45 | 749 |
| 46 | 1542 |
| 47 | 487 |
| 48 | 897 |
| 49 | 338 |
| 50 | 1728 |
| 51 | 783 |
| 52 | 232 |
| 53 | 521 |

TABLE 1-continued

| Example | AAK1 IC$_{50}$ (nM) |
|---|---|
| 54 | 785 |
| 55 | 1786 |
| 56 | 620 |
| 57 | 1551 |
| 58 | 40 |
| 59 | 7 |
| 60 | 8 |
| 61 | 8 |
| 62 | 12 |
| 63 | 14 |
| 64 | 16 |
| 65 | 26 |
| 66 | 45 |
| 67 | 49 |
| 68 | 50 |
| 69 | 57 |
| 70 | 61 |
| 71 | 70 |
| 72 | 108 |
| 73 | 180 |

TABLE 1-continued

| Example | AAK1 IC$_{50}$ (nM) |
|---|---|
| 74 | 228 |
| 75 | 244 |
| 76 | 350 |
| 77 | 436 |
| 78 | 510 |
| 79 | 591 |
| 80 | 697 |
| 81 | 1433 |
| 82 | 1803 |
| 83 | 71 |
| 84 | 438 |
| 85 | 833 |
| 86 | 2311 |
| 87 | 92 |
| 88 | 62 |
| 89 | 327 |
| 90 | 818 |
| 91 | 391 |
| 92 | 1701 |
| 93 | 136 |
| 94 | 294 |
| 95 | 100 |
| 96 | 797 |
| 97 | 116 |
| 98 | 44 |
| 99 | 105 |
| 100 | 1017 |
| 101 | 34 |
| 102 | 680 |

TABLE 1-continued

| Example | AAK1 IC$_{50}$ (nM) |
|---|---|
| 103 | 158 |
| 104 | 381 |
| 105 | 150 |
| 106 | 115 |
| 107 | 16 |
| 108 | 60 |
| 109 | 428 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula (I)

(I)

or a pharmaceutically acceptable salt thereof, wherein
one of $a$ and $b$ a double bond and the other is a single bond;
when $a$ is a double bond, X is N;
when $a$ is a single bond, X is selected from NR$^4$, O, and S;
when $b$ is a double bond, Y is N;
when $b$ is a single bond, Y is selected from NR$^4$, O, and S;
R$^1$ is selected from C$_3$-C$_6$cycloalkyl optionally substituted with one or two methyl groups; C$_3$-C$_6$cycloalkylC$_1$-C$_3$alkyl, wherein the C$_1$-C$_3$alkyl part is optionally substituted with an amino or methylamino group and wherein the C$_3$-C$_6$cycloalkyl part is optionally substituted with a methyl group;

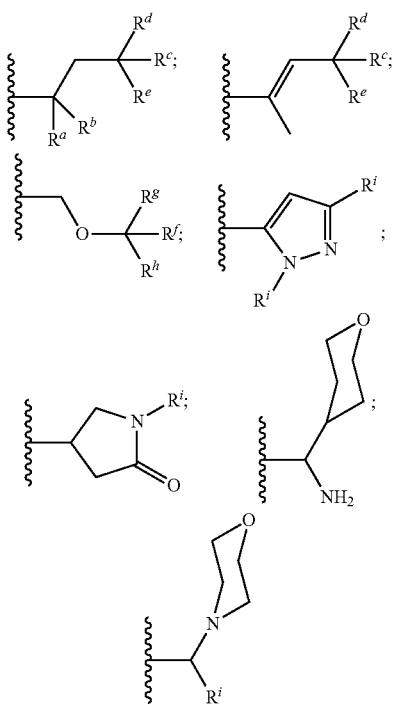

wherein
R$^a$ is selected from hydrogen, amino, aminomethyl, methoxyethylamino, methyl, methylamino, trifluoroacetyl, and 2,2,2-trifluoroethyl;
R$^b$ is selected from hydrogen and methyl;
R$^c$ is selected from hydrogen, fluoro, and methyl;
R$^d$ is selected from methyl and trifluoromethyl;
R$^e$ is selected from hydrogen, methyl, trifluoromethyl;
R$^f$ is selected from hydrogen and methyl;
R$^g$ is selected from hydrogen and methyl;
R$^h$ is methyl; and
R$^i$ is C$_1$-C$_6$alkyl;
R$^2$ is pyridinyl, oxazolyl or pyrazolyl, wherein said pyridinyl, oxazolyl or pyrazolyl is optionally substituted with one or two groups independently selected from acylamino, C$_1$-C$_3$alkoxy, C$_1$-C$_3$alkyl, amino, cyano, dimethylamino, halo, methyl, and methylamino;
R$^3$ is selected from hydrogen, C$_1$-C$_3$alkoxy, C$_1$-C$_3$alkyl, and halo; and
R$^4$ is selected from hydrogen, C$_1$-C$_3$alkoxyC$_1$-C$_3$alkyl, C$_1$-C$_3$alkyl, haloC$_1$-C$_3$alkyl, hydroxyC$_1$-C$_3$alkyl.

2. A compound of claim 1 wherein R$^1$ is

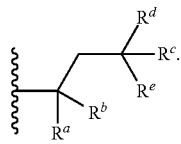

3. A compound of claim 1 wherein R$^2$ is optionally substituted pyridinyl.
4. A compound of claim 1 wherein R$^2$ is optionally substituted oxazolyl.
5. A compound of claim 1 wherein R$^2$ is pyrazolyl.
6. A compound selected from
(R)-3-methyl-1-(5-(pyridin-4-yl)-1H-benzo[d]imidazol-2-yl)butan-1-amine;
(S)-3-methyl-1-(6-(pyridin-4-yl)-1H-benzo[d]imidazol-2-yl)butan-1-amine;
(R)-1-(5-(1 H-pyrazol-3-yl)-1H-benzo[d]imidazol-2-yl)-3-methylbutan-1-amine;
(R)-3-methyl-1-(5-(oxazol-5-yl)-1H-benzo[d]imidazol-2-yl)butan-1-amine;
(S)-3-methyl-1-(5-(oxazol-5-yl)-1H-benzo[d]imidazol-2-yl)butan-1-amine;
(R)-1-(5-(1H-pyrrolo[2,3-b]pyridin-4-yl)-1H-benzo[d]imidazol-2-yl)-3-methylbutan-1-amine;
(R)-1-(5-(1H-pyrazolo[3,4-b]pyridin-4-yl)-1H-benzo[d]imidazol-2-yl)-3-methylbutan-1-amine;
(R)-1-(5-(7H-pyrrolo[2,3-d]pyrimidin-4-yl)-1H-benzo[d]imidazol-2-yl)-3-methylbutan-1-amine;
(R)-3-methyl-1-(5-(quinolin-4-yl)-1H-benzo[d]imidazol-2-yl)butan-1-amine;
(R)-1-(5-(3-fluoropyridin-4-yl)-1H-benzo[d]imidazol-2-yl)-3-methylbutan-1-amine;
(R)-1-(5-(3-methoxypyridin-4-yl)-1H-benzo[d]imidazol-2-yl)-3-methylbutan-1-amine;
(R)-1-(5-(2-fluoropyridin-4-yl)-1H-benzo[d]imidazol-2-yl)-3-methylbutan-1-amine;
(R)-1-(5-(2-methoxypyridin-4-yl)-1H-benzo[d]imidazol-2-yl)-3-methylbutan-1-amine;
(R)-4-(2-(1-amino-3-methylbutyl)-1H-benzo[d]imidazol-5-yl)-N,N-dimethylpyrimidin-2-amine;
(R)-4-(2-(1-amino-3-methylbutyl)-1H-benzo[d]imidazol-5-yl)picolinonitrile;
(R)-4-(2-(1-amino-3-methylbutyl)-1H-benzo[d]imidazol-5-yl)pyrimidin-2-amine;
(R)-1-(5-(2,6-difluoropyridin-4-yl)-1H-benzo[d]imidazol-2-yl)-3-methylbutan-1-amine;
(R)-4-(2-(1-amino-3-methylbutyl)-1H-benzo[d]imidazol-5-yl)pyridin-2-amine;
(R)-1-(5-(3,5-dimethyl-1H-pyrazol-4-yl)-1H-benzo[d]imidazol-2-yl)-3-methylbutan-1-amine;
(R)-1-(5-(5-fluoro-2-methoxypyridin-4-yl)-1H-benzo[d]imidazol-2-yl)-3-methylbutan-1-amine;
(R)-1-(7-methoxy-5-(oxazol-5-yl)-1H-benzo[d]imidazol-2-yl)-3-methylbutan-1-amine;
(R)-1-(7-methoxy-5-(pyridin-4-yl)-1H-benzo[d]imidazol-2-yl)-3-methylbutan-1-amine;
(R)-1-(7-methoxy-5-(3-methoxypyridin-4-yl)-1H-benzo[d]imidazol-2-yl)-3-methylbutan-1-amine;
(R)-1-(7-methoxy-5-(2-methoxypyridin-4-yl)-1H-benzo[d]imidazol-2-yl)-3-methylbutan-1-amine;
2-isopentyl-4-methoxy-6-(pyridin-4-yl)-1H-benzo[d]imidazole;
5-(2-isopentyl-4-methoxy-1H-benzo[d]imidazol-6-yl)oxazole;
(R)-1-(6-methoxy-5-(3-methoxypyridin-4-yl)-1H-benzo[d]imidazol-2-yl)-3-methylbutan-1-amine;
(R)-1-(6-methoxy-5-(2-methoxypyridin-4-yl)-1H-benzo[d]imidazol-2-yl)-3-methylbutan-1-amine;
(R)-1-(5-methoxy-6-(oxazol-5-yl)-1H-benzo[d]imidazol-2-yl)-3-methylbutan-1-amine;
(R)-1-(6-fluoro-5-(pyridin-4-yl)-1H-benzo[d]imidazol-2-yl)-3-methylbutan-1-amine;
(R)-1-(5-fluoro-6-(oxazol-5-yl)-1H-benzo[d]imidazol-2-yl)-3-methylbutan-1-amine;
(R)-1-(1-ethyl-6-(oxazol-5-yl)-1H-benzo[d]imidazol-2-yl)-3-methylbutan-1-amine;
(R)-1-(1-ethyl-6-(pyridin-4-yl)-1H-benzo[d]imidazol-2-yl)-3-methylbutan-1-amine;
(R)-1-(1-ethyl-6-(1 H-pyrazol-4-yl)-1H-benzo[d]imidazol-2-yl)-3-methylbutan-1-amine;

(R)-1-(6-(3-methoxypyridin-4-yl)-1-(2,2,2-trifluoro-ethyl)-1H-benzo[d]imidazol-2-yl)-3-methylbutan-1-amine;
(R)-3-methyl-1-(6-(oxazol-5-yl)-1-(2,2,2-trifluoroethyl)-1H-benzo[d]imidazol-2-yl)butan-1-amine;
(R)-3-methyl-1-(6-(pyridin-4-yl)-1-(2,2,2-trifluoroethyl)-1H-benzo[d]imidazol-2-yl)butan-1-amine;
(R)-1-(1-(2-methoxyethyl)-6-(pyridin-4-yl)-1H-benzo[d]imidazol-2-yl)-3-methylbutan-1-amine;
(R)-1-(1-(2-methoxyethyl)-6-(oxazol-5-yl)-1H-benzo[d]imidazol-2-yl)-3-methylbutan-1-amine;
(R)-2-(2-(1-amino-3-methylbutyl)-6-(pyridin-4-yl)-1H-benzo[d]imidazol-1-yl)ethanol;
(R)-2-(2-(1-amino-3-methylbutyl)-6-(oxazol-5-yl)-1H-benzo[d]imidazol-1-yl)ethanol;
(R)-3-methyl-1-(1-methyl-6-(pyridin-4-yl)-1H-benzo[d]imidazol-2-yl)butan-1-amine;
(R)-3-methyl-1-(1-propyl-6-(pyridin-4-yl)-1H-benzo[d]imidazol-2-yl)butan-1-amine;
(R)-1-(1-isopropyl-6-(pyridin-4-yl)-1H-benzo[d]imidazol-2-yl)-3-methylbutan-1-amine;
(R)-1-(1-ethyl-5-(pyridin-4-yl)-1H-benzo[d]imidazol-2-yl)-3-methylbutan-1-amine;
(R)-1-(1-ethyl-5-(oxazol-5-yl)-1H-benzo[d]imidazol-2-yl)-3-methylbutan-1-amine;
(R)-1-(5-methoxy-6-(pyridin-4-yl)-1H-benzo[d]imidazol-2-yl)-3-methylbutan-1-amine;
2-(2-methylcyclopropyl)-6-(pyridin-4-yl)-1H-benzo[d]imidazole;
2-(2,2-dimethylcyclopropyl)-6-(pyridin-4-yl)-1H-benzo[d]imidazole;
2-(3-(tert-butyl)-1-methyl-1H-pyrazol-5-yl)-6-(pyridin-4-yl)-1H-benzo[d]imidazole;
1-isopropyl-4-(6-(pyridin-4-yl)-1H-benzo[d]imidazol-2-yl)pyrrolidin-2-one;
3,3,3-trifluoro-2-methyl-1-(6-(pyridin-4-yl)-1H-benzo[d]imidazol-2-yl)propan-1-amine;
3,3,3-trifluoro-2-methyl-1-(6-(pyridin-4-yl)-1H-benzo[d]imidazol-2-yl)propan-1-amine;
2-(isopropoxymethyl)-6-(pyridin-4-yl)-1H-benzo[d]imidazole;
2-(tert-butoxymethyl)-6-(pyridin-4-yl)-1H-benzo[d]imidazole;
2-isopentyl-5-(3-methoxypyridin-4-yl)-1H-benzo[d]imidazole;
2-isopentyl-5-(2-methoxypyridin-4-yl)-1H-benzo[d]imidazole;
2-(4-methylpentan-2-yl)-5-(pyridin-4-yl)-1H-benzo[d]imidazole;
(R)-4-(2-(3-methyl-1-(methylamino)butyl)-1H-benzo[d]imidazol-5-yl)pyridin-2-amine;
(R)-1-Cyclohexyl-N-methyl-1-(5-(pyridin-4-yl)-1H-benzo[d]imidazol-2-yl)methanamine;
(R)-N-methyl-4-(2-(3-methyl-1-(methylamino) butyl)-1H-benzo[d]imidazol-5-yl) pyridin-2-amine;
N,3-dimethyl-1-(5-(pyridin-4-yl)-1H-benzo[d]imidazol-2-yl)butan-1-amine;
(R)-N-(4-(2-(3-methyl-1-(methylamino)butyl)-1H-benzo[d]imidazol-5-yl)pyridin-2-yl)acetamide;
(R)-cyclohexyl(6-methoxy-5-(oxazol-5-yl)-1H-benzo[d]imidazol-2-yl)methanamine;
4-methyl-2-(5-(oxazol-5-yl)-1H-benzo[d]imidazol-2-yl)pentan-1-amine;
3-methyl-1-(5-(pyridin-4-yl)-1H-benzo[d]imidazol-2-yl)-N-(2,2,2-trifluoroethyl)butan-1-amine;
4-methyl-2-(5-(pyridin-4-yl)-1H-benzo[d]imidazol-2-yl)pentan-1-amine;
(R)-cyclopentyl (6-methoxy-5-(oxazol-5-yl)-1H-benzo[d]imidazol-2-yl) methanamine;
5-(2-(cyclopentylmethyl)-6-methoxy-1H-benzo[d]imidazol-5-yl) oxazole;
(R)-2-cyclopropyl-1-(5-(pyridin-4-yl)-1H-benzo[d]imidazol-2-yl) ethanamine;
2-cyclopentyl-1-(6-methoxy-5-(oxazol-5-yl)-1H-benzo[d]imidazol-2-yl)ethanamine;
2-(cyclohexylmethyl)-5-(pyridin-4-yl)-1H-benzo[d]imidazole;
1-(6-methoxy-5-(pyridin-4-yl)-1H-benzo[d]imidazol-2-yl)-N,3-dimethylbutan-1-amine;
(R)-cyclopropyl (5-(pyridin-4-yl)-1H-benzo[d]imidazol-2-yl)methanamine;
(R)-N,N-dimethyl-4-(2-(3-methyl-1-(methylamino) butyl)-1H-benzo[d]imidazol-5-yl) pyridin-2-amine;
3-fluoro-3-methyl-1-(5-(pyridin-4-yl)-1H-benzo[d]imidazol-2-yl)butan-1-amine;
(R)-(5-(pyridin-4-yl)-1H-benzo[d]imidazol-2-yl) (tetrahydro-2H-pyran-4-yl) 180 methanamine;
(R)-1-(5-(3,5-dimethylisoxazol-4-yl)-1H-benzo[d]imidazol-2-yl)-3-methylbutan-1-amine;
4-(1-(5-bromo-1H-benzo[d]imidazol-2-yl) ethyl) morpholine;
(R)-2,2,2-trifluoro-N-(3-methyl-1-(5-(pyridin-4-yl)-1H-benzo[d]imidazol-2-yl)butyl)acetamide;
2-(3-methylcyclohexyl)-6-(pyridin-4-yl)-1H-benzo[d]imidazole;
(R)-cyclopentyl(6-methoxy-5-(pyridin-4-yl)-1H-benzo[d]imidazol-2-yl)methanamine;
3-methyl-1-(5-(pyridin-4-yl)benzo[d]oxazol-2-yl)butan-1-amine;
3-methyl-1-(6-(pyridin-4-yl)benzo[d]oxazol-2-yl)butan-1-amine;
2-isopentyl-6-(pyridin-4-yl)benzo[d]oxazole;
(E)-2-(4-methylpent-2-en-2-yl)-5-(pyridin-4-yl)benzo[d]oxazole;
2-(4-methylpentan-2-yl)-6-(pyridin-4-yl)benzo[d]oxazole;
2-(4-methylpentan-2-yl)-5-(pyridin-4-yl)benzo[d]oxazole;
2-isopentyl-5-(pyridin-4-yl)benzo[d]oxazole;
2-(cyclopentylmethyl)-5-(pyridin-4-yl)benzo[d]oxazole;
4,4,4-trifluoro-1-(5-(pyridin-4-yl)benzo[d]oxazol-2-yl)-3-(trifluoromethyl)butan-1-amine;
2-(2-cyclopentylethyl)-5-(pyridin-4-yl)benzo[d]oxazole;
4,4,4-trifluoro-1-(5-(pyridin-4-yl)benzo[d]oxazol-2-yl) butan-1-amine;
1-(5-(3-methoxypyridin-4-yl)benzo[d]oxazol-2-yl)-3-methylbutan-1-amine;
3-methyl-1-(5-(pyridin-4-yl)benzo[d]thiazol-2-yl)butan-1-amine;
(R)-3-methyl-1-(5-(pyridin-4-yl)benzo[d]thiazol-2-yl)butan-1-amine;
(S)-3-methyl-1-(5-(pyridin-4-yl)benzo[d]thiazol-2-yl)butan-1-amine;
3-methyl-1-(6-(pyridin-4-yl)benzo[d]thiazol-2-yl)butan-1-amine;
2-(cyclopentylmethyl)-5-(pyridin-4-yl)-1H-benzo[d]imidazole;
2-isopentyl-6-(oxazol-5-yl)benzo[d]oxazole;
(R)-N,3-dimethyl-1-(6-(oxazol-5-yl)-1H-benzo[d]imidazol-2-yl)butan-1-amine;
(R)-N-(2-methoxyethyl)-3-methyl-1-(5-(oxazol-5-yl)-1H-benzo[d]imidazol-2-yl)butan-1-amine;
4-methyl-2-(6-(oxazol-5-yl)-1H-benzo[d]imidazol-2-yl)pentan-2-amine;

4,4,4-trifluoro-1-(6-(oxazol-5-yl)-1H-benzo[d]imidazol-2-yl)-3-(trifluoromethyl)butan-1-amine;

4,4,4-trifluoro-1-(6-(oxazol-5-yl)-1H-benzo[d]imidazol-2-yl)butan-1-amine;

2-isopentyl-6-(pyridin-4-yl)-1H-benzo[d]imidazole;

1-(6-methoxy-5-(oxazol-5-yl)-1H-benzo[d]imidazol-2-yl)-N,3-dimethylbutan-1-amine;

2-(6-methoxy-5-(oxazol-5-yl)-1H-benzo[d]imidazol-2-yl)-4-methylpentan-2-amine; and (R)-N,3-dimethyl-1-(5-(pyridazin-4-yl)-1H-benzo[d]imidazol-2-yl)butan-1-amine;

or a pharmaceutically acceptable salt thereof.

7. A composition comprising a pharmaceutically acceptable amount of a compound of claim 1, or a pharmaceutically acceptable salt thereof, and a pharmaceutically acceptable carrier.

8. A method of inhibiting adaptor associated kinase 1 (AAK1) activity, comprising contacting AAK1 with a compound of claim 1, or a pharmaceutically acceptable salt thereof.

9. A method for treating or managing a disease or a disorder mediated by AAK1 activity, the method comprising administering to a patient having said disease or disorder a therapeutically effective amount of a compound of claim 1, or a pharmaceutically acceptable salt thereof.

10. The method of claim 9, wherein the disease or disorder is selected from Alzheimer's disease, bipolar disorder, pain, Parkinson's disease, and schizophrenia.

11. The method of claim 10 wherein the pain is neuropathic pain.

12. The method of claim 11 wherein the neuropathic pain is fibromyalgia or peripheral neuropathy.

* * * * *

UNITED STATES PATENT AND TRADEMARK OFFICE
CERTIFICATE OF CORRECTION

PATENT NO. : 10,035,777 B2
APPLICATION NO. : 15/500116
DATED : July 31, 2018
INVENTOR(S) : Dzierba et al.

It is certified that error appears in the above-identified patent and that said Letters Patent is hereby corrected as shown below:

In the Claims

Claim 1, Column 158, Lines 42-49:

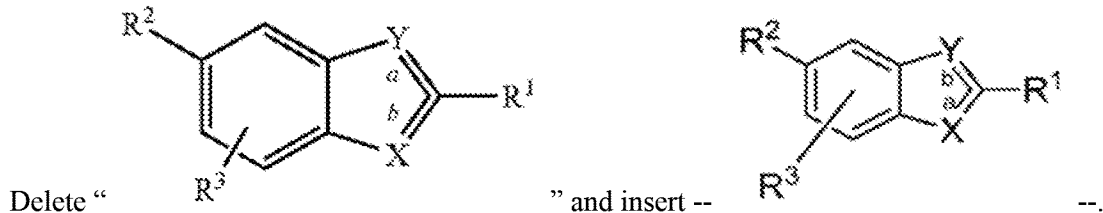

Delete " [structure] " and insert -- [structure] --.

Claim 1, Column 158, Line 52:
Before "a" insert -- is --.

Claim 6, Column 160, Line 3:
Delete "(1 H-" and insert -- (1H- --.

Claim 6, Column 160, Line 66:
Delete "(1 H-" and insert -- (1H- --.

Claim 6, Column 162, Line 20:
Delete "-yl) 180 methanamine;" and insert -- -yl)methanamine; --.

Signed and Sealed this
Eleventh Day of December, 2018

Andrei Iancu
*Director of the United States Patent and Trademark Office*